US011591334B2

(12) United States Patent
Wang et al.

(10) Patent No.: US 11,591,334 B2
(45) Date of Patent: Feb. 28, 2023

(54) SUBSTITUTED PYRROLIZINES FOR THE TREATMENT OF HEPATITIS B

(71) Applicant: SHANGHAI LONGWOOD BIOPHARMACEUTICALS CO., LTD., Shanghai (CN)

(72) Inventors: Zhe Wang, Shanghai (CN); Guoqin Fan, Shanghai (CN); Cenbin Lu, Shanghai (CN); Sai Yang, Shanghai (CN); Xiaoguang Wang, Shanghai (CN)

(73) Assignee: SHANGHAI LONGWOOD BIOPHARMACEUTICALS CO., LTD., Shanghai (CN)

( * ) Notice: Subject to any disclaimer, the term of this patent is extended or adjusted under 35 U.S.C. 154(b) by 502 days.

(21) Appl. No.: 16/610,400

(22) PCT Filed: May 4, 2018

(86) PCT No.: PCT/CN2018/085695

§ 371 (c)(1),
(2) Date: Aug. 3, 2020

(87) PCT Pub. No.: WO2018/202155

PCT Pub. Date: Nov. 8, 2018

(65) Prior Publication Data

US 2020/0354366 A1 Nov. 12, 2020

(30) Foreign Application Priority Data

May 4, 2017 (CN) ........................ 201710308759.X

(51) Int. Cl.

| | |
|---|---|
| ***A61K 31/167*** | (2006.01) |
| ***C07C 233/57*** | (2006.01) |
| ***C07D 487/04*** | (2006.01) |
| ***A61P 31/20*** | (2006.01) |
| ***C07D 471/04*** | (2006.01) |
| ***C07D 519/00*** | (2006.01) |

(52) U.S. Cl.

CPC ............ *C07D 487/04* (2013.01); *A61P 31/20* (2018.01); *C07D 471/04* (2013.01); *C07D 519/00* (2013.01)

(58) Field of Classification Search

CPC ............................ A61K 31/167; C07C 233/57
USPC ........................................... 514/613; 564/123
See application file for complete search history.

(56) References Cited

U.S. PATENT DOCUMENTS 4,208,210 A 6/1980 Sakai et al.
4,334,004 A 6/1982 Scheler

FOREIGN PATENT DOCUMENTS

CN 101001856 A 7/2007
CN 103224466 A 7/2013

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
El-Moghazy Aly, et al. Saudi Pharmaceutical Journal, 17(1), 2009, 3-18.*
English Translation of the International Search Report dated Aug. 13, 2018 corresponding to PCT/CN2018/085695 filed May 4, 2018; 3 pages.
Kleymann, Gerald et al., "A Generally Applicable, High-Throughput Screening-Compatible Assay to Identify, Evaluate, and Optimize Antimicrobial Agents for Drug Therapy," *Journal of Biomolecular Screening* (Feb. 9, 2004); 9(7):578-587.

* cited by examiner

*Primary Examiner* — Douglas M Willis
(74) *Attorney, Agent, or Firm* — Mintz Levin Cohn Ferris Glovsky and Popeo, P.C.

(57) ABSTRACT

The present invention relates to a bicyclic nucleocapsid inhibitor and the use of the same as a drug in the treatment of hepatitis B. In particular, disclosed is a compound having a structure shown by the following formula (A1):

(A1)

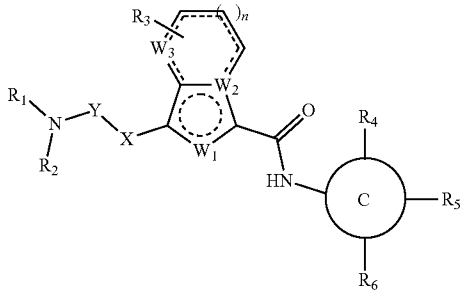

or a stereoisomer or a tautomer thereof, or a pharmaceutically acceptable salt, a hydrate, or a solvate thereof, that can be used as an HBV inhibitor, wherein the definition of each group is as described in detail in the description. The present invention also relates to a pharmaceutical composition comprising the compound and the use of the same in the treatment of hepatitis B.

12 Claims, No Drawings

SUBSTITUTED PYRROLIZINES FOR THE TREATMENT OF HEPATITIS B

CROSS-REFERENCES TO RELATED APPLICATIONS

This application is a U.S. National Phase Application of International Application No. PCT/CN2018/085695 filed May 4, 2018, which claims priority to Chinese Patent Application No. CN201710308759.X filed May 4, 2017, each of which is incorporated herein in its entirety for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

FIELD OF THE INVENTION

The present invention belongs to the field of medicine, and in particular, the present invention relates to fused-aryl amide compounds for treatment of hepatitis B and uses thereof.

BACKGROUND OF THE INVENTION

Hepatitis B virus (HBV) is an enveloped virus of hepatotropic virus DNA family (Hepadnaviridae) with partially double-stranded DNA (dsDNA). The genome thereof contains 4 overlapped reading frames: precore/core gene, polymerase gene, UM and S genes (which encode three envelope proteins), and X gene. In the early stage of infection, the partially double-stranded DNA genome (open-loop DNA, rcDNA) in the host cell nucleus is transformed into covalently closed circular DNA (cccDNA) and transcribed into virus mRNA. Once encapsulated, the pre-genome RNA (pgRNA) (which encodes the core protein and Pol encoded) serves as a template for reverse transcription, which regenerates this partially dsDNA genome (rcDNA) in the nucleocapsid.

HBV causes epidemics in certain areas of Asia and Africa, and is endemic in China. HBV has infected about 2 billion people worldwide, of which about 350 million people have developed into chronic infectious diseases. The virus causes hepatitis B disease and chronic infectious diseases are associated with a highly increased risk of development of cirrhosis and liver cancer.

The spread of hepatitis B virus is caused by exposure to infectious blood or body fluid, and the virus is detected in the saliva, tears, and urine of chronic carriers with high DNA titers in the serum.

Although there is currently an effective and well tolerated vaccine, the option of direct treatment is currently limited to interferon and the following antiviral drugs: tenofovir, lamivudine, adefovir, entecavir and telbivudine.

Additionally, heteroaryl dihydropyrimidines (HAPs) are identified as a class of HBV inhibitors in tissue cultivation and animal models. WO2013/006394 (published on Jan. 10, 2013) and WO 2013/096744 (published on Jun. 27, 2013) also disclosed sulfamoyl-arylamides having anti-HBV activity. However, these direct HBV antiviral drugs still have problems such as toxicity, mutagenicity, lack of selectivity, poor efficacy, poor bioavailability, and difficulty in synthesis.

Therefore, there is a need in the art to develop HBV inhibitors with advantages such as high potency and lower toxicity.

BRIEF SUMMARY OF THE INVENTION

The object of the present invention is to provide a class of HBV inhibitors having high potency and lower toxicity.

In the first aspect of the invention, it provides a compound of formula A, or a stereoisomer thereof, a tautomer thereof, or a pharmaceutically acceptable salt, hydrate or solvent thereof,

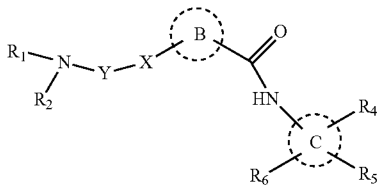

A wherein the B ring is a substituted or unsubstituted 8-20 membered fused bicyclic ring structure; wherein said "substituted" means that one or more hydrogen atoms on the group are substituted by a substituent selected from the group consisting of halogen, —CN, hydroxyl, amino, carboxyl, —(C═O)-substituted or unsubstituted C1-C8 alkyl, substituted or unsubstituted C1-C8 alkyl, substituted or unsubstituted C2-C6 alkenyl, substituted or unsubstituted C2-C6 alkynyl, substituted or unsubstituted C1-C8 alkylamino, substituted or unsubstituted C1-C8 alkoxy, substituted or unsubstituted C3-C10 cycloalkyl, substituted or unsubstituted 3-10 membered heterocycloalkyl having 1-3 heteroatoms selected from the group consisting of N, S and O, substituted or unsubstituted C6-C10 aryl, and substituted or unsubstituted 5-10 membered heteroaryl having 1-3 heteroatoms selected from the group consisting of N, S and O;

C ring is a substituted or unsubstituted 5-12 membered ring;

$R_1$ and $R_2$ are each independently selected from the group consisting of hydrogen, substituted or unsubstituted C1-C8 alkyl, substituted or unsubstituted C3-C10 cycloalkyl (including monocyclic, fused or bridged ring structures), substituted or unsubstituted 3-10 membered heterocyclic group (including monocyclic, fused or bridged ring structures) with 1-3 heteroatoms selected from N, S and O, substituted or unsubstituted C6-C10 aryl, and substituted or unsubstituted 5-10 membered heteroaryl having 1-3 heteroatoms selected from the group consisting of N, S and O;

or $R_1$ and $R_2$ together with the nitrogen atom to which they are attached form a substituted or unsubstituted 3-10 membered heterocyclic group (including monocyclic, fused or bridged ring structures) comprising one N atom and 0-3 heteroatoms selected from N, S and O;

$R_4$, $R_5$ and $R_6$ are each independently a substituent on any site of C ring selected from the group consisting of hydrogen, halogen, —CN, hydroxyl, amino, carboxyl, —(C═O)-substituted or unsubstituted C1-C8 alkyl, substituted or unsubstituted C1-C8 alkyl, substituted or unsubstituted C2-C6 alkenyl, substituted or unsubstituted C2-C6 alkynyl, substituted or unsubstituted C1-C8 alkylamino, substituted or unsubstituted C1-C8 alkoxy, substituted or unsubstituted C3-C10 cycloalkyl, substituted or unsubstituted 3-10 membered heterocycloalkyl having 1-3 heteroatoms selected from the group consisting of N, S and O, substituted or unsubstituted C6-C10 aryl, and substituted or unsubstituted 5-10 membered heteroaryl having 1-3 heteroatoms selected from the group consisting of N, S and O;

X is none, O, $NR_9$, halogenated C1-C4 alkylene (such as $CF_2$) or hydroxyl oxime (═N—OH); wherein $R_9$ is hydrogen, substituted or unsubstituted C1-C8 alkyl, or substituted or unsubstituted C3-C8 cycloalkyl; wherein the term "substituted" means substitution by one or more (for example 2, 3, 4, etc.) substituents selected from the group consisting of halogen, C1-C6 alkyl, C1-C6 haloalkyl, —CN, hydroxyl, amino, and carboxyl;

Y is carbonyl (—(CO)—), sulfonyl (—$SO_2$—), or sulfonimido (—SONH—);

unless otherwise indicated, the term "substituted" means substitution by one or more (for example 2, 3, 4, etc.) substituents selected from the group consisting of halogen, C1-C6 alkyl, C1-C6 haloalkyl, C1-C6 alkoxy, C1-C6 haloalkoxy, C3-C8 cycloalkyl, C3-C8 halocycloalkyl, oxo, —CN, hydroxyl, hydroxy-C1-C6 alkyl, amino, carboxyl, C6-C10 aryl, halogenated C6-C10 aryl, and 5-10 membered heteroaryl having 1-3 heteroatoms selected from N, S and O which is unsubstituted or substituted with a substituent selected from the group consisting of halogen and phenyl.

In another preferred embodiment, X is none.

In another preferred embodiment, the 3-10 membered heterocyclic group is selected from the group consisting of monocyclic group, bicyclic group, fused ring group, bridged ring group, and spiro ring group.

In another preferred embodiment, the C ring is a substituted or unsubstituted benzene ring, or a substituted or unsubstituted 5-7 membered heteroaryl ring.

In another preferred embodiment, the B ring is a ring fused by a five-membered ring and a five-membered ring.

In another preferred embodiment, the B ring is a ring fused by a five-membered ring and a six-membered ring.

In another preferred embodiment, the B ring is a ring fused by a six-membered ring with six-membered ring.

In another preferred embodiment, the B ring is a ring fused by a five-member and a seven-membered ring.

In another preferred embodiment, the B ring is a saturated ring, a partially unsaturated ring or an aromatic ring.

In another preferred embodiment, the C ring is a 5-7 membered ring.

In another preferred embodiment, each of $R_4$, $R_5$ and $R_6$ is independently a substituent at any site on the C ring selected from the group consisting of hydrogen, halogen, —CN, hydroxyl, amino, carboxyl, and substituted or unsubstituted C1-C8 alkyl.

In another preferred embodiment, each of the chiral centers in the compound of formula I is independently R or S.

In another preferred embodiment, the compound has a structure shown by the following formula A1:

A1

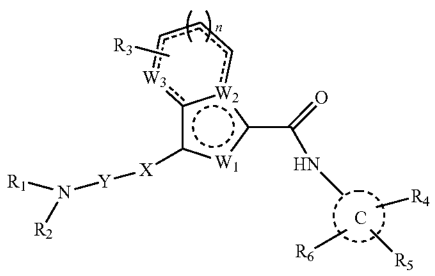

wherein, $W_1$ is selected from the group consisting of $CR_{10}R_{11}$, $CR_{10}$, O, S, and $NR_{12}$;

$W_2$ is selected from the group consisting of $CR_{10}$ or N;

$W_3$ is $CR_{10}R_{11}$, $CR_{10}$, N or $NR_{12}$;

n is 0, 1 or 2;

dashed line is a chemical bond or none.

$R_{10}$ and $R_{11}$ are each independently a substituent selected from the group consisting of hydrogen, halogen, —CN, hydroxyl, amino, carboxyl, —(C═O)-substituted or unsubstituted C1-C8 alkyl, substituted or unsubstituted C1-C8 alkyl, substituted or unsubstituted C2-C6 alkenyl, substituted or unsubstituted C2-C6 alkynyl, substituted or unsubstituted C1-C8 alkylamino, substituted or unsubstituted C1-C8 alkoxy, substituted or unsubstituted C3-C10 cycloalkyl, substituted or unsubstituted 3-10 membered heterocycloalkyl having 1-3 heteroatoms selected from the group consisting of N, S and O, substituted or unsubstituted C6-C10 aryl, and substituted or unsubstituted 5-10 membered heteroaryl having 1-3 heteroatoms selected from the group consisting of N, S and O;

$R_{12}$ is each independently a substituent selected from the group consisting of hydrogen, —CN, hydroxyl, amino, carboxyl, —(C═O)-substituted or unsubstituted C1-C8 alkyl, substituted or unsubstituted C1-C8 alkyl, substituted or unsubstituted C2-C6 alkenyl, substituted or unsubstituted C2-C6 alkynyl, substituted or unsubstituted C1-C8 alkylamino, substituted or unsubstituted C1-C8 alkoxy, substituted or unsubstituted C3-C10 cycloalkyl, substituted or unsubstituted 3-10 membered heterocycloalkyl having 1-3 heteroatoms selected from the group consisting of N, S and O, substituted or unsubstituted C6-C10 aryl, and substituted or unsubstituted 5-10 membered heteroaryl having 1-3 heteroatoms selected from the group consisting of N, S and O;

$R_3$ is one or more (preferably 1, 2, 3, 4 or 5) substituents on the bicyclic structure selected from the group consisting of H, halogen, —CN, hydroxyl, amino, carboxyl, —(C═O)-substituted or unsubstituted C1-C8 alkyl, substituted or unsubstituted C1-C8 alkyl, substituted or unsubstituted C2-C6 alkenyl, substituted or unsubstituted C2-C6 alkynyl, substituted or unsubstituted C1-C8 alkylamino, substituted or unsubstituted C1-C8 alkoxy, substituted or unsubstituted C3-C10 cycloalkyl, substituted or unsubstituted 3-10 membered heterocycloalkyl having 1-3 heteroatoms selected from the group consisting of N, S and O, substituted or unsubstituted C6-C10 aryl, and substituted or unsubstituted 5-10 membered heteroaryl having 1-3 heteroatoms selected from the group consisting of N, S and O.

In another preferred embodiment, when n=2, the compound has a structure shown by the following formula A2:

A2

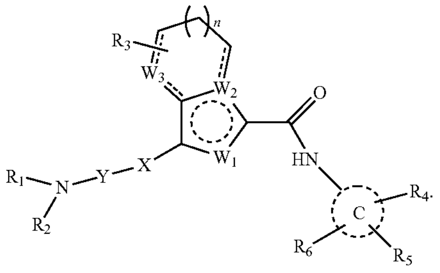

In another preferred embodiment, $R_3$ is one or more substituents on the bicyclic structure selected from the group consisting of H, halogen, —CN, hydroxyl, amino, carboxyl, —(C═O)-substituted or unsubstituted C1-C4 alkyl, C1-C4 alkyl, C2-C4 alkenyl, C2-C4 alkynyl, C1-C4 alkylamino, and C1-C4 alkoxy.

In another preferred embodiment, the compound is selected from the group consisting of A-1, A-2, A-3 or A-4:

A-1

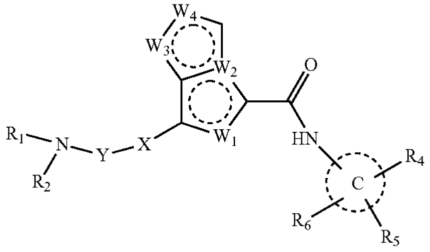

A-2

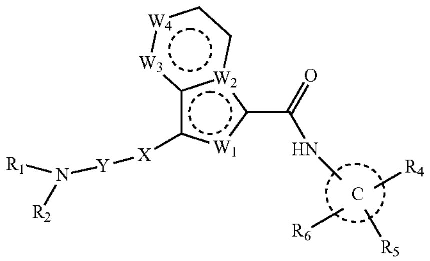

A-3

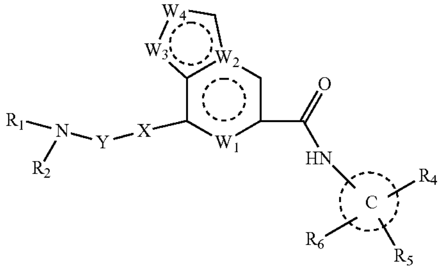

-continued

A-4

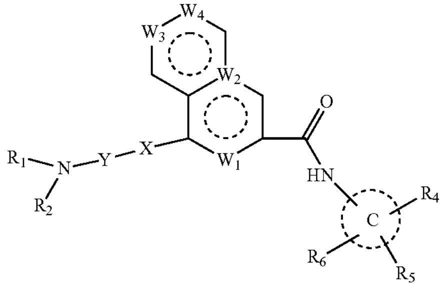

In another preferred embodiment, the compound has a structure selected from the group consisting of I, II, III, IV, V, VI, VII, VIII, IX, and X:

I

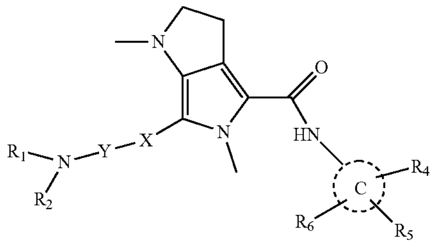

II

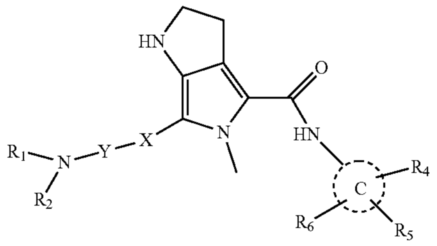

III

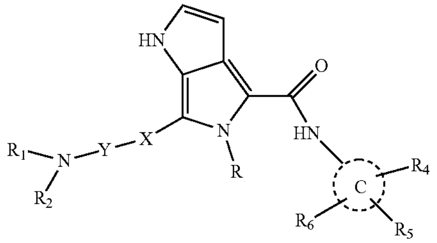

IV

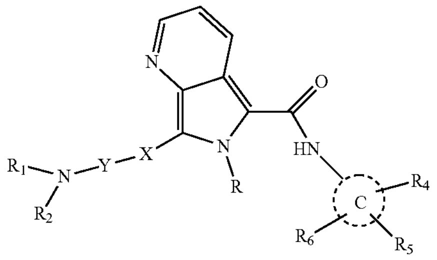

-continued

V

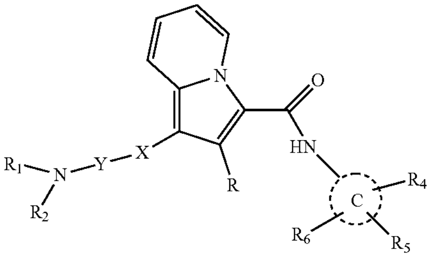

VI

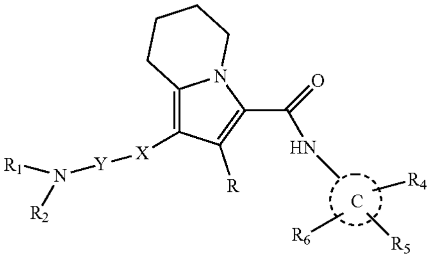

VII

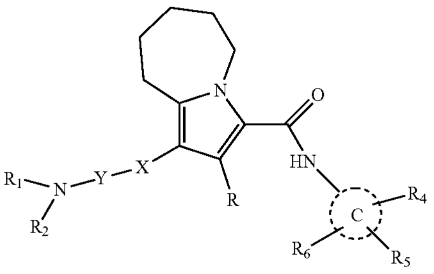

VIII

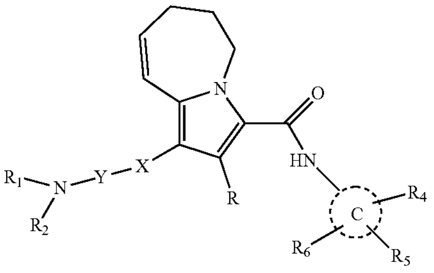

IX

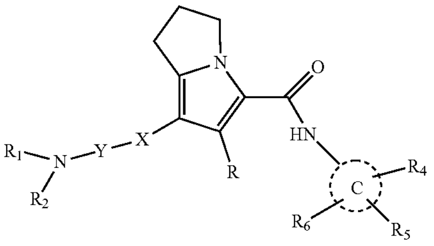

X

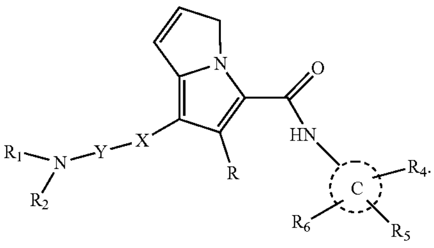

wherein R is selected from the group consisting of halogen, and C1-C4 alkyl.

In another preferred embodiment, the C ring is a 5-7 membered ring.

In another preferred embodiment, the C ring is a saturated ring, a partially unsaturated ring or an aromatic ring.

In another preferred embodiment, the C ring is a benzene ring or a pyridine ring.

In another preferred embodiment, the $R_1$ is a halogenated or hydroxyl substituted C1-C4 alkyl group, and the $R_2$ is H.

In another preferred embodiment, the compound is a compound as described in Table 1.

In the second aspect of the invention, it provides a pharmaceutical composition, which comprises (1) a compound, or a stereoisomer or tautomer thereof, or a pharmaceutically acceptable salt, hydrate or solvate thereof according to the first aspect of the invention; and (2) a pharmaceutically acceptable carrier.

In another preferred embodiment, the pharmaceutical composition further comprises other medicine for preventing and/or treating hepatitis B virus infection.

In another preferred embodiment, the other medicine for preventing and/or treating hepatitis B virus infection is selected from the group consisting of immunomodulators (e.g., interferon-α (IFN-α), pegylated interferon-α) or stimulant of the innate immune system (such as Toll-like receptors 7 and/or 8 agonists).

In another preferred embodiment, the other medicine for preventing and/or treating hepatitis B virus infection is selected from the group consisting of tenofovir, lamivudine, adefovir, entecavir, telbivudine, or combinations thereof.

In the third aspect of the invention, it provides a use of compound, or a stereoisomer or tautomer thereof, or a pharmaceutically acceptable salt, hydrate or solvate thereof according to the first aspect of the invention, or a use of the pharmaceutical composition according to the second aspect of the invention, in the preparation of a medicine for the prevention and/or treatment of Hepatitis B infection.

In the fourth aspect of the invention, it provides an inhibitor of hepatitis B virus, which comprises the compound of the formula I, or a stereoisomer thereof, a tautomer thereof, or a pharmaceutically acceptable salt, hydrate or solvent thereof according to the first aspect of the present invention.

In the fifth aspect of the present invention, it provides an intermediate compound of the following formula:

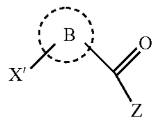

wherein,

X' is selected from the group consisting of $—NO_2$, $—SO_2—NR_1R_2$, $—SO_2—Cl$, and $—NH_2$;

Z is selected from the group consisting of —OH, —O—C1-C4 alkyl, and

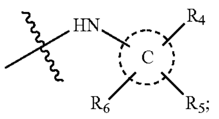

while the remaining groups are as defined in the first aspect of the present invention.

In the sixth aspect of the present invention, it provides a use of an intermediate compound of the fifth aspect of the invention in the preparation of a compound according to the first aspect of the invention.

In the seventh aspect of the invention, it provides a method for preparing a compound of the formula I, or a stereoisomer thereof, a tautomer thereof, or a pharmaceutically acceptable salt, hydrate or solvent thereof according to the first aspect of the present invention, wherein the formula A compound is a compound of formula XIII-1, and the method comprises the steps:

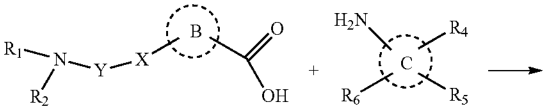

Aa1 Aa2

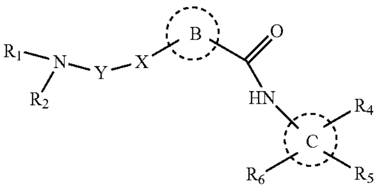

A in an inert solvent, reacting compound of formula Aa1 with a a compound formula Aa2, thereby obtaining the compound of formula A.

In another preferred embodiment, the method further comprises the following steps:

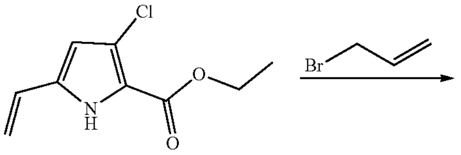

I-1

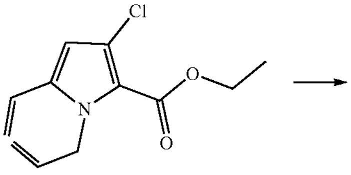

I-2

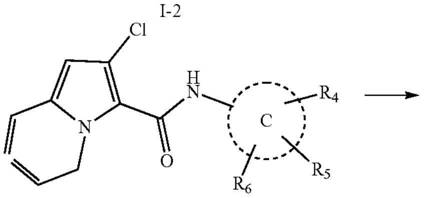

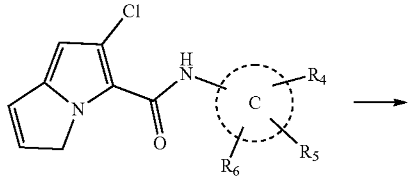

I-4

-continued

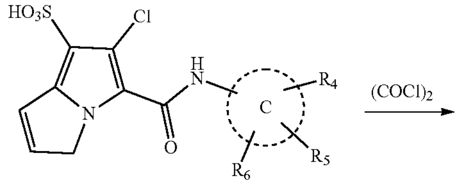

I-5

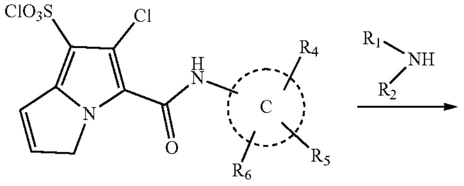

I-6

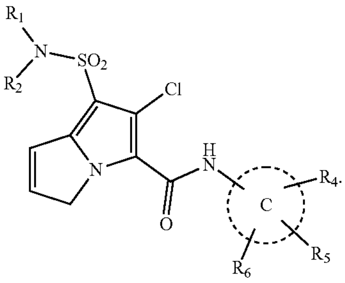

I-7

In another preferred embodiment, the compound of formula A is a compound of formula II-7, and the method comprises the following steps:

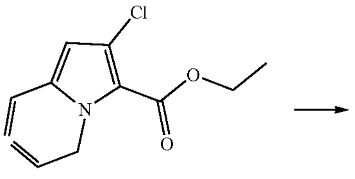

II-1

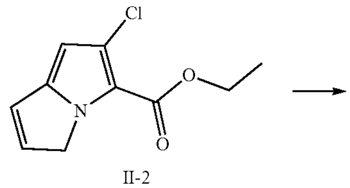

II-2

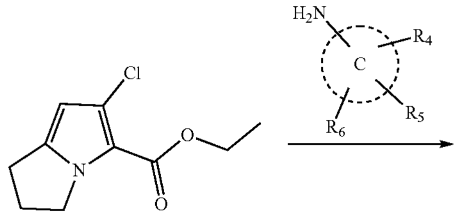

II-3

-continued
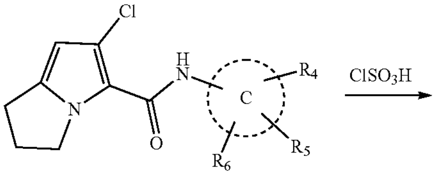
II-4
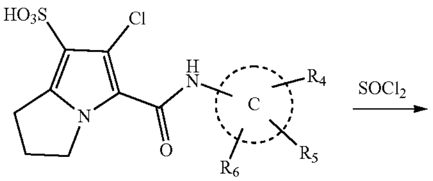
II-5
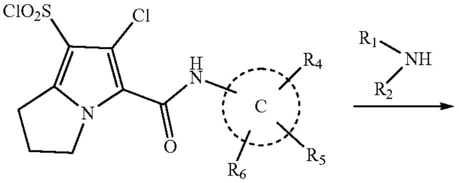
II-6
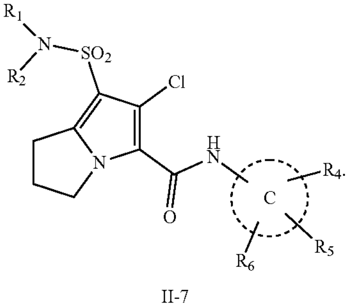
II-7
In another preferred embodiment, the compound of the formula A is a compound of formula III-7 and the method comprises the following steps:
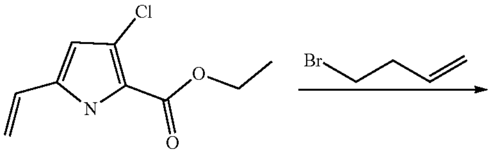
III-1
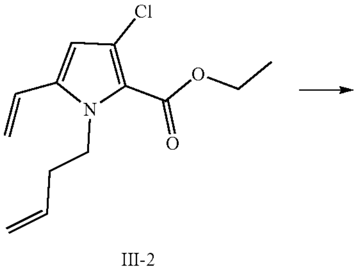
III-2
-continued
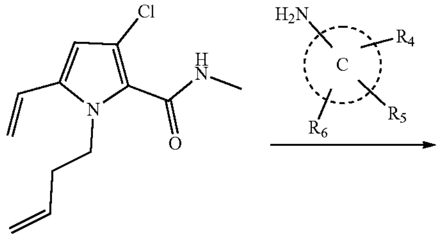
III-3
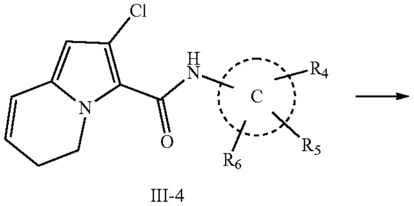
III-4
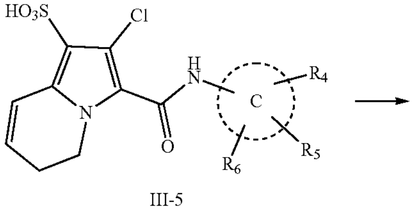
III-5
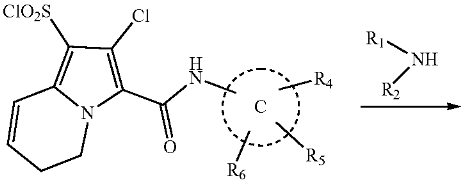
III-6
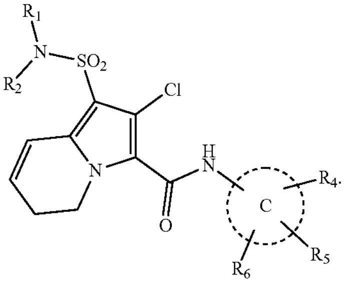
III-7
In another preferred embodiment, the compound of formula A is a compound of formula IV-7, and the method comprises the following steps:
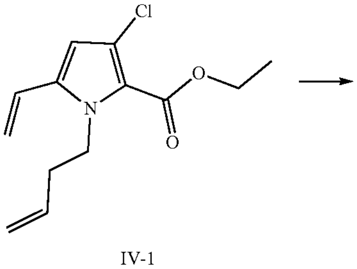
IV-1

-continued
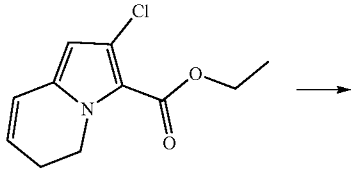
IV-2
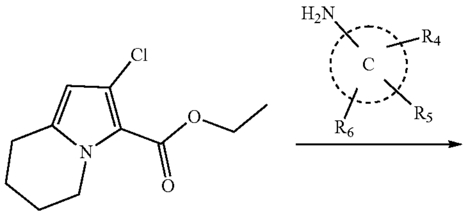
IV-3
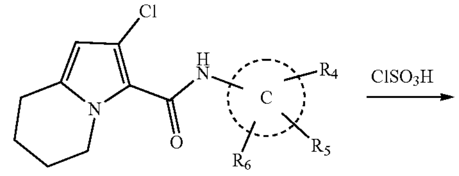
IV-4
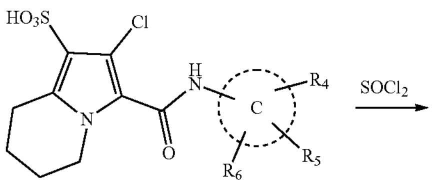
IV-5
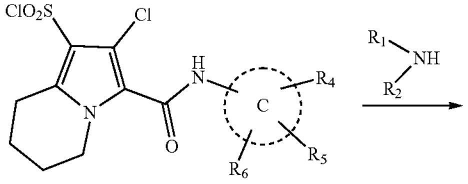
IV-6
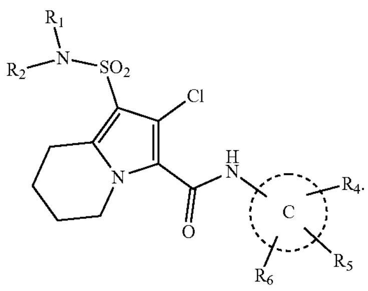
IV-7
In another preferred embodiment, the compound of the formula A is a compound of formula V-7, and the method comprises the following steps:
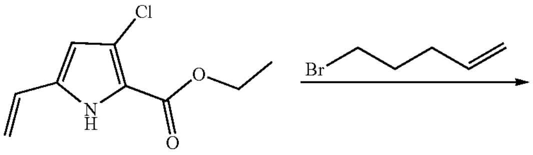
V-1
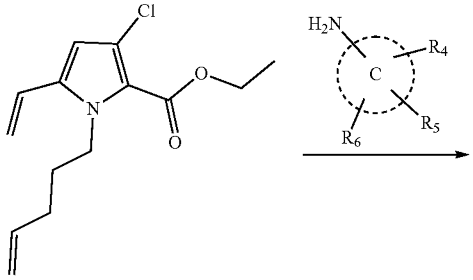
V-2
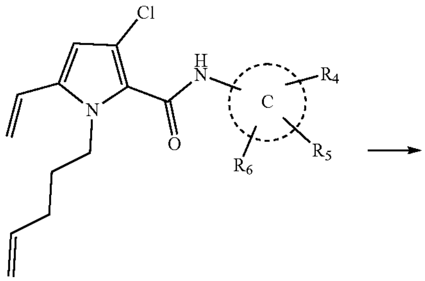
V-3
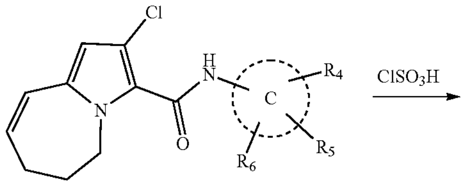
V-4
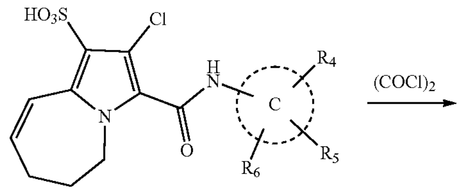
V-5
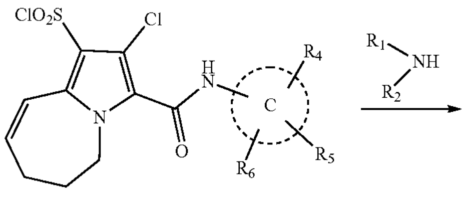
V-6

-continued
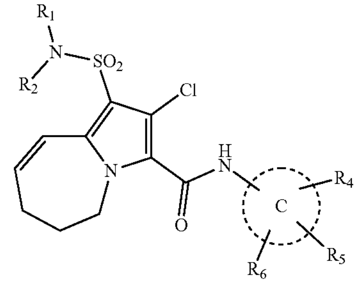
V-7
In another preferred embodiment, the compound of formula A is a compound of formula VI-7, and the method comprises the following steps:
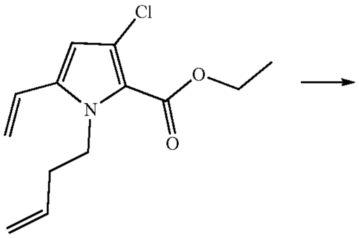
VI-1
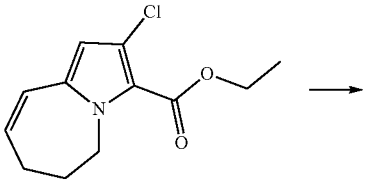
VI-2
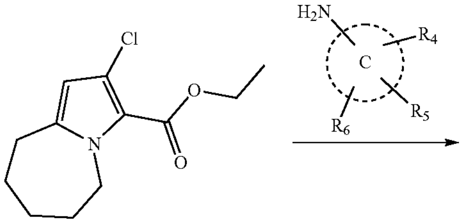
VI-3
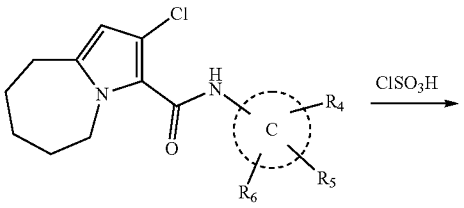
VI-4
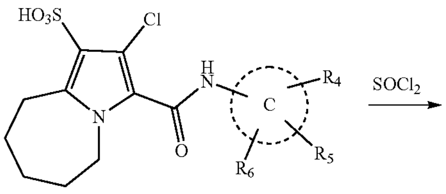
VI-5
-continued
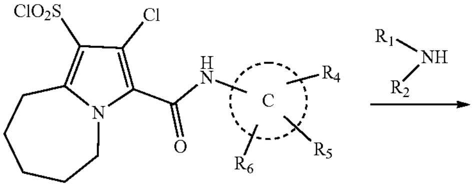
VI-6
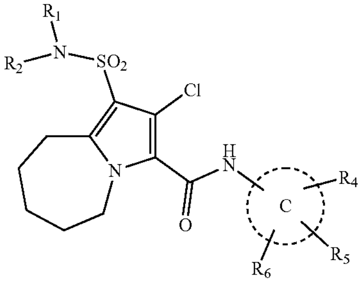
VI-7
In another preferred embodiment, the compound of the formula A is a compound of formula VII-11, and the method comprises the following steps:
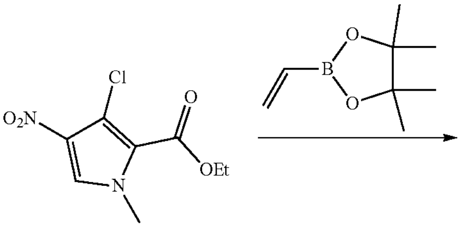
VII-1
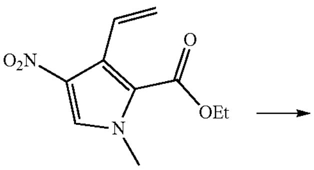
VII-2
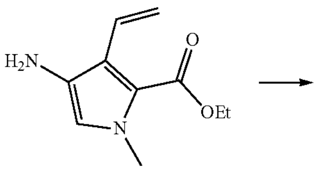
VII-3
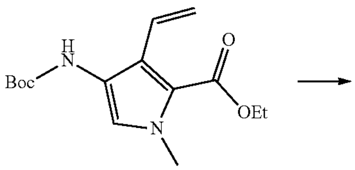
VII-4

-continued
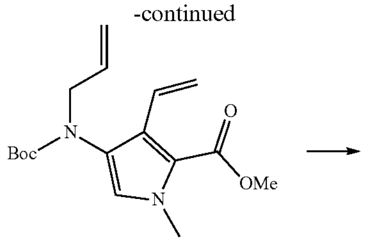
VII-5
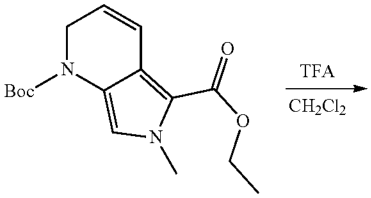
VII-6
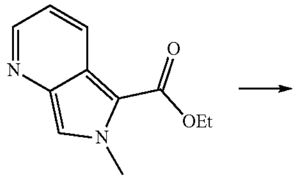
VII-7
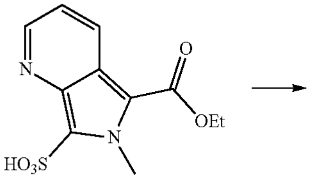
VII-8
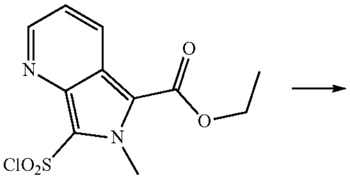
VII-9
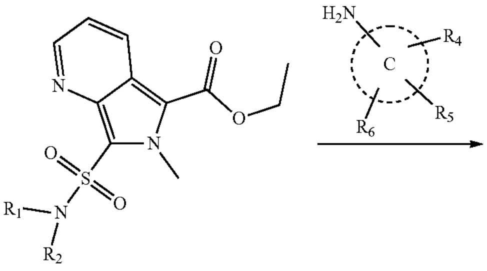
VII-10
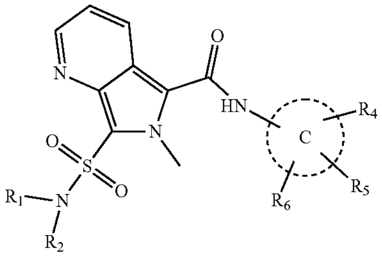
VII-11
In another preferred embodiment, the compound of the formula A is a compound of formula VII-11, and the method comprising the following steps:
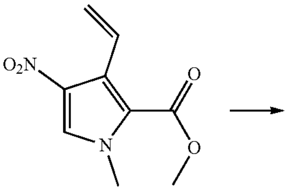
VIII-1
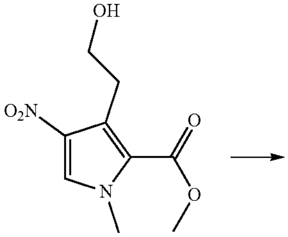
VIII-2
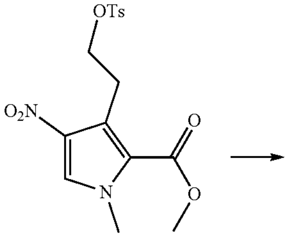
VIII-3
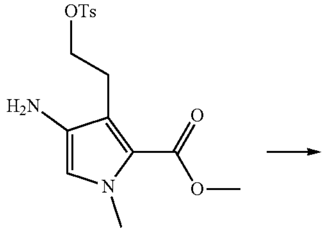
VIII-4
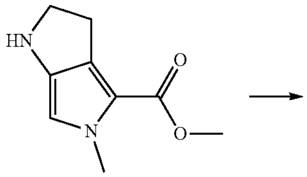
VIII-5
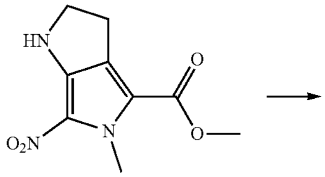
VIII-6

-continued

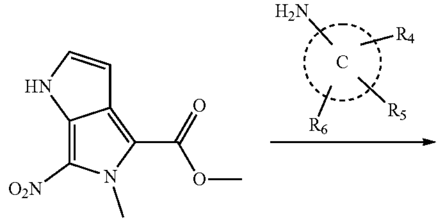

VIII-7

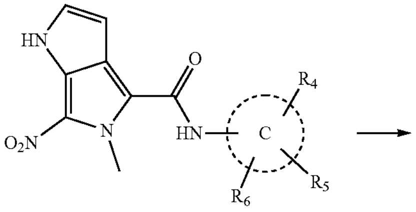

VIII-8

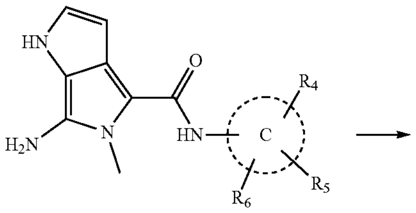

VIII-9

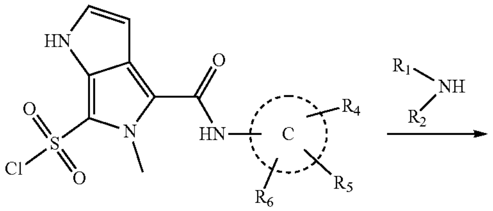

VIII-10

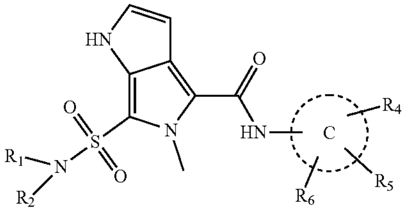

VIII-11

In another preferred embodiment, the compound of formula A is a compound of formula IX-4, and the method comprises the following steps:

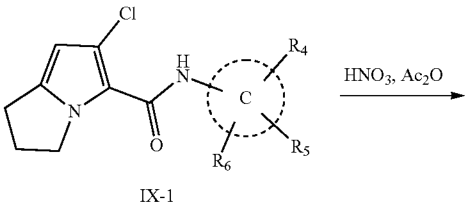

IX-1

-continued

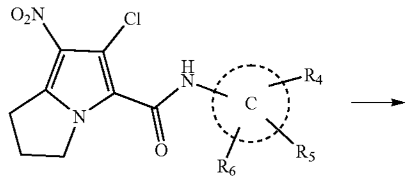

IX-2

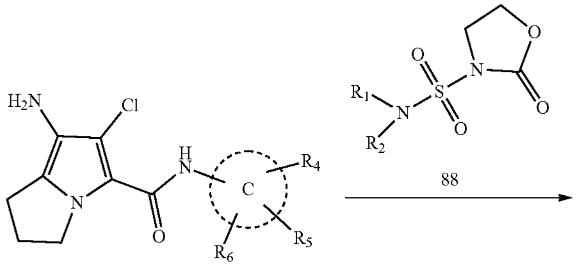

IX-3

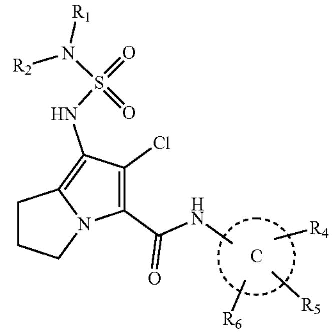

IX-4

In another preferred embodiment, the compound of the formula A is a compound of X-2, and the method comprises the following steps:

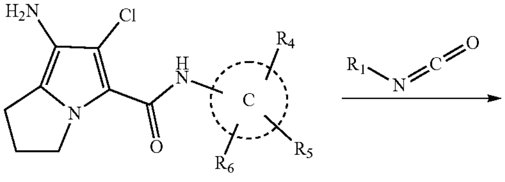

X-1

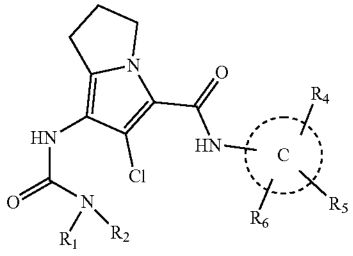

X-2

In the eighth aspect of the invention, it provides a method for the prevention and/or treatment of hepatitis B, which comprises the steps: administrating a compound, or a stereoisomer or tautomer thereof, or a pharmaceutically acceptable salt, hydrate or solvate thereof according to the first aspect of the invention, or the pharmaceutical composition according to the second aspect of the invention to a subject in need thereof.

In the ninth aspect of the invention, it provides a method for in vitro inhibiting hepatitis B virus, which comprises the steps: contacting a compound, or a stereoisomer or tautomer thereof, or a pharmaceutically acceptable salt, hydrate or solvate thereof according to the first aspect of the invention with hepatitis B virus, thereby inhibiting hepatitis B virus.

It should be understood that, in the present invention, each of the technical features specifically described above and below (such as those in the Examples) can be combined with each other, thereby constituting new or preferred technical solutions which are not necessarily specified one by one herein.

BRIEF DESCRIPTION OF THE DRAWINGS

Not Applicable

DETAILED DESCRIPTION OF THE INVENTION

After extensive and intensive research, the inventors have found a novel class of compounds having excellent therapeutic effects on hepatitis B. The inventors have completed the present invention on this basis.

Definitions

As used herein, the term "alkyl" includes straight or branched alkyl groups. For example, $C_1$-$C_8$ alkyl refers to a straight or branched alkyl having from 1-8 carbon atoms, such as methyl, ethyl, propyl, isopropyl, butyl, isobutyl, tert-butyl, and the like.

As used herein, the term "alkenyl" includes straight or branched alkenyl groups. For example, $C_2$-$C_6$ alkenyl refers to a straight or branched alkenyl group having 2-6 carbon atoms, such as vinyl, allyl, 1-propenyl, isopropenyl, 1-butenyl, 2-butenyl, and the like.

As used herein, the term "alkynyl" includes straight or branched alkynyl groups. For example, "$C_2$-$C_6$ alkynyl" refers to a straight or branched alkynyl having 2-6 carbon atoms, such as ethynyl, propynyl, butynyl, and the like.

As used herein, the term "$C_3$-$C_{10}$ cycloalkyl" refers to cycloalkyl group having 3 to 10 carbon atoms. It may be a monocyclic ring, such as cyclopropyl, cyclobutyl, cyclopentyl, cyclohexyl, and the like. It may also be of bicyclic form, such as bridged or spiro ring form.

As used herein, the term "$C_1$-$C_8$ alkylamino" refers to an amine group substituted by $C_1$-$C_8$ alkyl, which may be monosubstituted or di-substituted; for example, methylamino, ethylamino, propylamine, isopropylamino, butylamino, isobutylamino, tert-butylamino, dimethylamino, diethylamino, dipropylamino, diisopropylamino, dibutylamino, diisobutylamino, di(tert-butyl)amine, and the like.

As used herein, the term "$C_1$-$C_8$ alkoxy" refers to straight or branched alkoxy groups having 1-8 carbon atoms; for example, methoxy, ethoxy, propoxy, isopropoxy, butoxy, isobutoxy, tert-butoxy, and the like.

As used herein, the term "3-10 membered heterocycloalkyl having 1-3 heteroatoms selected from N, S and O" refers to a saturated or partially saturated cyclic group comprising 3-10 atoms, in which 1-3 atoms are selected from N, S and O heteroatom. It may be a monocyclic ring or bicyclic form, such as bridged or spiro ring form. Specific examples may be oxetane, azetidine, tetrahydro-2H-pyranyl, piperidinyl, tetrahydrofuranyl, morpholinyl and pyrrolidinyl, and the like.

As used herein, the term "$C_6$-$C_{10}$ aryl" refers to an aryl group having 6 to 10 carbon atoms, such as phenyl, naphthyl, and the like.

As used herein, the term "5-10 membered heterocycloalkyl having 1-3 heteroatoms selected from N, S and O" refers to a cyclic group aromatic group comprising 5-10 atoms, in which 1-3 atoms are selected from heteroatoms N, S and O. It may be a monocyclic ring or fused ring form. Specific examples may be pyridyl, pyridazinyl, pyrimidinyl, pyrazinyl, triazinyl, pyrrolyl, pyrazolyl, imidazolyl, (1,2,3)-triazolyl and (1,2,4)-triazolyl, tetrazyl, furyl, thienyl, isoxazolyl, thiazolyl, oxazolyl, etc.

Unless otherwise specified as "substituted or unsubstituted", all the groups described in the present invention may be substituted with a substituent selected from the group consisting of halogen, nitrile, nitro, hydroxyl, amino, $C_1$-$C_6$ alkyl-amine, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_2$-$C_6$ haloalkenyl, $C_2$-$C_6$ haloalkynyl, $C_1$-$C_6$ haloalkoxy, allyl, benzyl, $C_6$-$C_{12}$ aryl, $C_1$-$C_6$ alkoxy-$C_1$-$C_6$ alkyl, $C_1$-$C_6$ alkoxy-carbonyl, phenoxycarbonyl, $C_2$-$C_6$ alkynyl-carbonyl, $C_2$-$C_6$ alkenyl-carbonyl, $C_3$-$C_6$ cycloalkyl-carbonyl, $C_1$-$C_6$ alkyl-sulfonyl, etc.

As used herein, "halogen" or "halogen atom" refers to F, Cl, Br, and I. More preferably, the halogen or halogen atom is selected from F, Cl and Br. "Halogenated" means substitution by an atom selected from the group consisting of F, Cl, Br, and I.

Unless otherwise specified, the structural formula described herein is intended to include all isomeric forms (such as enantiomeric, diastereomeric, and geometric isomers (or conformational isomers)): for example, R, S configuration having an asymmetrical center, (Z), (E) isomers of double bonds, etc. Therefore, the single stereochemical isomer or enantiomer, diastereomer or geometric isomer (or conformer) of the compound of the invention, or mixtures thereof all fall within the scope of the invention.

As used herein, the term "tautomer" means that structural isomers having different energies can exceed the low energy barrier and thereby transform between each other. For example, proton tautomers (proton shift) include interconversion by proton transfer, such as 1H-carbazole and 2H-carbazole. Valence tautomers include interconversion through some bonding electron recombination.

As used herein, the term "solvate" refers to a complex of specific ratio formed by a compound of the invention coordinating to a solvent molecule.

As used herein, the term "hydrate" refers to a complex formed by the coordination of a compound of the invention with water.

Active Ingredients

As used herein, "compound of the invention" refers to the compound of formula (A), as well as various crystal forms of the compound of formula (A), or the pharmaceutically acceptable salts, hydrate or solvates thereof.

A

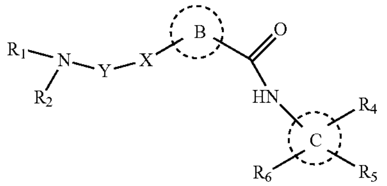

As used herein, the "pharmaceutically acceptable salts" refers to salts suitable for use in pharmaceutical which is formed by a compound of the present invention with an acid or base. The pharmaceutically acceptable salts include inorganic and organic salts. Preferred types of salts are salts formed by the compounds of the present invention and acid. Suitable salt-forming acids include, but are not limited to: inorganic acids such as hydrochloric acid, hydrobromic acid, hydrofluoric acid, sulfuric acid, nitric acid, phosphoric acid and the like; organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, toluenesulfonic acid, benzenesulfonic acid and the like; and acidic amino acids such as aspartic acid, glutamic acid.

In another preferred embodiment, the B ring, C ring, X, Y, $R_1$, $R_2$, $R_4$, $R_5$ and $R_6$ are each independently a group corresponding to each compound in Table 1.

Preferred compounds of the invention are shown in Table 1:

| Compound | Structure | Mass Spectrometry. ESI-MS, (M + H) |
|---|---|---|
| 10a | 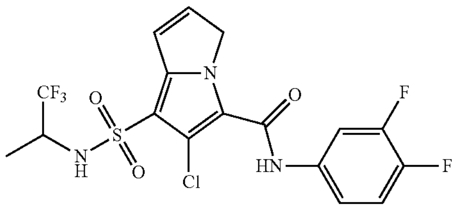 (R) | 470 |
| 10b | 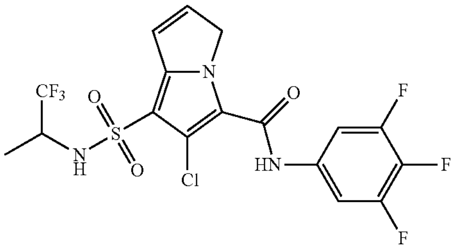 (R) | 488 |
| 10c | 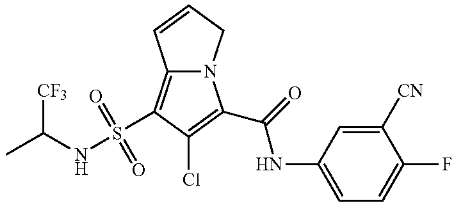 (R) | 477 |
| 10d | 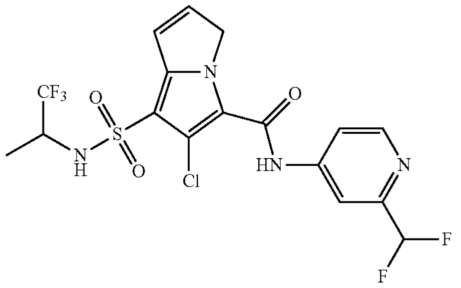 (R) | 485 |
| 10e | 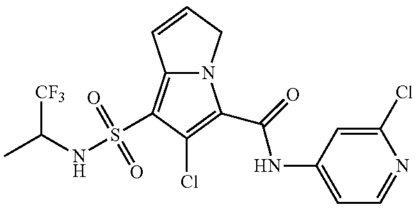 (R) | 469 |

-continued
| Compound | Structure | Mass Spectrometry. ESI-MS, (M + H) |
| --- | --- | --- |
| 10f | 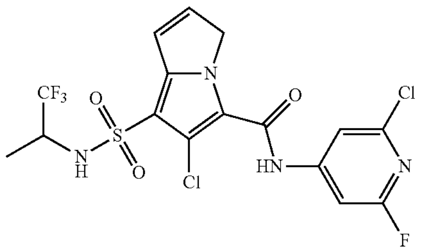 (R) | 478 |
| 10g | 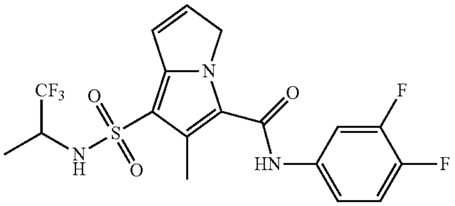 (R) | 450 |
| 10h | 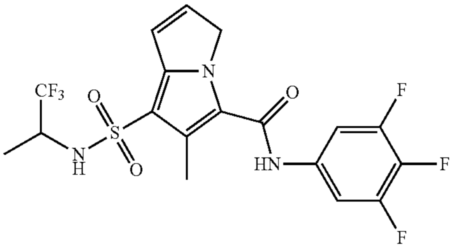 (R) | 468 |
| 10i | 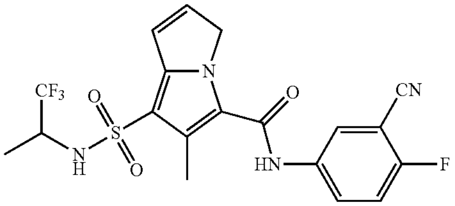 (R) | 457 |
| 10j | 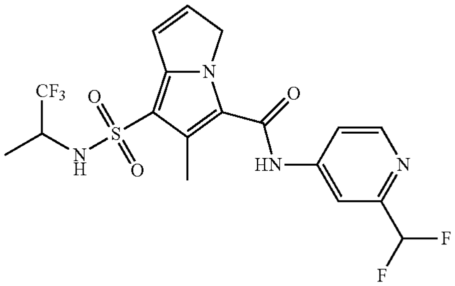 (R) | 465 |
| 10k | 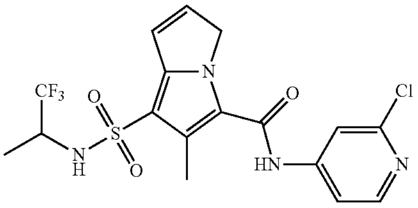 (R) | 449 |

-continued
| Compound | Structure | Mass Spectrometry. ESI-MS, (M + H) |
|---|---|---|
| 10l | 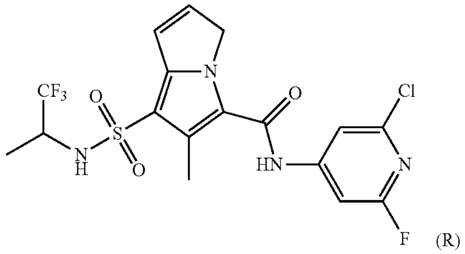 | 458 |
| 10m | 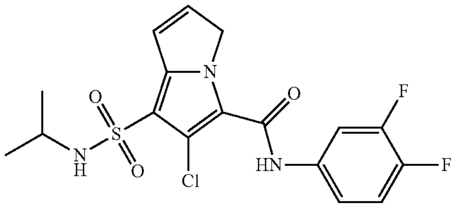 [SMILES: CC(C)NS(=O)(=O)c1c(Cl)c(C(=O)Nc2ccc(F)c(F)c2)n2c1C=CC2] | 416 |
| 10n | 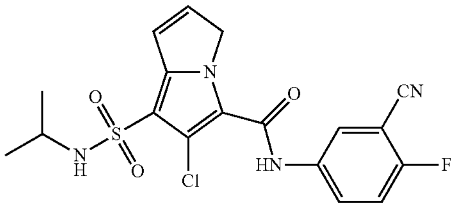 [SMILES: CC(C)NS(=O)(=O)c1c(Cl)c(C(=O)Nc2ccc(F)c(C#N)c2)n2c1C=CC2] | 423 |
| 10o | 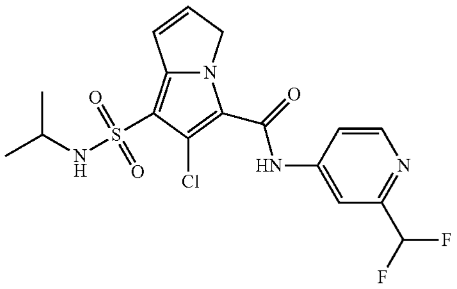 [SMILES: CC(C)NS(=O)(=O)c1c(Cl)c(C(=O)Nc2ccnc(C(F)F)c2)n2c1C=CC2] | 431 |
| 10p | 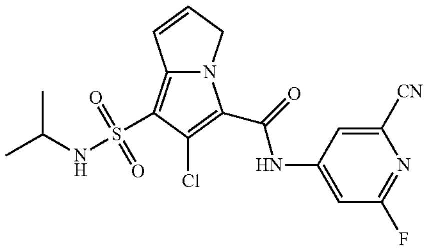 | 424 |
| 10q | 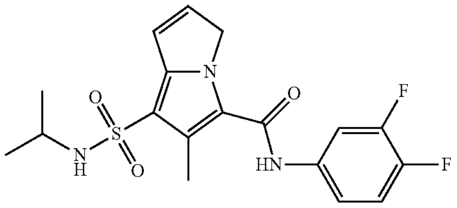 [SMILES: Cc1c(S(=O)(=O)NC(C)C)c2n(c1C(=O)Nc1ccc(F)c(F)c1)CC=C2] | 396 |

-continued
| Compound | Structure | Mass Spectrometry. ESI-MS, (M + H) |
|---|---|---|
| 10r | 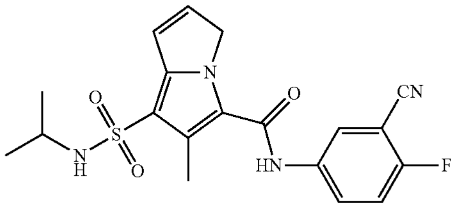 [SMILES: Cc1c(S(=O)(=O)NC(C)C)c2n(c1C(=O)Nc1ccc(F)c(C#N)c1)CC=C2] | 403 |
| 10s | 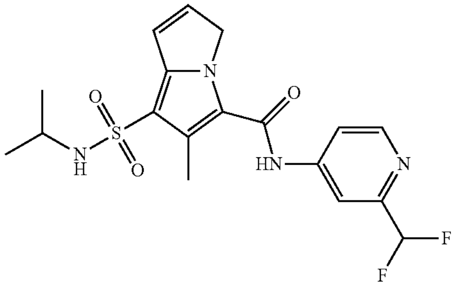 | 411 |
| 10t | 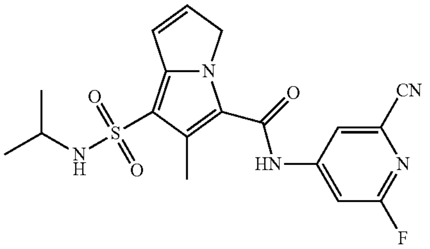 [SMILES: Cc1c(S(=O)(=O)NC(C)C)c2n(c1C(=O)Nc1cc(F)nc(C#N)c1)CC=C2] | 404 |
| 10u | 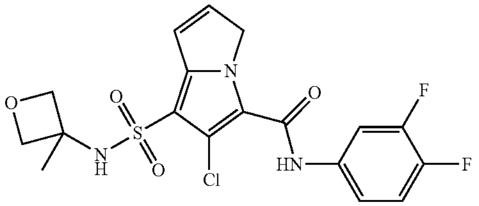 [SMILES: CC1(NS(=O)(=O)c2c(Cl)c(C(=O)Nc3ccc(F)c(F)c3)n3c2C=CC3)COC1] | 444 |
| 10v | 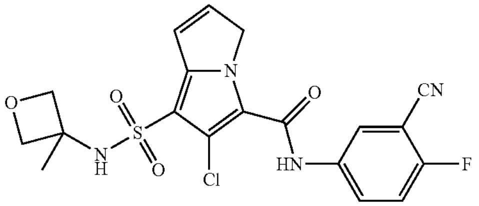 [SMILES: CC1(NS(=O)(=O)c2c(Cl)c(C(=O)Nc3ccc(F)c(C#N)c3)n3c2C=CC3)COC1] | 451 |
| 10w | 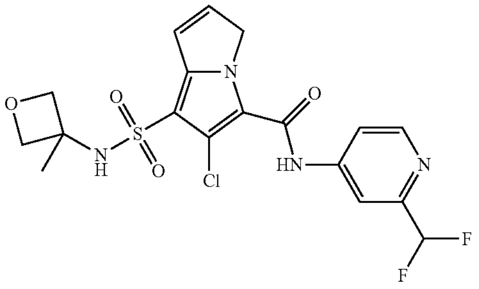 [SMILES: CC1(NS(=O)(=O)c2c(Cl)c(C(=O)Nc3ccnc(C(F)F)c3)n3c2C=CC3)COC1] | 459 |

-continued
| Compound | Structure | Mass Spectrometry. ESI-MS, (M + H) |
|---|---|---|
| 10x | 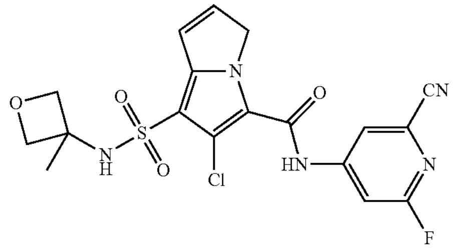 [SMILES: CC1(NS(=O)(=O)c2c(Cl)c(C(=O)Nc3cc(F)nc(C#N)c3)n3c2C=CC3)COC1] | 452 |
| 10y | 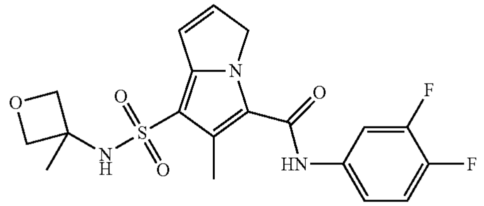 [SMILES: Cc1c(S(=O)(=O)NC2(C)COC2)c2n(c1C(=O)Nc1ccc(F)c(F)c1)CC=C2] | 424 |
| 10z | 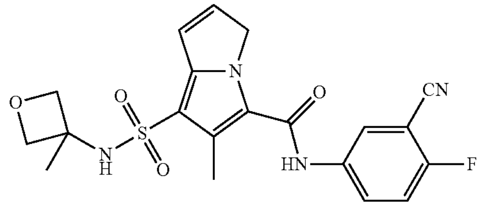 [SMILES: Cc1c(S(=O)(=O)NC2(C)COC2)c2n(c1C(=O)Nc1ccc(F)c(C#N)c1)CC=C2] | 431 |
| 10aa | 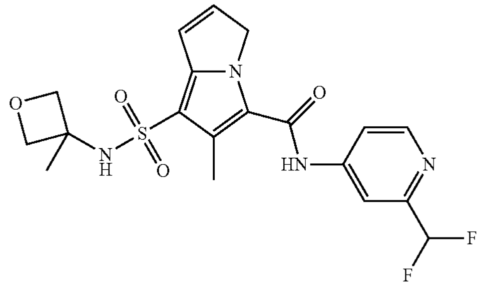 [SMILES: Cc1c(S(=O)(=O)NC2(C)COC2)c2n(c1C(=O)Nc1ccnc(C(F)F)c1)CC=C2] | 439 |
| 10bb | 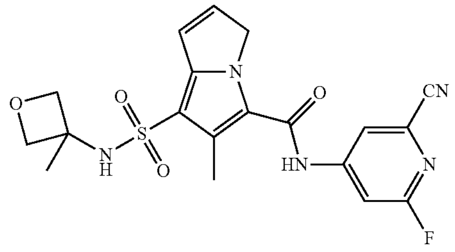 [SMILES: Cc1c(S(=O)(=O)NC2(C)COC2)c2n(c1C(=O)Nc1cc(F)nc(C#N)c1)CC=C2] | 432 |
| 10cc | 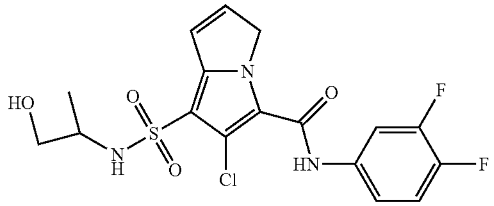 [SMILES: CC(CO)NS(=O)(=O)c1c(Cl)c(C(=O)Nc2ccc(F)c(F)c2)n2c1C=CC2] | 432 |

-continued
| Compound | Structure | Mass Spectrometry. ESI-MS, (M + H) |
|---|---|---|
| 10dd | 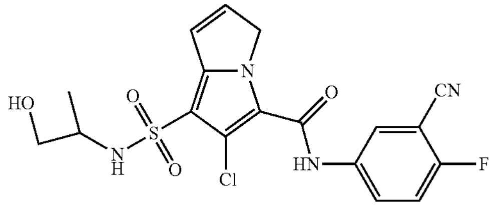 [SMILES: CC(CO)NS(=O)(=O)c1c(Cl)c(C(=O)Nc2ccc(F)c(C#N)c2)n2c1C=CC2] | 439 |
| 10ee | 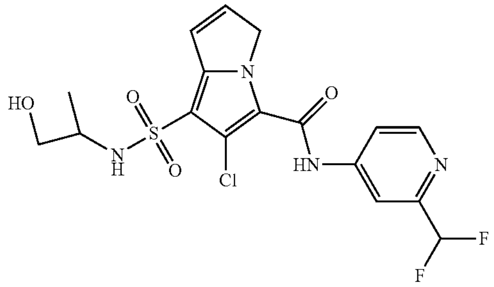 [SMILES: CC(CO)NS(=O)(=O)c1c(Cl)c(C(=O)Nc2ccnc(C(F)F)c2)n2c1C=CC2] | 447 |
| 10ff | 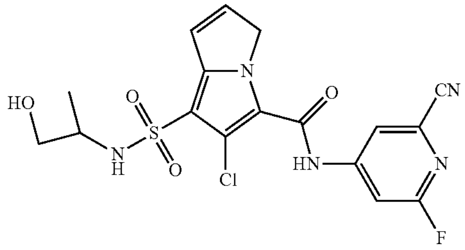 [SMILES: CC(CO)NS(=O)(=O)c1c(Cl)c(C(=O)Nc2cc(F)nc(C#N)c2)n2c1C=CC2] | 440 |
| 10gg | 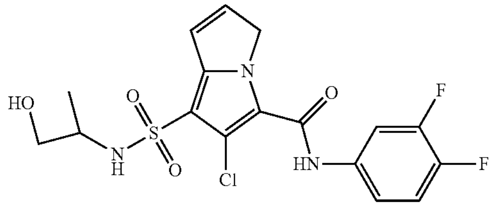 [SMILES: CC(CO)NS(=O)(=O)c1c(Cl)c(C(=O)Nc2ccc(F)c(F)c2)n2c1C=CC2] | 412 |
| 10hh | 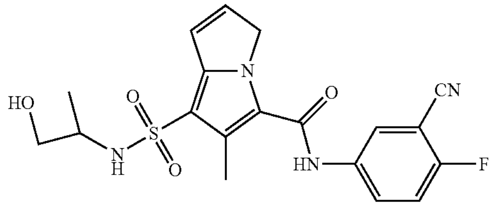 [SMILES: Cc1c(S(=O)(=O)NC(C)CO)c2n(c1C(=O)Nc1ccc(F)c(C#N)c1)CC=C2] | 419 |
| 10ii | 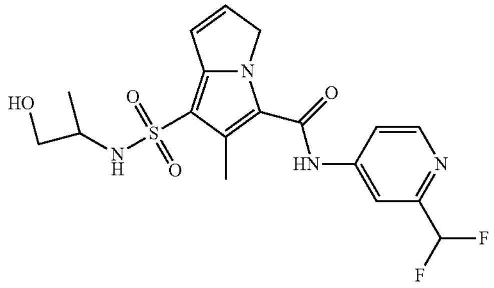 [SMILES: Cc1c(S(=O)(=O)NC(C)CO)c2n(c1C(=O)Nc1ccnc(C(F)F)c1)CC=C2] | 427 |

-continued
| Compound | Structure | Mass Spectrometry. ESI-MS, (M + H) |
|---|---|---|
| 10jj | 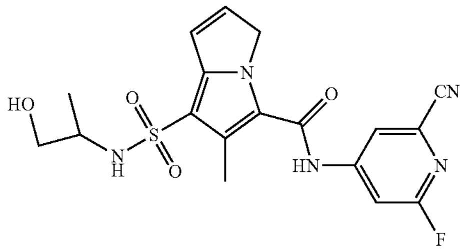 | 420 |
| 10kk | 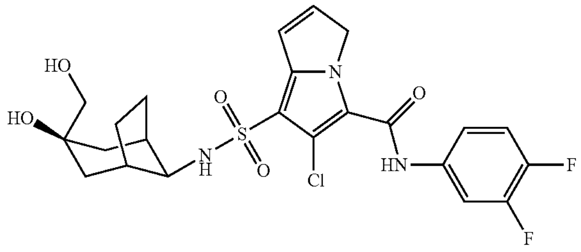 | 528 |
| 10ll | 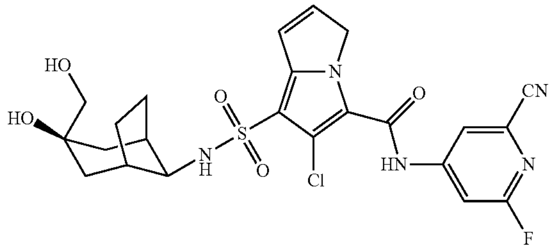 | 536 |
| 10mm | 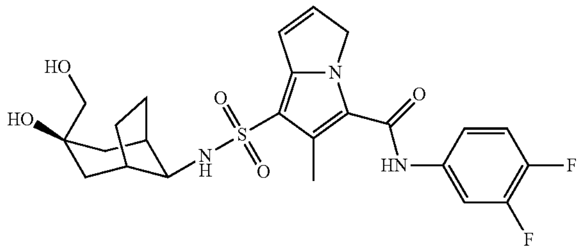 | 508 |
| 10nn | 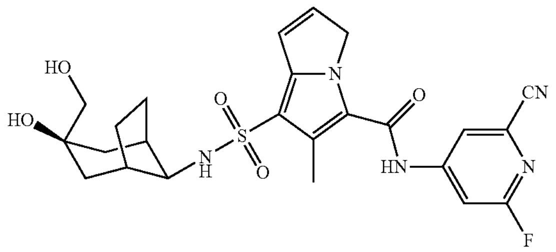 | 516 |
| 10oo | 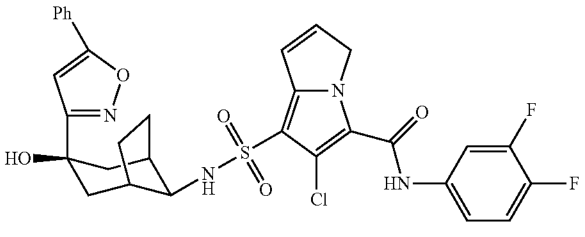 | 641 |

-continued
| Compound | Structure | Mass Spectrometry. ESI-MS, (M + H) |
|---|---|---|
| 10pp | 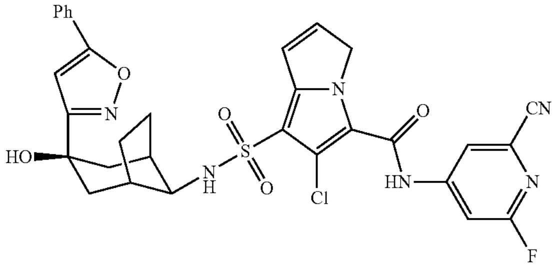 | 649 |
| 10qq | 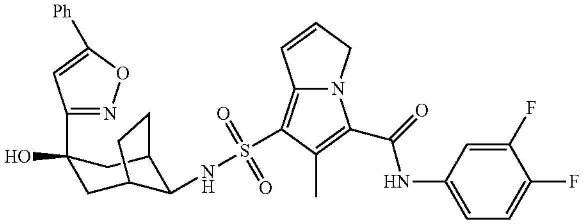 | 621 |
| 10rr | 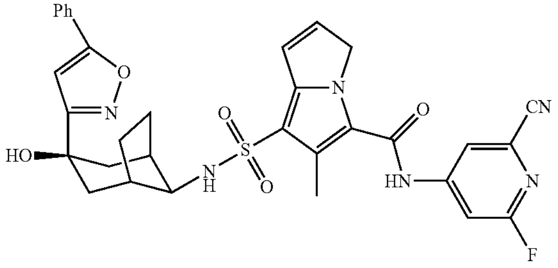 | 629 |
| 10ss | 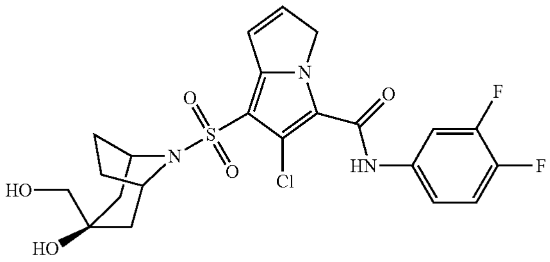 | 514 |
| 10tt | 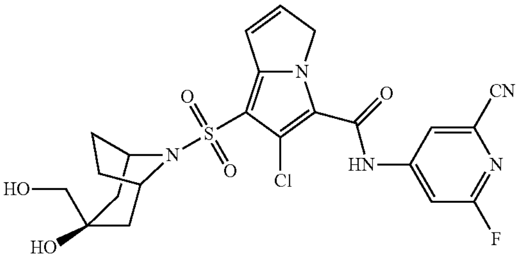 | 522 |
| 10uu | 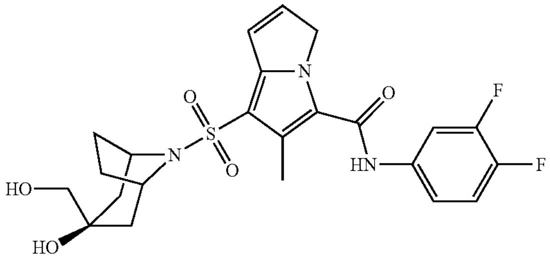 | 494 |

-continued
| Compound | Structure | Mass Spectrometry. ESI-MS, (M + H) |
|---|---|---|
| 10vv | 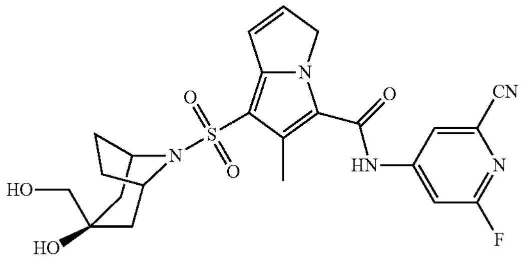 | 502 |
| 10ww | 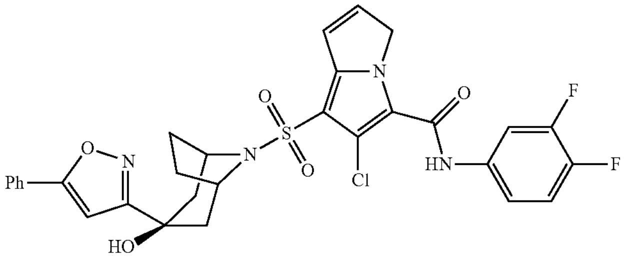 | 627 |
| 10xx | 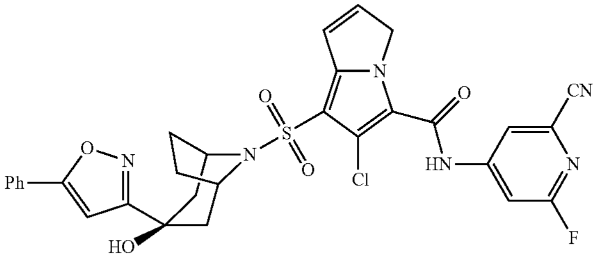 | 635 |
| 10yy | 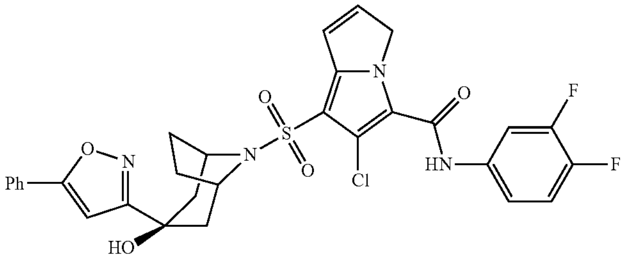 | 607 |
| 10zz | 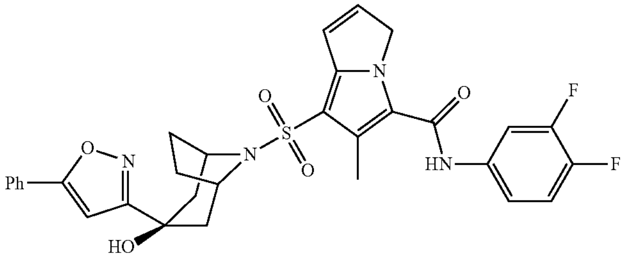 | 615 |
| 20a | 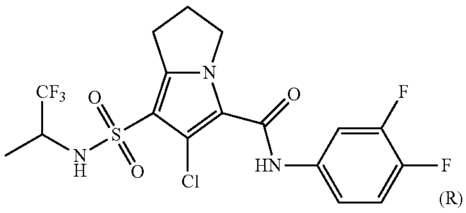 | 472 |

-continued
| Compound | Structure | Mass Spectrometry. ESI-MS, (M + H) |
|---|---|---|
| 20b | 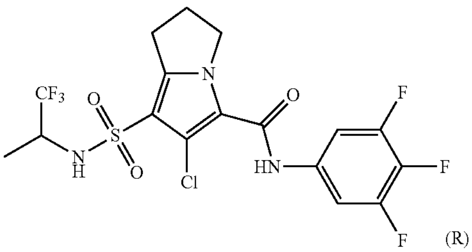 (R) | 490 |
| 20c | 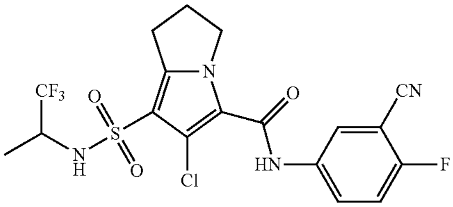 (R) | 479 |
| 20d | 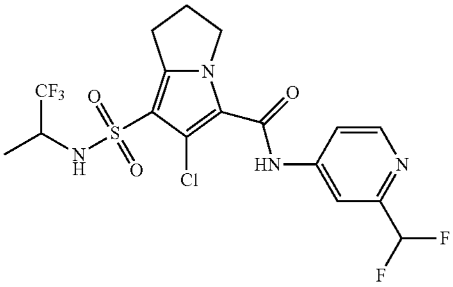 (R) | 487 |
| 20e | 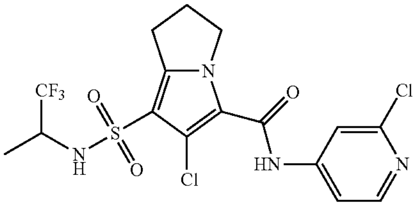 (R) | 471 |
| 20f | 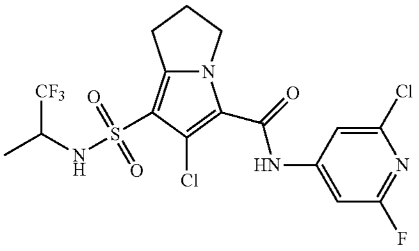 (R) | 480 |
| 20g | 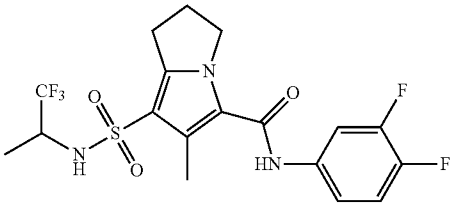 (R) | 452 |

-continued
| Compound | Structure | Mass Spectrometry. ESI-MS, (M + H) |
|---|---|---|
| 20h | 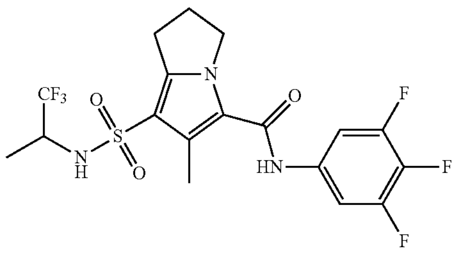 (R) | 470 |
| 20i | 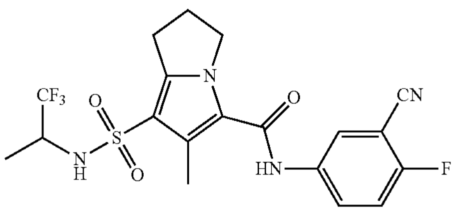 (R) | 459 |
| 20j | 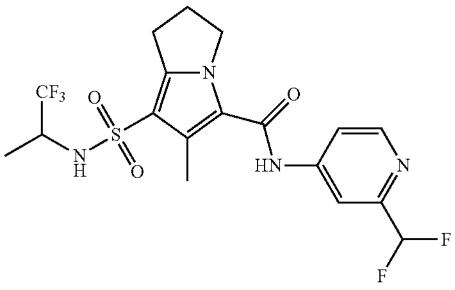 (R) | 467 |
| 20k | 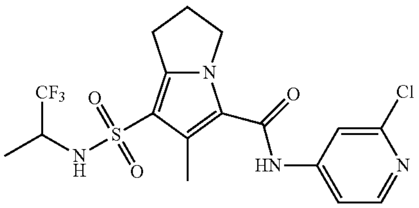 (R) | 451 |
| 20l | 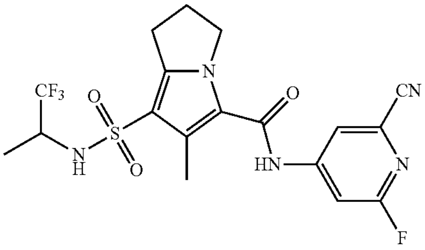 (R) | 460 |
| 20m | 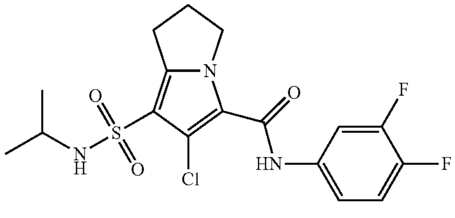 | 418 |

-continued
| Compound | Structure | Mass Spectrometry. ESI-MS, (M + H) |
| --- | --- | --- |
| 20n | 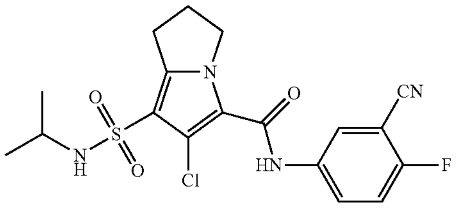 [SMILES: CC(C)NS(=O)(=O)c1c(Cl)c(C(=O)Nc2ccc(F)c(C#N)c2)n2c1CCC2] | 425 |
| 20o | 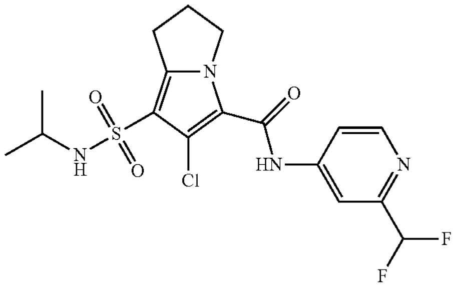 | 433 |
| 20p | 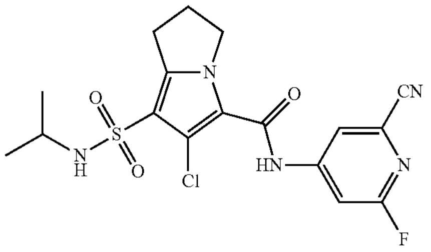 [SMILES: CC(C)NS(=O)(=O)c1c(Cl)c(C(=O)Nc2cc(F)nc(C#N)c2)n2c1CCC2] | 426 |
| 20q | 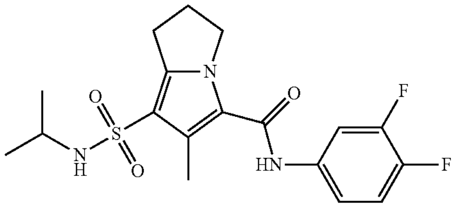 [SMILES: Cc1c(S(=O)(=O)NC(C)C)c2n(c1C(=O)Nc1ccc(F)c(F)c1)CCC2] | 398 |
| 20r | 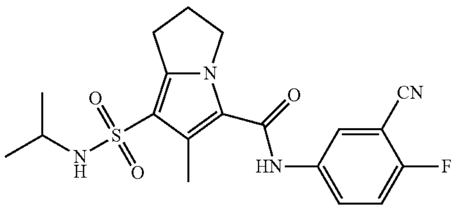 [SMILES: Cc1c(S(=O)(=O)NC(C)C)c2n(c1C(=O)Nc1ccc(F)c(C#N)c1)CCC2] | 405 |
| 20s | 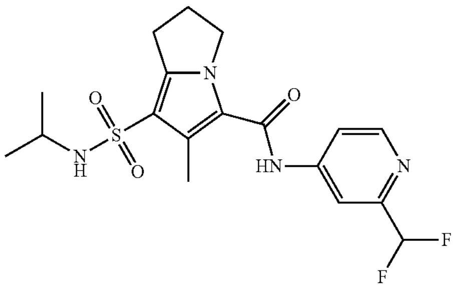 [SMILES: Cc1c(S(=O)(=O)NC(C)C)c2n(c1C(=O)Nc1ccnc(C(F)F)c1)CCC2] | 413 |

-continued
| Compound | Structure | Mass Spectrometry. ESI-MS, (M + H) |
|---|---|---|
| 20t | 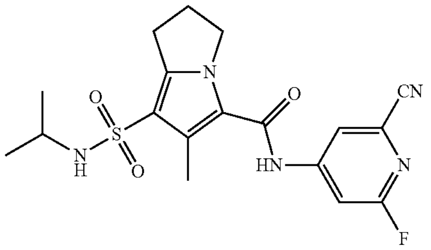 [SMILES: Cc1c(S(=O)(=O)NC(C)C)c2n(c1C(=O)Nc1cc(F)nc(C#N)c1)CCC2] | 406 |
| 20u | 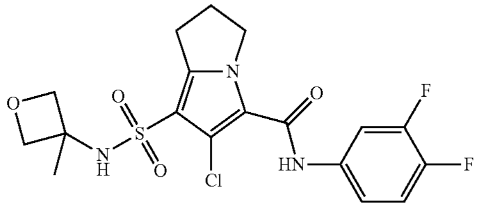 [SMILES: CC1(NS(=O)(=O)c2c(Cl)c(C(=O)Nc3ccc(F)c(F)c3)n3c2CCC3)COC1] | 446 |
| 20v | 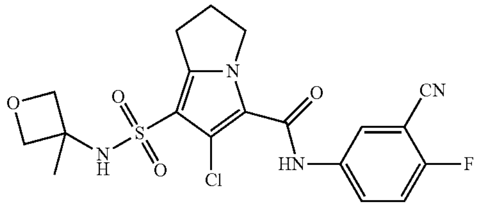 [SMILES: CC1(NS(=O)(=O)c2c(Cl)c(C(=O)Nc3ccc(F)c(C#N)c3)n3c2CCC3)COC1] | 453 |
| 20w | 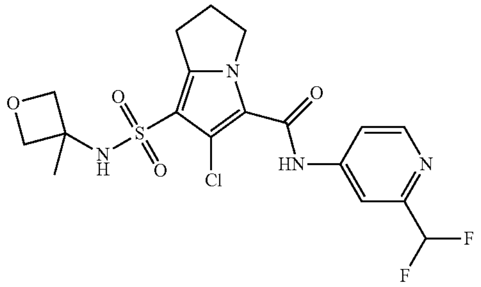 [SMILES: CC1(NS(=O)(=O)c2c(Cl)c(C(=O)Nc3ccnc(C(F)F)c3)n3c2CCC3)COC1] | 461 |
| 20x | 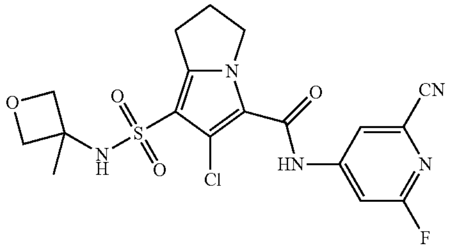 [SMILES: CC1(NS(=O)(=O)c2c(Cl)c(C(=O)Nc3cc(F)nc(C#N)c3)n3c2CCC3)COC1] | 454 |
| 20y | 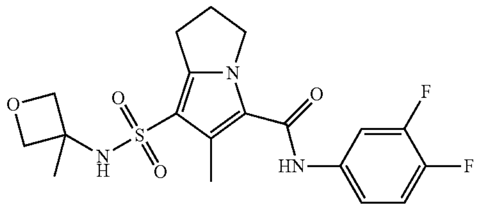 [SMILES: Cc1c(S(=O)(=O)NC2(C)COC2)c2n(c1C(=O)Nc1ccc(F)c(F)c1)CCC2] | 426 |

-continued
| Compound | Structure | Mass Spectrometry. ESI-MS, (M + H) |
|---|---|---|
| 20z | 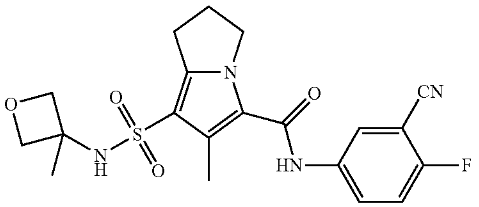 [SMILES: Cc1c(S(=O)(=O)NC2(C)COC2)c2n(c1C(=O)Nc1ccc(F)c(C#N)c1)CCC2] | 433 |
| 20aa | 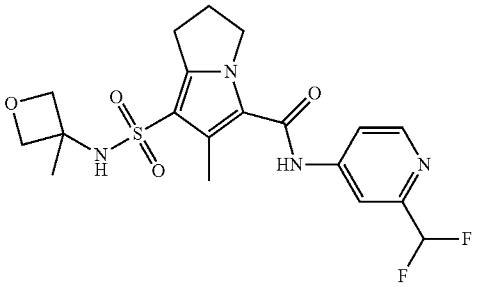 [SMILES: Cc1c(S(=O)(=O)NC2(C)COC2)c2n(c1C(=O)Nc1ccnc(C(F)F)c1)CCC2] | 441 |
| 20bb | 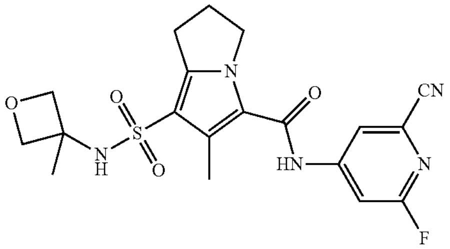 [SMILES: Cc1c(S(=O)(=O)NC2(C)COC2)c2n(c1C(=O)Nc1cc(F)nc(C#N)c1)CCC2] | 434 |
| 20cc | 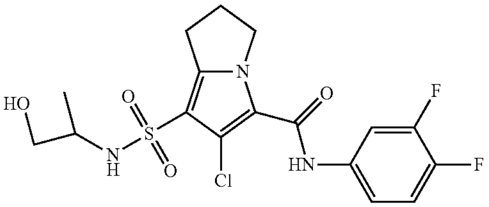 | 434 |
| 20dd | 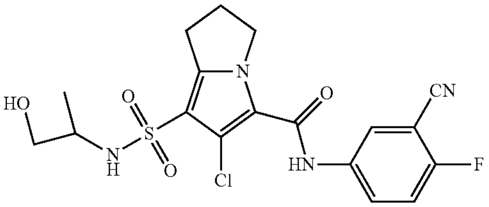 [SMILES: CC(CO)NS(=O)(=O)c1c(Cl)c(C(=O)Nc2ccc(F)c(C#N)c2)n2c1CCC2] | 441 |
| 20ee | 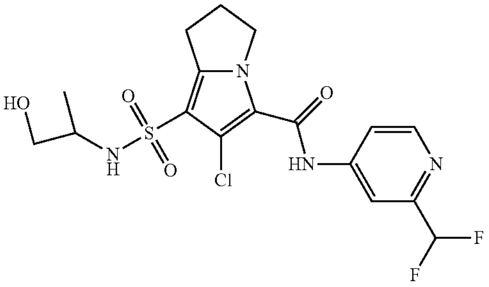 [SMILES: CC(CO)NS(=O)(=O)c1c(Cl)c(C(=O)Nc2ccnc(C(F)F)c2)n2c1CCC2] | 449 |

-continued
| Compound | Structure | Mass Spectrometry. ESI-MS, (M + H) |
|---|---|---|
| 20ff | 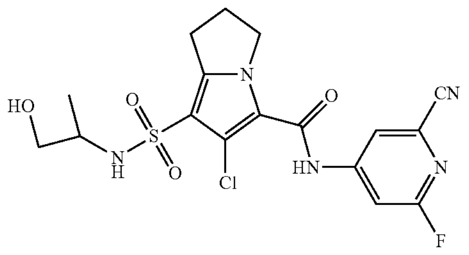 [SMILES: CC(CO)NS(=O)(=O)c1c(Cl)c(C(=O)Nc2cc(F)nc(C#N)c2)n2c1CCC2] | 442 |
| 20gg | 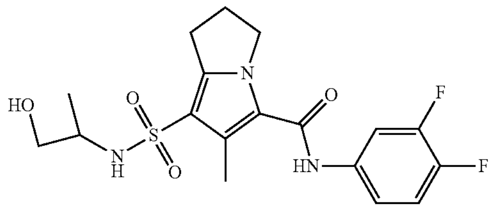 [SMILES: Cc1c(S(=O)(=O)NC(C)CO)c2n(c1C(=O)Nc1ccc(F)c(F)c1)CCC2] | 414 |
| 20hh | 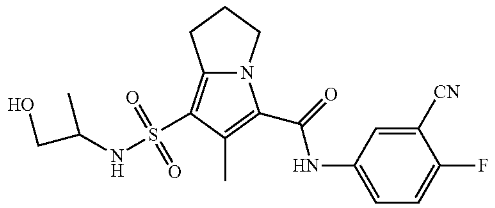 [SMILES: Cc1c(S(=O)(=O)NC(C)CO)c2n(c1C(=O)Nc1ccc(F)c(C#N)c1)CCC2] | 421 |
| 20ii | 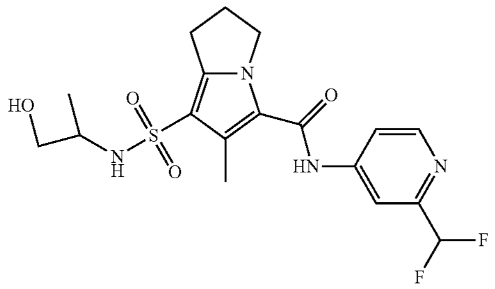 [SMILES: Cc1c(S(=O)(=O)NC(C)CO)c2n(c1C(=O)Nc1ccnc(C(F)F)c1)CCC2] | 429 |
| 20jj | 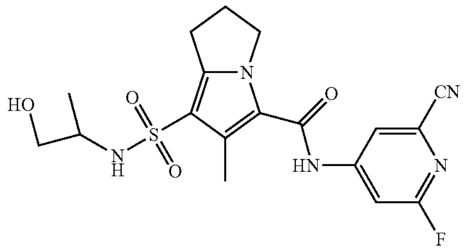 [SMILES: Cc1c(S(=O)(=O)NC(C)CO)c2n(c1C(=O)Nc1cc(F)nc(C#N)c1)CCC2] | 422 |
| 20kk | 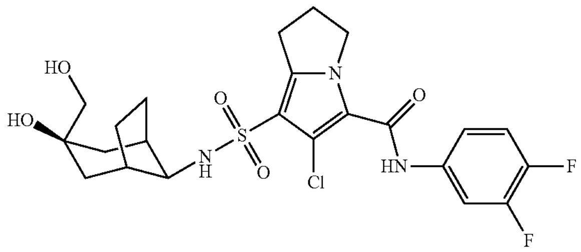 | 530 |

-continued
| Compound | Structure | Mass Spectrometry. ESI-MS, (M + H) |
|---|---|---|
| 220ll | 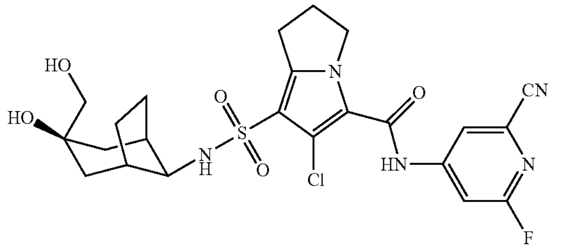 | 538 |
| 20mm | 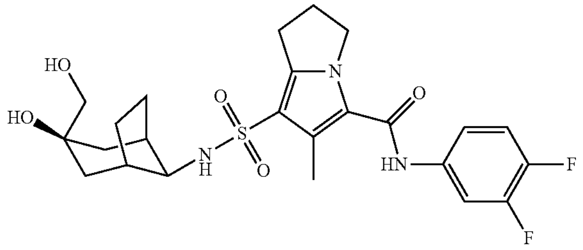 | 510 |
| 20nn | 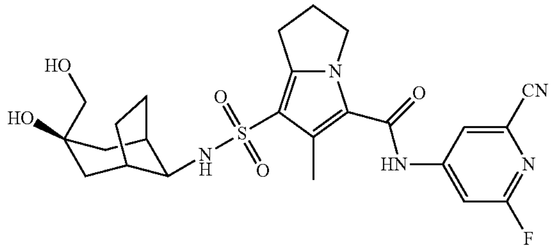 | 516 |
| 20oo | 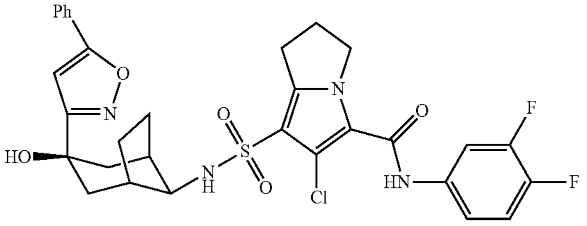 | 643 |
| 20pp | 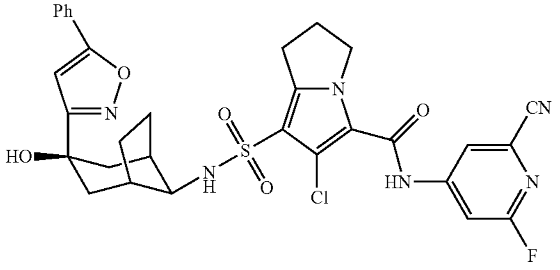 | 651 |
| 20qq | 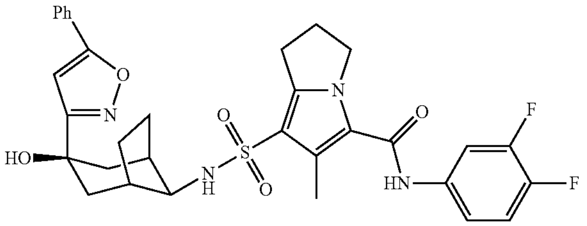 | 621 |

-continued
| Compound | Structure | Mass Spectrometry. ESI-MS, (M + H) |
| --- | --- | --- |
| 20rr | 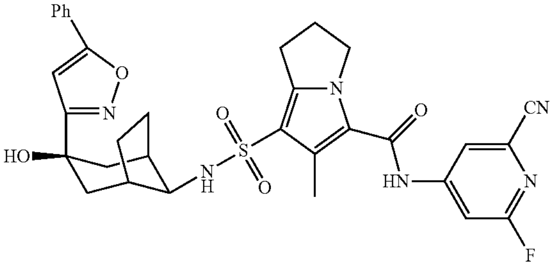 | 631 |
| 20ss | 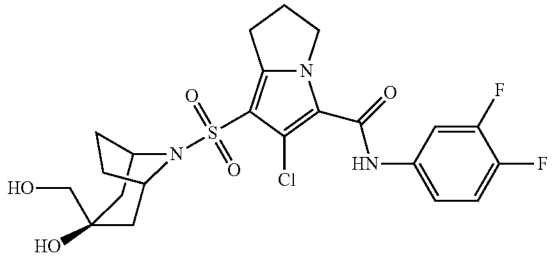 | 516 |
| 20tt | 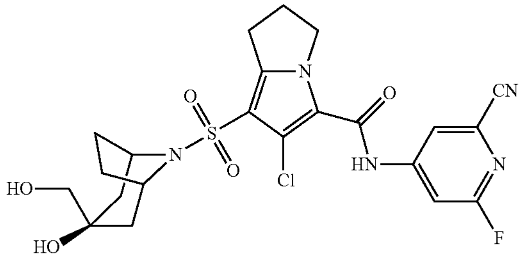 | 524 |
| 20uu | 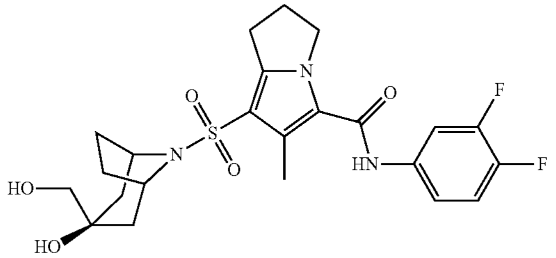 | 496 |
| 20vv | 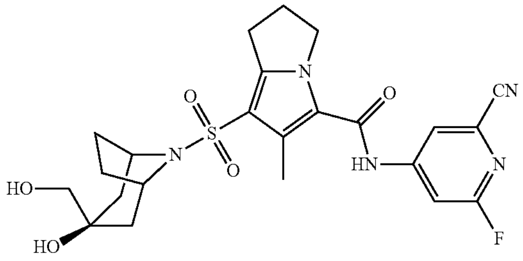 | 504 |

-continued
| Compound | Structure | Mass Spectrometry. ESI-MS, (M + H) |
|---|---|---|
| 20ww | 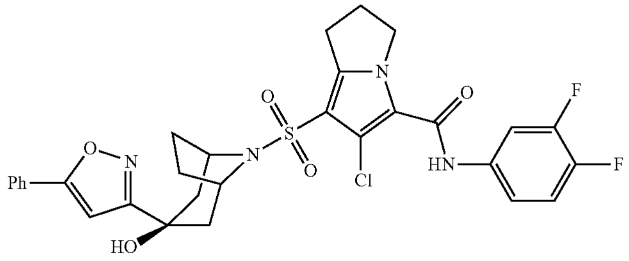 | 629 |
| 20xx | 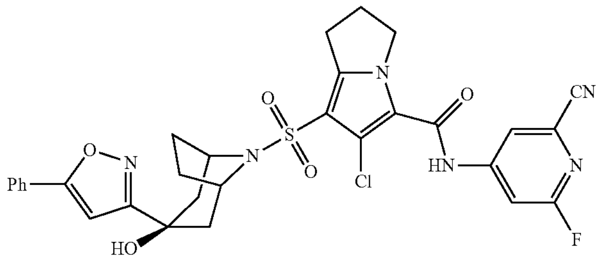 | 637 |
| 20yy | 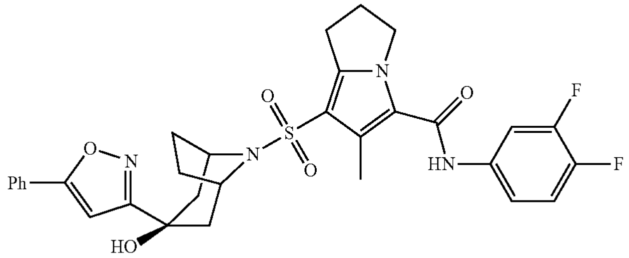 | 609 |
| 20zz | 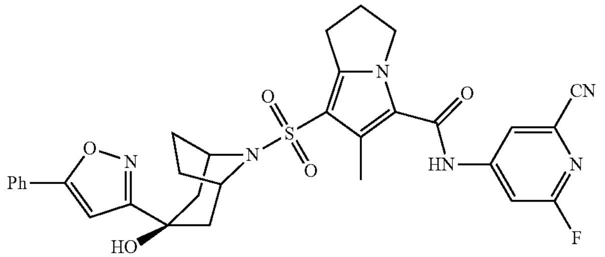 | 617 |
| 30a | 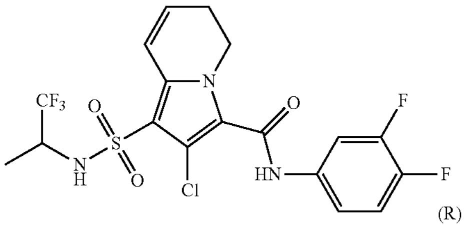 | 484 |
| 30b | 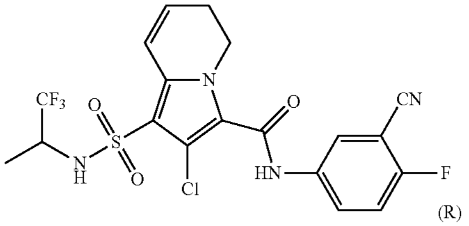 | 491 |

-continued
| Compound | Structure | Mass Spectrometry. ESI-MS, (M + H) |
|---|---|---|
| 30c | 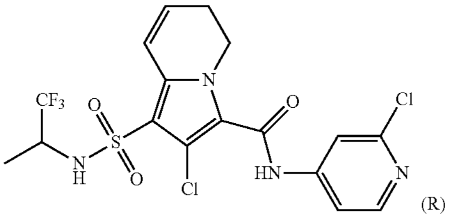 | 483 |
| 30d | 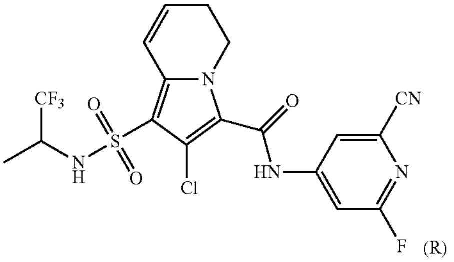 | 492 |
| 30e | 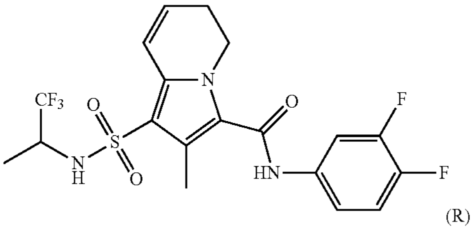 | 464 |
| 30f | 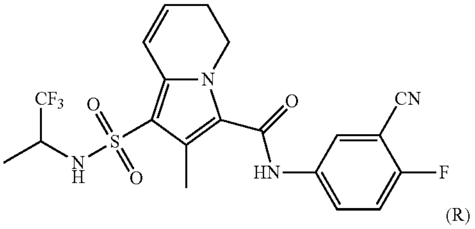 | 471 |
| 30g | 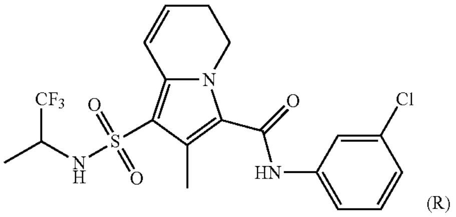 | 463 |
| 30h | 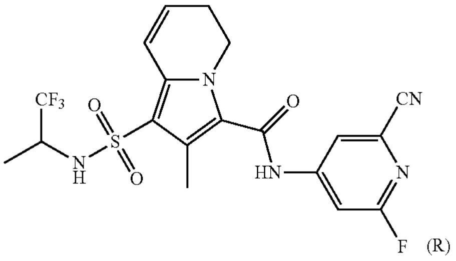 | 472 |

-continued
| Compound | Structure | Mass Spectrometry. ESI-MS, (M + H) |
|---|---|---|
| 30i | 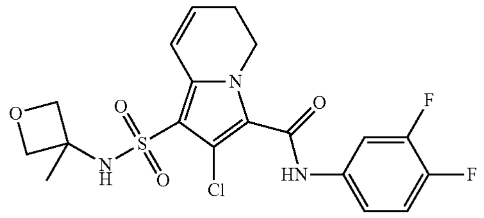 [SMILES: CC1(NS(=O)(=O)c2c(Cl)c(C(=O)Nc3ccc(F)c(F)c3)n3c2C=CCC3)COC1] | 458 |
| 30j | 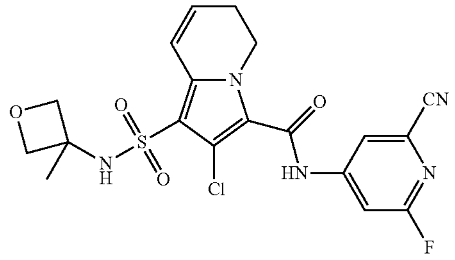 [SMILES: CC1(NS(=O)(=O)c2c(Cl)c(C(=O)Nc3cc(F)nc(C#N)c3)n3c2C=CCC3)COC1] | 466 |
| 30k | 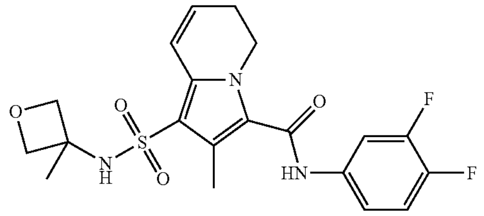 [SMILES: Cc1c(S(=O)(=O)NC2(C)COC2)c2n(c1C(=O)Nc1ccc(F)c(F)c1)CCC=C2] | 438 |
| 30l | 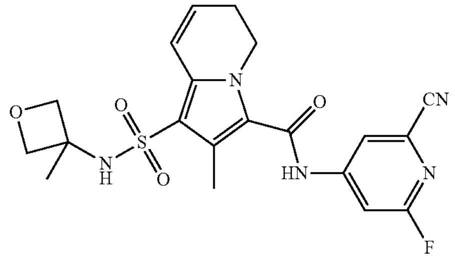 [SMILES: Cc1c(S(=O)(=O)NC2(C)COC2)c2n(c1C(=O)Nc1cc(F)nc(C#N)c1)CCC=C2] | 446 |
| 30m | 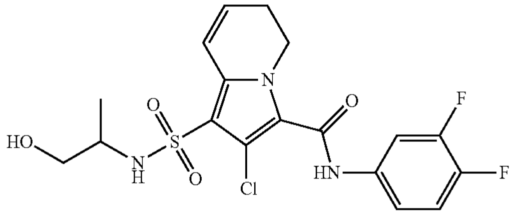 [SMILES: CC(CO)NS(=O)(=O)c1c(Cl)c(C(=O)Nc2ccc(F)c(F)c2)n2c1C=CCC2] | 446 |
| 30n | 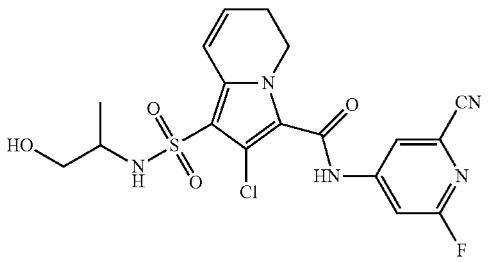 [SMILES: CC(CO)NS(=O)(=O)c1c(Cl)c(C(=O)Nc2cc(F)nc(C#N)c2)n2c1C=CCC2] | 454 |

-continued
| Compound | Structure | Mass Spectrometry. ESI-MS, (M + H) |
|---|---|---|
| 30o | 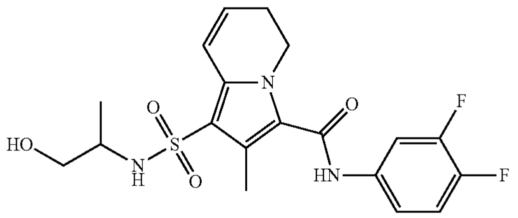 | 426 |
| 30p | 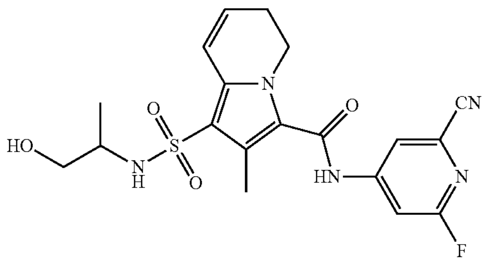 [SMILES: Cc1c(S(=O)(=O)NC(C)CO)c2n(c1C(=O)Nc1cc(F)nc(C#N)c1)CCC=C2] | 434 |
| 30q | 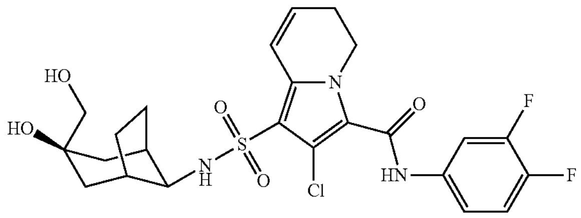 | 542 |
| 30r | 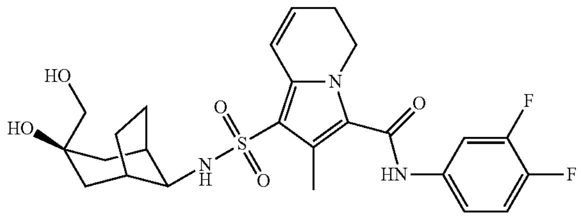 | 522 |
| 30s | 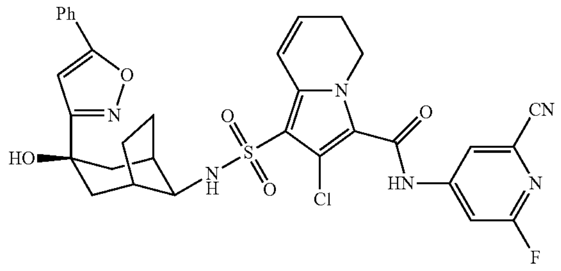 | 663 |
| 30t | 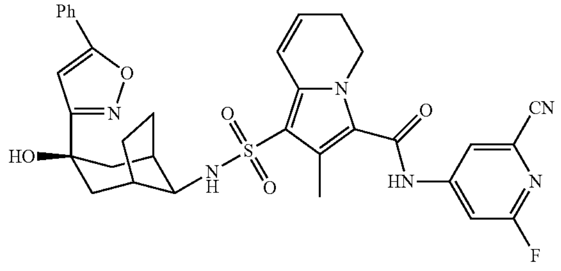 | 643 |

-continued
| Compound | Structure | Mass Spectrometry. ESI-MS, (M + H) |
| --- | --- | --- |
| 30u | 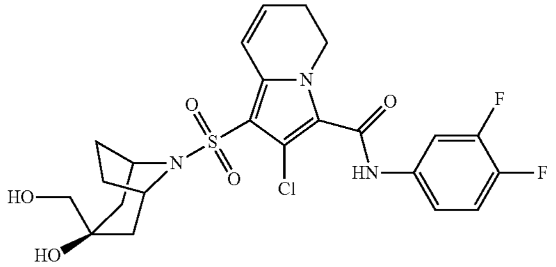 | 528 |
| 30v | 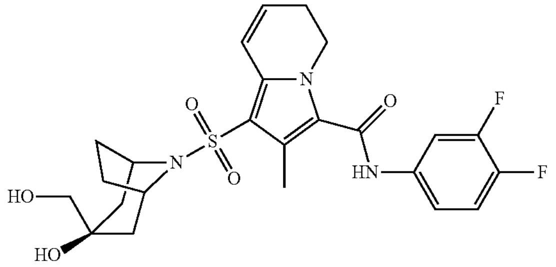 | 508 |
| 30w | 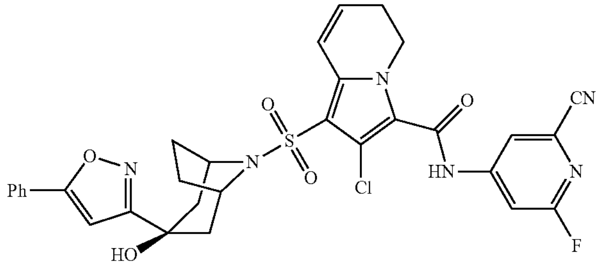 | 649 |
| 30x | 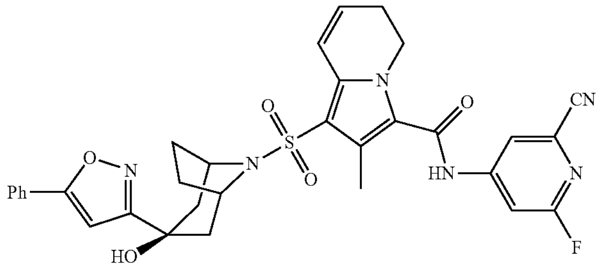 | 628 |
| 40a | 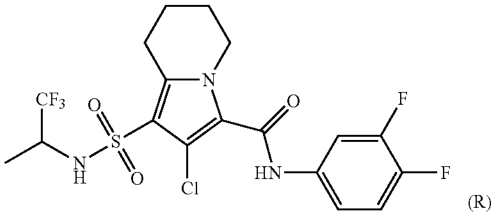 | 486 |
| 40b | 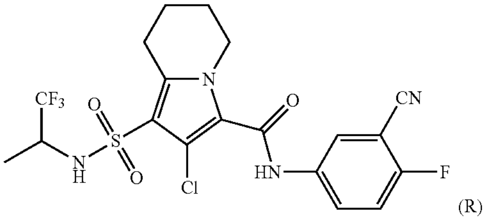 | 493 |

-continued
| Compound | Structure | Mass Spectrometry. ESI-MS, (M + H) |
|---|---|---|
| 40c | 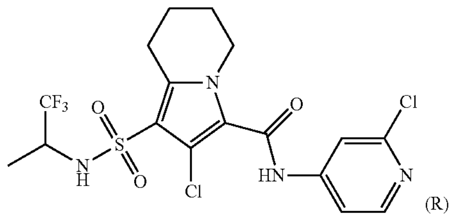 | 485 |
| 40d | 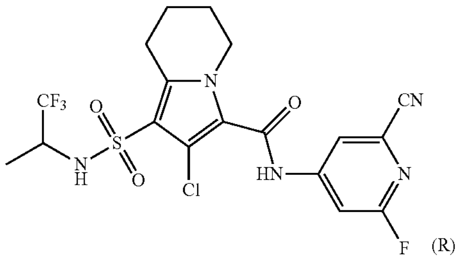 | 494 |
| 40e | 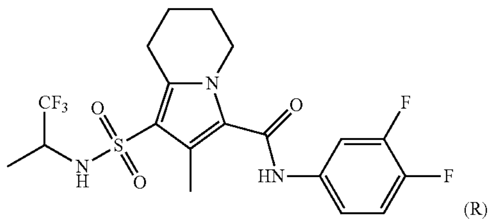 | 466 |
| 40f | 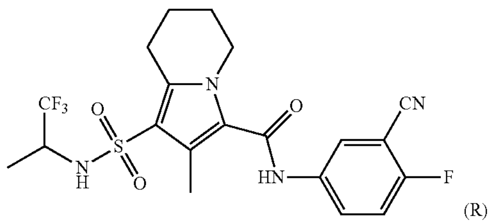 | 473 |
| 40g | 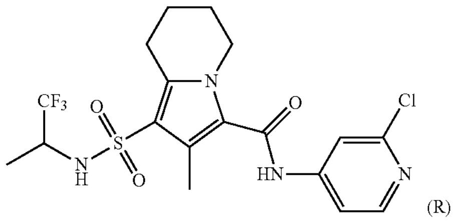 | 465 |
| 40h | 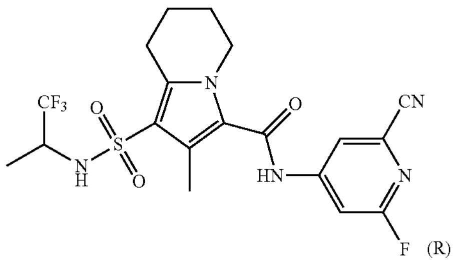 | 474 |

-continued
| Compound | Structure | Mass Spectrometry. ESI-MS, (M + H) |
| --- | --- | --- |
| 40i | 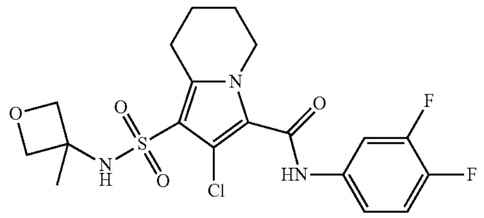 [SMILES: CC1(NS(=O)(=O)c2c(Cl)c(C(=O)Nc3ccc(F)c(F)c3)n3c2CCCC3)COC1] | 460 |
| 40j | 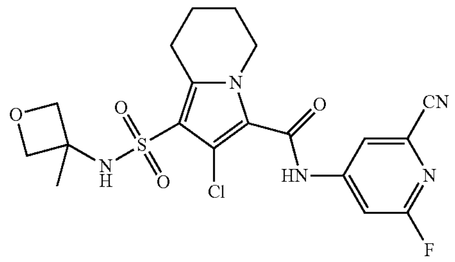 [SMILES: CC1(NS(=O)(=O)c2c(Cl)c(C(=O)Nc3cc(F)nc(C#N)c3)n3c2CCCC3)COC1] | 468 |
| 40k | 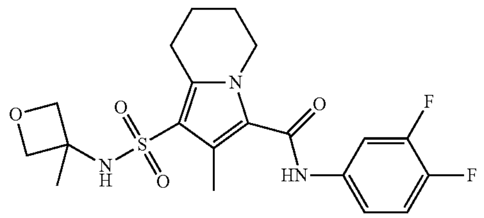 [SMILES: Cc1c(S(=O)(=O)NC2(C)COC2)c2n(c1C(=O)Nc1ccc(F)c(F)c1)CCCC2] | 440 |
| 40l | 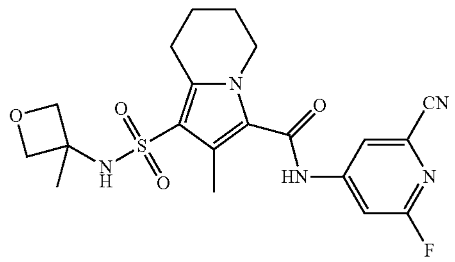 [SMILES: Cc1c(S(=O)(=O)NC2(C)COC2)c2n(c1C(=O)Nc1cc(F)nc(C#N)c1)CCCC2] | 448 |
| 40m | 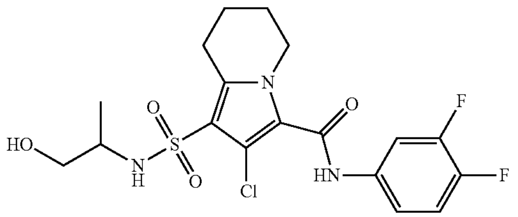 [SMILES: CC(CO)NS(=O)(=O)c1c(Cl)c(C(=O)Nc2ccc(F)c(F)c2)n2c1CCCC2] | 448 |
| 40n | 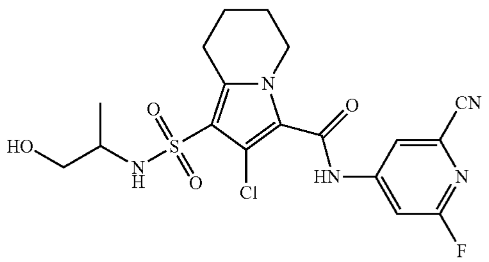 [SMILES: CC(CO)NS(=O)(=O)c1c(Cl)c(C(=O)Nc2cc(F)nc(C#N)c2)n2c1CCCC2] | 456 |

-continued
| Compound | Structure | Mass Spectrometry. ESI-MS, (M + H) |
| --- | --- | --- |
| 40o | 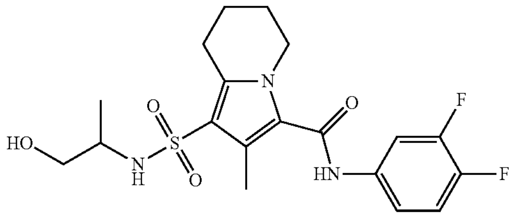 [SMILES: Cc1c(S(=O)(=O)NC(C)CO)c2n(c1C(=O)Nc1ccc(F)c(F)c1)CCCC2] | 428 |
| 40p | 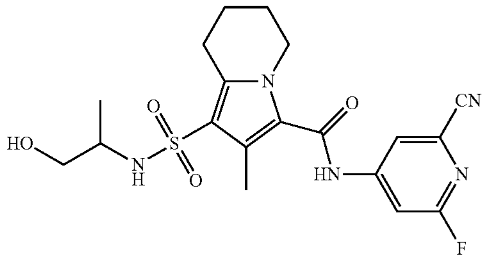 [SMILES: Cc1c(S(=O)(=O)NC(C)CO)c2n(c1C(=O)Nc1cc(F)nc(C#N)c1)CCCC2] | 436 |
| 40q | 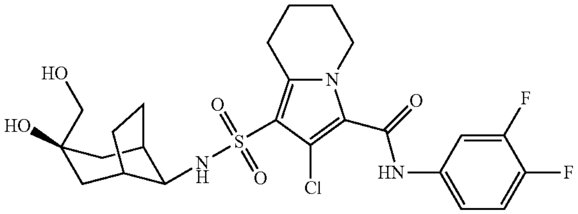 | 544 |
| 40r | 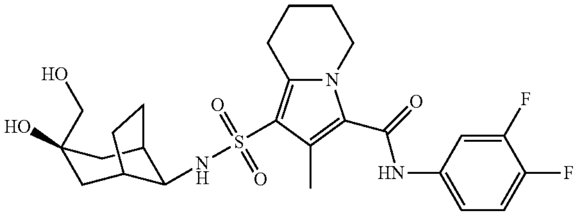 | 524 |
| 40s | 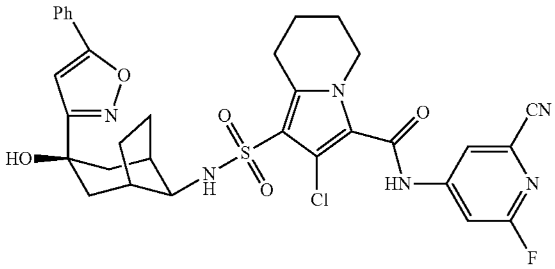 | 666 |
| 40t | 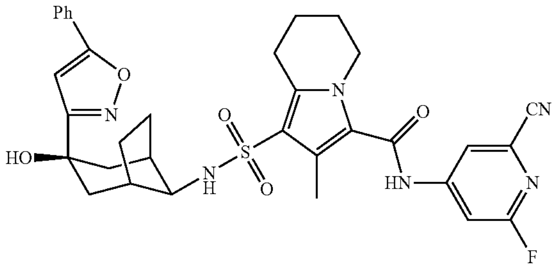 | 645 |

-continued
| Compound | Structure | Mass Spectrometry. ESI-MS, (M + H) |
| --- | --- | --- |
| 40u | 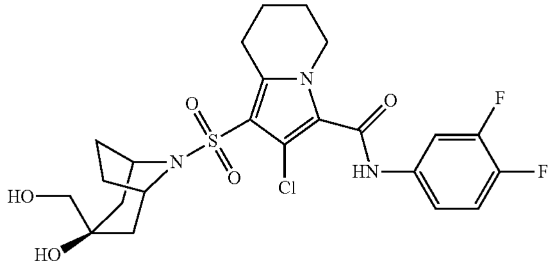 | 530 |
| 40v | 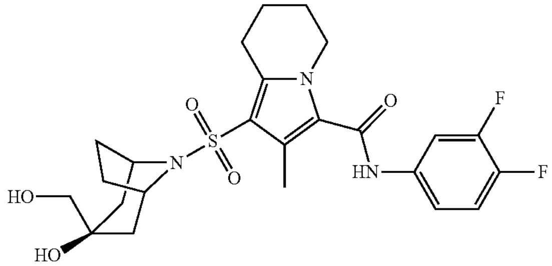 | 510 |
| 40w | 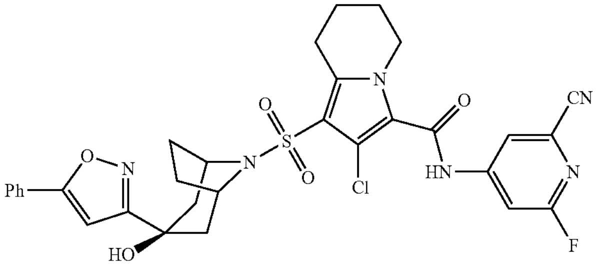 | 651 |
| 40x | 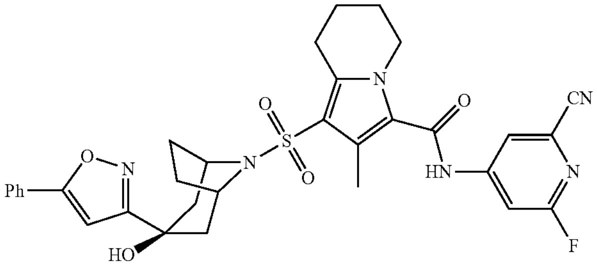 | 630 |
| 50a | 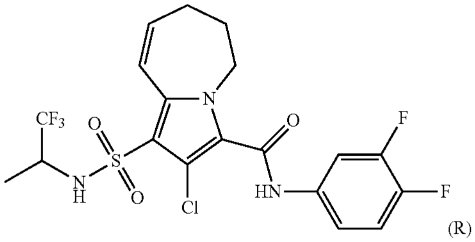 (R) | 498 |

-continued
| Compound | Structure | Mass Spectrometry. ESI-MS, (M + H) |
|---|---|---|
| 50b | 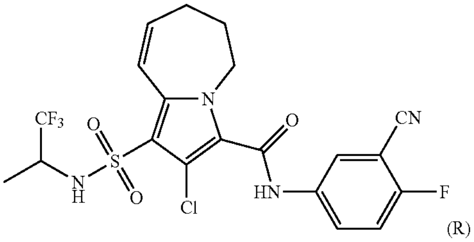 (R) | 505 |
| 50c | 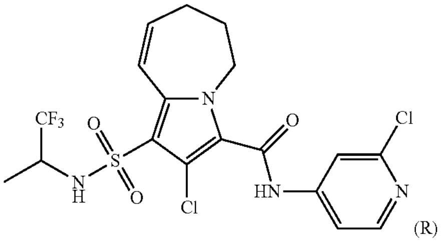 (R) | 497 |
| 50d | 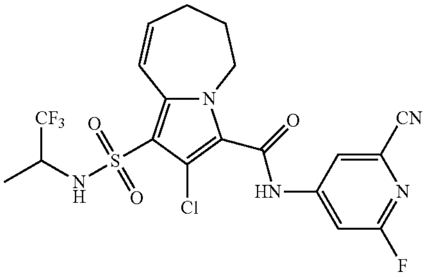 (R) | 506 |
| 50e | 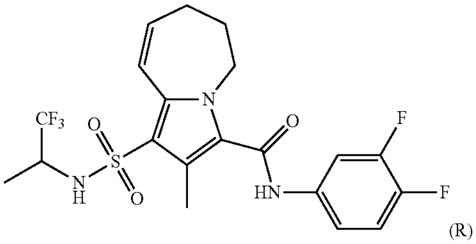 (R) | 478 |
| 50f | 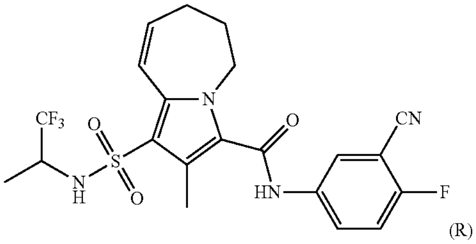 (R) | 485 |
| 50g | 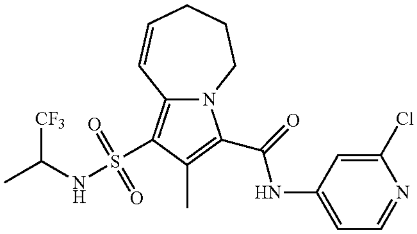 (R) | 477 |

-continued
| Compound | Structure | Mass Spectrometry. ESI-MS, (M + H) |
|---|---|---|
| 50h | 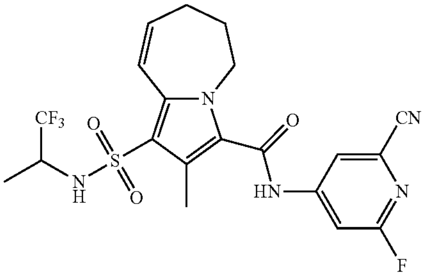 (R) | 486 |
| 50i | 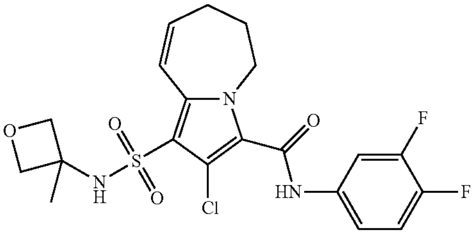 | 472 |
| 50j | 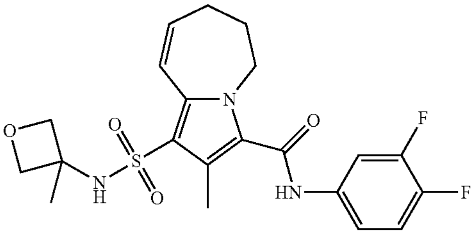 | 452 |
| 50k | 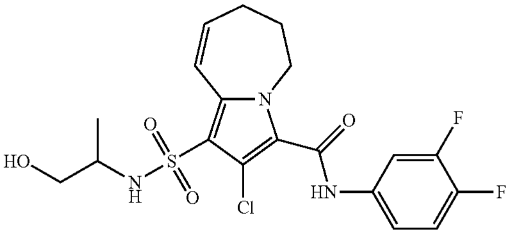 | 460 |
| 50l | 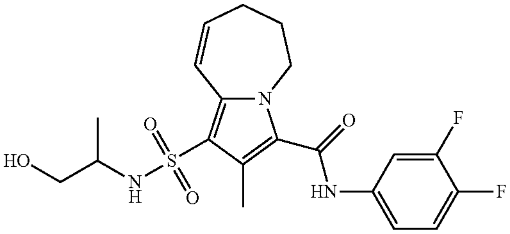 | 440 |
| 50m | 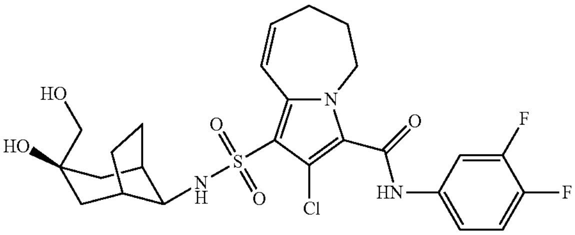 | 556 |

-continued
| Compound | Structure | Mass Spectrometry. ESI-MS, (M + H) |
|---|---|---|
| 50n | 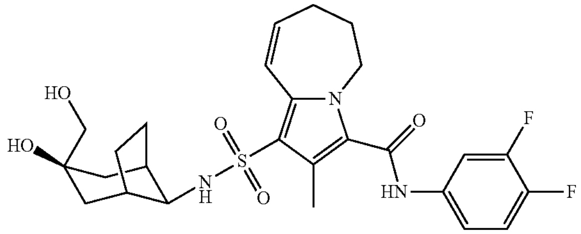 | 536 |
| 50o | 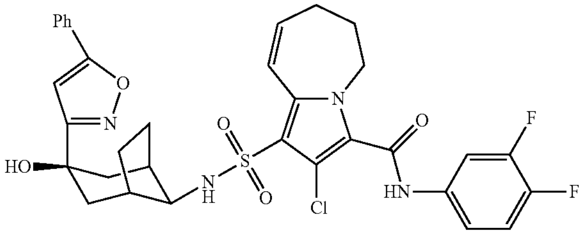 | 669 |
| 50p | 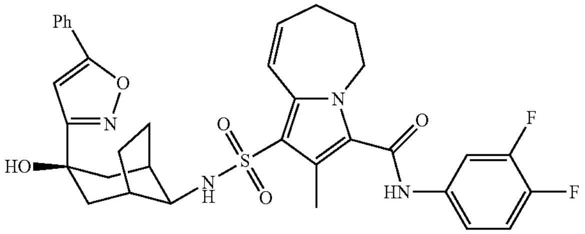 | 649 |
| 50q | 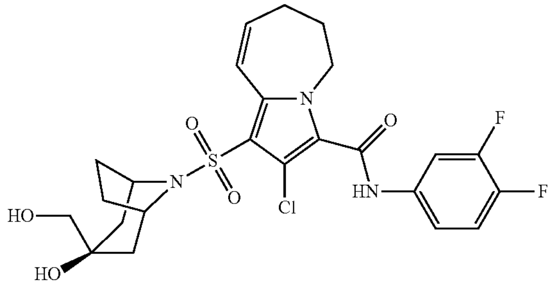 | 542 |
| 50r | 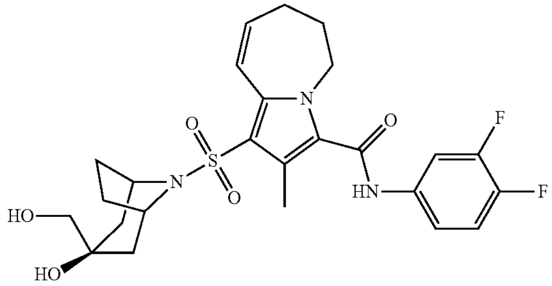 | 522 |

-continued
| Compound | Structure | Mass Spectrometry. ESI-MS, (M + H) |
|---|---|---|
| 50s | 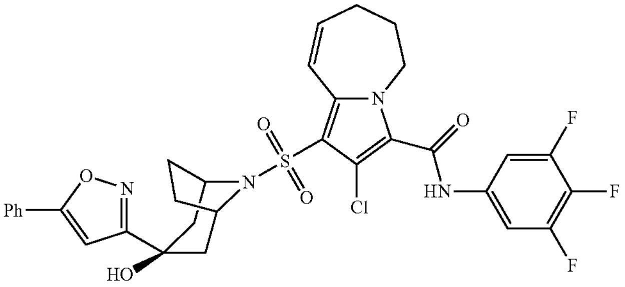 | 673 |
| 50t | 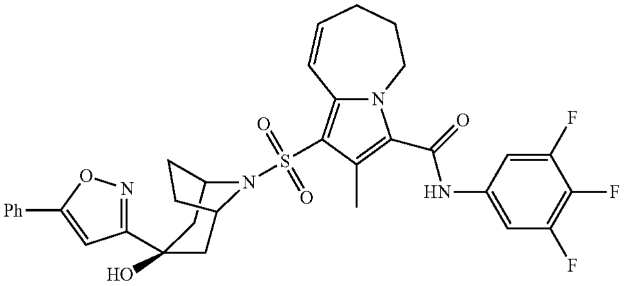 | 653 |
| 60a | 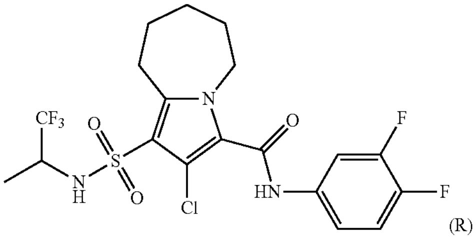 | 500 |
| 60b | 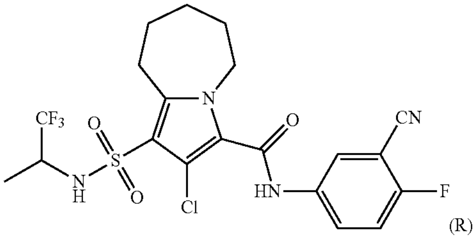 | 507 |
| 60c | 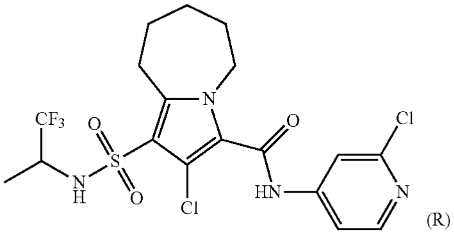 | 499 |

-continued
| Compound | Structure | Mass Spectrometry. ESI-MS, (M + H) |
| --- | --- | --- |
| 60d | 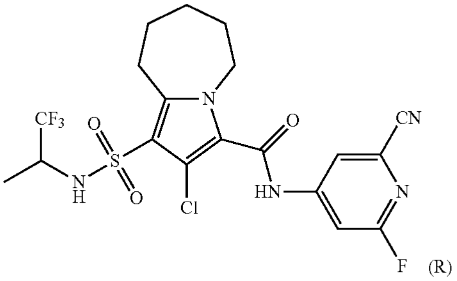 | 508 |
| 60e | 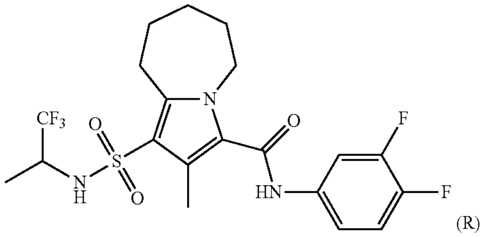 | 480 |
| 60f | 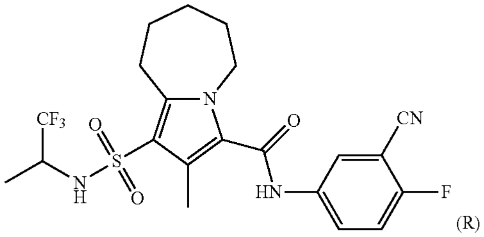 | 487 |
| 60g | 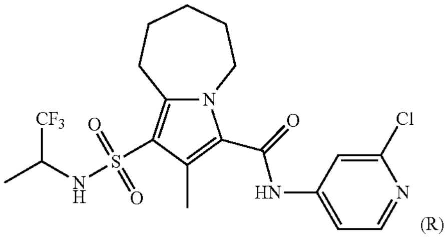 | 479 |
| 60h | 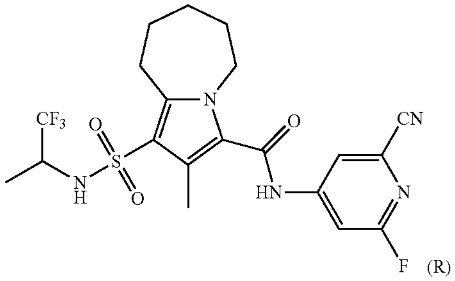 | 488 |
| 60i | 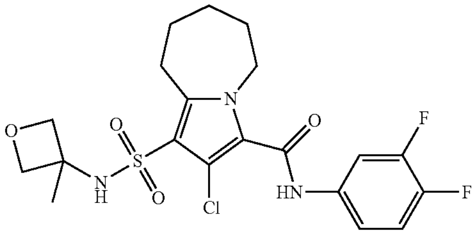 [SMILES: CC1(NS(=O)(=O)c2c(Cl)c(C(=O)Nc3ccc(F)c(F)c3)n3c2CCCCC3)COC1] | 474 |

-continued
| Compound | Structure | Mass Spectrometry. ESI-MS, (M + H) |
|---|---|---|
| 60j | 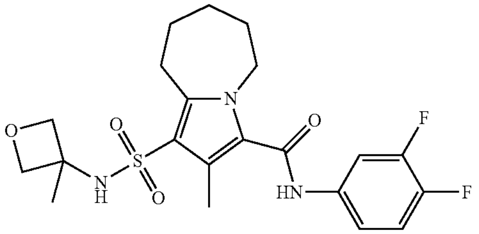 [SMILES: Cc1c(S(=O)(=O)NC2(C)COC2)c2n(c1C(=O)Nc1ccc(F)c(F)c1)CCCCC2] | 454 |
| 60k | 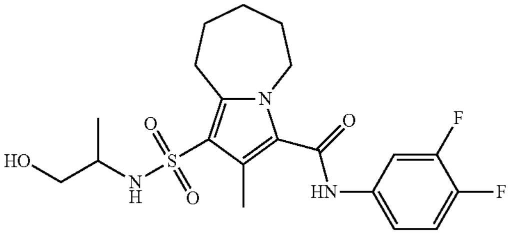 [SMILES: Cc1c(S(=O)(=O)NC(C)CO)c2n(c1C(=O)Nc1ccc(F)c(F)c1)CCCCC2] | 462 |
| 60l | 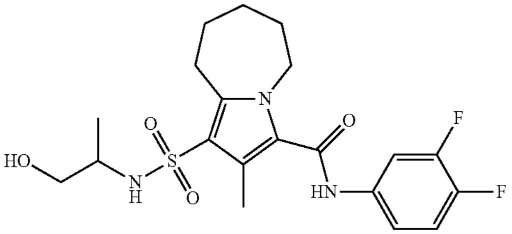 [SMILES: Cc1c(S(=O)(=O)NC(C)CO)c2n(c1C(=O)Nc1ccc(F)c(F)c1)CCCCC2] | 442 |
| 60m | 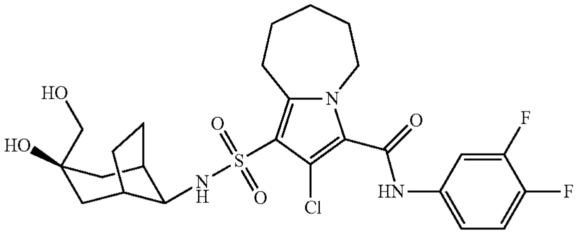 | 558 |
| 60n | 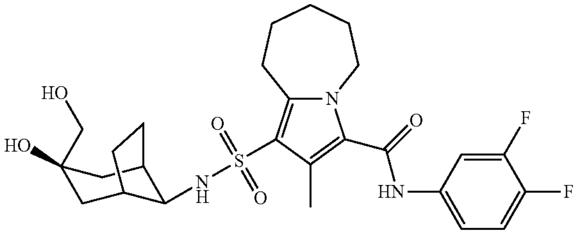 | 538 |
| 60o | 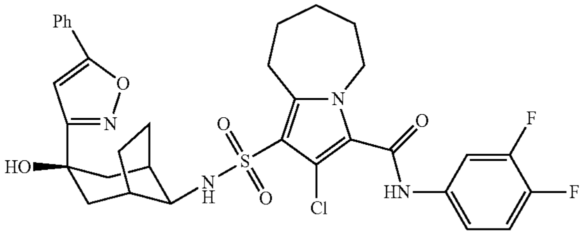 | 671 |

-continued
| Compound | Structure | Mass Spectrometry. ESI-MS, (M + H) |
|---|---|---|
| 60p | 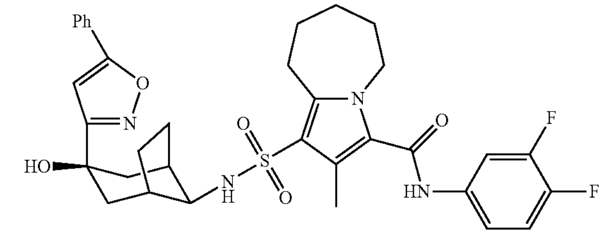 | 651 |
| 60q | 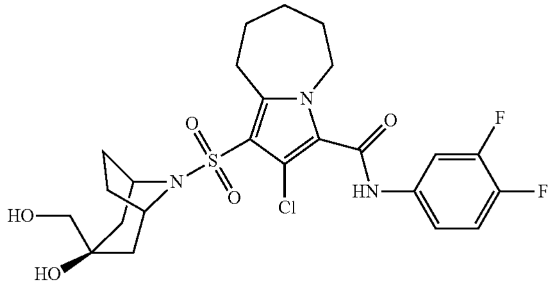 | 544 |
| 60r | 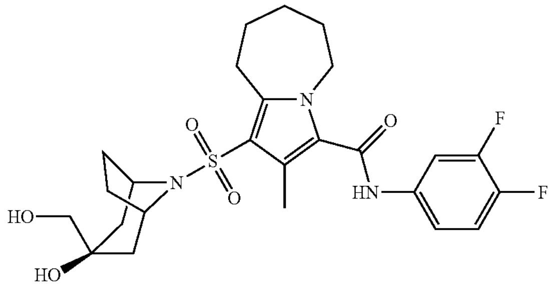 | 524 |
| 60s | 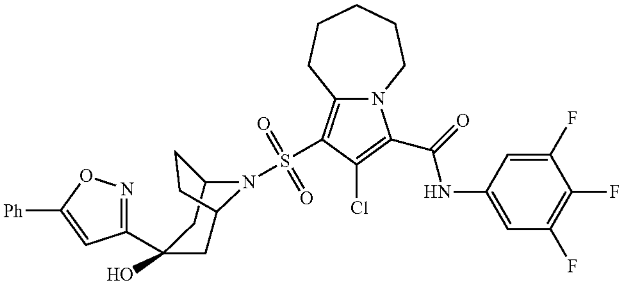 | 675 |
| 60t | 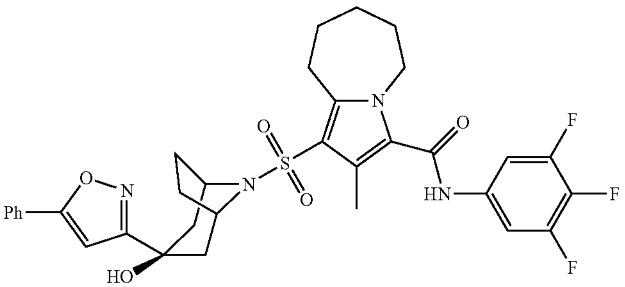 | 655 |

-continued
| Compound | Structure | Mass Spectrometry. ESI-MS, (M + H) |
|---|---|---|
| 70a | 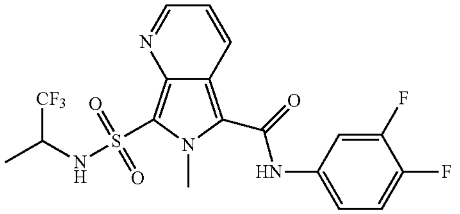 [SMILES: CC(NS(=O)(=O)c1c2ncccc2c(C(=O)Nc2ccc(F)c(F)c2)n1C)C(F)(F)F] | 463 |
| 70b | 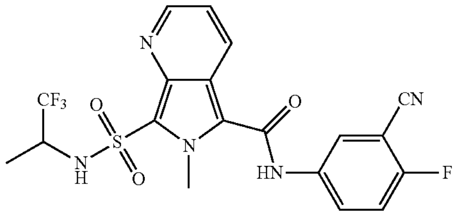 (R) | 470 |
| 70c | 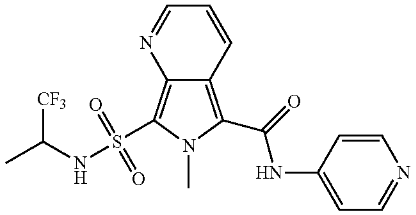 (R) | 428 |
| 70d | 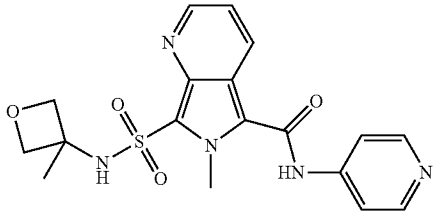 [SMILES: Cn1c(C(=O)Nc2ccncc2)c2cccnc2c1S(=O)(=O)NC1(C)COC1] | 437 |
| 70e | 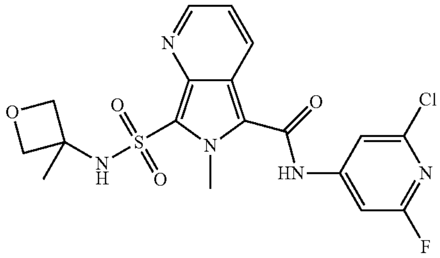 [SMILES: Cn1c(C(=O)Nc2cc(F)nc(Cl)c2)c2cccnc2c1S(=O)(=O)NC1(C)COC1] | 454 |
| 70f | 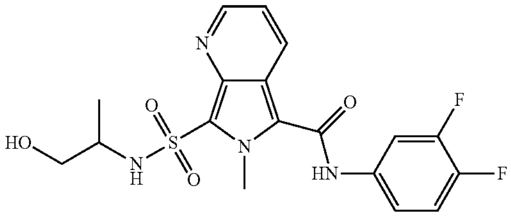 [SMILES: CC(CO)NS(=O)(=O)c1c2ncccc2c(C(=O)Nc2ccc(F)c(F)c2)n1C] | 425 |

-continued
| Compound | Structure | Mass Spectrometry. ESI-MS, (M + H) |
| --- | --- | --- |
| 70g | 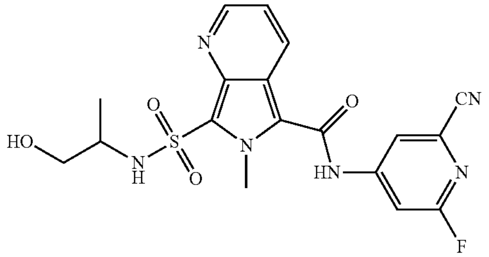 [SMILES: CC(CO)NS(=O)(=O)c1c2ncccc2c(C(=O)Nc2cc(F)nc(C#N)c2)n1C] | 433 |
| 70h | 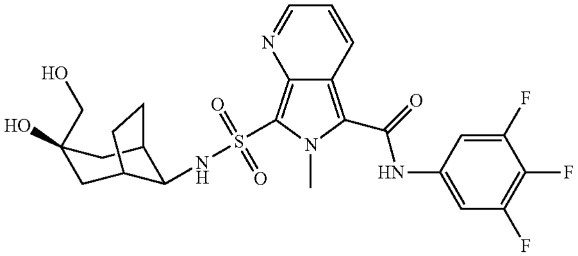 | 539 |
| 70i | 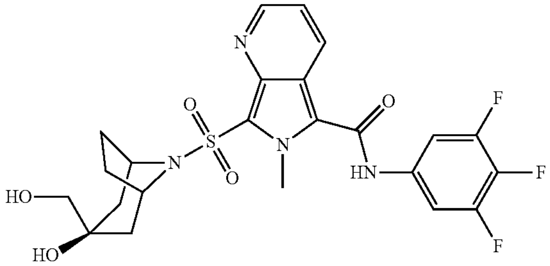 | 525 |
| 70j | 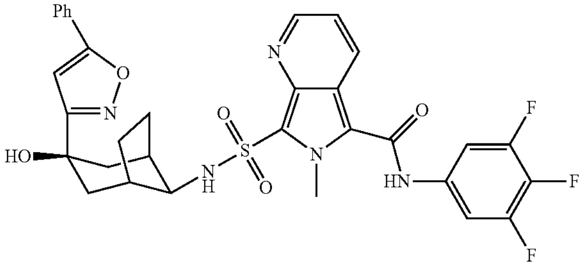 | 652 |
| 70k | 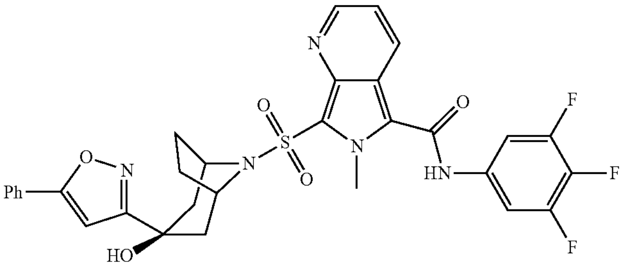 | 638 |
| 80a | 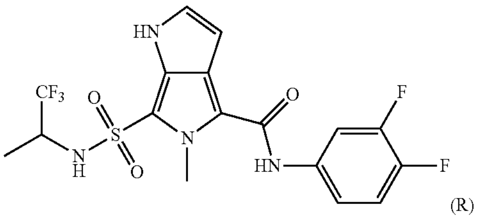 | 451 |

-continued
| Compound | Structure | Mass Spectrometry. ESI-MS, (M + H) |
|---|---|---|
| 80b | 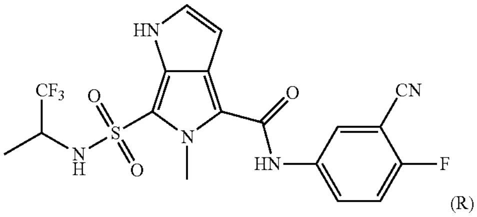 (R) | 458 |
| 80c | 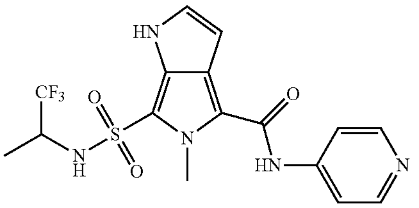 (R) | 416 |
| 80d | 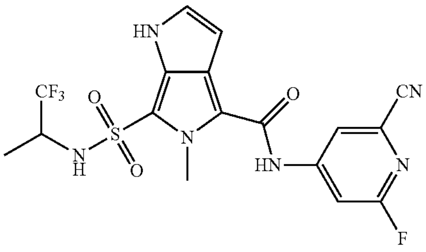 (R) | 459 |
| 80e | 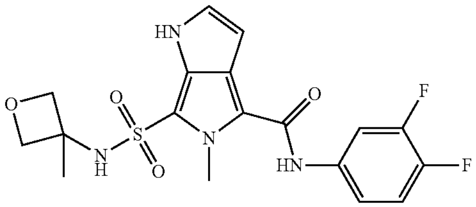 | 425 |
| 80f | 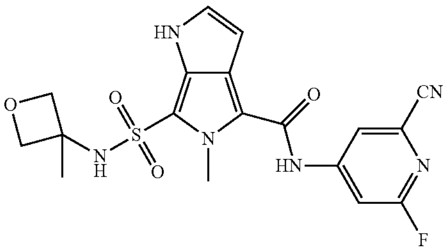 | 433 |
| 80g | 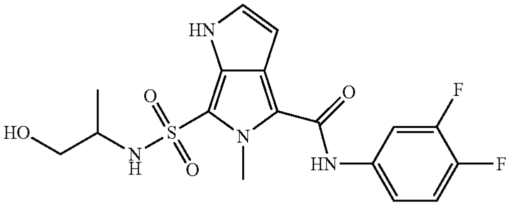 | 413 |

-continued
| Compound | Structure | Mass Spectrometry. ESI-MS, (M + H) |
|---|---|---|
| 80h | 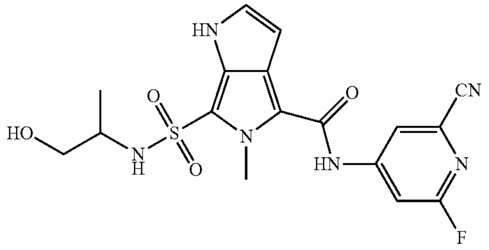 [SMILES: CC(CO)NS(=O)(=O)c1c2[nH]ccc2c(C(=O)Nc2cc(F)nc(C#N)c2)n1C] | 421 |
| 80i | 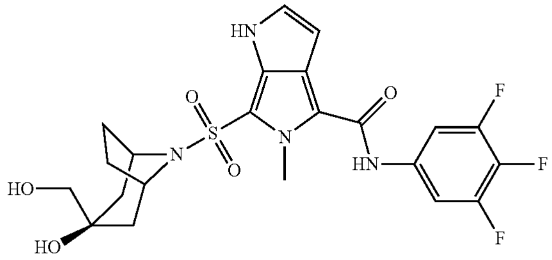 | 513 |
| 80j | 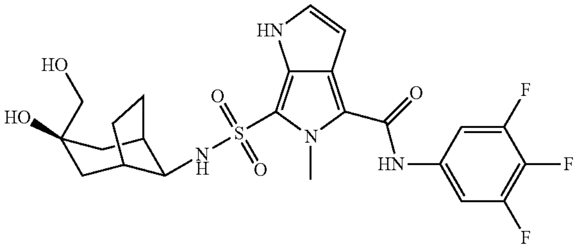 | 527 |
| 80k | 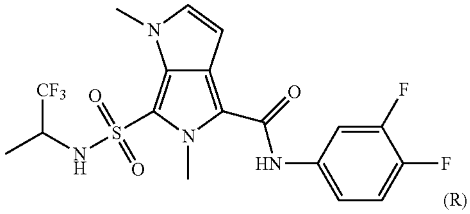 (R) | 465 |
| 80l | 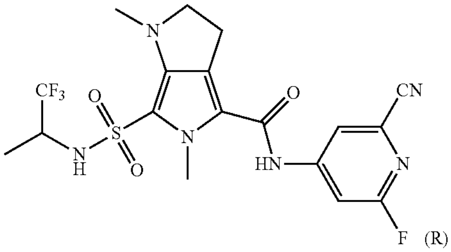 (R) | 475 |
| 80m | 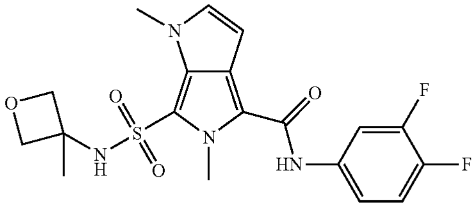 [SMILES: Cn1c(C(=O)Nc2ccc(F)c(F)c2)c2ccn(C)c2c1S(=O)(=O)NC1(C)COC1] | 439 |

-continued
| Compound | Structure | Mass Spectrometry. ESI-MS, (M + H) |
|---|---|---|
| 80n | 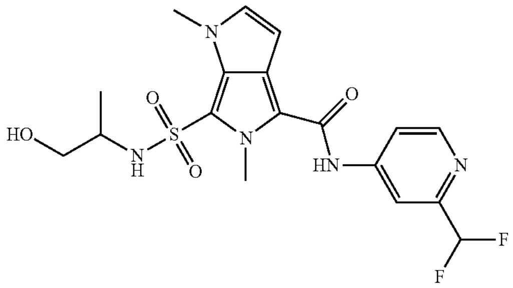 [SMILES: CC(CO)NS(=O)(=O)c1c2c(ccn2C)c(C(=O)Nc2ccnc(C(F)F)c2)n1C] | 442 |
| 80o | 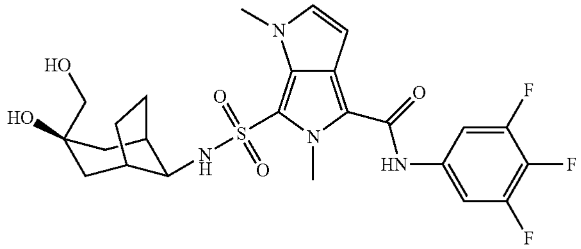 | 541 |
| 80p | 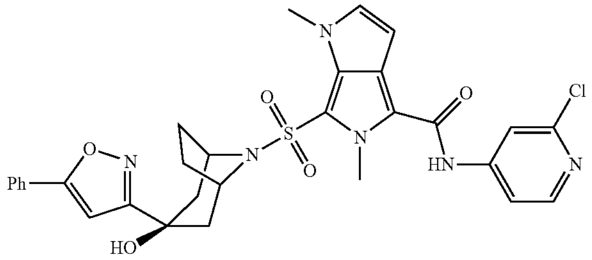 | 621 |
| 90a | 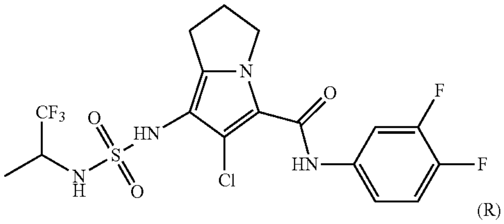 (R) | 487 |
| 90b | 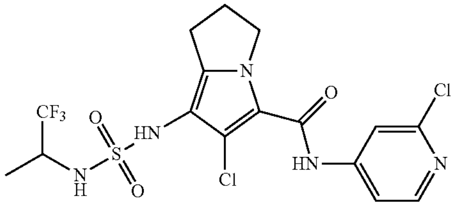 (R) | 486 |
| 90c | 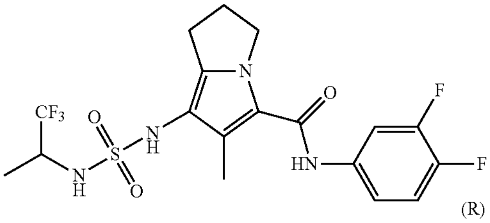 (R) | 467 |

-continued
| Compound | Structure | Mass Spectrometry. ESI-MS, (M + H) |
|---|---|---|
| 90d | 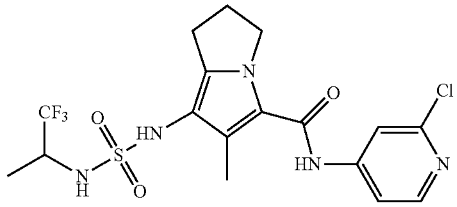 (R) | 466 |
| 90e | 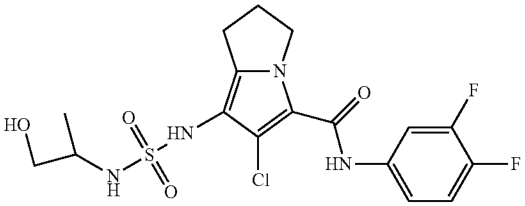 | 449 |
| 90f | 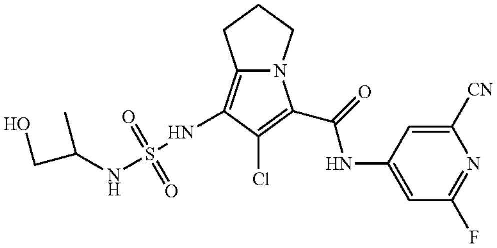 | 457 |
| 90g | 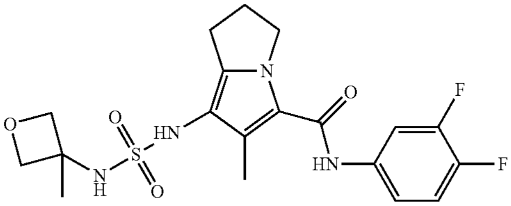 | 441 |
| 90h | 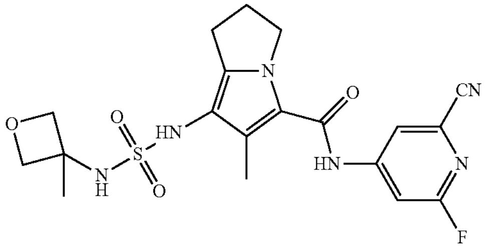 | 449 |
| 90i | 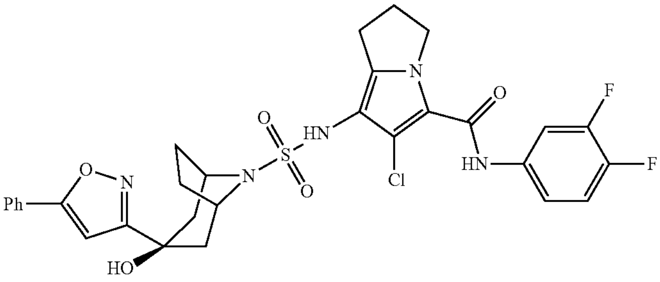 | 644 |

-continued
| Compound | Structure | Mass Spectrometry. ESI-MS, (M + H) |
|---|---|---|
| 90j | 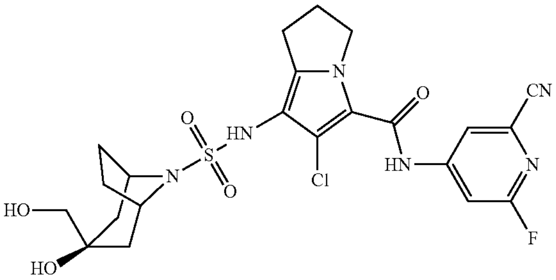 | 539 |
| 90k | 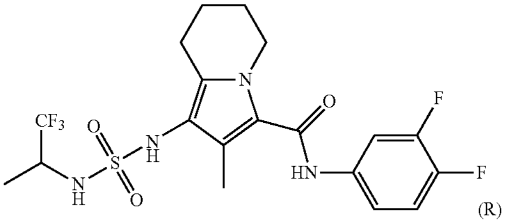 (R) | 481 |
| 90l | 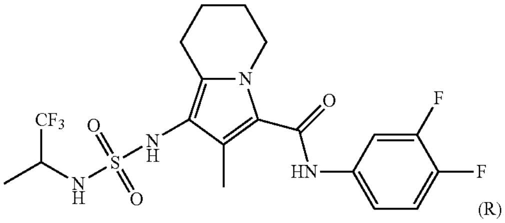 (R) | 480 |
| 90m | 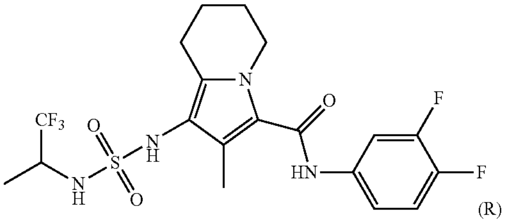 (R) | 501 |
| 90n | 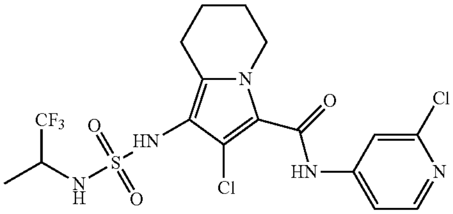 (R) | 500 |
| 90o | 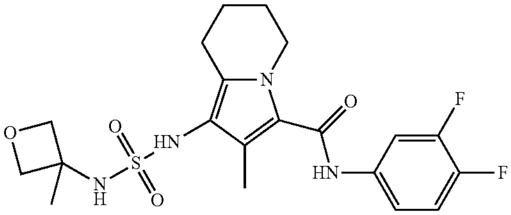 [SMILES: Cc1c(NS(=O)(=O)NC2(C)COC2)c2n(c1C(=O)Nc1ccc(F)c(F)c1)CCCC2] | 455 |

-continued
| Compound | Structure | Mass Spectrometry. ESI-MS, (M + H) |
|---|---|---|
| 90p | 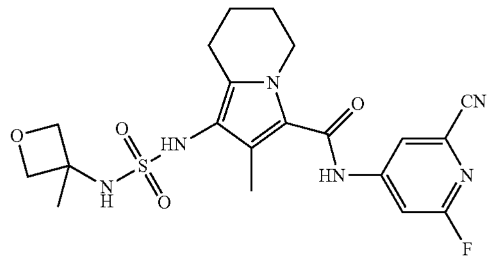 [SMILES: Cc1c(NS(=O)(=O)NC2(C)COC2)c2n(c1C(=O)Nc1cc(F)nc(C#N)c1)CCCC2] | 463 |
| 90r | 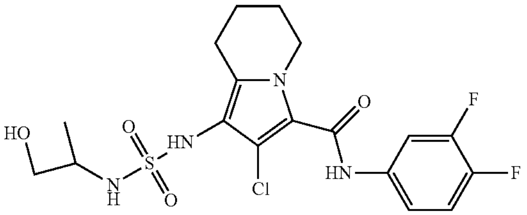 [SMILES: CC(CO)NS(=O)(=O)Nc1c(Cl)c(C(=O)Nc2ccc(F)c(F)c2)n2c1CCCC2] | 463 |
| 90s | 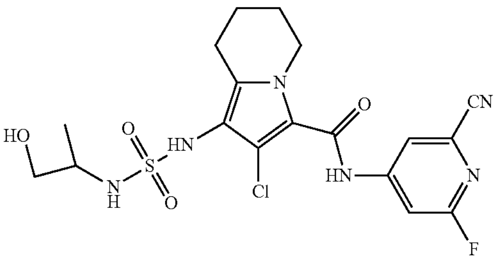 [SMILES: CC(CO)NS(=O)(=O)Nc1c(Cl)c(C(=O)Nc2cc(F)nc(C#N)c2)n2c1CCCC2] | 471 |
| 90t | 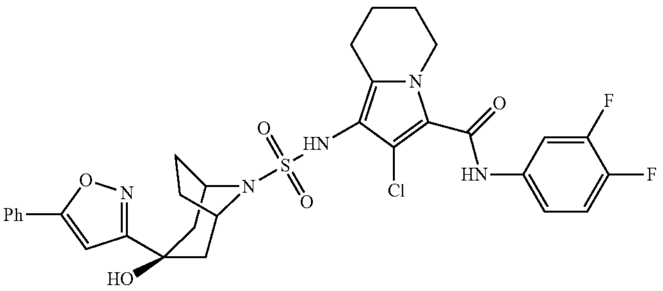 | 658 |
| 90u | 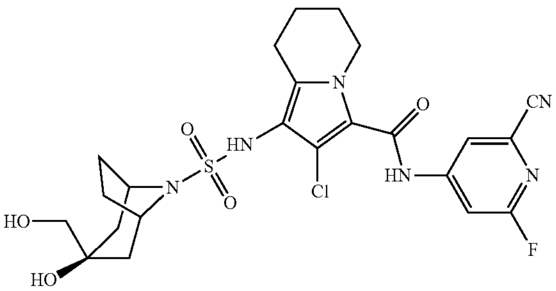 | 553 |
| 90v | 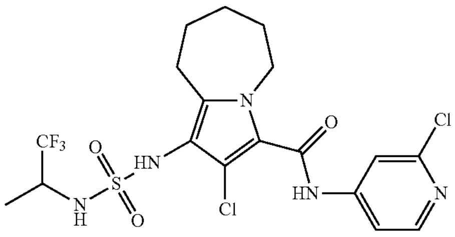 [SMILES: CC(NS(=O)(=O)Nc1c(Cl)c(C(=O)Nc2ccnc(Cl)c2)n2c1CCCCC2)C(F)(F)F] | 514 |

-continued
| Compound | Structure | Mass Spectrometry. ESI-MS, (M + H) |
|---|---|---|
| 90w | 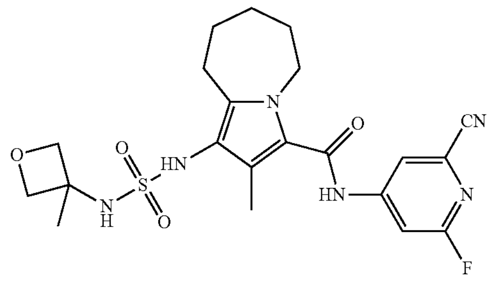 [SMILES: Cc1c(NS(=O)(=O)NC2(C)COC2)c2n(c1C(=O)Nc1cc(F)nc(C#N)c1)CCCCC2] | 477 |
| 90x | 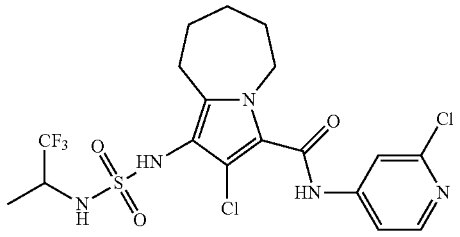 (R) | 514 |
| 90y | 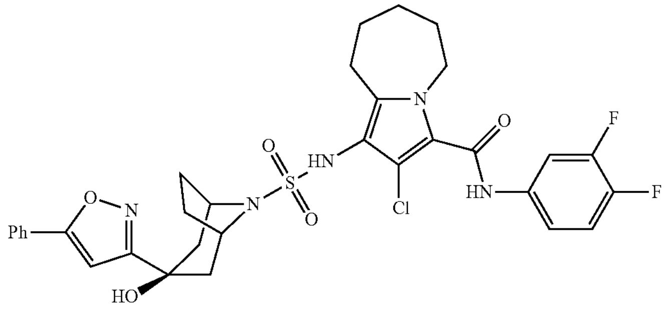 | 672 |
| 90z | 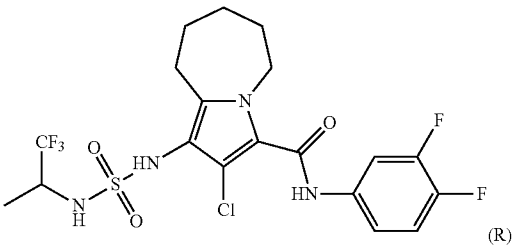 (R) | 497 |
| 90aa | 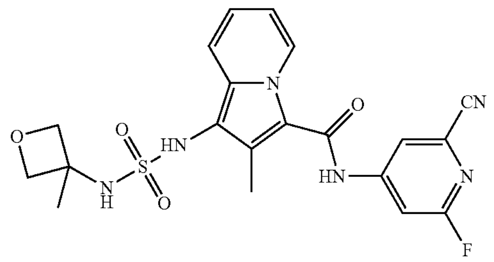 [SMILES: Cc1c(NS(=O)(=O)NC2(C)COC2)c2ccccn2c1C(=O)Nc1cc(F)nc(C#N)c1] | 459 |

-continued
| Compound | Structure | Mass Spectrometry. ESI-MS, (M + H) |
|---|---|---|
| 90bb | 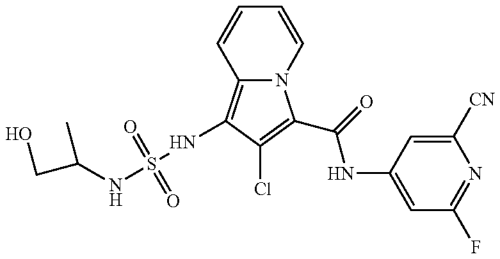 [SMILES: CC(CO)NS(=O)(=O)Nc1c(Cl)c(C(=O)Nc2cc(F)nc(C#N)c2)n2ccccc12] | 467 |
| 90cc | 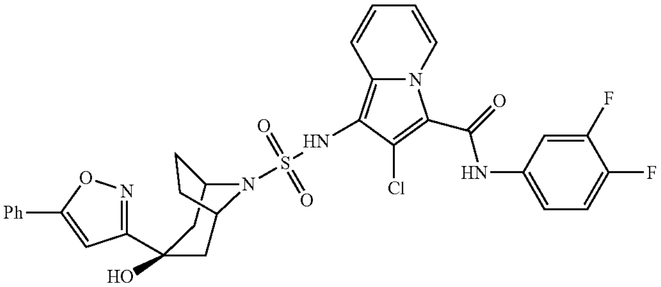 | 654 |
| 90dd | 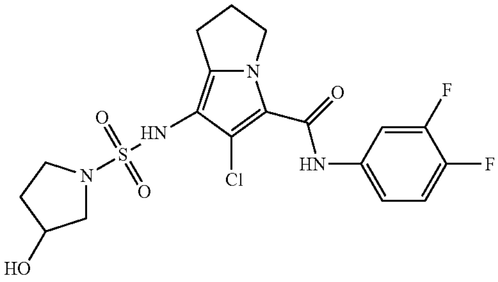 [SMILES: O=C(Nc1ccc(F)c(F)c1)c1c(Cl)c(NS(=O)(=O)N2CCC(O)C2)c2n1CCC2] | 461 |
| 90ee | 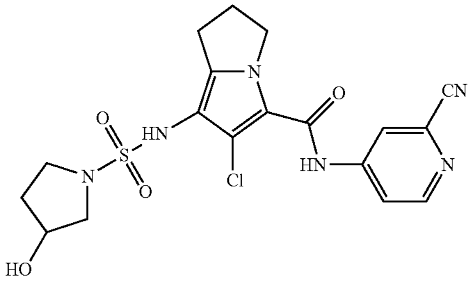 [SMILES: N#Cc1cc(NC(=O)c2c(Cl)c(NS(=O)(=O)N3CCC(O)C3)c3n2CCC3)ccn1] | 451 |
| 90ff | 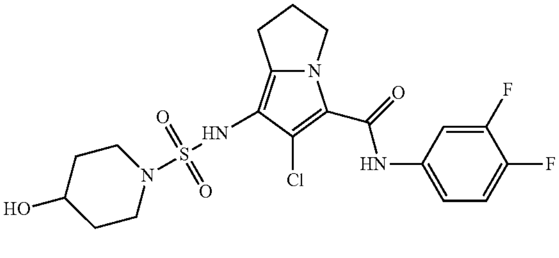 [SMILES: O=C(Nc1ccc(F)c(F)c1)c1c(Cl)c(NS(=O)(=O)N2CCC(O)CC2)c2n1CCC2] | 474 |

-continued
| Compound | Structure | Mass Spectrometry. ESI-MS, (M + H) |
|---|---|---|
| 90gg | 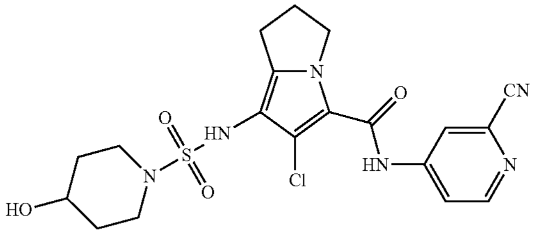 [SMILES: N#Cc1cc(NC(=O)c2c(Cl)c(NS(=O)(=O)N3CCC(O)CC3)c3n2CCC3)ccn1] | 465 |
| 90hh | 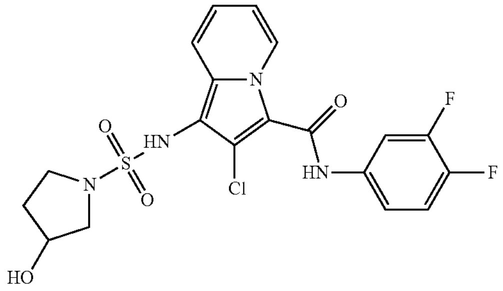 [SMILES: O=C(Nc1ccc(F)c(F)c1)c1c(Cl)c(NS(=O)(=O)N2CCC(O)C2)c2ccccn12] | 471 |
| 90ii | 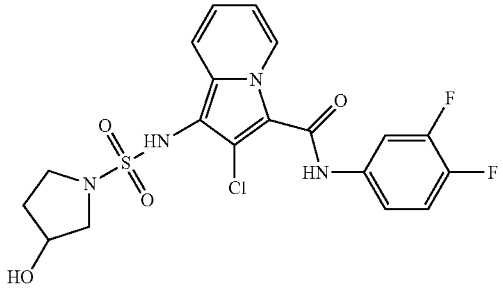 [SMILES: O=C(Nc1ccc(F)c(F)c1)c1c(Cl)c(NS(=O)(=O)N2CCC(O)C2)c2ccccn12] | 461 |
| 100b | 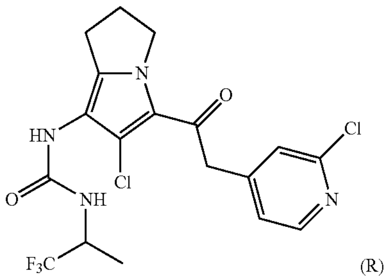 [SMILES: CC(NC(=O)Nc1c(Cl)c(C(=O)Cc2ccnc(Cl)c2)n2c1CCC2)C(F)(F)F ; "(R)"] (R) | 450 |
| 100d | 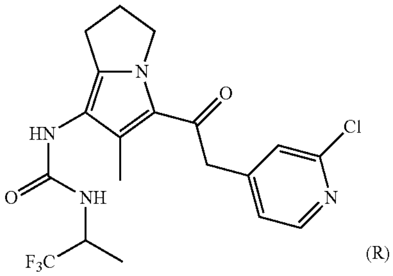 [SMILES: Cc1c(NC(=O)NC(C)C(F)(F)F)c2n(c1C(=O)Cc1ccnc(Cl)c1)CCC2 ; "(R)"] (R) | 430 |

-continued

| Compound | Structure | Mass Spectrometry. ESI-MS, (M + H) |
|---|---|---|
| 100p | 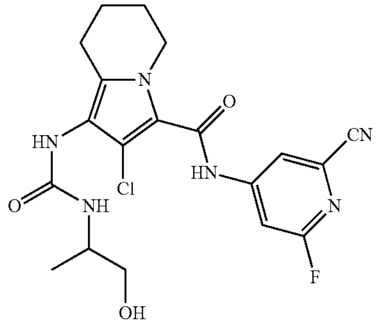 [SMILES: CC(CO)NC(=O)Nc1c(Cl)c(C(=O)Nc2cc(F)nc(C#N)c2)n2c1CCCC2] | 435 |
| 100q | 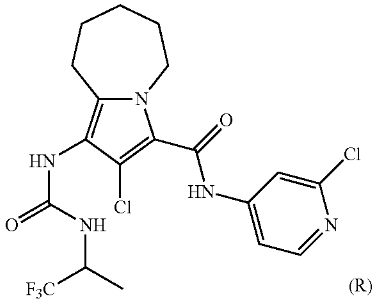 (R) | 478 |
| 100r | 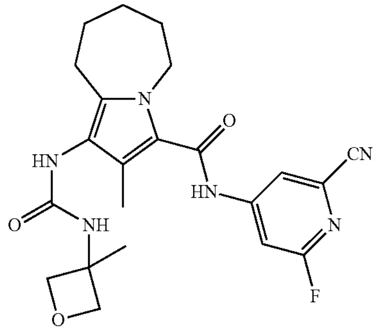 [SMILES: Cc1c(NC(=O)NC2(C)COC2)c2n(c1C(=O)Nc1cc(F)nc(C#N)c1)CCCCC2] | 441 |

Pharmaceutical Composition and Administration Mode

Since the compounds of the present invention have excellent inhibitory activity against hepatitis B virus (HBV), the various compounds of the present invention, pharmaceutically acceptable inorganic or organic salts, hydrates or solvates thereof, and a pharmaceutical composition containing a compound of the present invention as a main active ingredient can be used for the prevention and/or treatment (stabilization, alleviation or cure) of hepatitis B virus infection or for prevention and/or treatment (stabilize, alleviate or cure) hepatitis B virus-related diseases (for example, hepatitis B, progressive liver fibrosis, inflammation and necrosis which cause cirrhosis, end-stage liver disease, hepatitis B cancer).

The pharmaceutical composition of the invention comprises the compound of the present invention in a safe and effective dosage range and a pharmaceutically acceptable excipient or carrier. The term "safe and effective dosage" means that the amount of compound is sufficient to significantly improve the condition without causing serious side effects. Generally, the pharmaceutical composition contains 1-2000 mg compound of the invention per dose, preferably, 10-200 mg compound of the invention per dose. Preferably, the "one dose" is one capsule or one tablet.

"Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation on administration mode for the compound or pharmaceutical composition of the present invention, and the representative administration mode includes (but is not limited to): oral, parenteral (intravenous, intramuscular or subcutaneous) administration.

Solid dosage forms for oral administration include capsules, tablets, pills, powders and granules. In these solid dosage forms, the active compounds are mixed with at least one conventional inert excipient (or carrier), such as sodium citrate or $CaHPO_4$, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The compounds of the present invention can be administrated alone, or in combination with any other pharmaceutically acceptable compounds (such as anti-HBV agents).

In the case of co-administration, the pharmaceutical composition can also include one or more (2, 3, 4, or more) other pharmaceutically acceptable compounds (such as anti-HBV agents). One or more (2, 3, 4, or more) other pharmaceutically acceptable compounds (e.g., anti-HBV agents) may be used simultaneously, separately or sequentially with the compound of the present invention so as to prevent and/or treat HBV infection or HBV related diseases.

When the pharmaceutical composition is used, a safe and effective amount of compound of the present invention is administered to a mammal (such as human) in need of, wherein the dose of administration is a pharmaceutically effective dose. For a person weighed 60 kg, the daily dose is usually 1-2000 mg, preferably 20-500 mg. Of course, the particular dose should also depend on various factors, such as the route of administration, patient healthy status, which are well within the skills of an experienced physician.

The main advantages of the present invention include:

1. The compounds of the present invention are novel in structure and have an excellent anti-hepatitis B virus infection effect.

2. The compounds of the invention are low toxicity to normal cells.

3. The compound of the present invention and a pharmaceutical composition containing the compound of the present invention as a main active ingredient can be used for the prevention and/or treatment of hepatitis B virus infection.

4. The compound of the present invention and a pharmaceutical composition containing the compound of the present invention as a main active ingredient can be used for prevention and/or treatment of hepatitis B virus-related diseases (for example, hepatitis B, progressive liver fibrosis, inflammation and necrosis which cause liver cirrhosis, end-stage liver diseases, and hepatitis B liver cancer).

Terms

Unless otherwise defined, all technical and scientific terms used herein have the same meaning as commonly understood by one of ordinary skill in the art to which this invention belongs.

As used herein, when used in reference to a particular recited value, the term “about” means that the value can vary by no more than 1% from the recited value. For example, as used herein, the expression “about 100” includes all the values between 99 and 101 and (e.g., 99.1, 99.2, 99.3, 99.4, etc.).

As used herein, the terms “containing” or “including (comprising)” may be opened form, semi-closed form, or closed form. In other words, the terms also include situations such as “essentially consisting of . . . ” or “consisting of . . . .”

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer’s instructions. Unless indicated otherwise, parts and percentage are calculated by weight.

The experimental materials and reagents used in the following examples can be obtained from commercially available channels unless otherwise specified, and all temperatures are in Celsius degrees unless otherwise specified.

The following examples are the synthesis of 10 series of compounds:

Example 1 Synthesis of Compound 10a

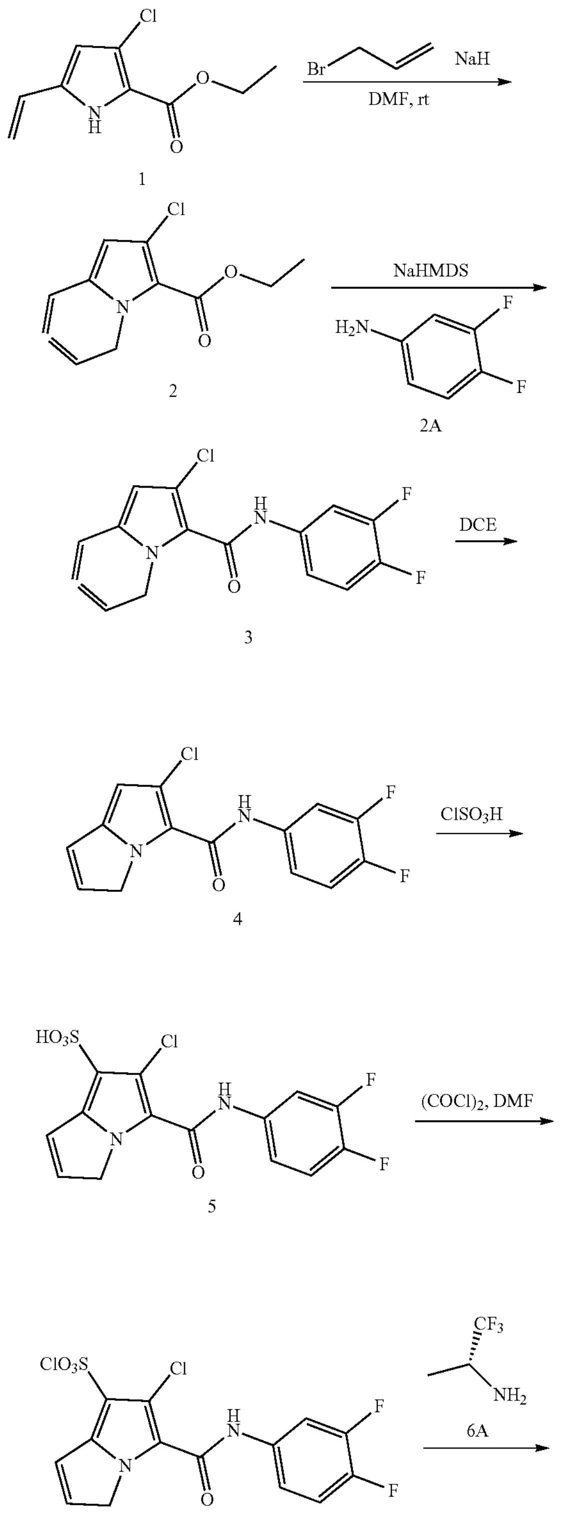

1, 2, 2A, 3, 4, 5, 6

-continued

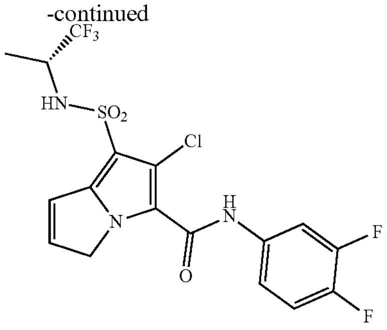

10a

Step 1:

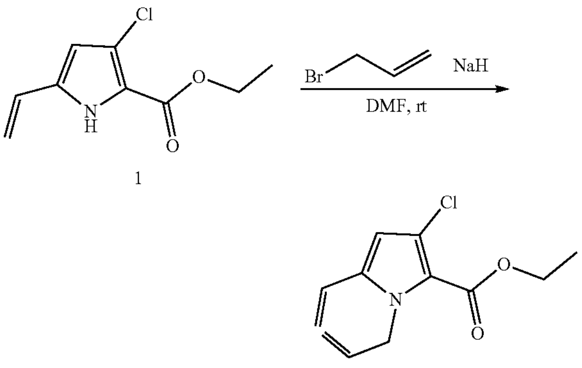

1, 2

Sodium hydride (43 mg, 1.5 equiv) was added into DMF (4 mL) at 0° C., and substrate 1 (143 mg, 1 equiv) was added into the reaction mixture, and allyl bromide (104.5 mg, 1.2 equiv) was added slowly dropwise. The reaction was carried out for two hours at room temperature. After the reaction was completed, the mixture was added into saturated aqueous solution of ammonium chloride and extracted with EA. After drying, it was column separated (heptane:EA=20:1) to provide 130 mg of product. ESI-MS (M+H)=240.

Step 2:

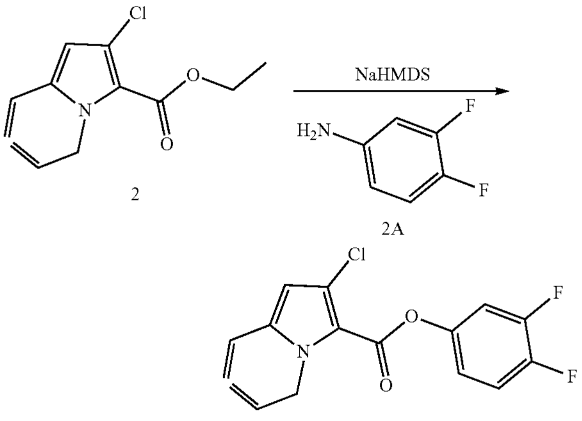

2, 2A, 3

Compound 2 (47 mg, 1 equiv) was dissolved in THF (15 ml/mmol), and air was replaced with nitrogen, and 3,4- difluoroaniline (51 mg, 2 equiv) was added. NaHMDS (0.4 ml, 4 equiv) was added at 0° C., and reacted in an ice bath. After the reaction was completed, the mixture was added into ice water, extracted with EA, dried and column separated (heptane:EA=3:1) to give 57 mg of product, ESI-MS (M+H=321).

Step 3:

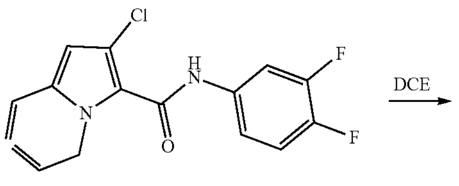

3

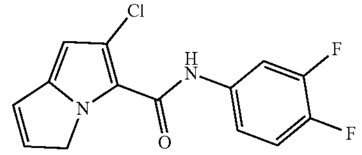

4

Under a nitrogen atmosphere, Zhan catalyst 1B (3 mg, 0.1 equiv) was added into a solution of Compound 3 (30 mg, 1 equiv) in DCE (30 ml, 0.1 ml/mg), reacted at room temperature, and after the reaction was completed, the organic phase was directly spin dried and column purified (heptane: EA=10:1) to provide 15 mg of product. ESI-MS (M+H=295)

Step 4:

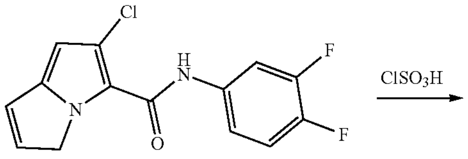

4

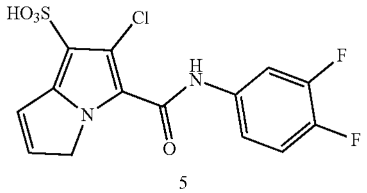

5

Compound 4 (300 mg, 1 equiv) was dissolved in anhydrous dichloromethane (15 ml) under nitrogen atmosphere, and then chlorosulfonic acid (116.52 mg, 1.1 equiv) was added at 0° C. After the reaction was completed, the mixture was suction filtered to give 200 mg of product, ESI-MS (M+H=375).

Step 5:

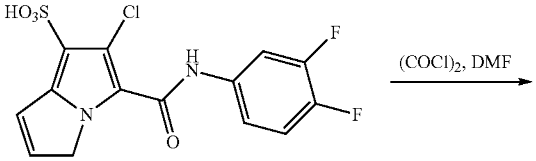

5

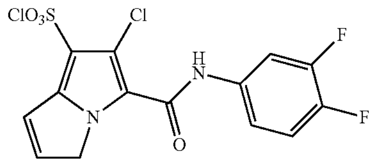

6

Under nitrogen atmosphere, oxalyl chloride (298.6 mg, 4 equiv) was added to a solution of Compound 5 (200 mg, 1 equiv) in DCM (8 ml), and reacted at room temperature. After the reaction was completed, the mixture was directly sampled and purified via column chromatography (heptane: EA=3:1) to provide 150 mg of product, ESI-MS (M+H=406.8).

Step 6:

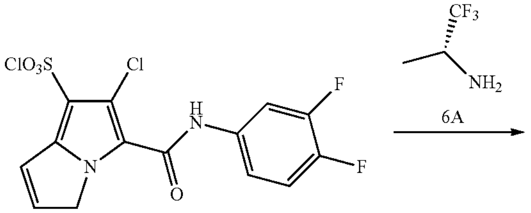

6

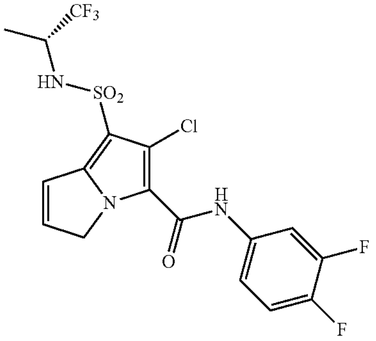

10a

Compound 6 (94 mg, 1 equiv) and amine (50 mg, 1.4 equiv) were dissolved in acetonitrile. Pyridine (94.8 mg, 4 equiv) was added under nitrogen atmosphere, and reacted overnight at 40° C. After extracted with ethyl acetate (3*20 mL), the solution was washed with HCl and water, dried, and column separated (heptane:EA=10:1) to give 120 mg of product. $^{1}$H NMR (400 MHz, DMSO-$d_6$) δ 9.95 (s, 1H), 3.60 (d, J=8.9 Hz, 1H), 7.99-7.77 (m, 1H), 7.59-7.35 (m, 2H), 6.94 (dd, J=46.5, 6.1 Hz, 2H), 4.97 (s, 2H), 3.99 (dq, J=15.5, 7.4 Hz, 1H), 1.19 (d, J=6.9 Hz, 3H). ESI-MS (M+H=470)

Example 2: Synthesis of Compound 10b

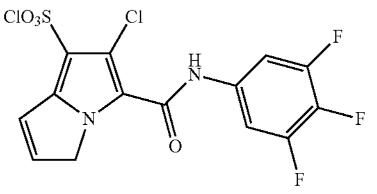

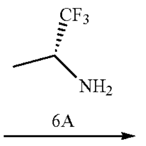

6b

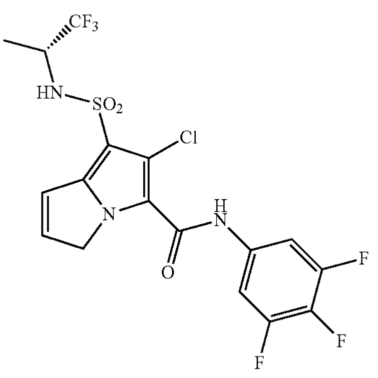

10b

The reaction was carried out according to the step 2 of example 1, all the conditions were the same except the compound 3,4,5-trifluoroaniline was used instead of 3,4-difluoroaniline. After purification via column chromatography (n-heptane:ethyl acetate=10:1) the target product 10b (15 mg) was provided. ESI-MS (M+H=488)

Example 3: Synthesis of Compound 10c

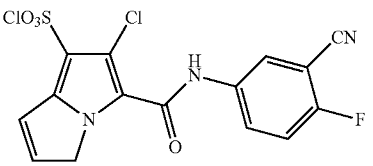

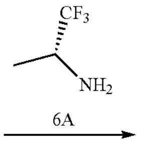

6c

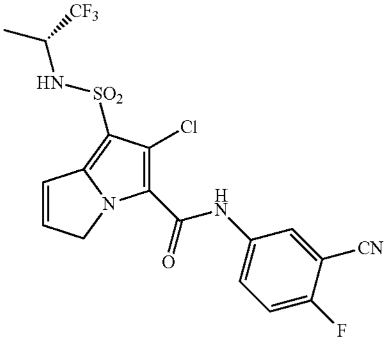

10c

The reaction was carried out according to the step 2 of example 1, all the conditions were the same except the compound 4-fluoro-3-cyanoaniline was used instead of 3,4-difluoroaniline. After purification via column chromatography (n-heptane:ethyl acetate=10:1) the target product 10c (10 mg) was provided. ESI-MS (M+H=488)

The following 10 series of compounds were synthesized according to the method of Example 1:

| Compound | Structure | Mass Spectrometry. ESI-MS, (M + H) |
|---|---|---|
| 10d | 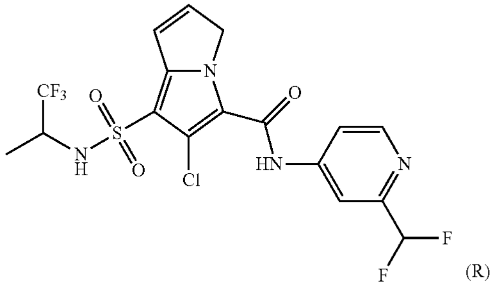 | 485 |
| 10e | 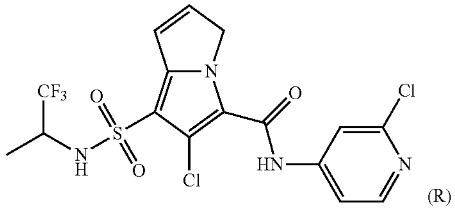 | 469 |

-continued
| Compound | Structure | Mass Spectrometry. ESI-MS, (M + H) |
|---|---|---|
| 10f | 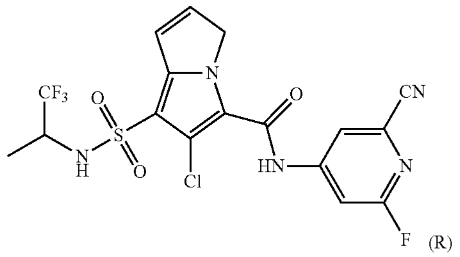 | 478 |
| 10g | 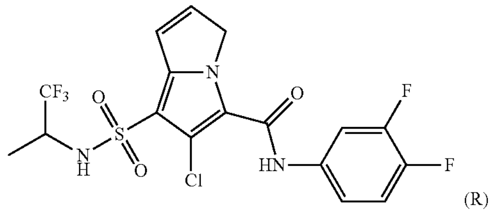 | 450 |
| 10h | 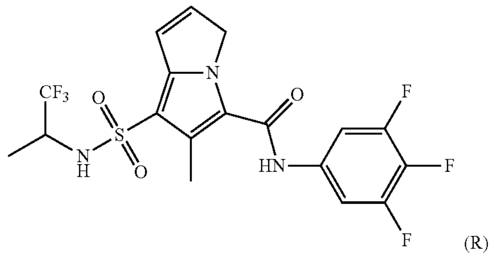 [SMILES: Cc1c(S(=O)(=O)NC(C)C(F)(F)F)c2n(c1C(=O)Nc1cc(F)c(F)c(F)c1)CC=C2 ; "(R)"] | 468 |
| 10i | 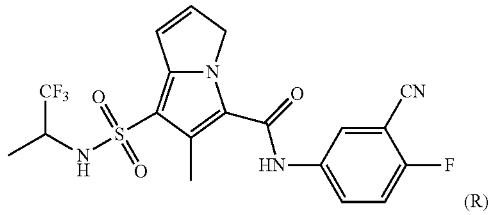 | 457 |
| 10j | 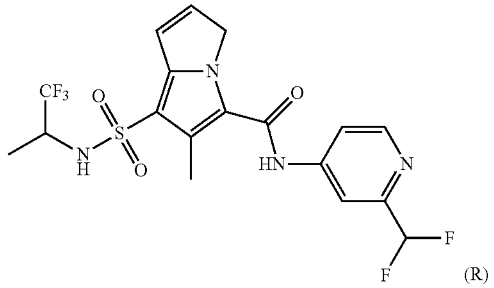 | 465 |
| 10k | 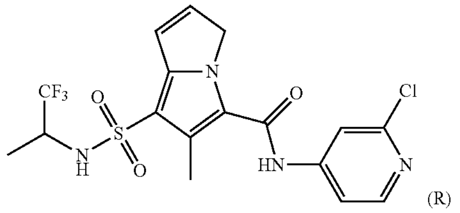 | 449 |

-continued
| Compound | Structure | Mass Spectrometry. ESI-MS, (M + H) |
| --- | --- | --- |
| 10l | 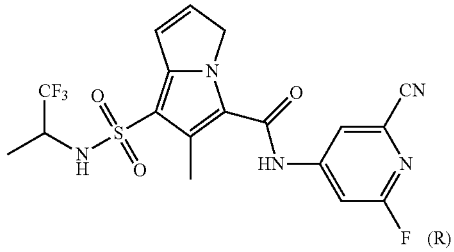 (R) | 458 |
| 10m | 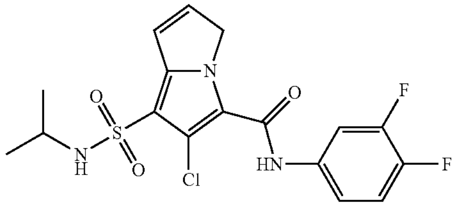 | 416 |
| 10n | 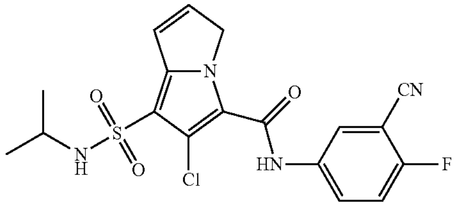 | 423 |
| 10o | 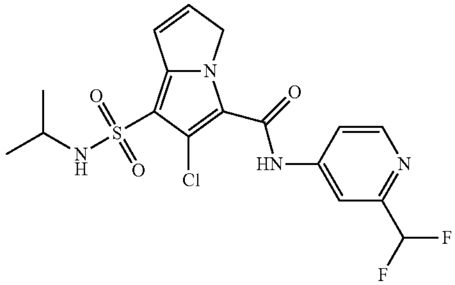 | 431 |
| 10p | 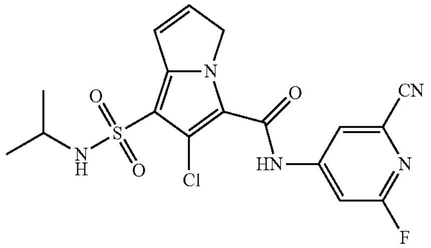 | 424 |
| 10q | 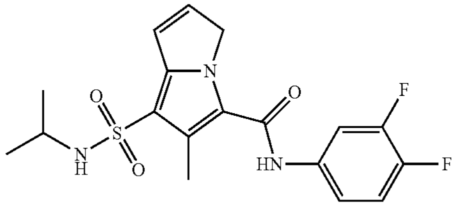 | 396 |

-continued
| Compound | Structure | Mass Spectrometry. ESI-MS, (M + H) |
|---|---|---|
| 10r | 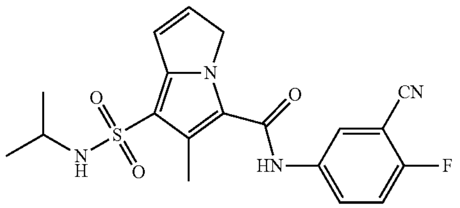 | 403 |
| 10s | 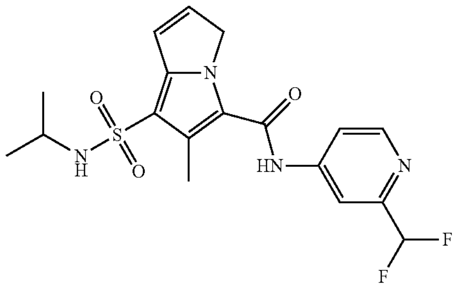 [SMILES: Cc1c(S(=O)(=O)NC(C)C)c2n(c1C(=O)Nc1ccnc(C(F)F)c1)CC=C2] | 411 |
| 10t | 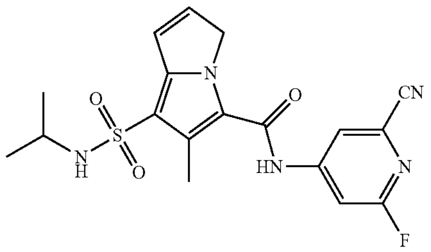 [SMILES: Cc1c(S(=O)(=O)NC(C)C)c2n(c1C(=O)Nc1cc(F)nc(C#N)c1)CC=C2] | 404 |
| 10u | 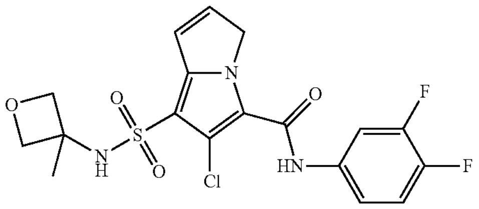 [SMILES: CC1(NS(=O)(=O)c2c(Cl)c(C(=O)Nc3ccc(F)c(F)c3)n3c2C=CC3)COC1] | 444 |
| 10v | 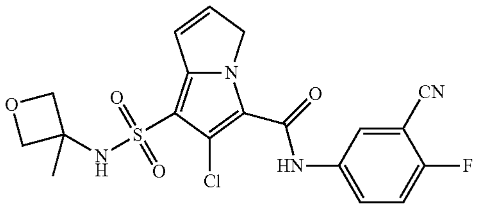 [SMILES: CC1(NS(=O)(=O)c2c(Cl)c(C(=O)Nc3ccc(F)c(C#N)c3)n3c2C=CC3)COC1] | 451 |
| 10w | 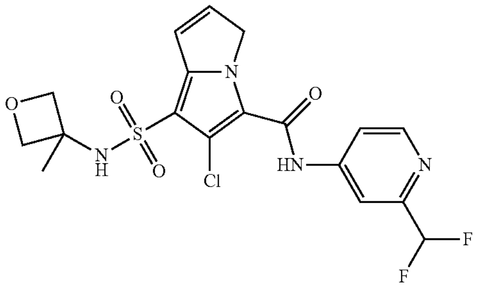 | 459 |

-continued
| Compound | Structure | Mass Spectrometry. ESI-MS, (M + H) |
|---|---|---|
| 10x | 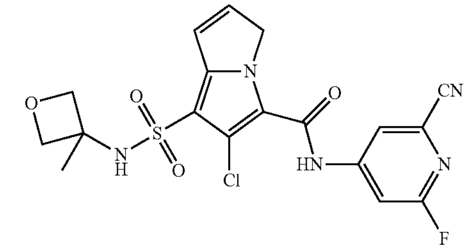 | 452 |
| 10y | 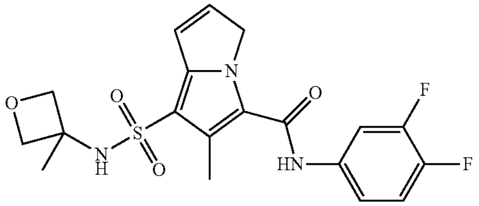 | 424 |
| 10z | 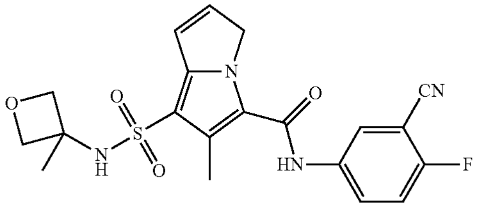 | 431 |
| 10aa | 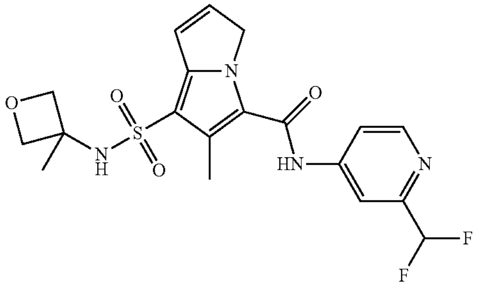 | 439 |
| 10bb | 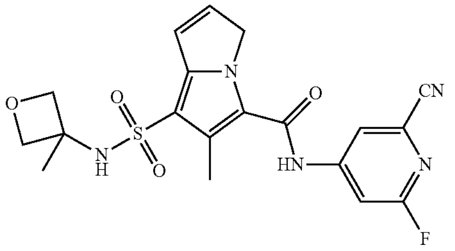 [SMILES: Cc1c(S(=O)(=O)NC2(C)COC2)c2n(c1C(=O)Nc1cc(F)nc(C#N)c1)CC=C2] | 432 |
| 10cc | 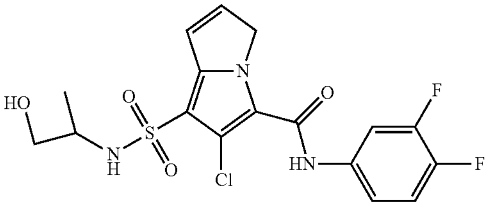 [SMILES: CC(CO)NS(=O)(=O)c1c(Cl)c(C(=O)Nc2ccc(F)c(F)c2)n2c1C=CC2] | 432 |

-continued
| Compound | Structure | Mass Spectrometry. ESI-MS, (M + H) |
|---|---|---|
| 10dd | 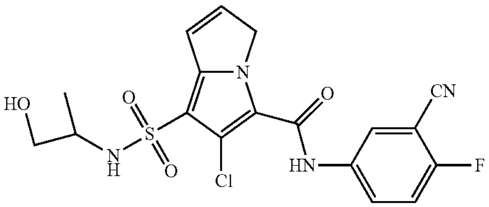 [SMILES: CC(CO)NS(=O)(=O)c1c(Cl)c(C(=O)Nc2ccc(F)c(C#N)c2)n2c1C=CC2] | 439 |
| 10ee | 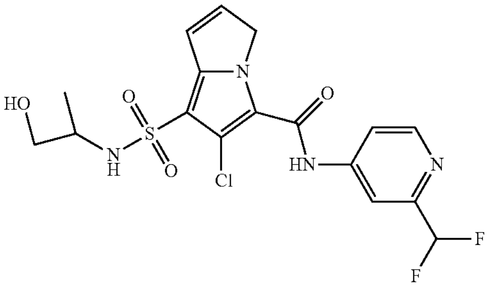 [SMILES: CC(CO)NS(=O)(=O)c1c(Cl)c(C(=O)Nc2ccnc(C(F)F)c2)n2c1C=CC2] | 447 |
| 10ff | 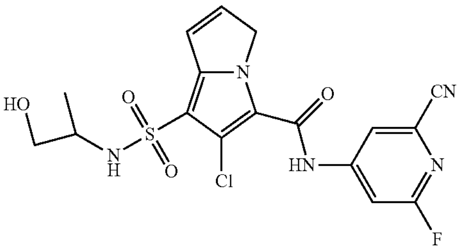 [SMILES: CC(CO)NS(=O)(=O)c1c(Cl)c(C(=O)Nc2cc(F)nc(C#N)c2)n2c1C=CC2] | 440 |
| 10gg | 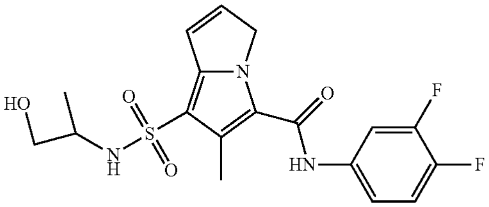 [SMILES: Cc1c(S(=O)(=O)NC(C)CO)c2n(c1C(=O)Nc1ccc(F)c(F)c1)CC=C2] | 412 |
| 10hh | 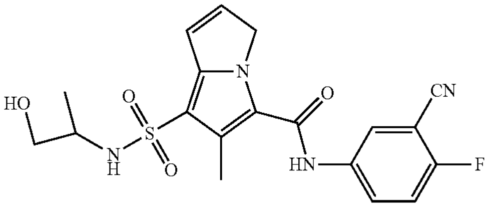 [SMILES: Cc1c(S(=O)(=O)NC(C)CO)c2n(c1C(=O)Nc1ccc(F)c(C#N)c1)CC=C2] | 419 |
| 10ii | 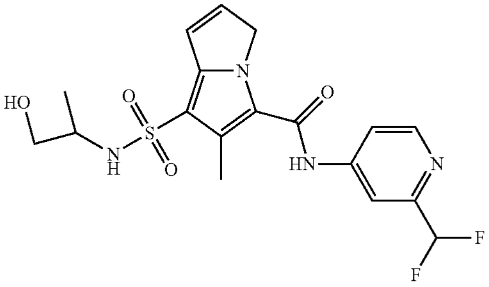 [SMILES: Cc1c(S(=O)(=O)NC(C)CO)c2n(c1C(=O)Nc1ccnc(C(F)F)c1)CC=C2] | 427 |

-continued
| Compound | Structure | Mass Spectrometry. ESI-MS, (M + H) |
|---|---|---|
| 10jj | 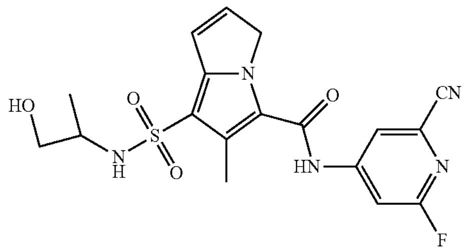 [SMILES: Cc1c(S(=O)(=O)NC(C)CO)c2n(c1C(=O)Nc1cc(F)nc(C#N)c1)CC=C2] | 420 |
| 10kk | 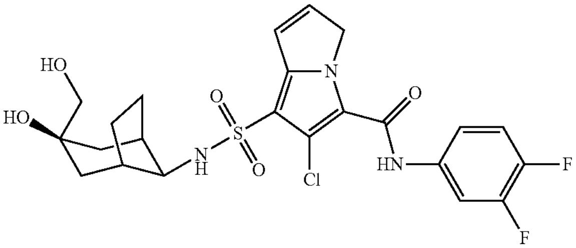 | 528 |
| 10ll | 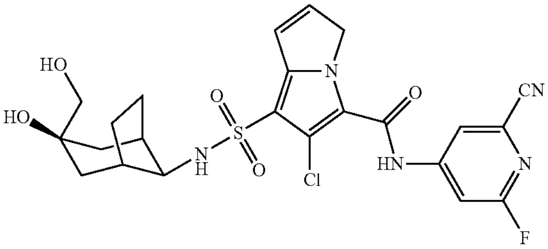 | 536 |
| 10mm | 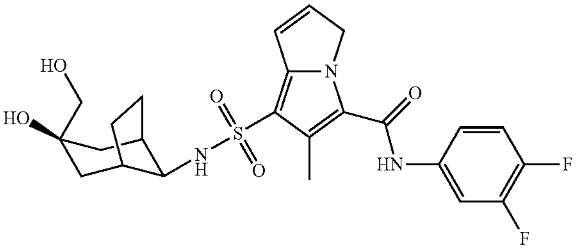 | 508 |
| 10nn | 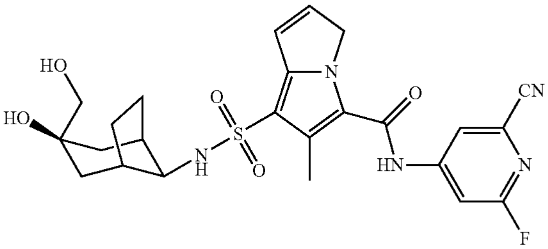 | 516 |
| 10oo | 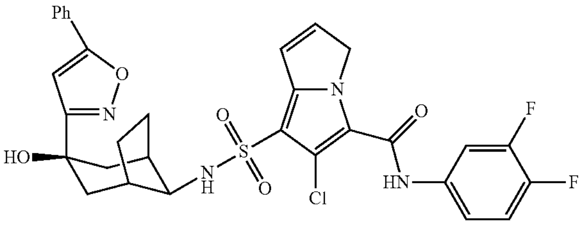 | 641 |

-continued
| Compound | Structure | Mass Spectrometry. ESI-MS, (M + H) |
|---|---|---|
| 10pp | 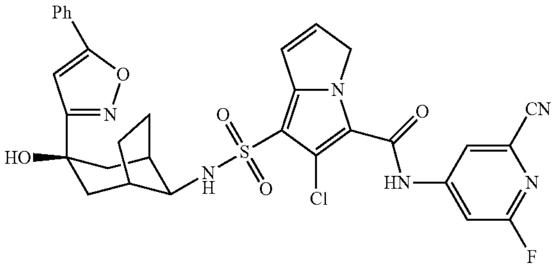 | 649 |
| 10qq | 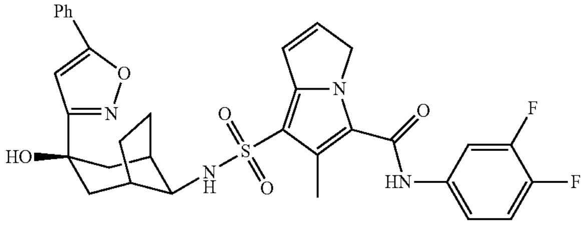 | 621 |
| l0rr | 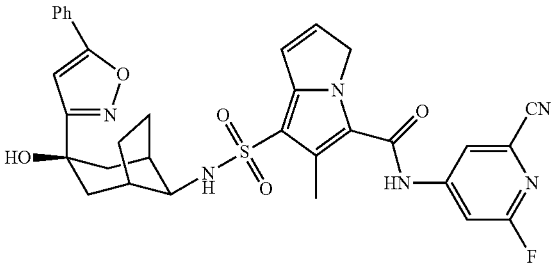 | 629 |
| 10ss | 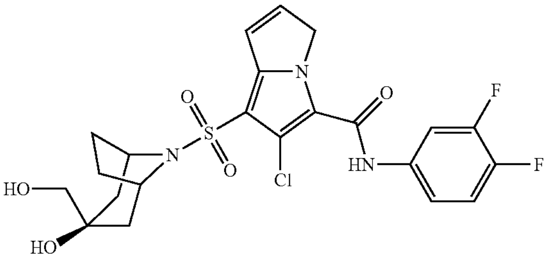 | 514 |
| 10tt | 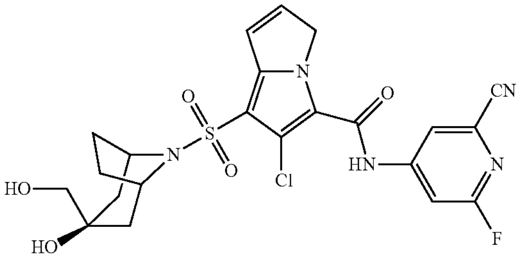 | 522 |
| 10uu | 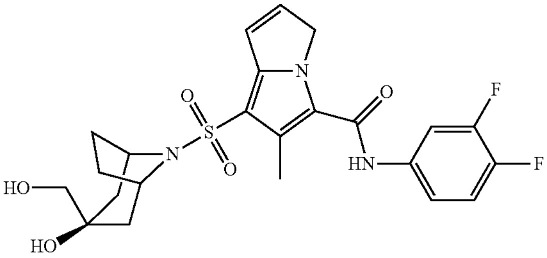 | 494 |

-continued
| Compound | Structure | Mass Spectrometry. ESI-MS, (M + H) |
| --- | --- | --- |
| 10vv | 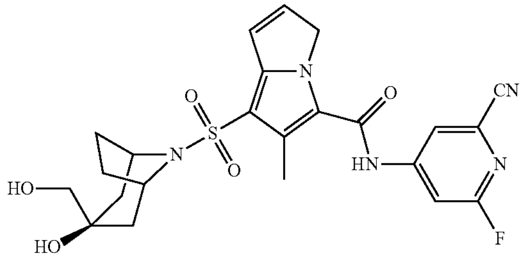 | 502 |
| 10ww | 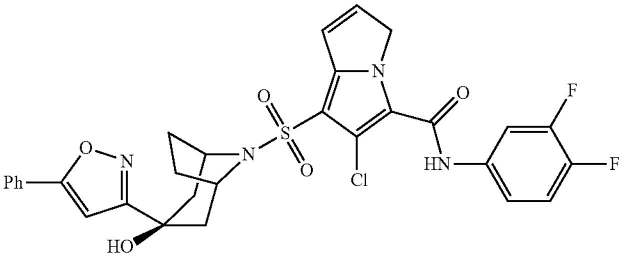 | 627 |
| 10xx | 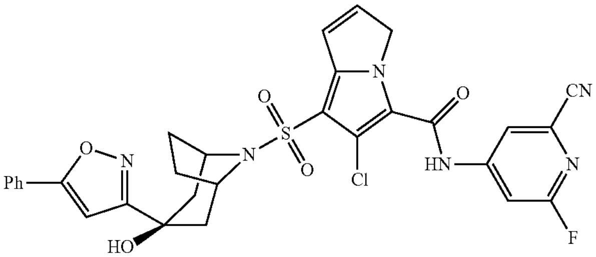 | 635 |
| 10yy | 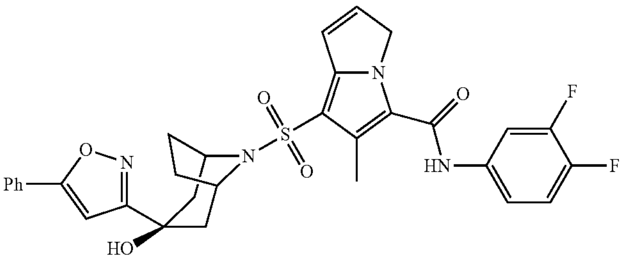 | 607 |
| 10zz | 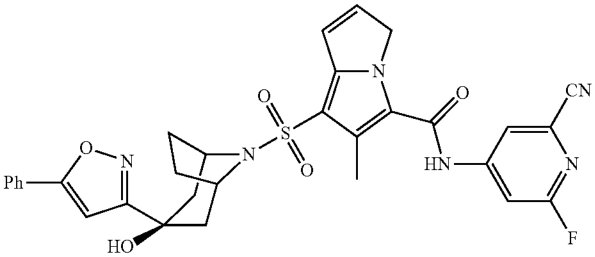 | 615 |

The following examples are the synthesis of 20 series of compounds:

Example 53 Synthesis of Compound 20a

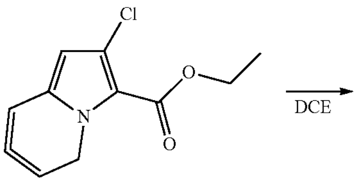

2

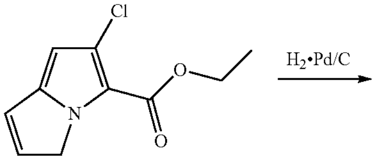

12

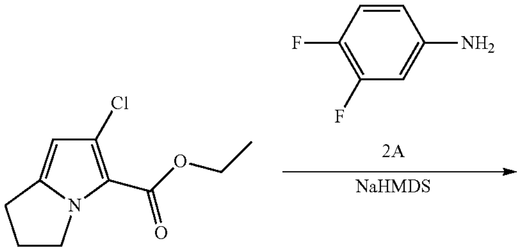

13

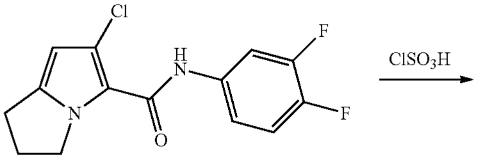

14

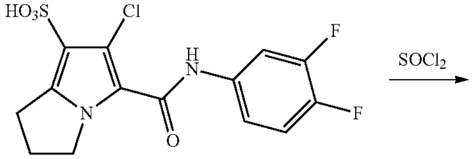

15

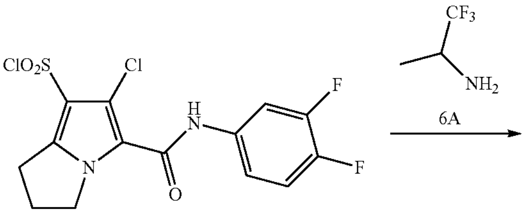

16

-continued

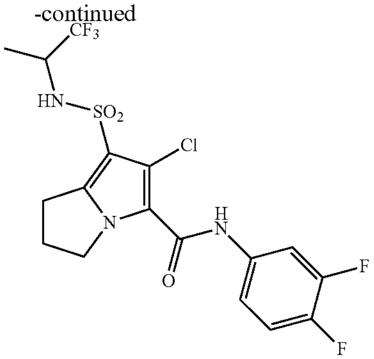

20a

Step 1:

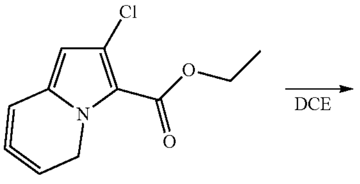

2

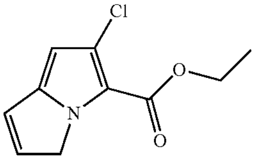

12

Under nitrogen atmosphere, Zhan catalyst 1B (6.5 mg) (0.1 equiv) was added into a solution of 2 (65 mg, 1 equiv) in DCE (10 mL) to react at room temperature. After the reaction was completed, the mixture was directly sampled and separated via column chromatography (heptane:EA=10:1) to obtain 29 mg of product, ESI-MS (M+H)=212 Step 2:

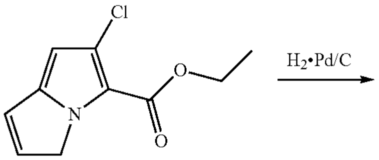

12

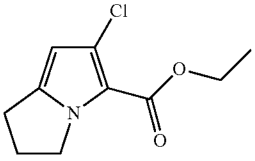

13

Under nitrogen atmosphere, Compound 2 (50 mg) was dissolved in EA (5 mL), and 10% Pd/C (0.1 equiv) was added. The air was replaced with hydrogen, and reaction was carried out at room temperature. After the reaction was completed, the mixture was filtered with the celite and concentrated to give 40 mg of product which was directly used in the next step, ESI-MS (M+H)=214.

Step 3:

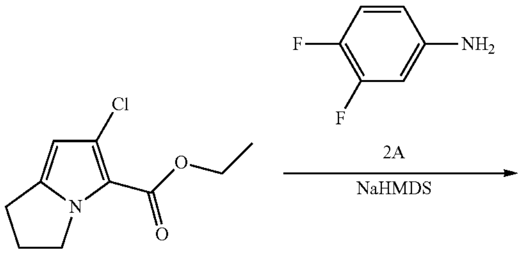

13

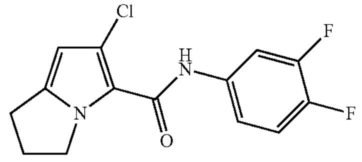

14

Compound 13 (40 mg, 1 equiv) was dissolved in THF (15 ml/mmol), and air was replaced with nitrogen, and 3,4-difluoroaniline (70 mg, 2 equiv) was added. 2M NaHMDS (0.3 ml, 2 equiv) was added at 0° C., and the reaction was carried out at room temperature. After the reaction was completed, the mixture was added into ice water, extracted with EA, dried and purified by column chromatography (heptane:EA=3:1) to give 40 mg compound, ESI-MS (M+H=297) Step 4:

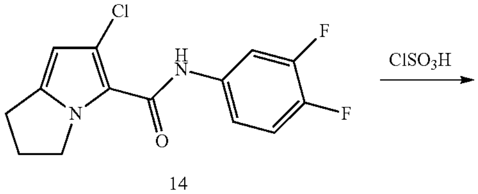

14

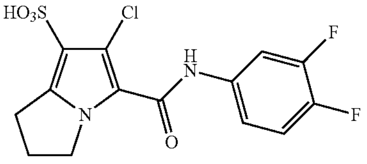

15

Compound 14 (300 mg, 1 equiv) was dissolved in anhydrous dichloromethane (15 ml) under nitrogen atmosphere, and then chlorosulfonic acid (116.52 mg, 1.1 equiv) was added at 0° C. After the reaction was completed, the mixture was suction filtered to give 200 mg of product, ESI-MS (M+H=377).

Step 5:

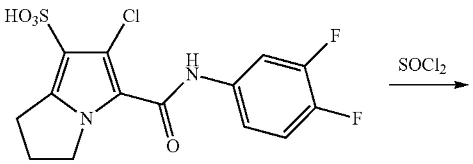

15

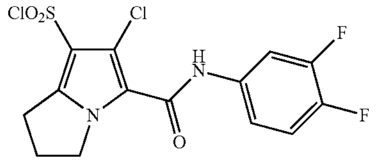

16

Under nitrogen atmosphere, oxalyl chloride (298.6 mg, 4 equiv) was added into a solution of Compound 15 (200 mg, 1 equiv) in DCM (8 ml) to react at room temperature. After the reaction was completed, the mixture was directly sampled and purified via column chromatography (heptane: EA=3:1) to provide 150 mg of product, ESI-MS (M+H=409)

Step 6:

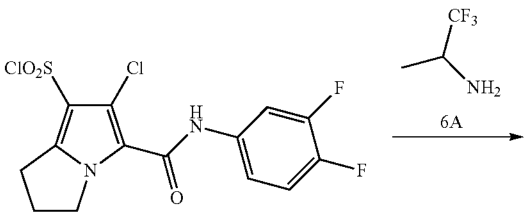

16

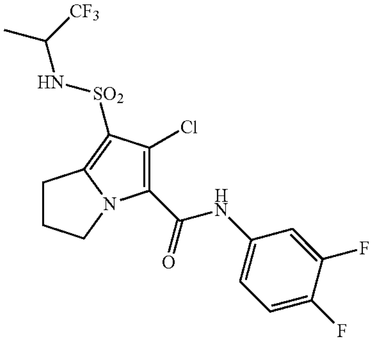

20a

Compound 16 (94 mg, 1 equiv) and amine (50 mg, 1.4 equiv) were dissolved in acetonitrile. Pyridine (94.8 mg, 4 equiv) was added under nitrogen atmosphere, and reacted at 40° C. overnight. After the reaction was completed, the mixture was extracted with ethyl acetate (3*20 mL), washed with HCl and water, dried, and separated by column chromatography (heptane:EA=10:1) to give Compound 20a (80 mg). $^1$H NMR (400 MHz, DMSO-$d_6$) δ 10.05 (s, 1H), 8.43 (d, J=8.9 Hz, 1H), 7.97-7.71 (m, 1H), 7.53-7.29 (m, 2H), 4.24 (t, J=7.1 Hz, 2H), 3.97 (dq, J=14.9, 7.3 Hz, 1H), 3.04 (h, J=9.7 Hz, 2H), 2.42 (p, J=7.5 Hz, 2H), 1.18 (d, J=6.9 Hz, 3H). ESI-MS (M+H=472)

Example 54: Synthesis of Compound 20b

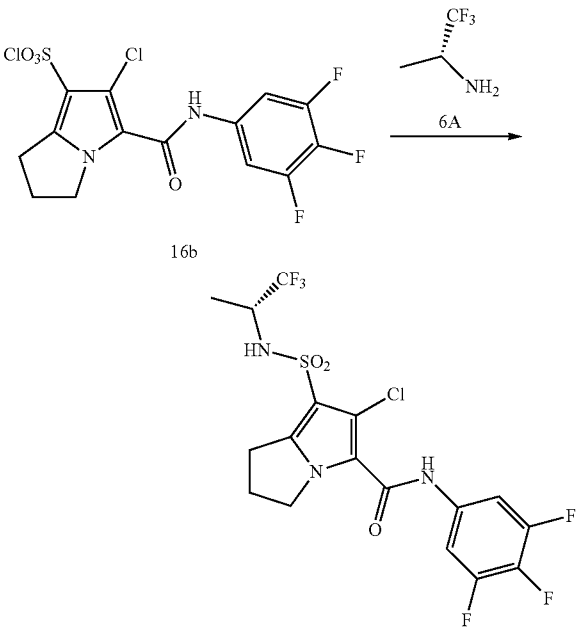

16b

20b

The reaction was carried out according to the step 3 of example 53, all the conditions were the same except the compound 3,4,5-trifluoroaniline was used instead of 3,4-difluoroaniline, After purification via column chromatography (n-heptane:ethyl acetate=10:1), the target product 20b (15 mg) was obtained. ESI-MS (M+H=490)

Example 55: Synthesis of Compound 20c

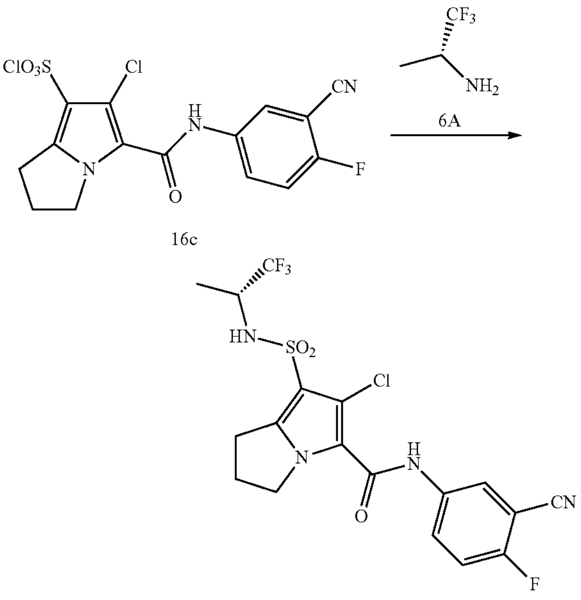

16c

20c

The reaction was carried out according to the step 3 of example 53, all the conditions were the same except the compound 4-fluoro-3-cyanoaniline was used instead of 3,4-difluoroaniline, After purification via column chromatography (n-heptane:ethyl acetate=10:1), the target product 20c (10 mg) was obtained. ESI-MS (M+H=480)

The following 20 series of compounds were synthesized according to the method of example 53:

| Compound | Structure | Mass Spectrometry. ESI-MS, (M + H) |
|---|---|---|
| 20d | 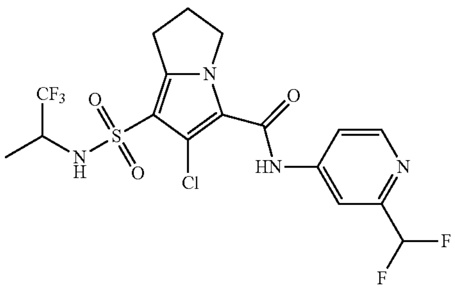 (R) | 487 |
| 20e | 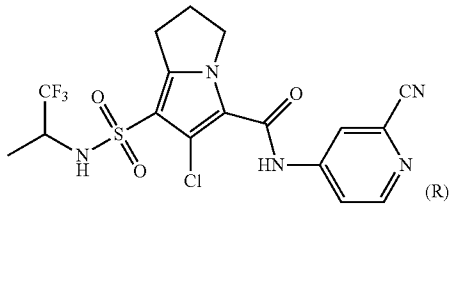 (R) | 471 |

-continued
| Compound | Structure | Mass Spectrometry. ESI-MS, (M + H) |
|---|---|---|
| 20f | 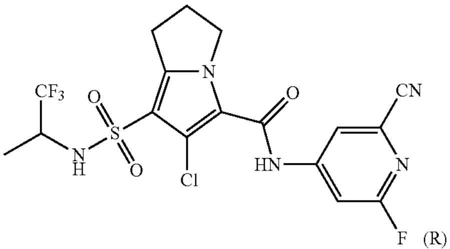 (R) | 480 |
| 20g | 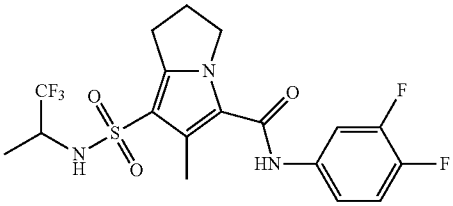 (R) | 452 |
| 20h | 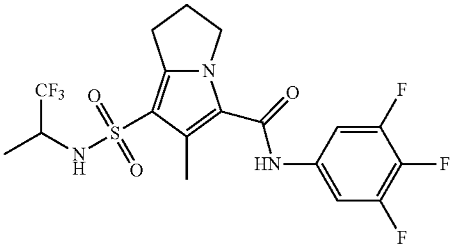 (R) | 470 |
| 20i | 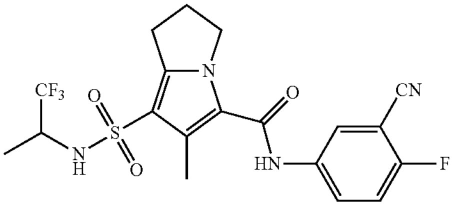 (R) | 459 |
| 20j | 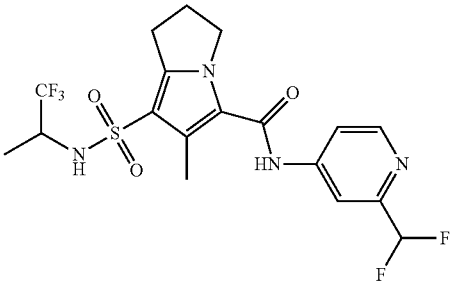 (R) | 467 |
| 20k | 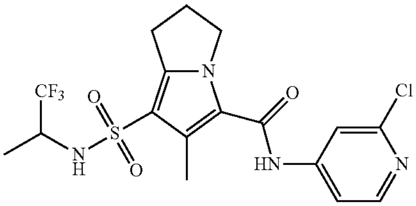 (R) | 451 |

-continued
| Compound | Structure | Mass Spectrometry. ESI-MS, (M + H) |
|---|---|---|
| 20l | 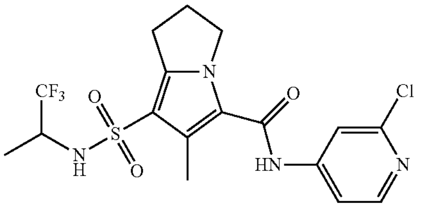 (R) | 460 |
| 20m | 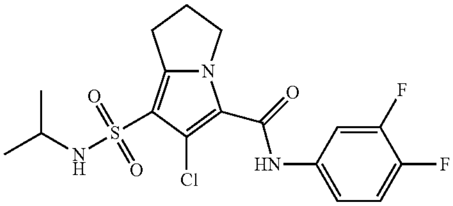 | 418 |
| 20n | 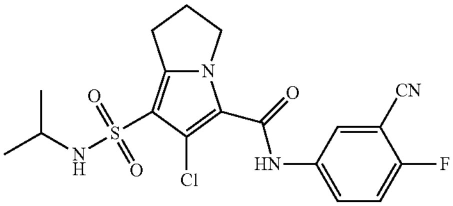 | 425 |
| 20o | 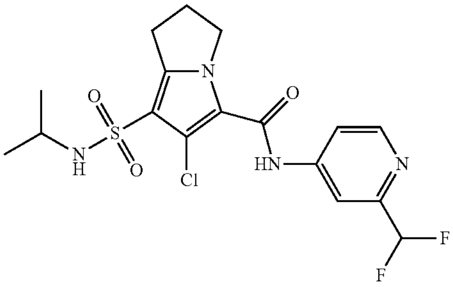 | 433 |
| 20p | 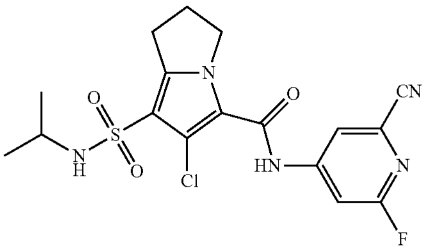 | 426 |
| 20q | 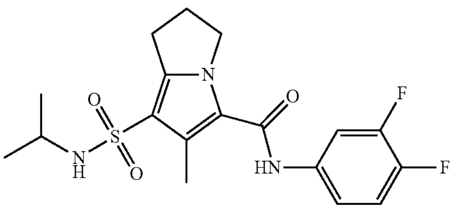 | 398 |

-continued
| Compound | Structure | Mass Spectrometry. ESI-MS, (M + H) |
|---|---|---|
| 20r | 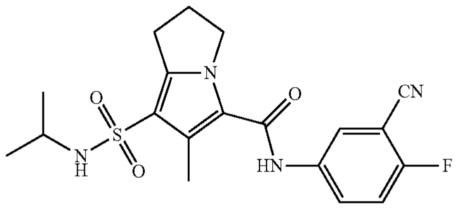 [SMILES: Cc1c(S(=O)(=O)NC(C)C)c2n(c1C(=O)Nc1ccc(F)c(C#N)c1)CCC2] | 405 |
| 20s | 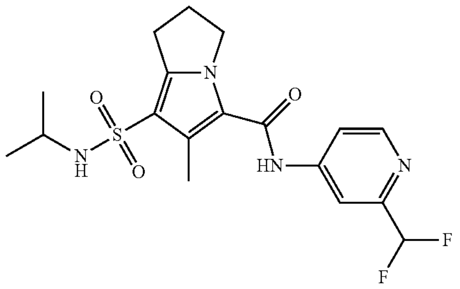 [SMILES: Cc1c(S(=O)(=O)NC(C)C)c2n(c1C(=O)Nc1ccnc(C(F)F)c1)CCC2] | 413 |
| 20t | 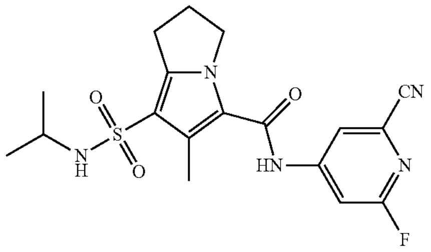 [SMILES: Cc1c(S(=O)(=O)NC(C)C)c2n(c1C(=O)Nc1cc(F)nc(C#N)c1)CCC2] | 406 |
| 20u | 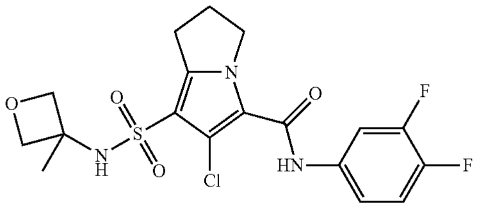 [SMILES: CC1(NS(=O)(=O)c2c(Cl)c(C(=O)Nc3ccc(F)c(F)c3)n3c2CCC3)COC1] | 446 |
| 20v | 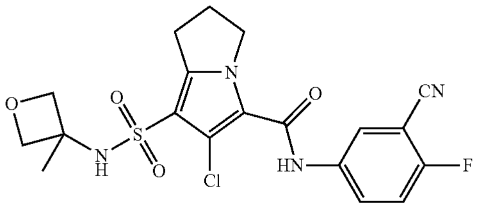 [SMILES: CC1(NS(=O)(=O)c2c(Cl)c(C(=O)Nc3ccc(F)c(C#N)c3)n3c2CCC3)COC1] | 453 |
| 20w | 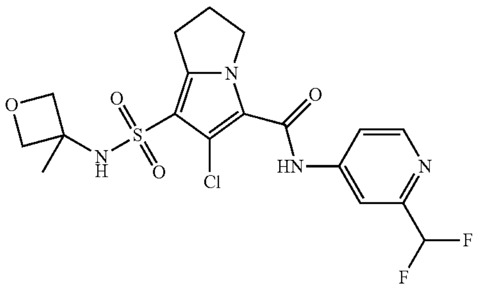 [SMILES: CC1(NS(=O)(=O)c2c(Cl)c(C(=O)Nc3ccnc(C(F)F)c3)n3c2CCC3)COC1] | 461 |

-continued
| Compound | Structure | Mass Spectrometry. ESI-MS, (M + H) |
|---|---|---|
| 20x | 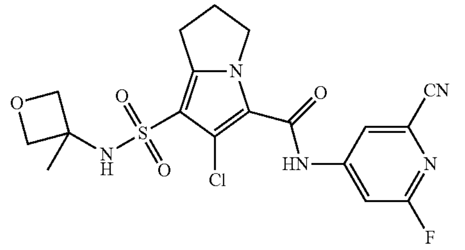 [SMILES: CC1(NS(=O)(=O)c2c(Cl)c(C(=O)Nc3cc(F)nc(C#N)c3)n3c2CCC3)COC1] | 454 |
| 20y | 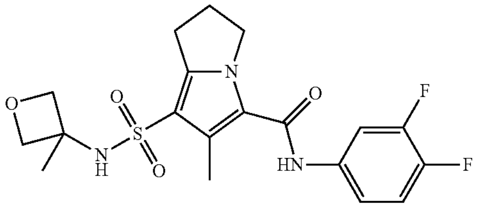 | 426 |
| 20z | 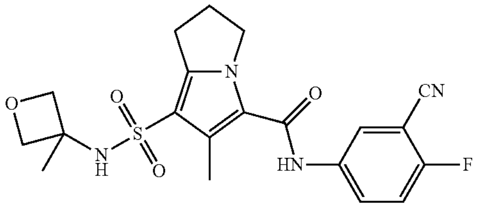 | 433 |
| 20aa | 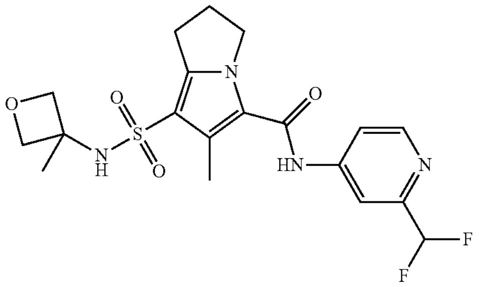 | 441 |
| 20bb | 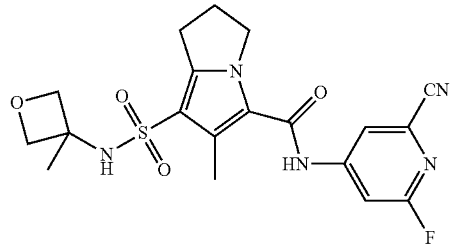 [SMILES: Cc1c(S(=O)(=O)NC2(C)COC2)c2n(c1C(=O)Nc1cc(F)nc(C#N)c1)CCC2] | 434 |
| 20cc | 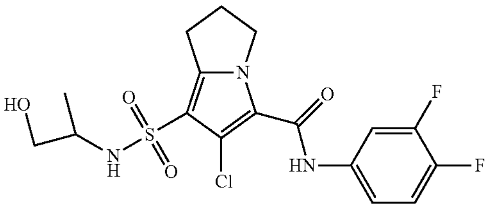 | 434 |

-continued
| Compound | Structure | Mass Spectrometry. ESI-MS, (M + H) |
|---|---|---|
| 20dd | 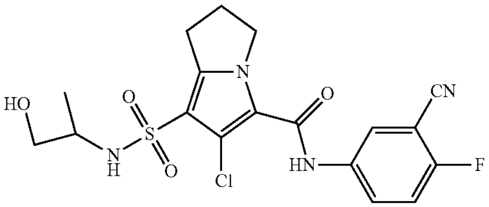 | 441 |
| 20ee | 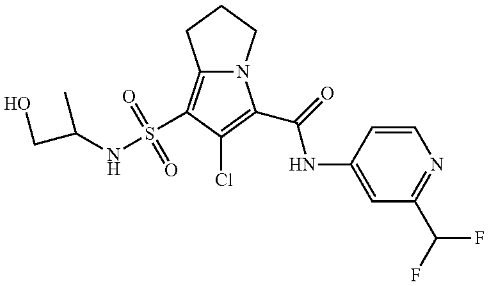 | 449 |
| 20ff | 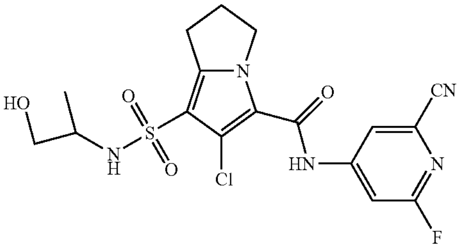 | 442 |
| 20gg | 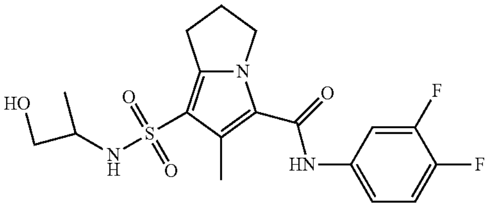 | 414 |
| 20hh | 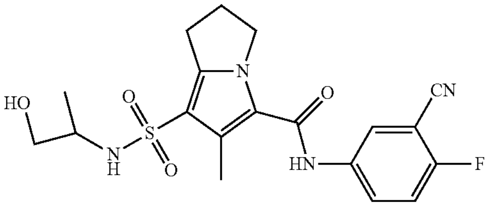 | 421 |
| 20ii | 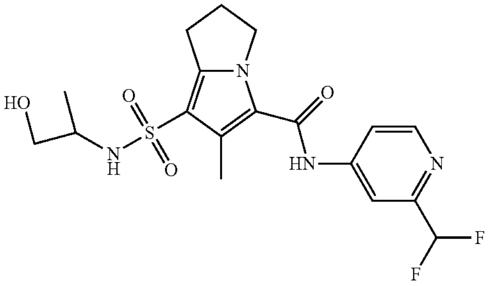 | 429 |

-continued
| Compound | Structure | Mass Spectrometry. ESI-MS, (M + H) |
|---|---|---|
| 20jj | 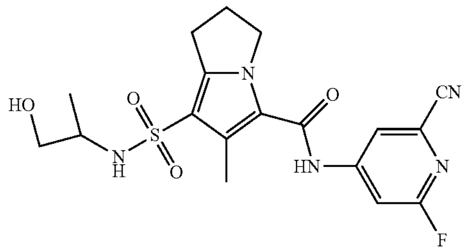 [SMILES: Cc1c(S(=O)(=O)NC(C)CO)c2n(c1C(=O)Nc1cc(F)nc(C#N)c1)CCC2] | 422 |
| 20kk | 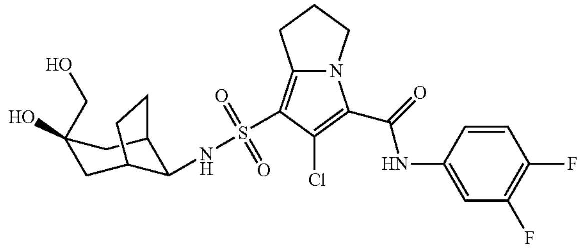 | 530 |
| 20ll | 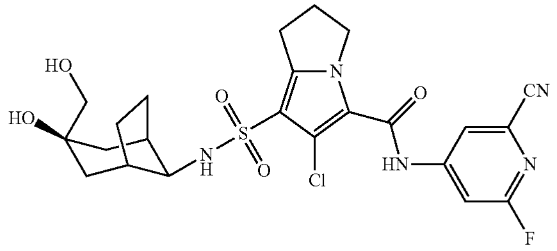 | 538 |
| 20mm | 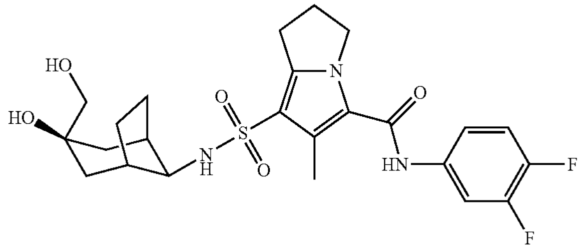 | 510 |
| 20nn | 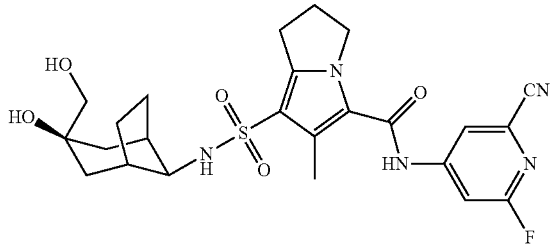 | 516 |
| 20oo | 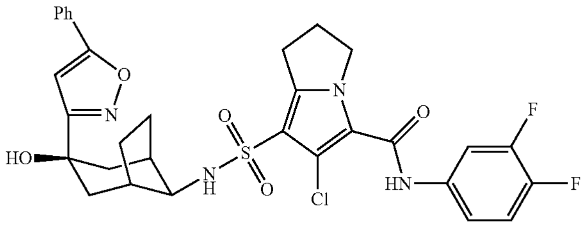 | 643 |

-continued
| Compound | Structure | Mass Spectrometry. ESI-MS, (M + H) |
|---|---|---|
| 20pp | 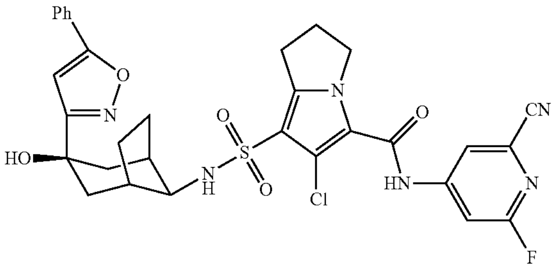 | 651 |
| 20qq | 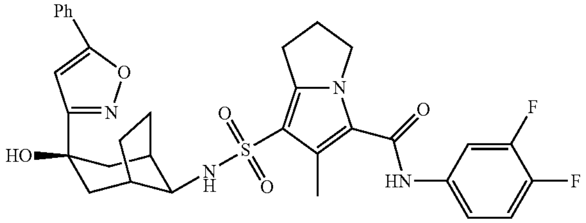 | 621 |
| 20rr | 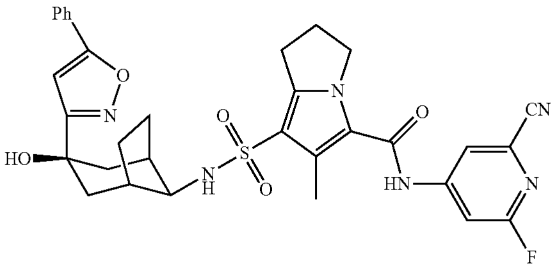 | 631 |
| 20ss | 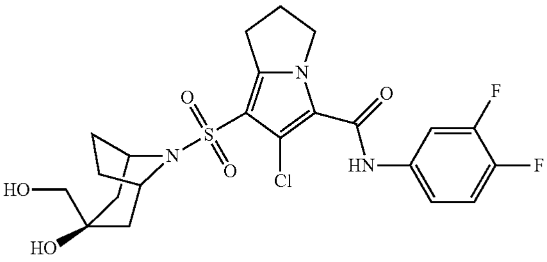 | 516 |
| 20tt | 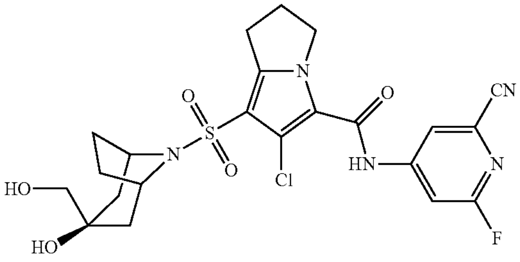 | 524 |
| 20uu | 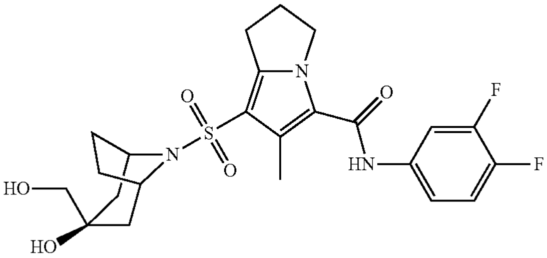 | 496 |

-continued
| Compound | Structure | Mass Spectrometry. ESI-MS, (M + H) |
|---|---|---|
| 20vv | 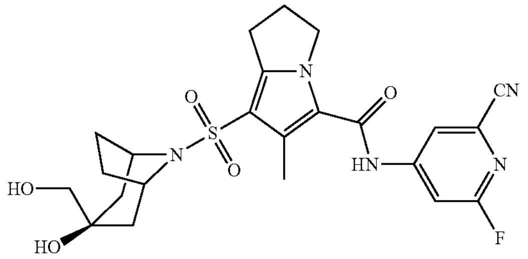 | 504 |
| 20ww | 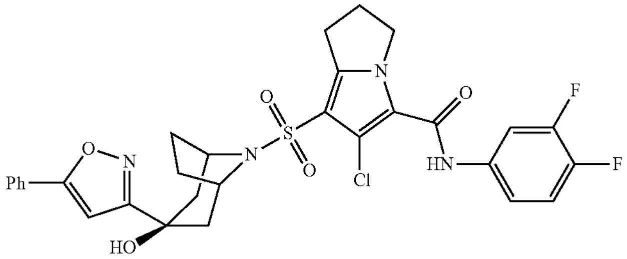 | 629 |
| 20xx | 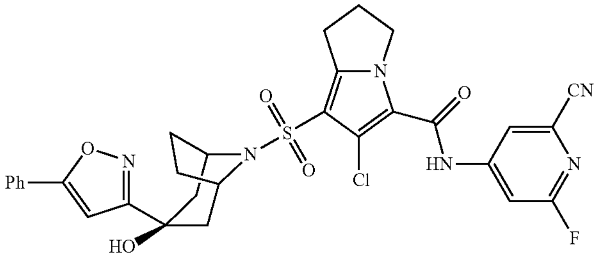 | 637 |
| 20yy | 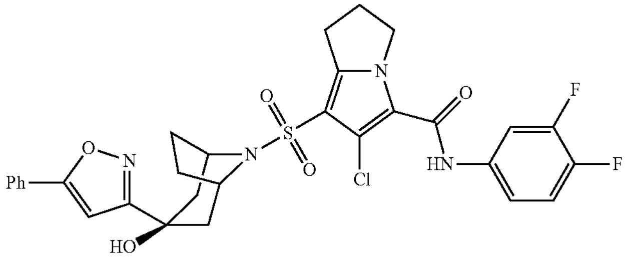 | 609 |
| 20zz | 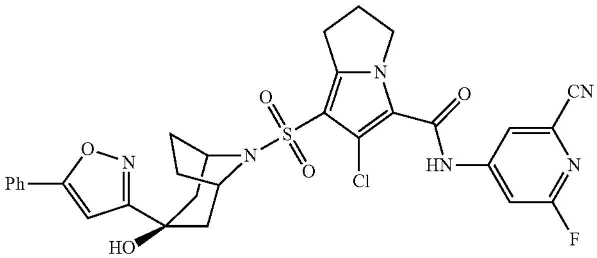 | 617 |

The following examples are the synthesis of 30 series of compounds:

Example 107 Synthesis of Compound 30a

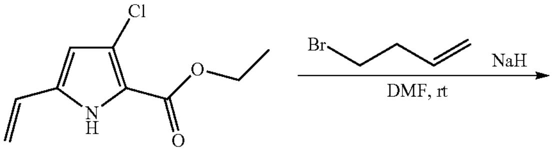

21

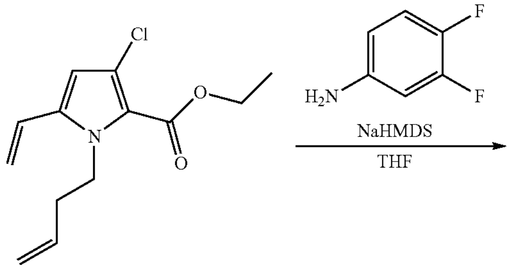

22

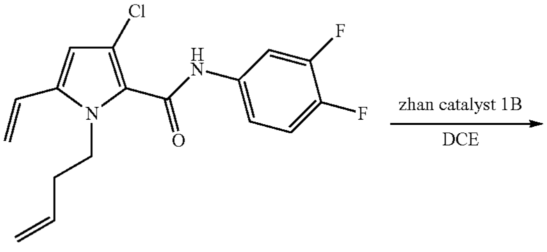

23

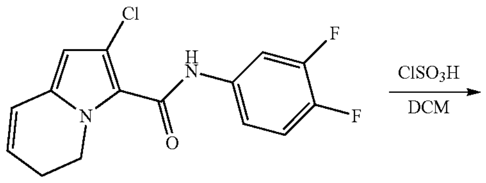

24

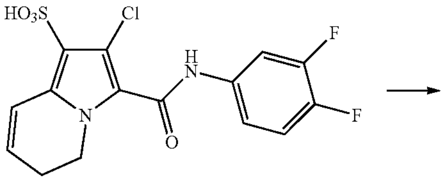

25

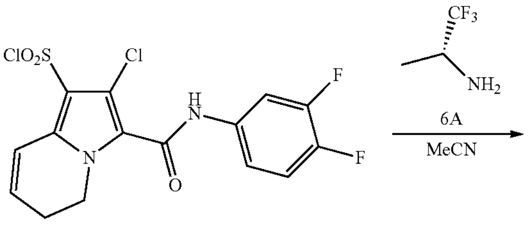

26

-continued

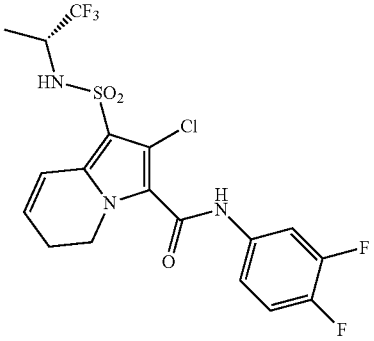

30a

Step 1:

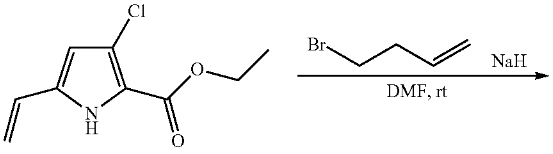

21

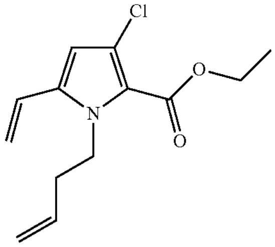

22

DMF (5 ml, 2 ml/mmol) was added into a reaction flask, and NaH (150 mg, 1.5 equiv) was added under ice bath, stirred for 10 min, and Compound 21 (500 mg, 1. equiv) was added and stirred for 30 min. 1-bromo-butene (405 mg) was added and reacted at room temperature. After the reaction was completed, the mixture was poured into ice water, extracted with EA, washed with saturated NaCl and dried over anhydrous sodium sulfate. 203 mg of product was provided by column separation (heptane:EA=15:1), ESI-MS (M+H=254)

Step 2:

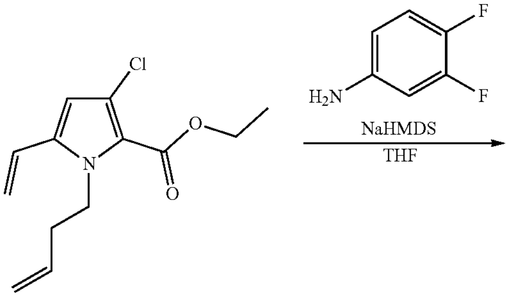

22

-continued

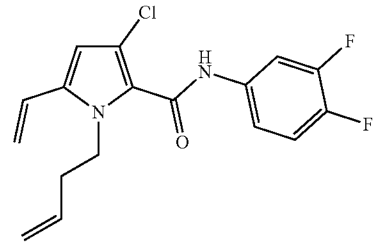

23

Compound 22 (200 mg, 1.0 equiv) was added into a reaction flask, and THF (5 ml/mmol), 3,4 difluoroaniline (203 mg, 2 equiv) were added, and NaHMDS (1.5 ml, 4 equiv) was added dropwise in an ice bath. After the reaction was completed, the mixture was poured into ice water, extracted with EA, washed with saturated NaCl and dried over anhydrous sodium sulfate. 225 mg of product was provided by column separation (heptane:EA=5:1), ESI-MS (M+H=337) Step 3:

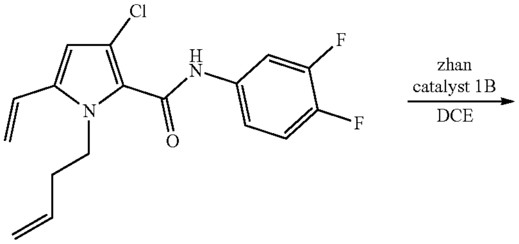

23

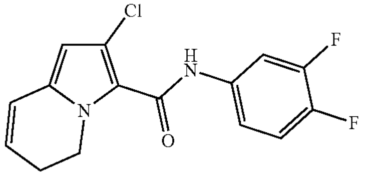

24

Compound 23 (225 mg, 1 equiv), Zhan catalyst (22.5 mg, 0.1 equiv) and DCE (22.5 ml, 0.1 ml/mg) were added into a reaction flask. After the reaction was completed, the reaction mixture was extracted with DCM, washed with saturated NaCl, and dried over anhydrous sodium sulfate. After column separation (heptane:EA=15:1), 192 mg of product was obtained.

ESI-MS (M+H=309)

Step 4:

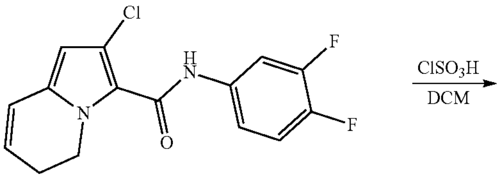

24

-continued

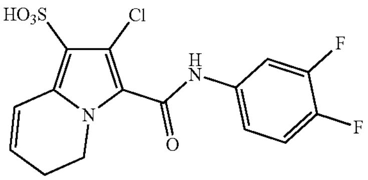

25

Compound 24 (300 mg, 1 equiv) was dissolved in anhydrous dichloromethane (15 ml) under nitrogen atmosphere, and then chlorosulfonic acid (116.52 mg, 1.1 equiv) was added at 0° C. After the reaction was completed, the mixture was suction filtered to give 200 mg of product, ESI-MS (M+H=389).

Step 5:

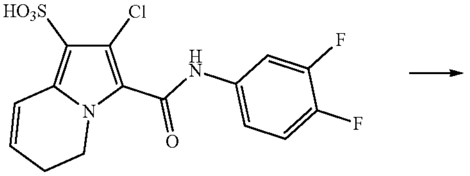

25

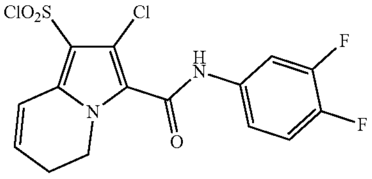

26

Under nitrogen atmosphere, oxalyl chloride (298.6 mg, 4 equiv) was added into a solution of Compound 25 (200 mg, 1 equiv) in DCM (8 ml) to react at room temperature. After the reaction was completed, the mixture was directly sampled and purified via column chromatography (heptane: EA=3:1) to provide 150 mg of product, ESI-MS (M+H=407)

Step 6:

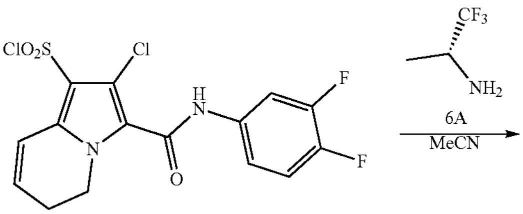

26

-continued

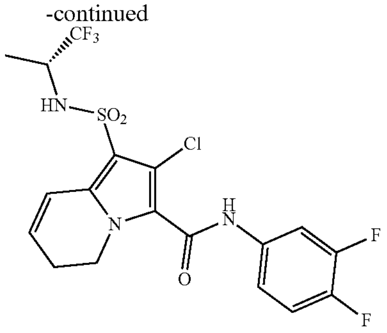

30a

-continued

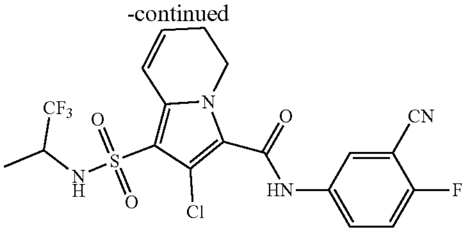

30b

Compound 26 (94 mg, 1 equiv) and amine (50 mg, 1.4 equiv) were dissolved in acetonitrile. Pyridine (94.8 mg, 4 equiv) was added under nitrogen atmosphere, and reacted overnight at 40° C. After reaction was completed, the mixture was extracted with ethyl acetate (3*20 mL), washed with HCl and water, dried, and column separated (heptane: EA=10:1) to give 120 mg of product. $^1$H NMR (400 MHz, DMSO-$d_6$) δ 10.64 (s, 1H), 8.57 (d, J=8.9 Hz, 1H), 7.85 (dd, J=13.1, 7.4 Hz, 1H), 7.50-7.30 (m, 2fH), 6.95 (dt, J=10.0, 1.8 Hz, 1H), 6.29 (dd, J=9.8, 4.8 Hz, 1H), 4.13 (t, J=7.7 Hz, 2H), 3.99 (tt, J=15.0, 7.3 Hz, 1H), 1.20 (d, J=7.0 Hz, 2H). ESI-MS (M+H=484)

Example 108: Synthesis of Compound 30b

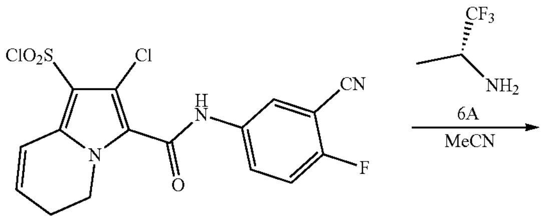

26b

The reaction was carried out according to the step 2 of example 107, all the conditions were the same except the compound 3,4,5-trifluoroaniline was used instead of 3,4-difluoroaniline. After purification via column chromatography (n-heptane:ethyl acetate=10:1), the target product 30b (25 mg) was obtained. ESI-MS (M+H=491)

Example 109: Synthesis of Compound 30c

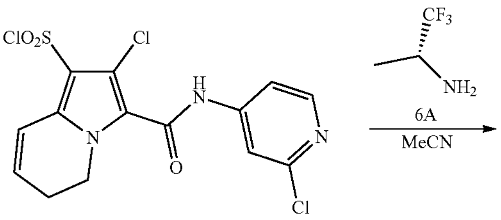

26c

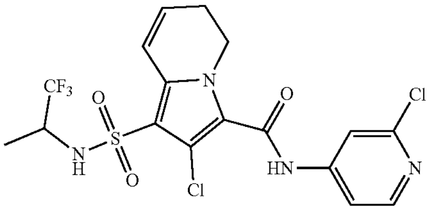

30c

The reaction was carried out according to the step 2 of example 107, all the conditions were the same except the compound 4-fluoro-3-cyanoaniline was used instead of 3,4-difluoroaniline. After purification via column chromatography (n-heptane:ethyl acetate=10:1), the target product 30c (10 mg) was obtained. ESI-MS (M+H=483)

The following 30 series compounds were synthesized according to the method of example 107:

| Compound | Structure | Mass Spectrometry. ESI-MS, (M + H) |
| --- | --- | --- |
| 30d | 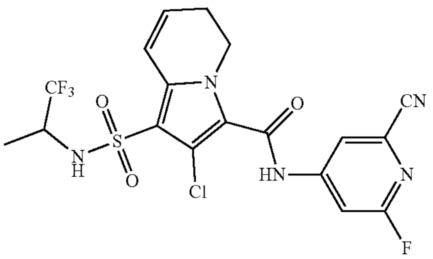 (R) | 492 |

-continued
| Compound | Structure | Mass Spectrometry. ESI-MS, (M + H) |
|---|---|---|
| 30e | 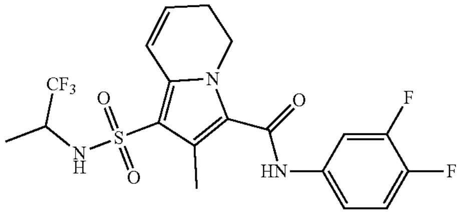 (R) | 464 |
| 30f | 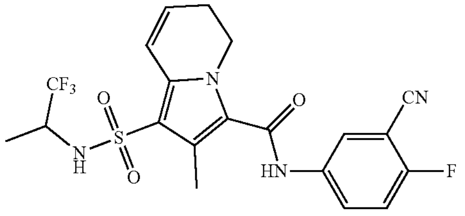 (R) | 471 |
| 30g | 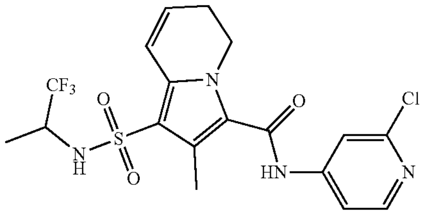 (R) | 463 |
| 30h | 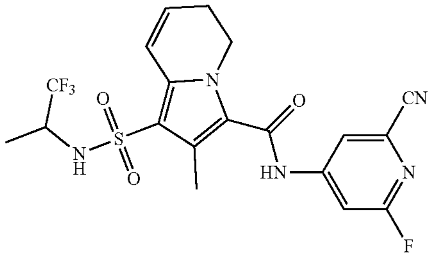 (R) | 472 |
| 30i | 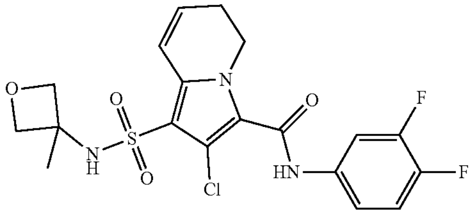 | 458 |
| 30j | 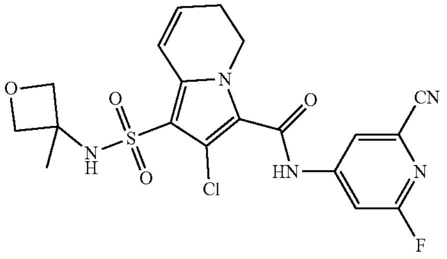 | 466 |

-continued
| Compound | Structure | Mass Spectrometry. ESI-MS, (M + H) |
|---|---|---|
| 30k | 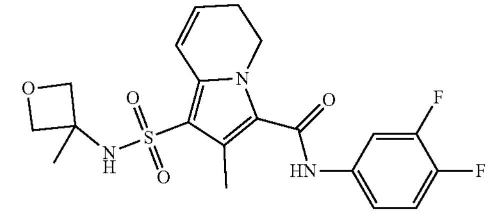 [SMILES: Cc1c(S(=O)(=O)NC2(C)COC2)c2n(c1C(=O)Nc1ccc(F)c(F)c1)CCC=C2] | 438 |
| 30l | 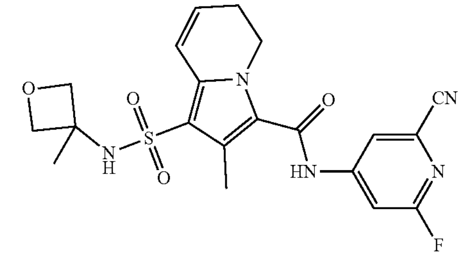 [SMILES: Cc1c(S(=O)(=O)NC2(C)COC2)c2n(c1C(=O)Nc1cc(F)nc(C#N)c1)CCC=C2] | 446 |
| 30m | 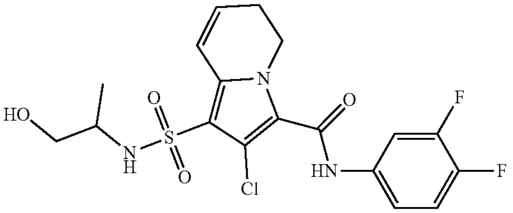 [SMILES: CC(CO)NS(=O)(=O)c1c(Cl)c(C(=O)Nc2ccc(F)c(F)c2)n2c1C=CCC2] | 446 |
| 30n | 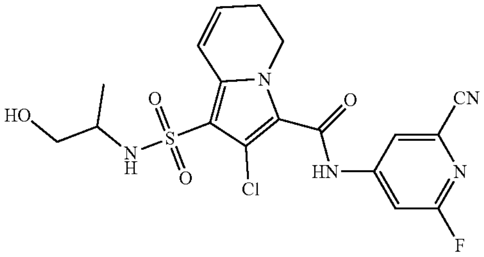 [SMILES: CC(CO)NS(=O)(=O)c1c(Cl)c(C(=O)Nc2cc(F)nc(C#N)c2)n2c1C=CCC2] | 454 |
| 30o | 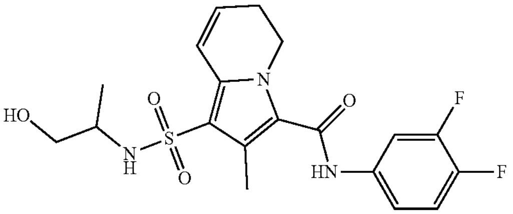 [SMILES: Cc1c(S(=O)(=O)NC(C)CO)c2n(c1C(=O)Nc1ccc(F)c(F)c1)CCC=C2] | 426 |
| 30p | 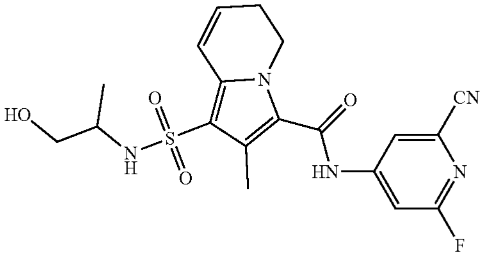 [SMILES: Cc1c(S(=O)(=O)NC(C)CO)c2n(c1C(=O)Nc1cc(F)nc(C#N)c1)CCC=C2] | 434 |

-continued
| Compound | Structure | Mass Spectrometry. ESI-MS, (M + H) |
|---|---|---|
| 30q | 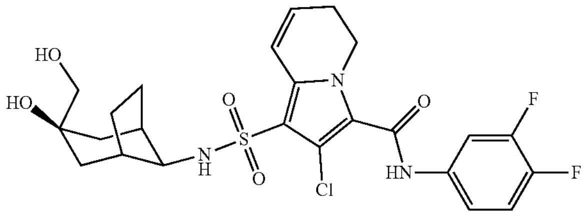 | 542 |
| 30r | 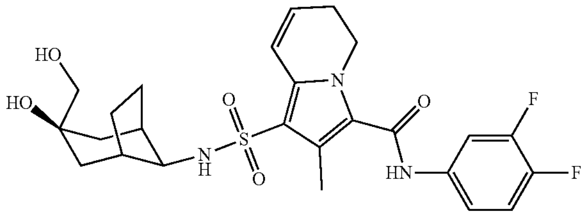 | 522 |
| 30s | 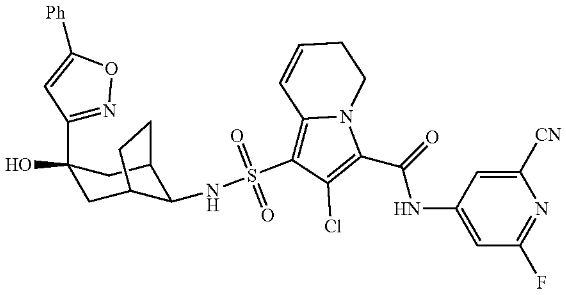 | 663 |
| 30t | 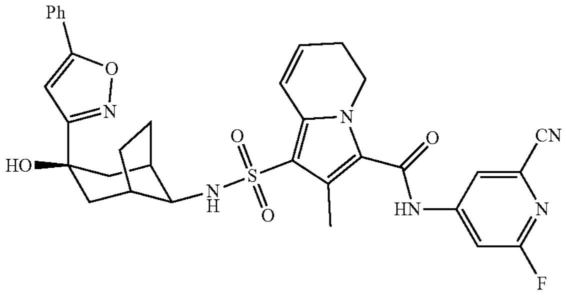 | 643 |
| 30u | 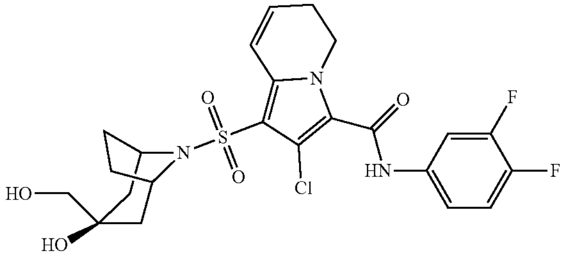 | 528 |
| 30v | 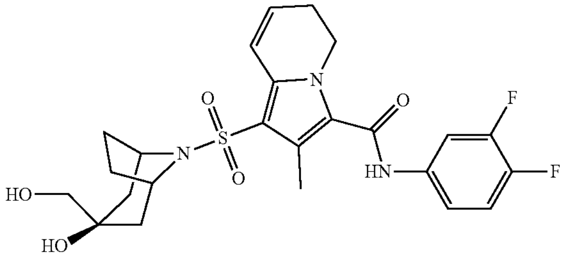 | 508 |

-continued
| Compound | Structure | Mass Spectrometry. ESI-MS, (M + H) |
| --- | --- | --- |
| 30w | 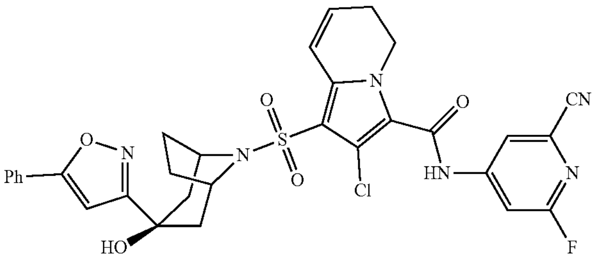 | 649 |
| 30x | 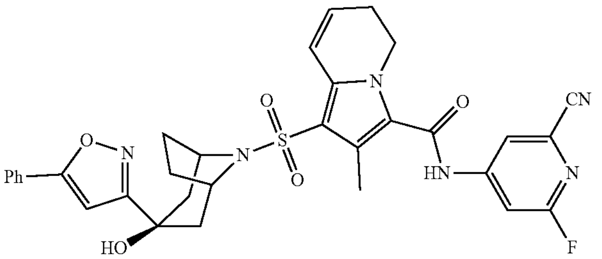 | 628 |
The following examples are the synthesis of 40 series of compounds:
Example 131 Synthesis of Compound 40a
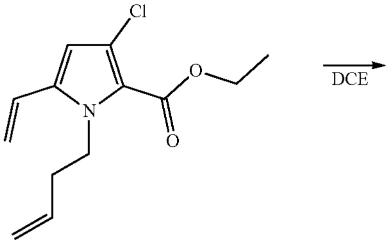
31
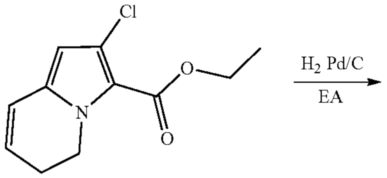
32
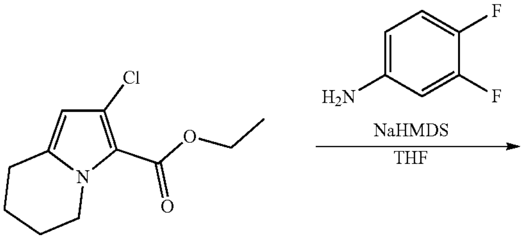
33
-continued
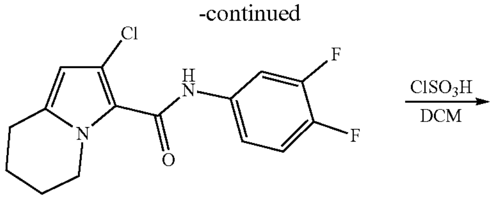
34
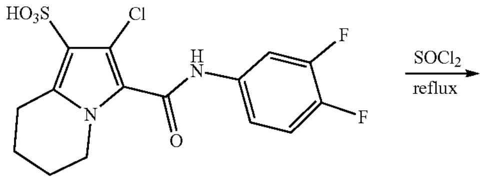
35
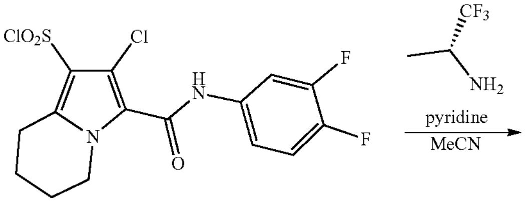
36

-continued

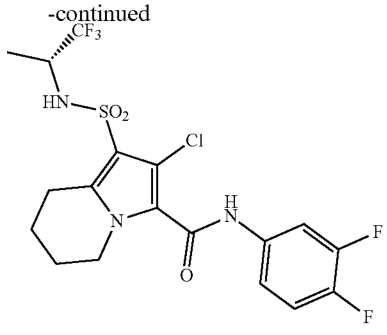

40a

Step 1:

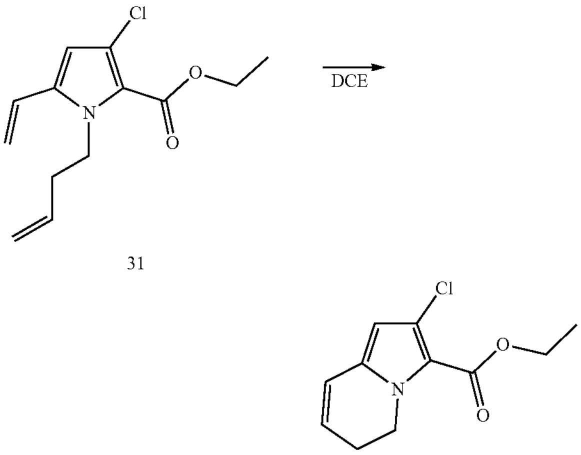

31

32

Under nitrogen atmosphere, Zhan catalyst B (6.5 mg) (0.1 equiv) was added into a solution of 31 (65 mg, 1 equiv) in DCE (10 mL) to react at room temperature. After the reaction was completed, the mixture was directly sampled. 29 mg of product was obtained by column chromatography (heptane:EA=10:1), ESI-MS (M+H)=226

Step 2:

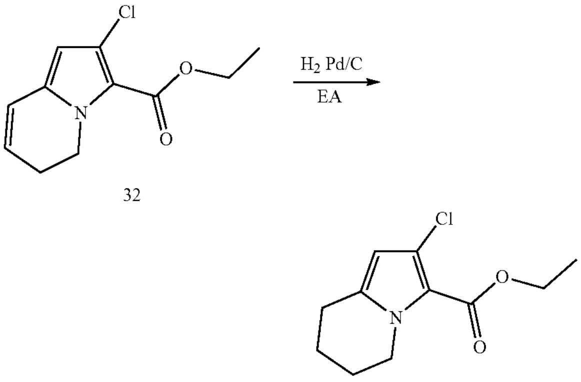

32

33

Under nitrogen atmosphere, compound 32 (50 mg) was dissolved in EA (5 mL), and 10% Pd/C (0.1 equiv) was added. The air was replaced with hydrogen, and reaction was carried out at room temperature. After the reaction was completed, the mixture was filtered with celite and concentrated to give 40 mg of product which was directly used in the next step, ESI-MS (M+H)=228.

Step 3:

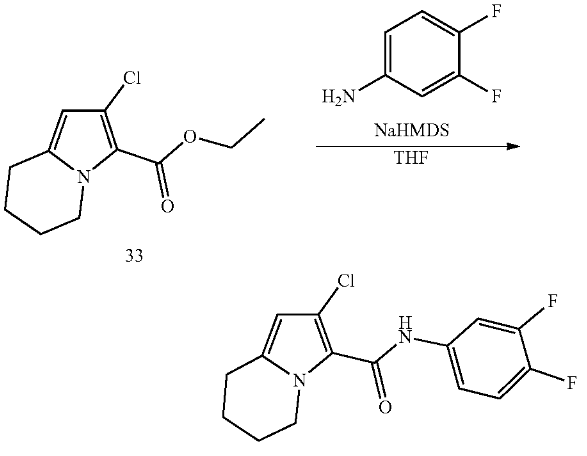

33

34

Compound 33 (40 mg, 1 equiv) was dissolved in THF (15 ml/mmol), and air was replaced with nitrogen. 3,4-difluoroaniline (70 mg, 2 equiv) was added. 2M NaHMDS (0.3 ml, 2 equiv) was added at 0° C., and the reaction was carried out at room temperature. After the reaction was completed, the mixture was added into ice water, extracted with EA, dried and purified by column chromatography (heptane:EA=3:1) to give 40 mg compound, ESI-MS (M+H=311)

Step 4:

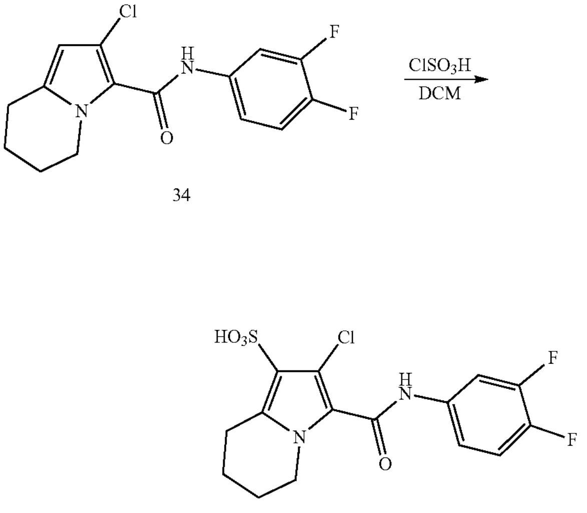

34

35

Compound 34 (300 mg, 1 equiv) was dissolved in anhydrous dichloromethane (15 ml) under nitrogen atmosphere, and then chlorosulfonic acid (116.52 mg, 1.1 equiv) was added at 0° C. After the reaction was completed, the mixture was suction filtered to give 200 mg of product, ESI-MS (M+H=391).

Step 5:

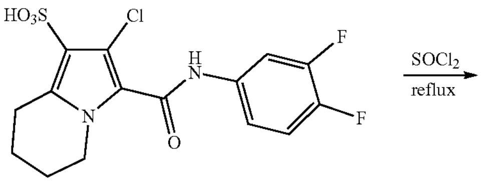

35

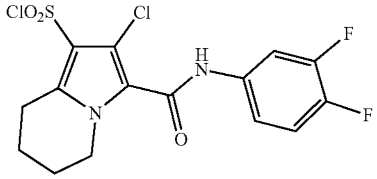

36

Under nitrogen atmosphere, oxalyl chloride (298.6 mg, 4 equiv) was added into a solution of 35 (200 mg, 1 equiv) in DCM (8 ml) to react at room temperature. After the reaction was completed, the mixture was directly sampled and purified via column chromatography (heptane:EA=3:1) to give 150 mg of product, ESI-MS (M+H=409)

Step 6:

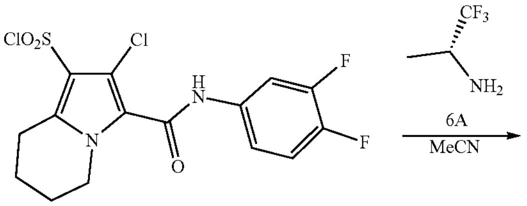

36

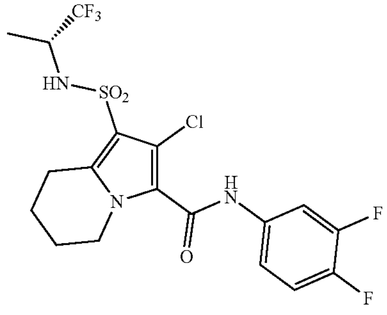

40a

Compound 36 (94 mg, 1 equiv) and amine (50 mg, 1.4 equiv) were dissolved in acetonitrile, pyridine (94.8 mg, 4 equiv) was added under nitrogen atmosphere, and the reaction was carried out at 40° C. overnight. After the reaction was completed, the mixture was extracted with ethyl acetate (3*20 mL), washed with HCl and water, dried and separated by column chromatography (heptane:EA=10:1) to give Compound 40a (80 mg). $^{1}H$ NMR (400 MHz, DMSO-$d_6$) δ 10.50 (s, 1H), 8.34 (d, J=9.0 Hz, 1H), 7.93-7.75 (m, 1H), 7.50-7.36 (m, 2H), 4.18-3.99 (m, 2H), 3.97 (d, J=7.7 Hz, 1H), 2.98 (t, J=6.4 Hz, 2H), 1.88 (p, J=5.9 Hz, 2H), 1.78 (dq, J=13.1, 6.2 Hz, 2H), 1.18 (d, J=6.9 Hz, 3H). ESI-MS (M+H=486)

Example 132: Synthesis of Compound 40b

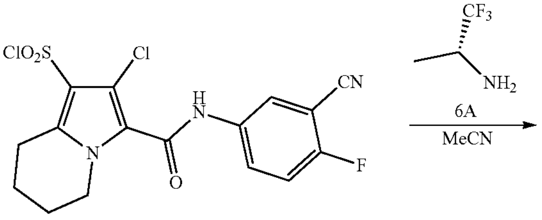

36b

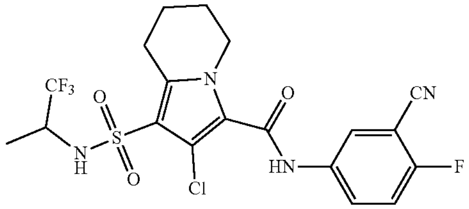

40b

The reaction was carried out according to the step 3 of example 131, all the conditions were the same except the compound 3,4,5-trifluoroaniline was used instead of 3,4-difluoroaniline. After purification via column chromatography (n-heptane:ethyl acetate=10:1), the target product 40b (15 mg) was obtained. ESI-MS (M+H=493)

Example 133: Synthesis of Compound 40c

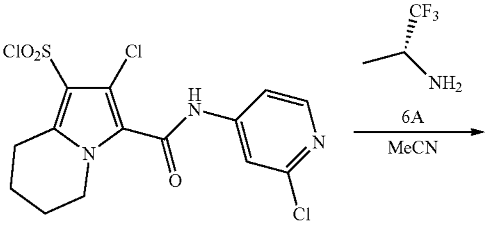

36c

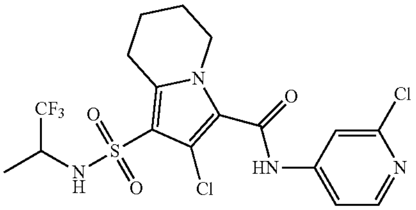

40c

The reaction was carried out according to the step 3 of example 131, all the conditions were the same except the compound 4-fluoro-3-cyanoaniline was used instead of 3,4-difluoroaniline. After purification via column chromatography (n-heptane:ethyl acetate=10:1), the target product 40c (10 mg) was obtained. ESI-MS (M+H=485)

The following 40 series of compounds were synthesized according to the method of example 131:

| Compound | Structure | Mass Spectrometry. ESI-MS, (M + H) |
|---|---|---|
| 40d | 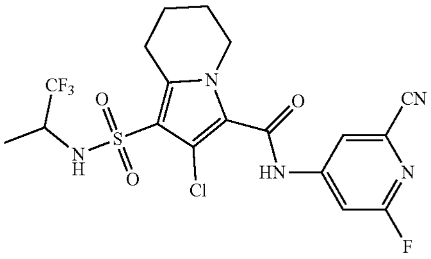 (R) | 494 |
| 40e | 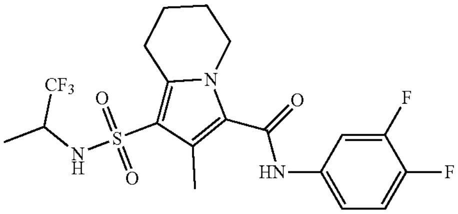 (R) | 466 |
| 40f | 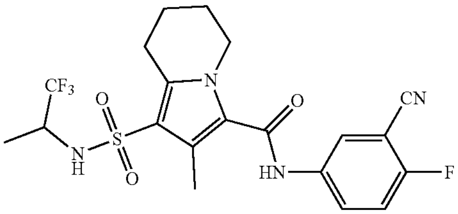 (R) | 473 |
| 40g | 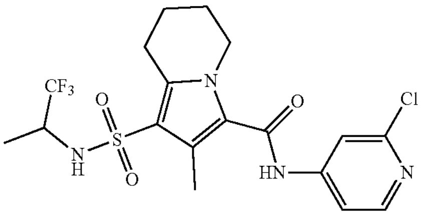 (R) | 465 |
| 40h | 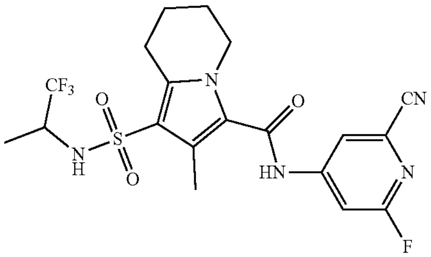 (R) | 474 |
| 40i | 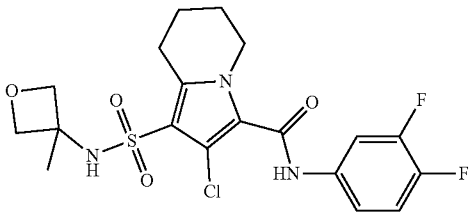 | 460 |

-continued
| Compound | Structure | Mass Spectrometry. ESI-MS, (M + H) |
|---|---|---|
| 40j | 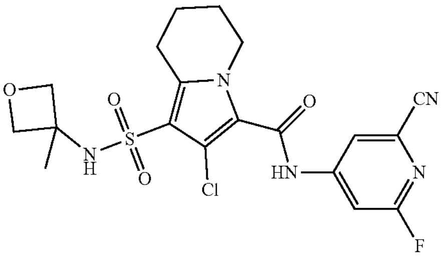 [SMILES: CC1(NS(=O)(=O)c2c(Cl)c(C(=O)Nc3cc(F)nc(C#N)c3)n3c2CCCC3)COC1] | 468 |
| 40k | 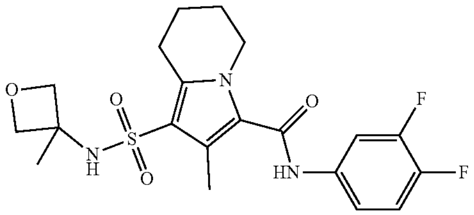 [SMILES: Cc1c(S(=O)(=O)NC2(C)COC2)c2n(c1C(=O)Nc1ccc(F)c(F)c1)CCCC2] | 440 |
| 40l | 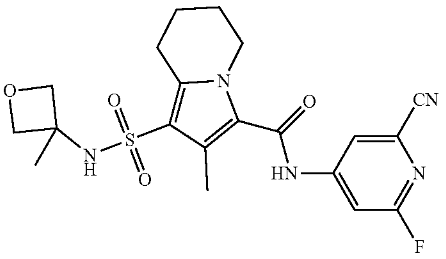 [SMILES: Cc1c(S(=O)(=O)NC2(C)COC2)c2n(c1C(=O)Nc1cc(F)nc(C#N)c1)CCCC2] | 448 |
| 40m | 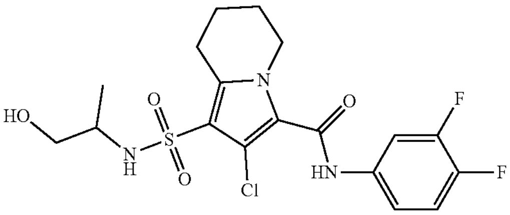 [SMILES: CC(CO)NS(=O)(=O)c1c(Cl)c(C(=O)Nc2ccc(F)c(F)c2)n2c1CCCC2] | 448 |
| 40n | 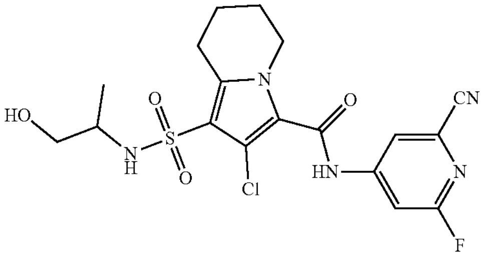 [SMILES: CC(CO)NS(=O)(=O)c1c(Cl)c(C(=O)Nc2cc(F)nc(C#N)c2)n2c1CCCC2] | 456 |
| 40o | 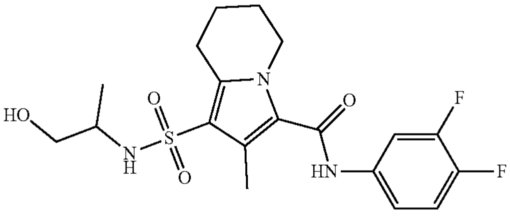 [SMILES: Cc1c(S(=O)(=O)NC(C)CO)c2n(c1C(=O)Nc1ccc(F)c(F)c1)CCCC2] | 428 |

-continued
| Compound | Structure | Mass Spectrometry. ESI-MS, (M + H) |
|---|---|---|
| 40p | 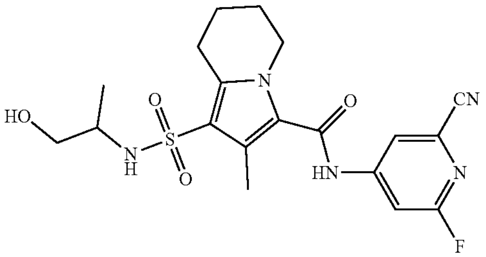 [SMILES: Cc1c(S(=O)(=O)NC(C)CO)c2n(c1C(=O)Nc1cc(F)nc(C#N)c1)CCCC2] | 436 |
| 40q | 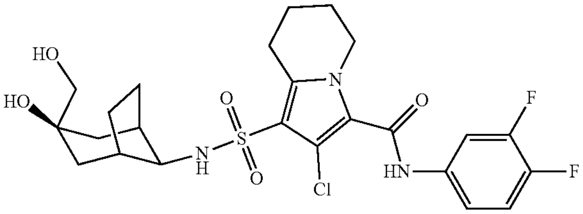 | 544 |
| 40r | 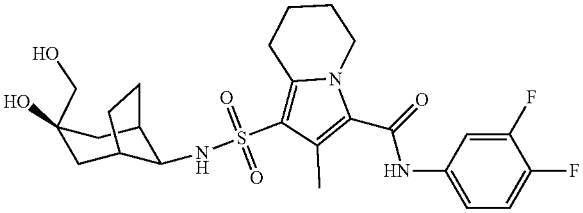 | 524 |
| 40s | 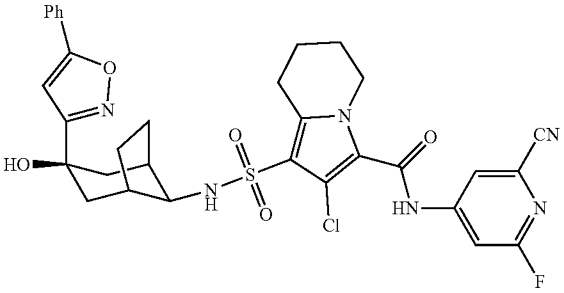 | 666 |
| 40t | 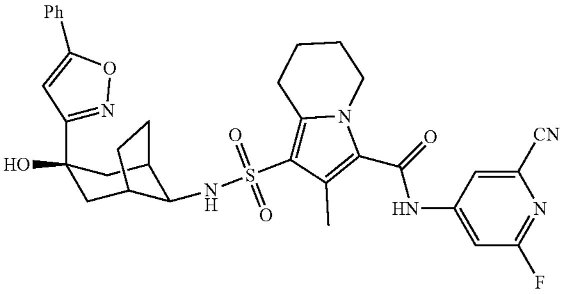 | 645 |
| 40u | 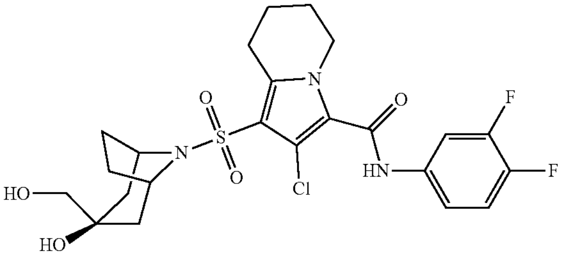 | 530 |

-continued
| Compound | Structure | Mass Spectrometry. ESI-MS, (M + H) |
|---|---|---|
| 40v | 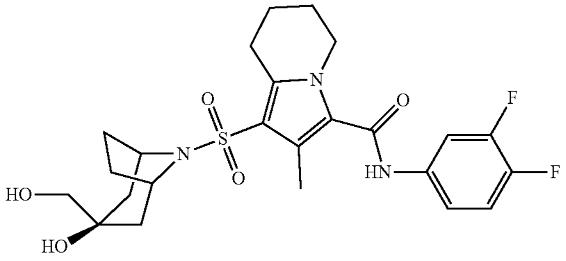 | 510 |
| 40w | 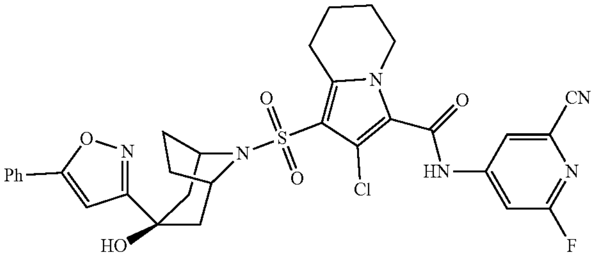 | 651 |
| 40x | 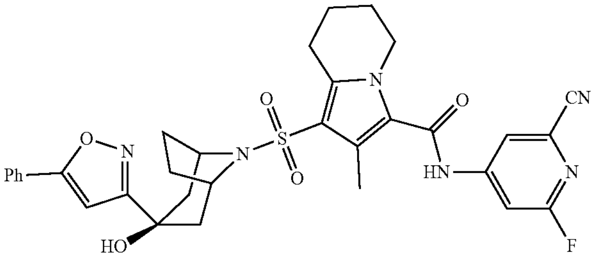 | 630 |
The following examples are the synthesis of 50 series of compounds:
Example 155 Synthesis of Compound 50a
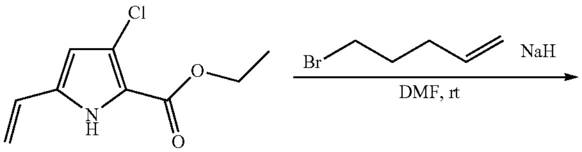
41
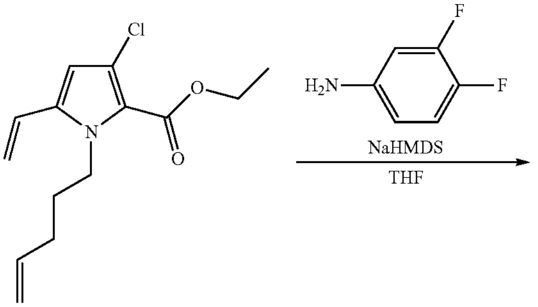
42
-continued
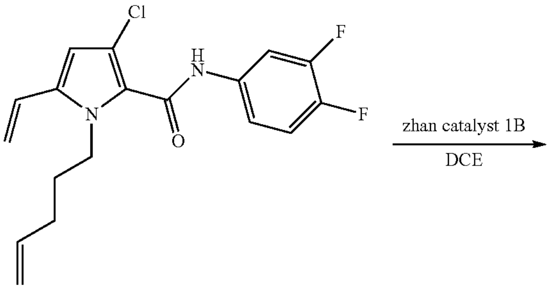
43
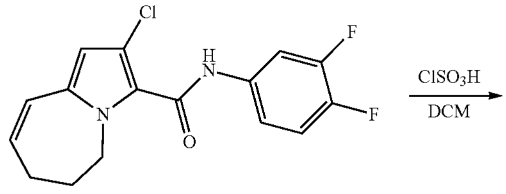
44

-continued

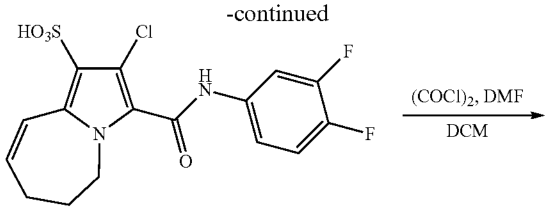

45

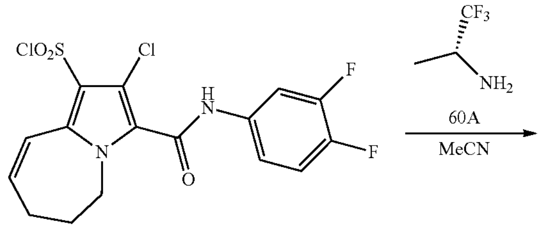

46

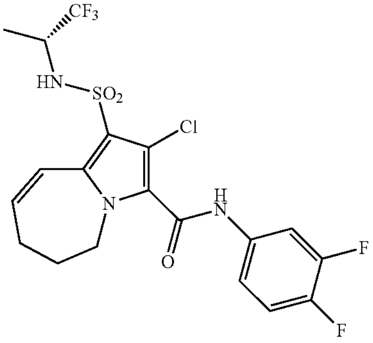

50a

Step 1:

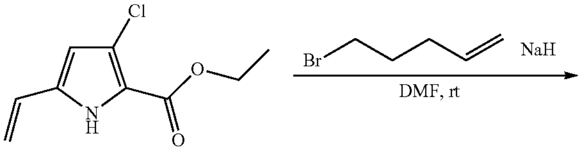

41

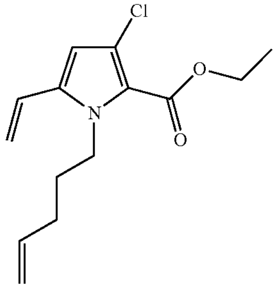

42

DMF (5 ml, 2 ml/mmol) was added into reaction flask, and NaH (150 mg, 1.5 equiv) was added under ice bath, stirred for 10 min, and Compound 41 (500 mg, 1. equiv) was added and stirred for 30 min. 1-bromo-butene (405 mg) was added and reacted at room temperature. After the reaction was completed, the mixture was poured into ice water, extracted with EA, washed with saturated NaCl and dried over anhydrous sodium sulfate. 203 mg of product was provided by column separation (heptane:EA=15:1), ESI-MS (M+H=268)

Step 2:

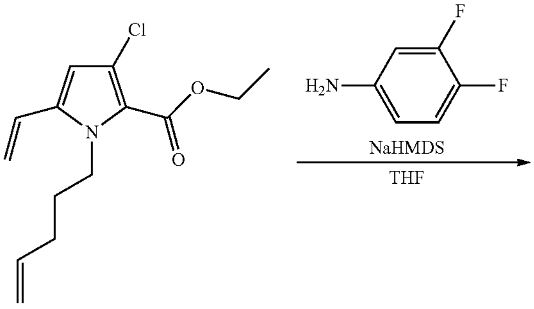

42

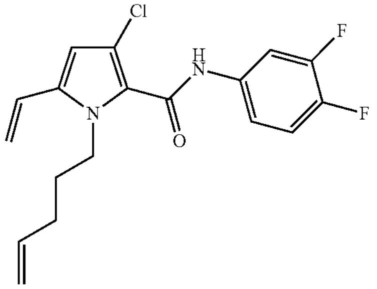

43

Compound 22 (200 mg, 1.0 equiv) was added into a reaction flask, and THF (5 ml/mmol), 3,4 difluoroaniline (203 mg, 2 equiv) were added, and NaHMDS (1.5 ml, 4 equiv) was added dropwise in an ice bath. After the reaction was completed, the mixture was poured into ice water, extract with EA, washed with saturated NaCl and dried over anhydrous sodium sulfate. 225 mg of product was provided by column separation (heptane:EA=5:1), ESI-MS (M+H=351)

Step 3:

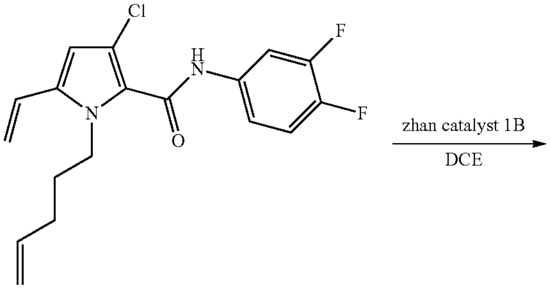

43

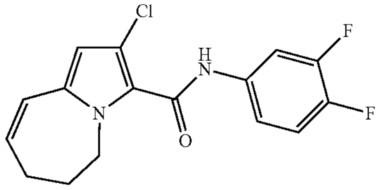

44

Compound 43 (225 mg, 1 equiv), Zhan catalyst (22.5 mg, 0.1 equiv) and DCE (22.5 ml, 0.1 ml/mg) were added into a reaction flask. After the reaction was completed, the reaction mixture was extracted with DCM, washed with saturated NaCl, and dried over anhydrous sodium sulfate. 192 mg of product was provided by column separation (heptane:EA=15:1), ESI-MS (M+H=323)

Step 4:

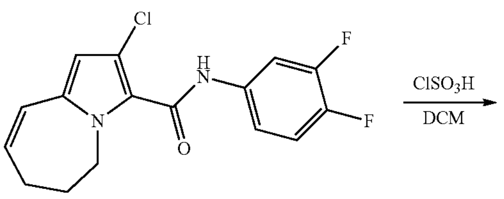

44

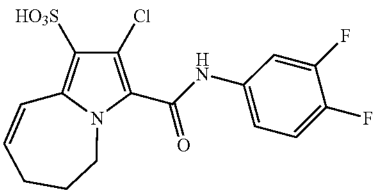

45

Compound 44 (300 mg, 1 equiv) was dissolved in anhydrous dichloromethane (15 ml) under nitrogen atmosphere, and then chlorosulfonic acid (116.52 mg, 1.1 equiv) was added at 0° C. After the reaction was completed, the mixture was suction filtered to give 200 mg of product, ESI-MS (M+H=403).

Step 5:

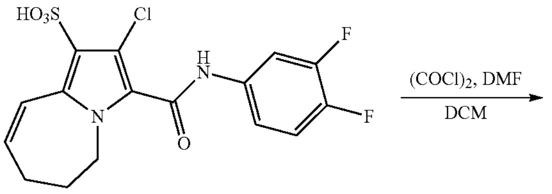

45

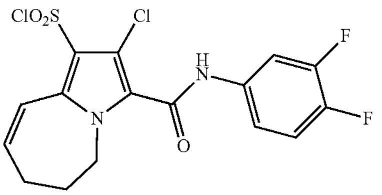

46

Under nitrogen atmosphere, oxalyl chloride (298.6 mg, 4 equiv) was added into a solution of Compound 45 (200 mg, 1 equiv) in DCM (8 ml) to react at room temperature. After the reaction was completed, the mixture was directly sampled and purified via column chromatography (heptane: EA=3:1) to give 150 mg of product, ESI-MS (M+H=421)

Step 6:

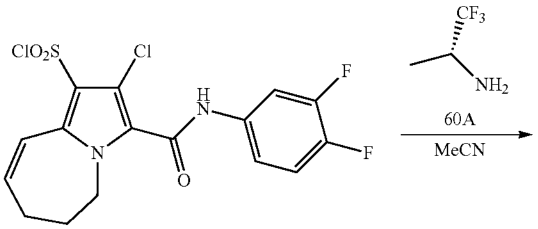

46

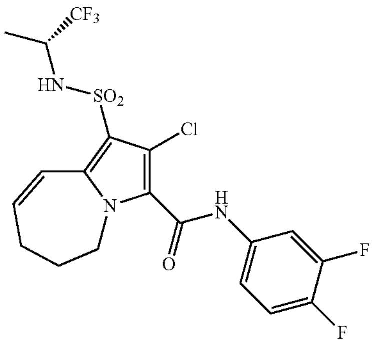

50a

Compound 46 (94 mg, 1 equiv) and amine (50 mg, 1.4 equiv) were dissolved in acetonitrile. Pyridine (94.8 mg, 4 equiv) was added under nitrogen atmosphere, and reacted overnight at 40° C. After the reaction was completed, the mixture was extracted with ethyl acetate (3*20 mL), washed with HCl and water, dried, and column separated (heptane: EA=10:1) to give 120 mg of product. $^{1}$H NMR (400 MHz, DMSO-$d_6$) δ 10.80 (s, 1H), 8.54 (d, J=8.9 Hz, 1H), 7.87 (dd, J=13.0, 7.4 Hz, 1H), 7.46 (q, J=5.1, 4.5 Hz, 2H), 6.96 (d, J=12.6 Hz, 1H), 6.14 (dt, J=12.6, 4.6 Hz, 1H), 4.24-4.07 (m, 2H), 3.94 (h, J=7.4 Hz, 1H), 2.01 (d, J=7.7 Hz, 2H), 1.18 (d, J=7.0 Hz, 2H). ESI-MS (M+H=498)

Example 156: Synthesis of Compound 50b

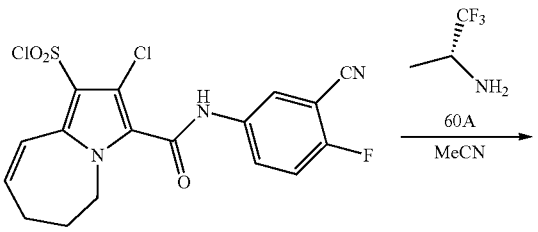

46b

-continued

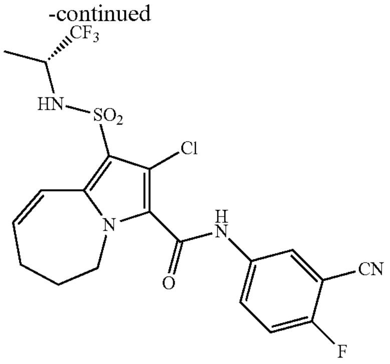

50b

-continued

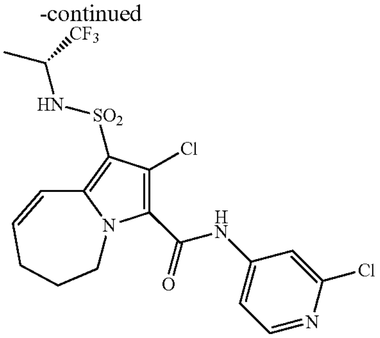

50c

The reaction was carried out according to the step 2 of example 155, all the conditions were the same except the compound 3,4,5-trifluoroaniline was used instead of 3,4-difluoroaniline. After purification via column chromatography (n-heptane:ethyl acetate=10:1), the target product 50b (25 mg) was obtained. ESI-MS (M+H=505)

Example 157: Synthesis of Compound 50c

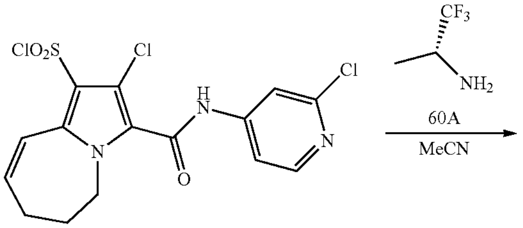

46c

The reaction was carried out according to the step 2 of example 155, all the conditions were the same except the compound 4-fluoro-3-cyanoaniline was used instead of 3,4-difluoroaniline. After purification via column chromatography (n-heptane:ethyl acetate=10:1), the target product 50c (10 mg) was obtained. ESI-MS (M+H=497)

The following 50 series of compounds were synthesized according to the method of example 155:

| Compound | Structure | Mass Spectrometry. ESI-MS, (M + H) |
|---|---|---|
| 50d | 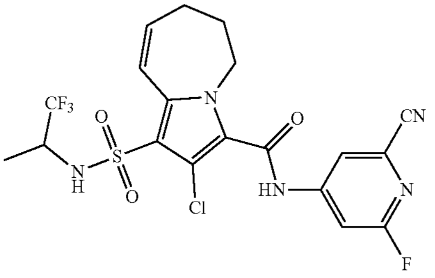 (R) | 506 |
| 50e | 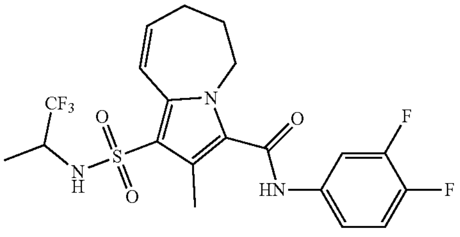 (R) | 478 |

-continued
| Compound | Structure | Mass Spectrometry. ESI-MS, (M + H) |
|---|---|---|
| 50f | 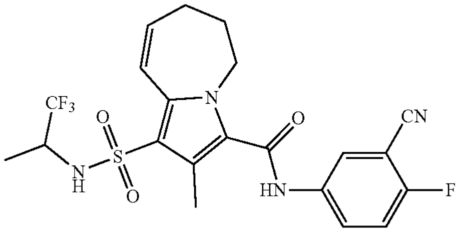 (R) | 485 |
| 50g | 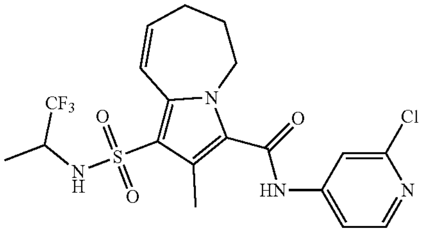 (R) | 477 |
| 50h | 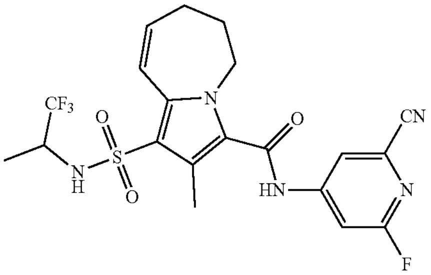 (R) | 486 |
| 50i | 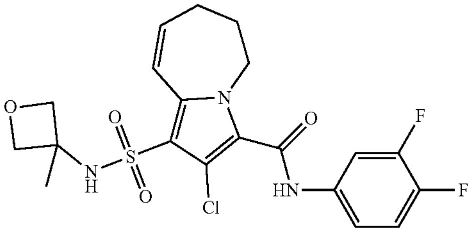 | 472 |
| 50j | 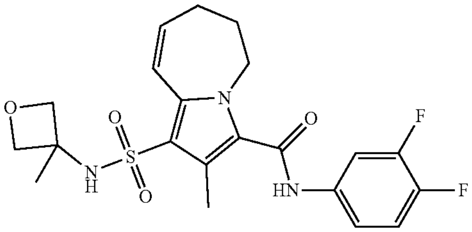 | 452 |
| 50k | 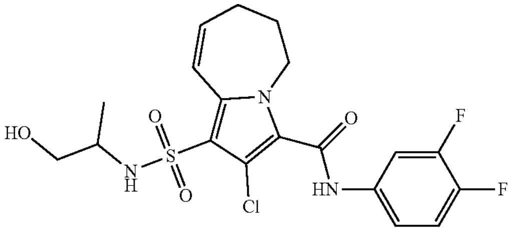 | 460 |

-continued
| Compound | Structure | Mass Spectrometry. ESI-MS, (M + H) |
|---|---|---|
| 50l | 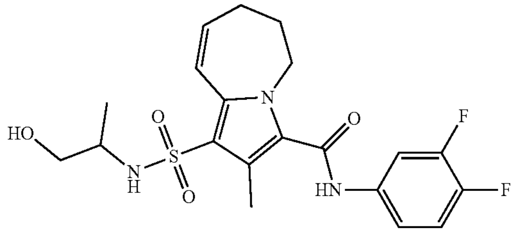 [SMILES: Cc1c(S(=O)(=O)NC(C)CO)c2n(c1C(=O)Nc1ccc(F)c(F)c1)CCCC=C2] | 440 |
| 50m | 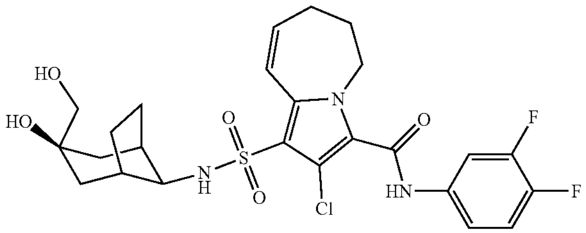 | 556 |
| 50n | 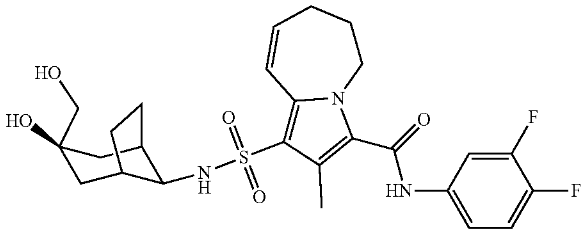 | 536 |
| 50o | 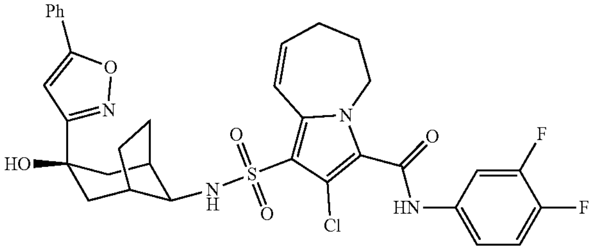 | 669 |
| 50p | 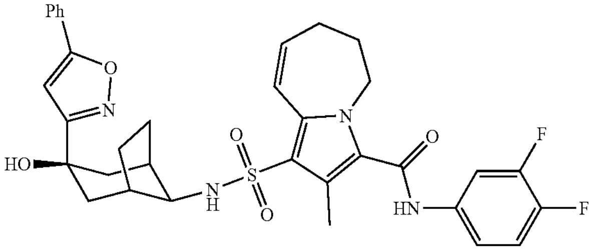 | 649 |
| 50q | 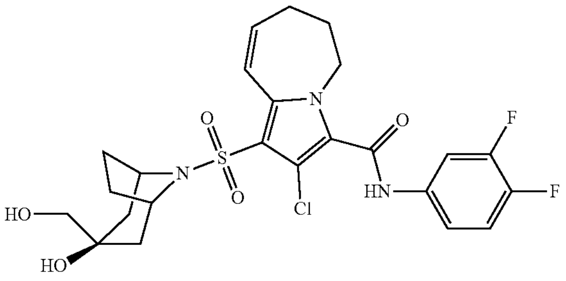 | 542 |

-continued
| Compound | Structure | Mass Spectrometry. ESI-MS, (M + H) |
|---|---|---|
| 50r | 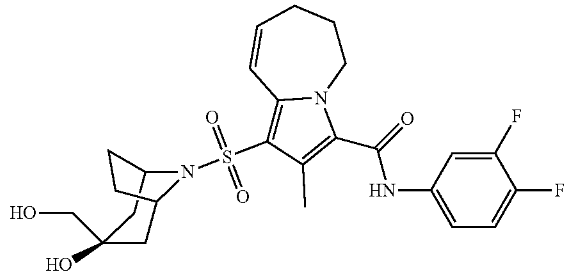 | 522 |
| 50s | 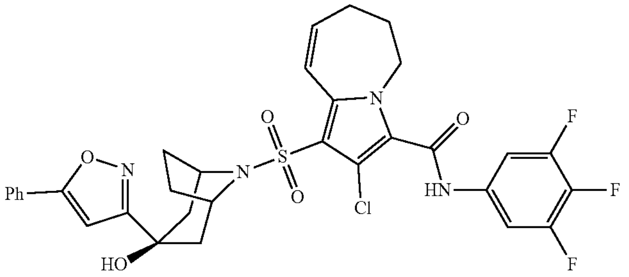 | 673 |
| 50t | 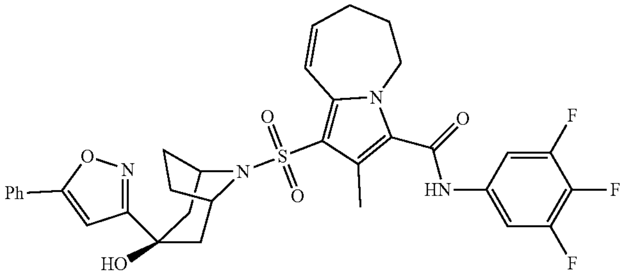 | 653 |
The following examples are the synthesis of 60 series of compounds:
Example 175 Synthesis of Compound 60a
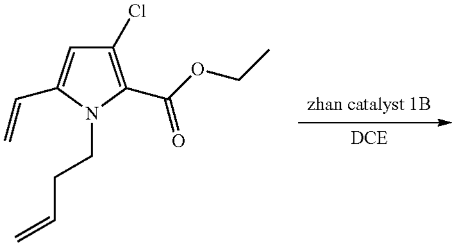
51
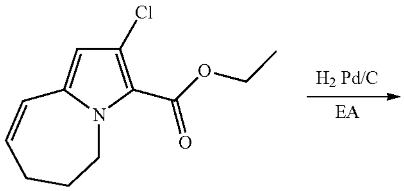
52
-continued
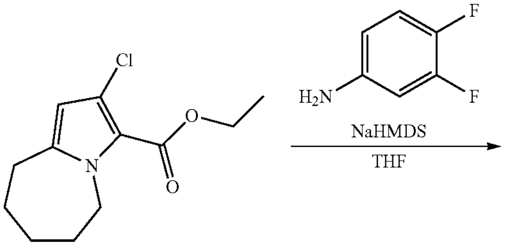
53
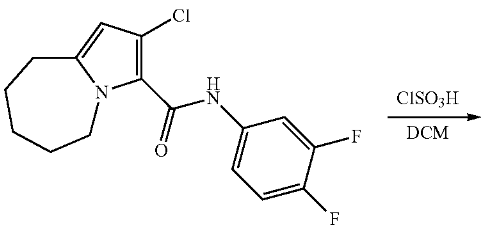
54

-continued

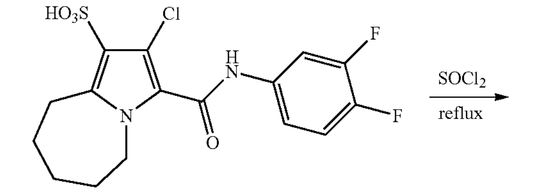

55

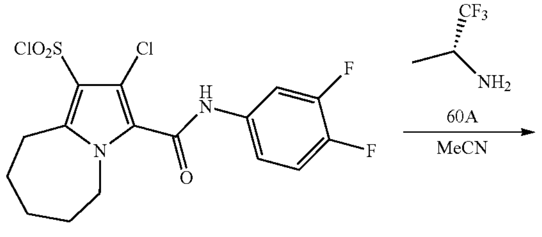

56

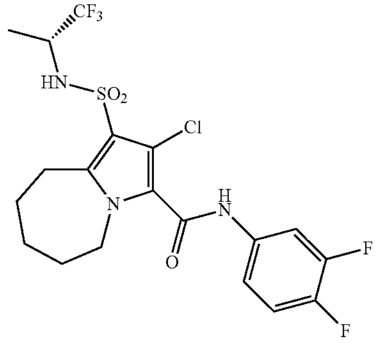

60a

Step 1:

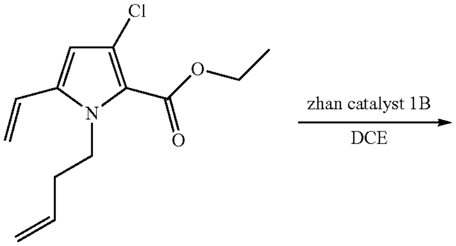

51

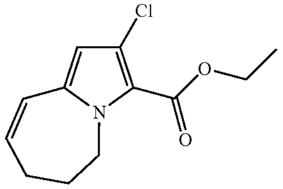

52

Under nitrogen atmosphere, Zhan catalyst 1B (6.5 mg) (0.1 equiv) was added to a solution of 51 (65 mg, 1 equiv) in DCE (10 mL) to react at room temperature. After the reaction was completed, the mixture was directly sampled. 29 mg of product was obtained by column chromatography (heptane:EA=10:1), ESI-MS (M+H)=240

Step 2:

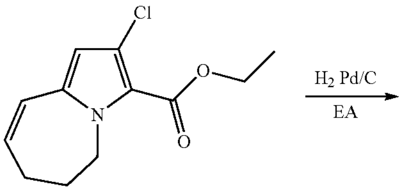

52

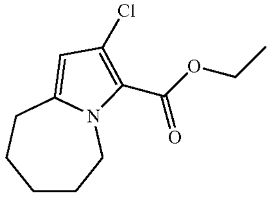

53

Under nitrogen atmosphere, compound 52 (50 mg) was dissolved in EA (5 mL), and 10% Pd/C (0.1 equiv) was added. The air was replaced with hydrogen, and reaction was carried out at room temperature. After the reaction was completed, the mixture was filtered with celite and concentrated to give 40 mg of product which was directly used in the next step, ESI-MS (M+H)=242.

Step 3:

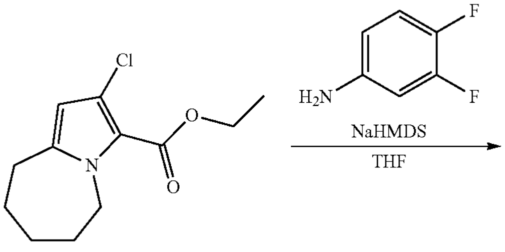

53

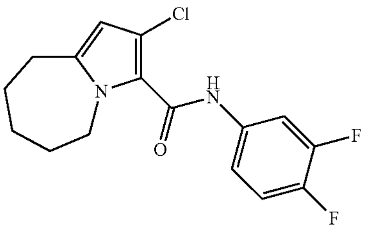

54

Compound 53 (40 mg, 1 equiv) was dissolved in THF (15 ml/mmol), and air was replaced with nitrogen. 3,4-difluoroaniline (70 mg, 2 equiv) was added. 2M NaHMDS (0.3 ml, 2 equiv) was added at 0° C., and the reaction was carried out at room temperature. After the reaction was completed, the mixture was added into ice water, extracted with EA, dried and purified by column chromatography (heptane:EA=3:1) to give 40 mg compound, ESI-MS (M+H=325)

Step 4:

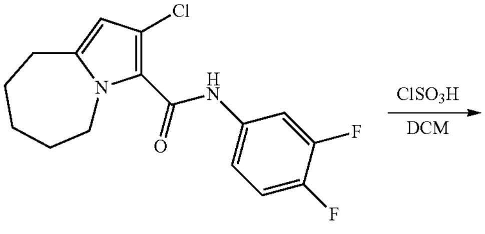

54

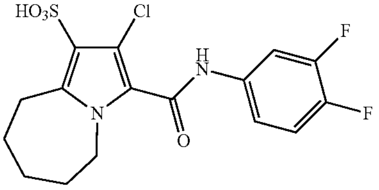

55

Compound 54 (300 mg, 1 equiv) was dissolved in anhydrous dichloromethane (15 ml) under nitrogen atmosphere, and then chlorosulfonic acid (116.52 mg, 1.1 equiv) was added at 0° C. After the reaction was completed, the mixture was suction filtered to give 200 mg of product, ESI-MS (M+H=405).

Step 5:

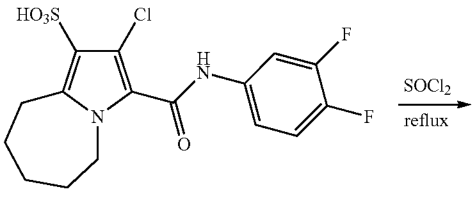

55

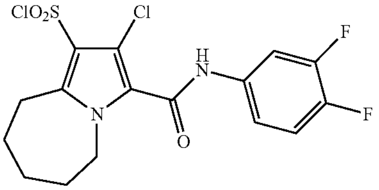

56

Under nitrogen atmosphere, oxalyl chloride (298.6 mg, 4 equiv) was added into a solution of Compound 55 (200 mg, 1 equiv) in DCM (8 ml) to react at room temperature. After the reaction was completed, the mixture was directly sampled and purified via column chromatography (heptane: EA=3:1) to give 150 mg of product, ESI-MS (M+H=423)

Step 6:

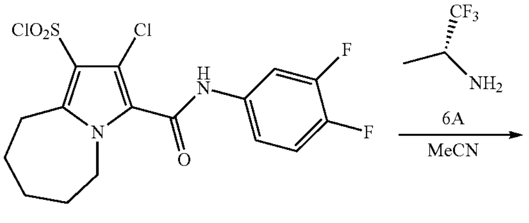

56

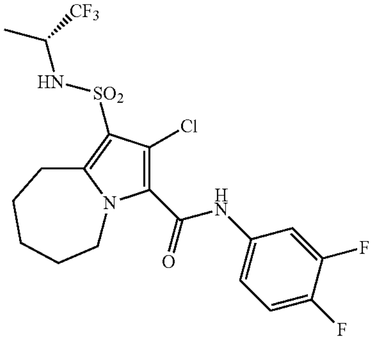

60a

Compound 56 (94 mg, 1 equiv) and amine (50 mg, 1.4 equiv) were dissolved in acetonitrile. Pyridine (94.8 mg, 4 equiv) was added under nitrogen atmosphere, and reaction was carried out at 40° C. overnight. After the reaction was completed, the mixture was extracted with ethyl acetate (3*20 mL), washed with HCl and water, dried, and separated by column chromatography (heptane:EA=10:1) to give Compound 60a (80 mg). $^1$H NMR (400 MHz, DMSO-d$_6$) δ 10.70 (s, 1H), 8.42 (d, J=8.9 Hz, 1H), 7.97-7.75 (m, 1H), 7.47-7.34 (m, 2H), 4.16 (d, J=6.8 Hz, 2H), 3.90 (dt, J=15.1, 7.5 Hz, 1H), 3.25-3.06 (m, 2H), 1.76 (s, 2H), 1.60 (d, J=32.7 Hz, 4H), 1.17 (d, J=7.0 Hz, 3H). ESI-MS (M+H=500)

Example 176: Synthesis of Compound 60b

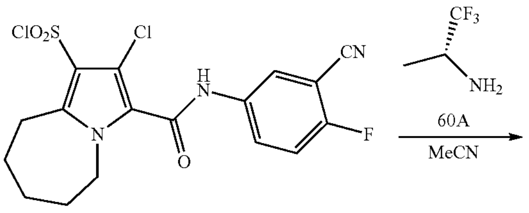

56b

-continued

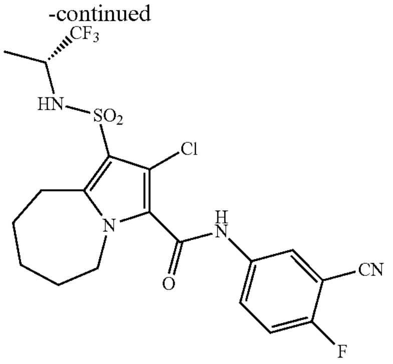

60 b

The reaction was carried out according to the step 3 of example 175, all the conditions were the same except the compound 3,4,5-trifluoroaniline was used instead of 3,4-difluoroaniline. After purification via column chromatography (n-heptane:ethyl acetate=10:1), the target product 60b (15 mg) was obtained. ESI-MS (M+H=507)

Example 177: Synthesis of Compound 60c

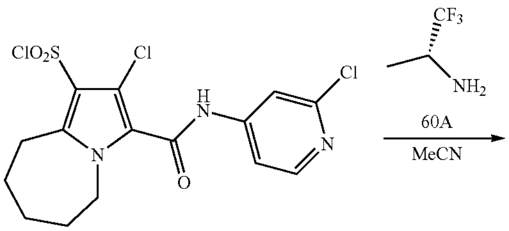

56c

-continued

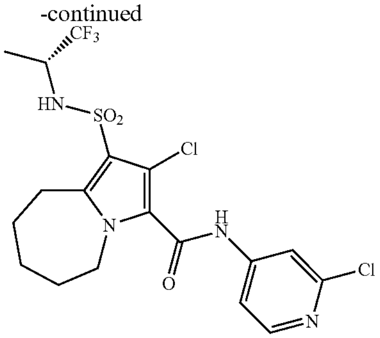

60 c

The reaction was carried out according to the step 3 of example 175, all the conditions were the same except the compound 4-fluoro-3-cyanoaniline was used instead of 3,4-difluoroaniline. After purification via column chromatography (n-heptane:ethyl acetate=10:1), the target product 60c (10 mg) was obtained. ESI-MS (M+H=499)

The following 60 series of compounds were synthesized according to the method of example 175:

| Compound | Structure | Mass Spectrometry. ESI-MS, (M + H) |
|---|---|---|
| 60a | 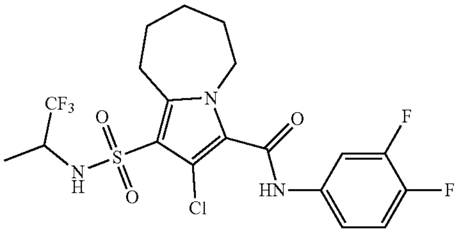 (R) | 500 |
| 60b | 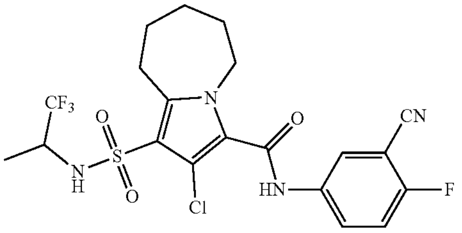 (R) | 507 |

-continued
| Compound | Structure | Mass Spectrometry. ESI-MS, (M + H) |
| --- | --- | --- |
| 60c | 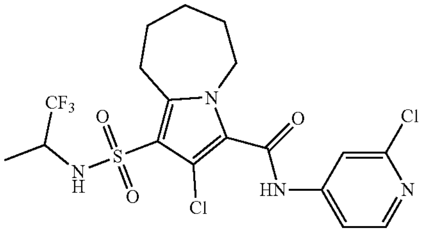 (R) | 499 |
| 60d | 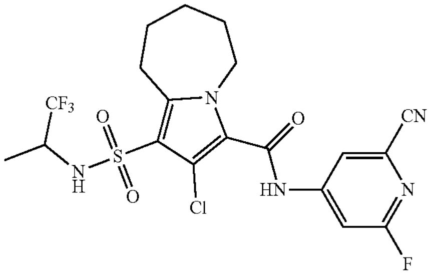 (R) | 508 |
| 60e | 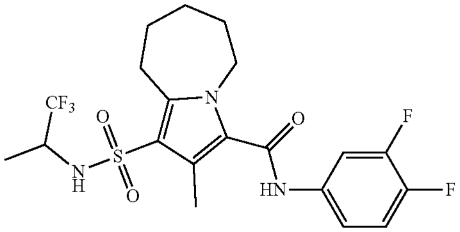 (R) | 480 |
| 60f | 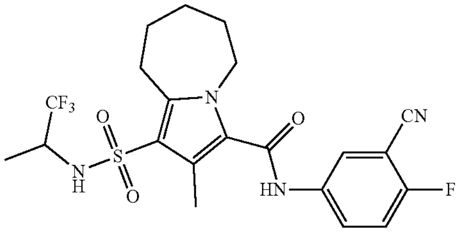 (R) | 487 |
| 60g | 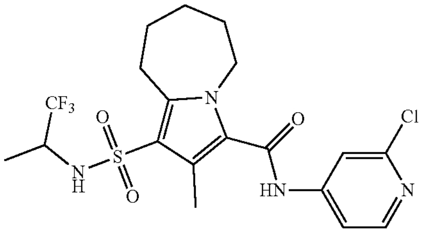 (R) | 479 |

-continued
| Compound | Structure | Mass Spectrometry. ESI-MS, (M + H) |
|---|---|---|
| 60h | 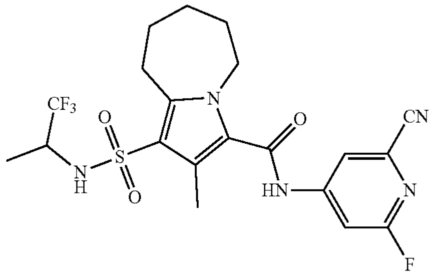 (R) | 488 |
| 60i | 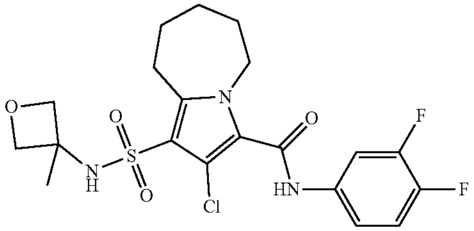 | 474 |
| 60j | 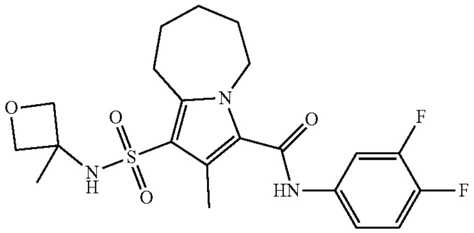 | 454 |
| 60k | 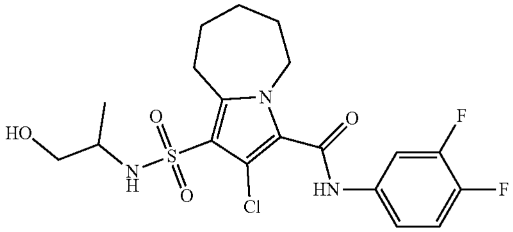 | 462 |
| 60l | 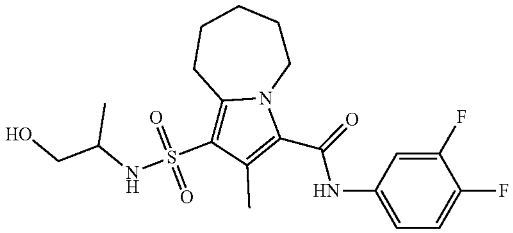 | 442 |
| 60m | 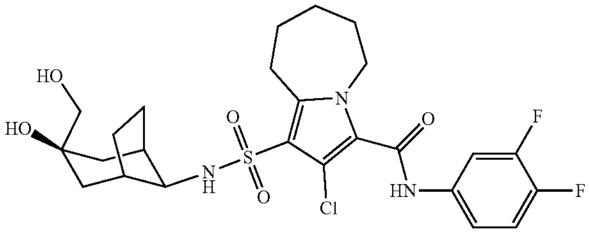 | 558 |

-continued
| Compound | Structure | Mass Spectrometry. ESI-MS, (M + H) |
|---|---|---|
| 60n | 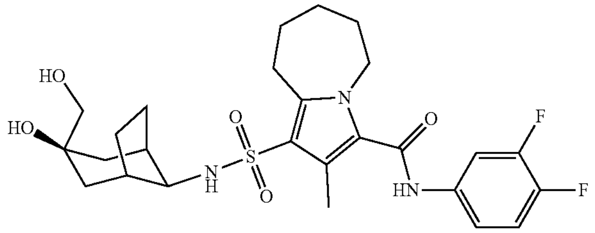 | 538 |
| 60o | 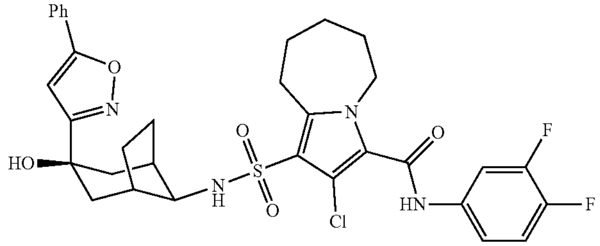 | 671 |
| 60p | 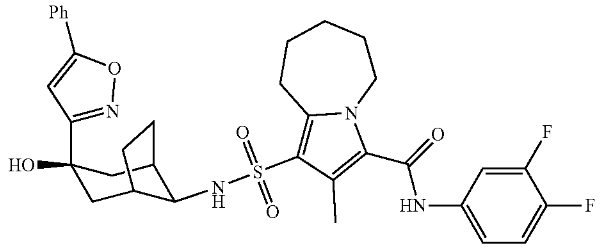 | 651 |
| 60q | 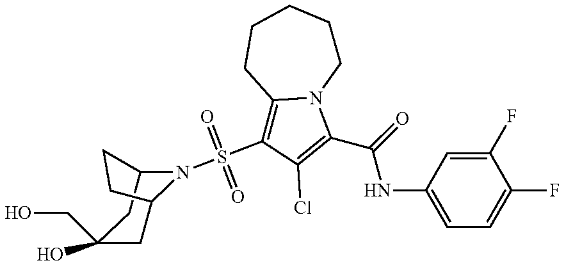 | 544 |
| 60r | 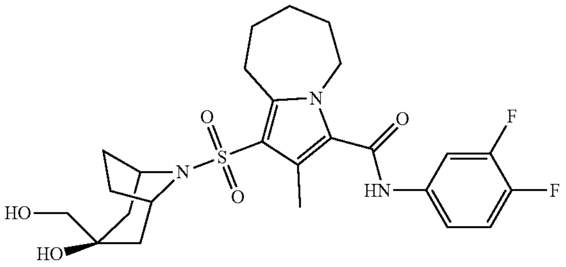 | 524 |
| 60s | 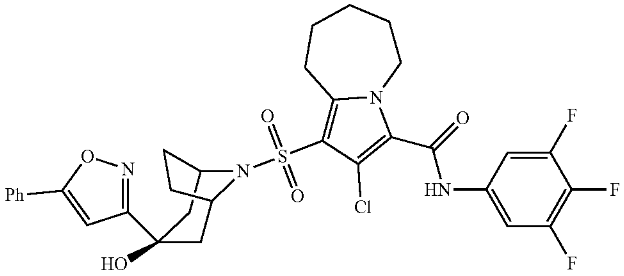 | 675 |

-continued
| Compound | Structure | Mass Spectrometry. ESI-MS, (M + H) |
|---|---|---|
| 60t | 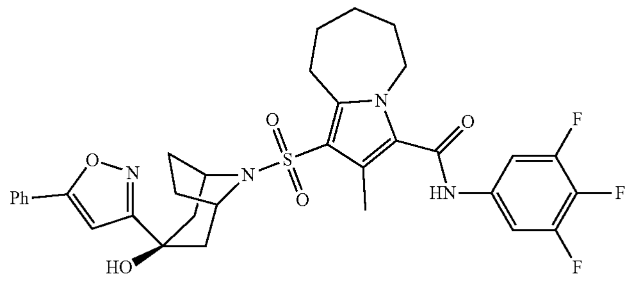 | 655 |
The following examples are the synthesis of 70 series of compounds:
Example 195 Synthesis of Compound 70a
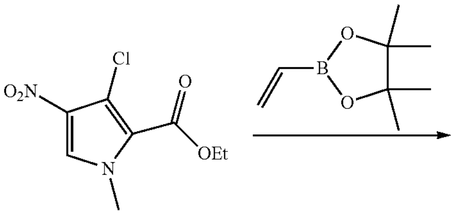
61
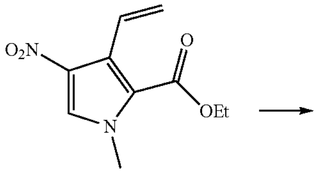
62
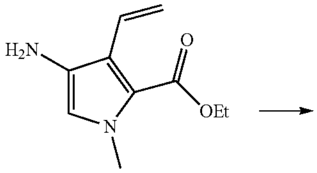
63
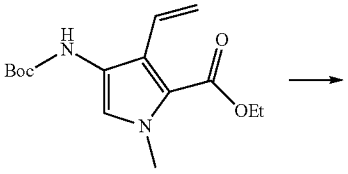
64
-continued
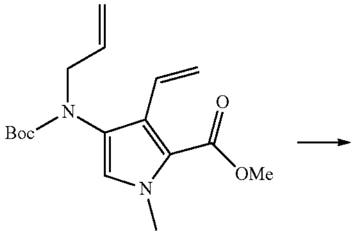
65
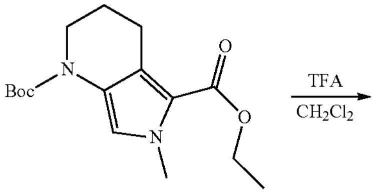
66
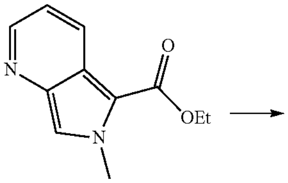
67
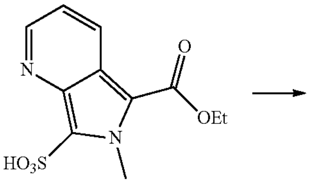
68
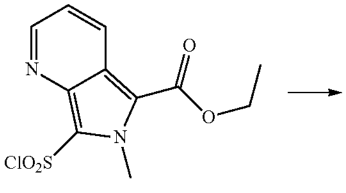
69

-continued

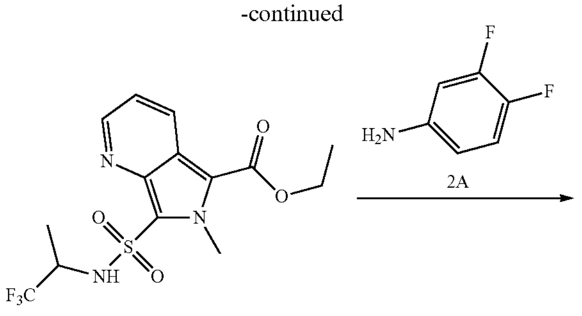

71

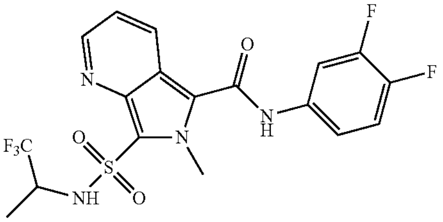

70a

Step 1:

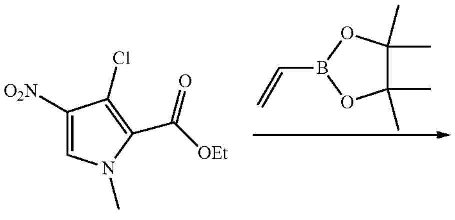

61

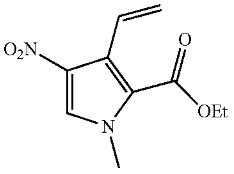

62

Compound 61 (1 g), pinacol vinyl borate (600 mg) and cesium carbonate (2.2 g) were dissolved in DMF (20 mL), then palladium acetate (130 mg) and Xphos (200 mg) were added into the reaction system. Under $N_2$ atmosphere, the mixture was reacted for 12 h, and water (30 mL) was added into the reaction system, which was then extracted with ethyl acetate (3*40 mL), dried over anhydrous sodium sulfate, spin dried and column chromatography purified to provide 800 mg of yellow solid, MS(M+1)=233.

Step 2:

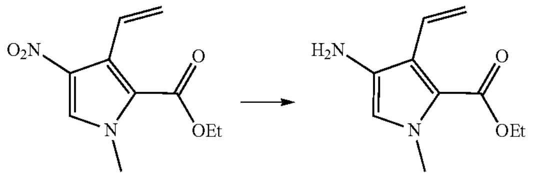

62 63

Compound 62 (4 g) was added into 50 mL of acetic acid, then 4.2 g of iron powder was added. After purged with argon for three times, and the mixture was stirred at room temperature for 20 h until TLC showed that the reaction was completed. The reaction mixture was extracted with ethyl acetate and water, the organic phase was washed with saturated sodium bicarbonate solution, dried over anhydrous sodium sulfate and purified via column chromatography to provide 1.45 g of brown oil. MS(M+1)=195.

Step 3:

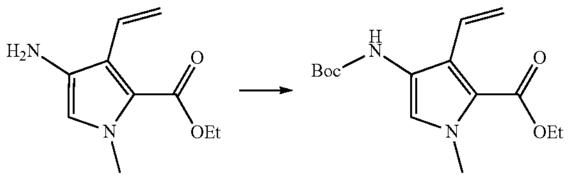

63 64

Compound 63 (1 g) was dissolved in dioxane (20 mL), and then $Boc_2O$ was added (2.25 g). After stirred uniformly, a potassium carbonate solution (2.13 g dissolved in 20 mL of water) was added dropwise. The reaction was carried out at room temperature for 3 h, TLC showed that the reaction was completed, then the mixture was extracted with ethyl acetate, dried over anhydrous sodium sulfate and purified via column chromatography to provide 967 mg of compound in a yield of 64%. MS(M+1)=295.

Step 4:

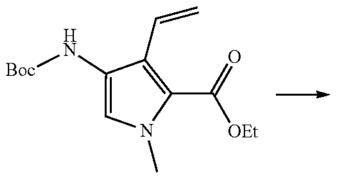

64

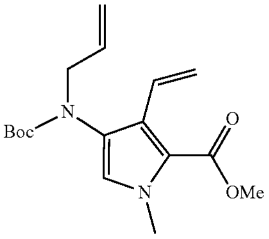

65

Under argon atmosphere, NaH (204 mg) was added into DMF, cooled to 0° C., and a solution of compound 64 (1 g in 5 mL) was added dropwise into the reaction mixture. The reaction was carried out at that temperature for 1 h, then 822 mg of allyl bromide was added. The reaction was continued for 1 h and TLC showed that the reaction was completed. The reaction solution was slowly added dropwise into saturated ammonium chloride, extracted with ethyl acetate, concentrated and purified via column chromatography to give a yellow solid 1.12 g. MS(M+1)=321.

Step 5:

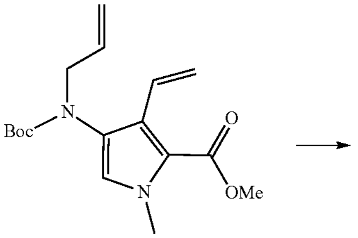

65

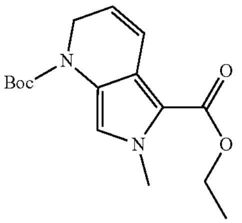

66

Compound 65 (900 mg) was dissolved in DCE (90 mL) and Zhan catalyst 1B (90 mg) was added. The mixture was refluxed for 2 h under argon atmosphere, concentrated and purified by PLC to give 320 mg of yellow solid. MS(M+1) =307.

Step 6:

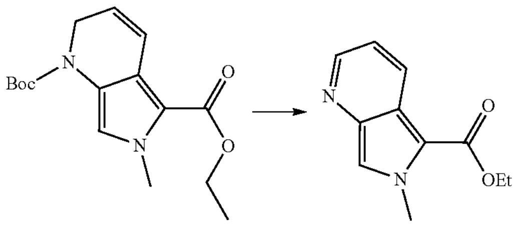

66 67

Compound 66 (320 mg) was dissolved in 20 mL of dichloromethane, and 2 drops of trifluoroacetic acid was added dropwise. The reaction was carried out under argon atmosphere for 2 h, and TLC showed that the reaction was completed. After concentration, the reaction mixture was purified by PLC to provide 200 g of crude product yellow solid, which was dissolved in ethyl acetate (10 mL) and water (10 mL), then the mixture was cooled to 0° C., then neutralized with 5% sodium hydroxide solution to pH=8-9, extracted with ethyl acetate (3*15 mL), dried over anhydrous sodium sulfate. The organic phase was spin dried and purified by column chromatography to give the compound (130 mg), MS (M+1)=205.

Step 7:

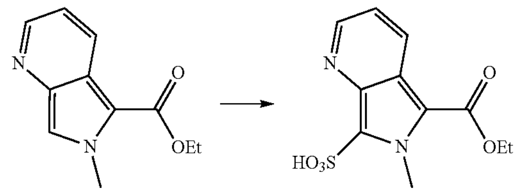

67 68

Compound 67 (130 mg) was dissolved in dichloromethane (5 mL), the system was cooled to 0° C., then chlorosulfonic acid (100 mg) was added into the reaction system and reacted at room temperature for 2 h. The reaction solution was spin dried to provide the crude product (150 mg), MS(M+1)=285.

Step 8:

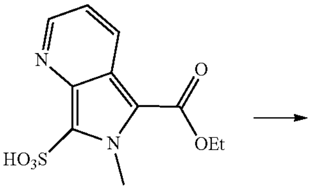

68

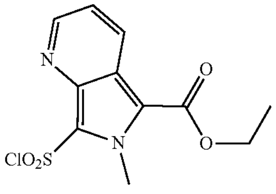

69

Compound 68 (150 mg) was dissolved in thionyl chloride (5 mL), the system was warmed to 90° C. for 2 h, and then silica gel was added into the reaction mixture, which was then spin dried and column purified to provide yellow powder. MS(M+1)=303.

Step 9:

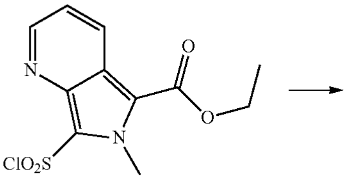

69

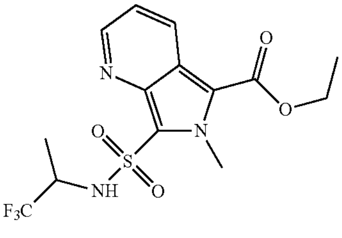

71

Compound 69 (60 mg) was dissolved in acetonitrile (3 mL), then trifluoroisopropylamine (26 mg) and pyridine (65 mg) were added into the reaction system. The system was warmed to 80° C. for 2 h, and then silica gel was added into the reaction mixture, which was then spin dried and column purified to provide yellow powder (22 mg). MS(M+1)=380.

Step 10

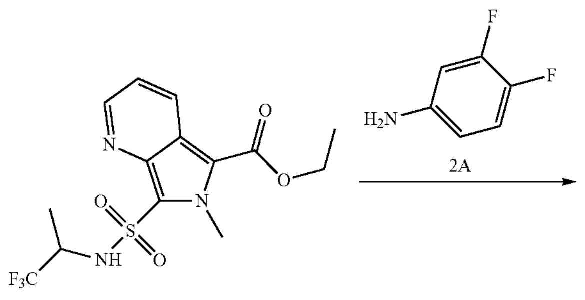

71

-continued

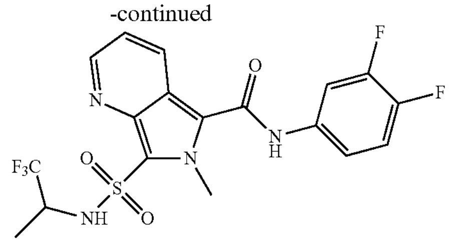

70a

Compound 7 (22 mg) and 3,4-difluoroaniline (13.6 mg) were dissolved in tetrahydrofuran (2 mL), the temperature of the system was reduced to 0° C., then NaHMDS (0.1 mL) was added dropwise into the reaction system, and reacted at room temperature for 2 h. The reaction mixture was separated by high performance liquid chromatography column to obtain Compound 70a (5 mg).

$^1$H-NMR (CDCl3,400 MHz) δ: 1.00 (d, J=2.8 Hz, 3H), 4.34 (s, 3H), 7.28-7.31 (m, 1H), 7.45-7.53 (m, 2H), 7.90-7.95 (m, 1H), 8.21-8.25 (m, 1H), 8.73 (s, 1H), 8.90-8.95 (m, 1H), 10.95 (s, 1H) Ms/ESI=463 (M+H).

The following 70 series of compounds were synthesized according to the method of example 195:

| Compound | Structure | Mass Spectrometry. ESI-MS, (M + H) |
|---|---|---|
| 70a | 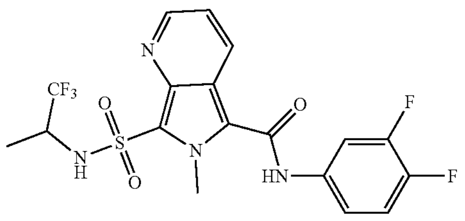 (R) | 463 |
| 70b | 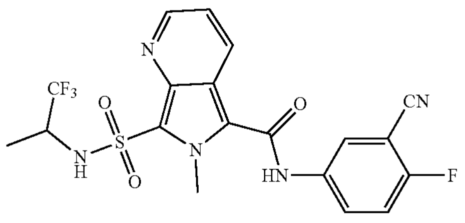 (R) | 470 |
| 70c | 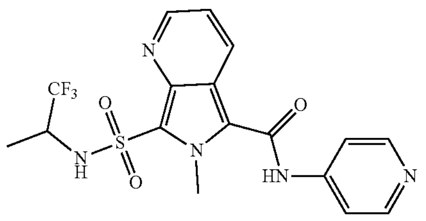 (R) | 428 |

-continued
| Compound | Structure | Mass Spectrometry. ESI-MS, (M + H) |
|---|---|---|
| 70d | 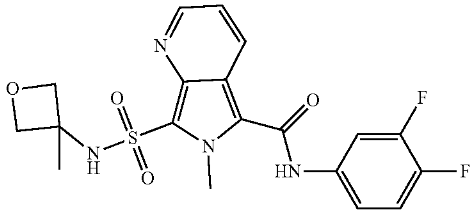 [SMILES: Cn1c(C(=O)Nc2ccc(F)c(F)c2)c2cccnc2c1S(=O)(=O)NC1(C)COC1] | 437 |
| 70e | 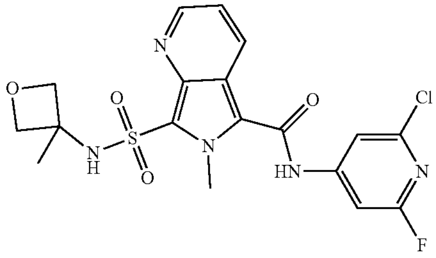 [SMILES: Cn1c(C(=O)Nc2cc(F)nc(Cl)c2)c2cccnc2c1S(=O)(=O)NC1(C)COC1] | 454 |
| 70f | 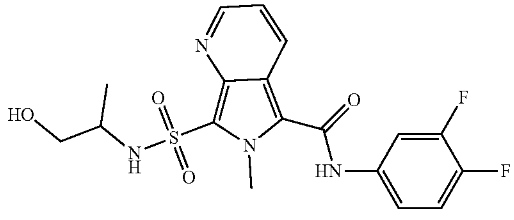 [SMILES: CC(CO)NS(=O)(=O)c1c2ncccc2c(C(=O)Nc2ccc(F)c(F)c2)n1C] | 425 |
| 70g | 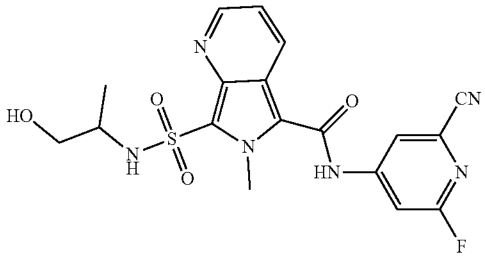 [SMILES: CC(CO)NS(=O)(=O)c1c2ncccc2c(C(=O)Nc2cc(F)nc(C#N)c2)n1C] | 433 |
| 70h | 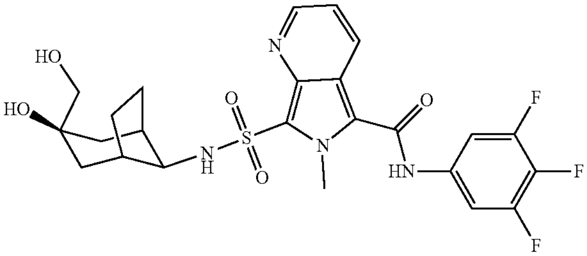 | 539 |
| 70i | 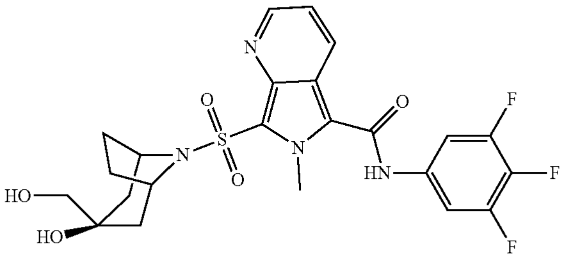 | 525 |

-continued
| Compound | Structure | Mass Spectrometry. ESI-MS, (M + H) |
|---|---|---|
| 70j | 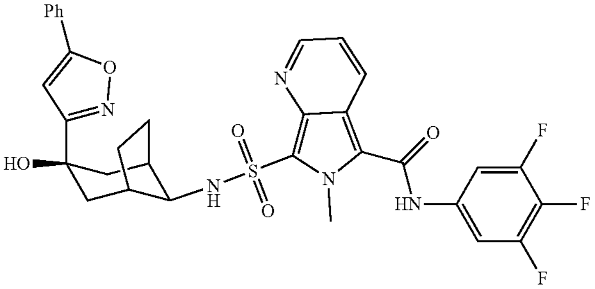 | 652 |
| 70k | 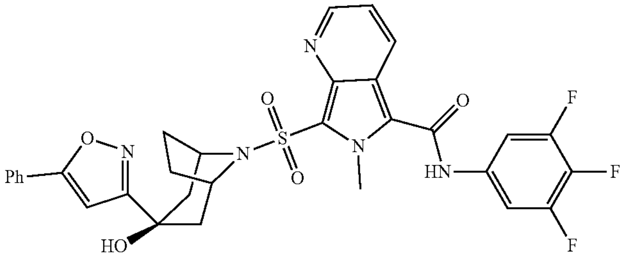 | 638 |
The following examples are the synthesis of 80 series of compounds:
Example 206: Synthesis of Compound 80a
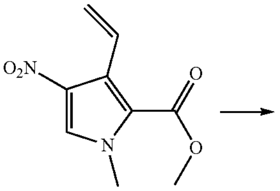
72
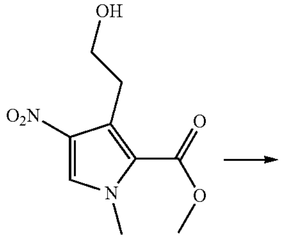
73
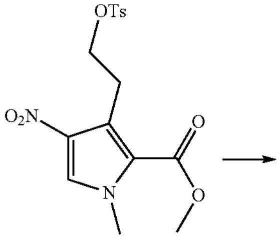
74
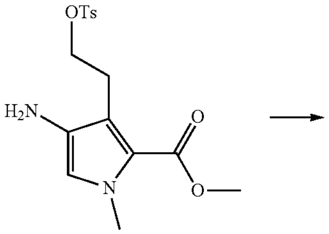
75
-continued
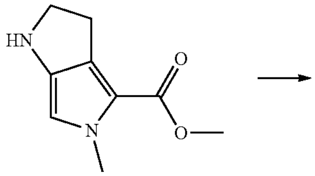
76
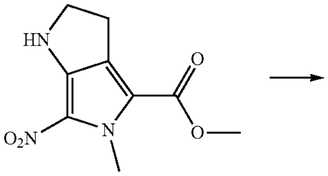
77
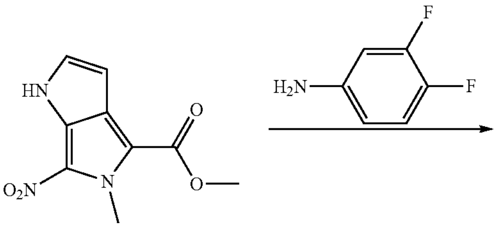
78
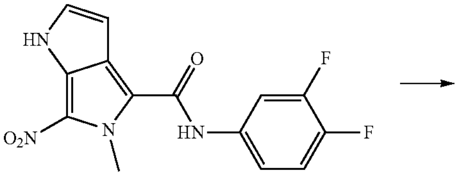
79

-continued

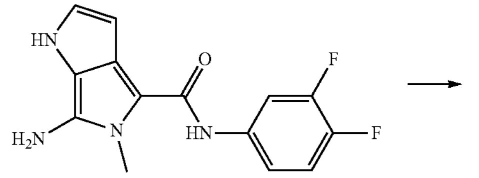

81

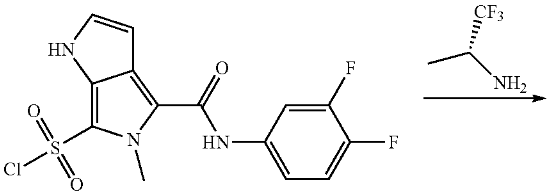

82

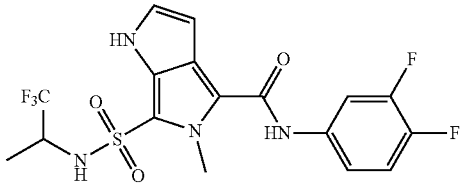

80a

Step 1:

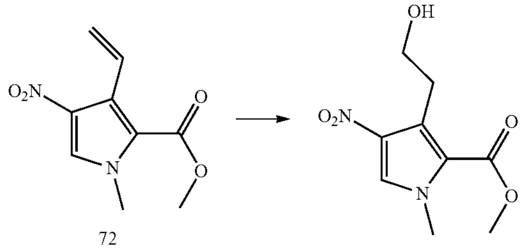

72

73

Compound 22 (10 g) was dissolved in THF (30 mL), and then the system was cooled to 0° C. 9-BBN (3.2 g) was added into the reaction system, stirred for 1 h, and $H_2O_2$ (5 mL) was added into the reaction system and reacted at room temperature for 3 h. Ethyl acetate (60 mL) and water (60 mL) was added into the reaction system, and the mixture was extracted with ethyl acetate (3*50 mL), dried over anhydrous sodium sulfate. The organic phase was spin dried, and the crude product was purified via column chromatography to obtain the compound 73. ESI-MS, (M+H=229)

Step 2:

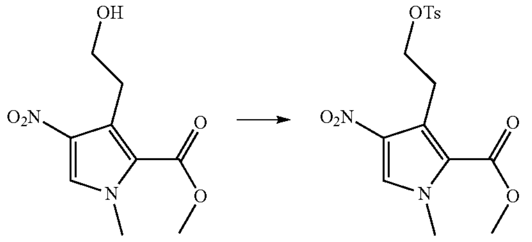

73

74

Compound 73 (8 g) was dissolved in dichloromethane (35 mL), then the system was cooled to 0° C., then p-toluenesulfonyl chloride (10 g) was added into the reaction system. The system was warmed to room temperature to react for 8 h, then the reaction system was added into ice water, extracted with ethyl acetate (3*30 mL), washed with saturated sodium hydrogen carbonate solution. The organic phase was dried over anhydrous sodium sulfate, and spin dried. The crude product was purified via column chromatography to give compound 74 (9 g), ESI-MS, (M+H=383)

Step 3:

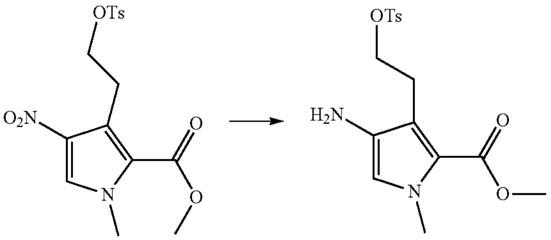

74

75

Compound 74 (9 g) was dissolved in acetic acid (50 mL), and iron powder (11 g) was added into the reaction system to react at room temperature for 3 h. Water (60 mL) was added into the reaction system, and mixture was extracted with ethyl acetate (3*50 mL), washed with saturated sodium bicarbonate, and dried over anhydrous sodium sulfate. The organic phase was spin dried and the crude product was purified by column chromatography to give a yellow solid 75 (7.2 g), ESI-MS, (M+H=353)

Step 4:

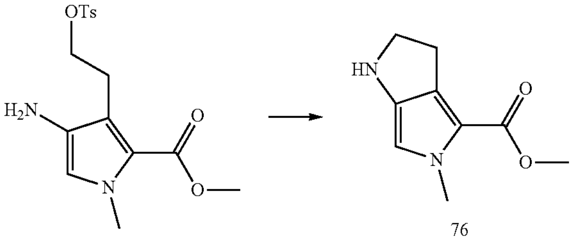

75

76

Compound 75 (7.2 g) was dissolved in ethanol (25 mL), then heated to reflux to react for 5 h. Then the reaction system was spin dried until little solvent was left, and water (25 mL) was added and mixture was extracted with ethyl acetate (3*15 mL), dried over anhydrous sodium sulfate. The organic phase was spin dried to provide yellow solid 76 (3 g), ESI-MS, (M+H=181).

Step 5:

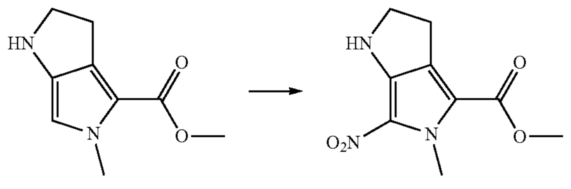

76 77

Compound 76 (3.0 g) was dissolved in acetic anhydride (10 mL), then cooled to −30° C., and concentrated nitric acid (5 mL) was added into the reaction system dropwise. After reacted for 2 h under 0° C., water (15 mL) and ethyl acetate (3*20 mL) were added to extract. The organic phase was dried over anhydrous sodium sulfate. The organic phase was spin dried, and the crude product was purified via column chromatography (n-heptane:ethyl acetate=10:1) to provide compound 77 (1.5 g), ESI-MS, (M+H=226)

Step 6:

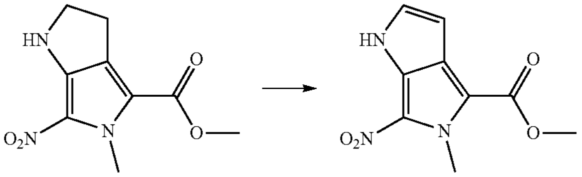

77 78

Compound 77 (1.5 g) was dissolved in chlorobenzene (12 mL), then DDQ (2.1 g) was added into the reaction system. Under nitrogen protection, the mixture was reacted overnight at 90° C., then extracted with water (25 mL) and ethyl acetate (3*25 mL), dried over anhydrous sodium sulfate. The organic phase was spin dried, and the crude product was purified by column chromatography (n-heptane:ethyl acetate=10:1) to provide Compound 78 (600 mg), ESI-MS, (M+H=224)

Step 7:

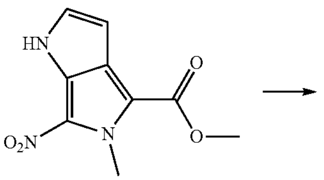

78

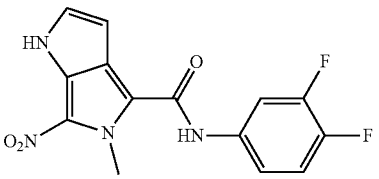

79

Compound 78 (0.6 g) and 4-fluoro-3-cyanoaniline (300 mg) were dissolved in tetrahydrofuran (10 mL), then NaHMDS (3.5 mL) was added into the reaction system. After reacting at room temperature for 8 h, the mixture was extracted with water (25 mL) and ethyl acetate (3*25 mL), dried with anhydrous sodium sulfate. The organic phase was spin dried, and the crude product was purified by column chromatography (n-Heptane:ethyl acetate=3:1) to provide compound 79 (400 mg). ESI-MS, (M+H=328)

Step 8:

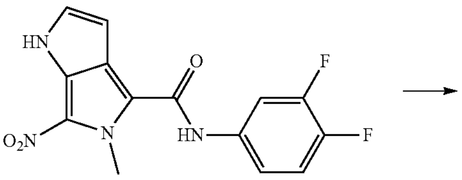

79

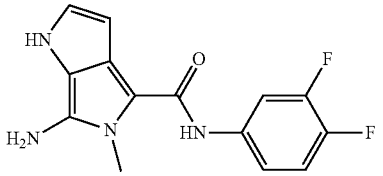

81

Compound 79 (0.4 g) was dissolved in acetic acid (5 mL), and iron powder (1.1 g) was added into the reaction system to react at room temperature for 3 h. Water (30 mL) was added into the reaction system, and the mixture was extracted with ethyl acetate (3*30 mL), washed with saturated sodium bicarbonate, and dried over anhydrous sodium sulfate. The organic phase was spin dried and the crude product was purified by column chromatography to give Compound 81 as a yellow solid (0.3 g), ESI-MS, (M+H=298)

Step 9:

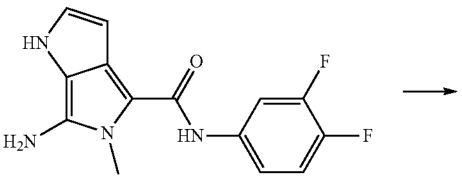

81

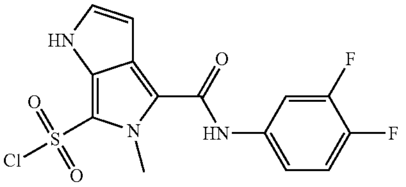

82

Compound 81 (0.3 g) was dissolved in concentrated hydrochloric acid (6 mL), then the system was cooled to −5° C., and sodium nitrite (0.11 g) was added into the reaction system, and reacted at −5° C. for 1 h. The mixture of thion chloride (0.12 g) and water (2 mL) was added into the reaction system, and reacted at 0° C. for 1.5 h. Icy water (25 mL) and ethyl acetate (3*25 mL) were added for extraction. After dried over anhydrous sodium sulfate, the organic phase was spin dried. The crude product was purified by column chromatography (n-Heptane:ethyl acetate=3:1) to provide compound 82 (150 mg). ESI-MS, (M+H=381)

Step 10:

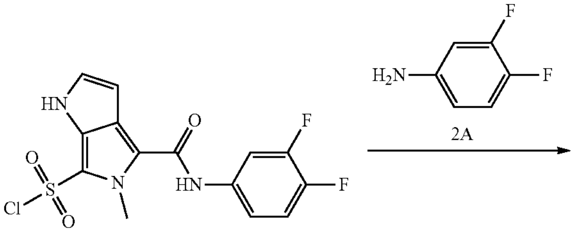
2A

82

-continued

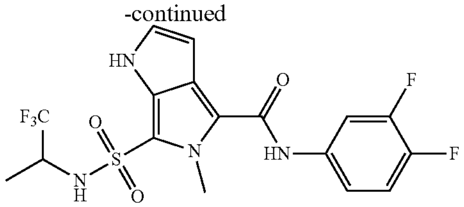

80a

Compound 82 (30 mg) and compound 33 (20 mg) were dissolved in acetonitrile (2 mL), and then pyridine (30 mg) was added into the reaction system to react at 50° C. for 5 h. The mixture was extracted with water (15 mL) and ethyl acetate (3*15 mL), dried with anhydrous sodium sulfate, and the organic phase was spin dried. The crude product was purified by column chromatography (n-heptane:ethyl acetate=1:1) to provide compound 80a. ESI-MS, (M+H=451)

The following 80 series of compounds were prepared according to the method of example 206:

| Compound | Structure | Mass Spectrometry. ESI-MS, (M + H) |
|---|---|---|
| 80b | 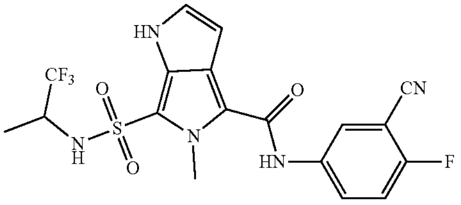 (R) | 458 |
| 80c | 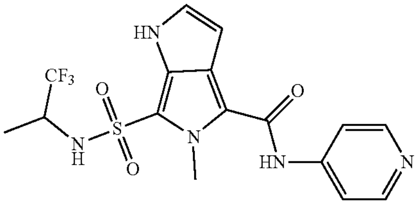 (R) | 416 |
| 80d | 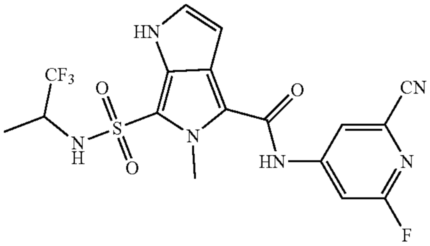 (R) | 459 |
| 80e | 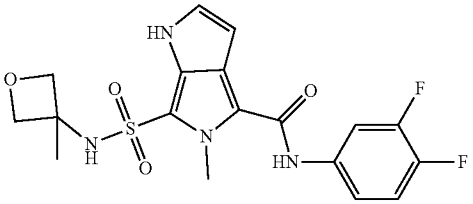 | 425 |

-continued
| Compound | Structure | Mass Spectrometry. ESI-MS, (M + H) |
|---|---|---|
| 80f | 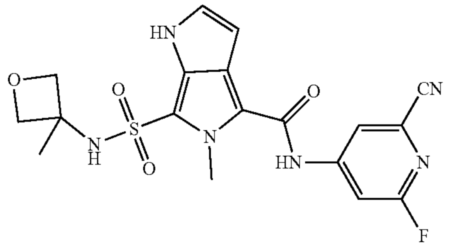 [SMILES: Cn1c(C(=O)Nc2cc(F)nc(C#N)c2)c2cc[nH]c2c1S(=O)(=O)NC1(C)COC1] | 433 |
| 80g | 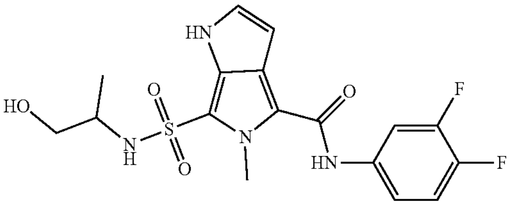 [SMILES: CC(CO)NS(=O)(=O)c1c2[nH]ccc2c(C(=O)Nc2ccc(F)c(F)c2)n1C] | 413 |
| 80h | 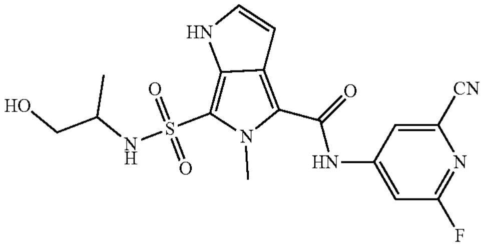 [SMILES: CC(CO)NS(=O)(=O)c1c2[nH]ccc2c(C(=O)Nc2cc(F)nc(C#N)c2)n1C] | 421 |
| 80i | 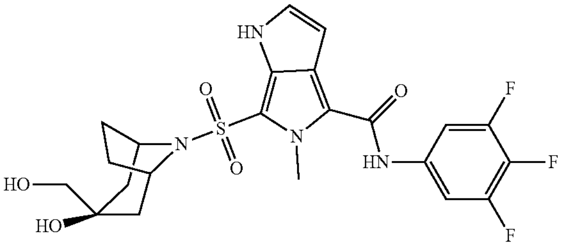 | 513 |
| 80j | 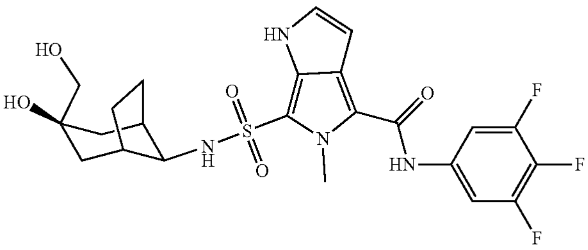 | 527 |
| 80k | 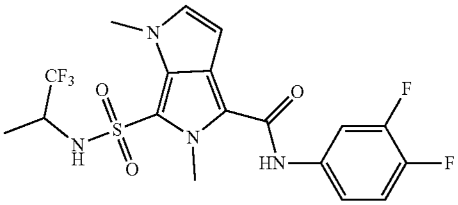 (R) | 465 |

-continued
| Compound | Structure | Mass Spectrometry. ESI-MS, (M + H) |
|---|---|---|
| 80l | 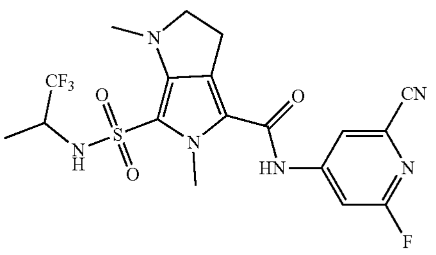 (R) | 475 |
| 80m | 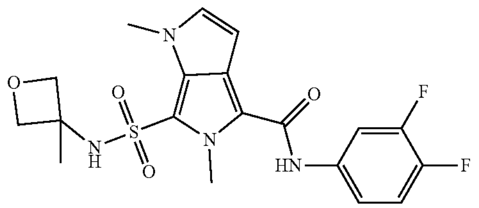 (R) | 439 |
| 80n | 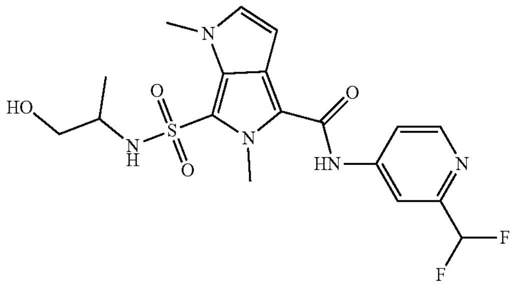 | 442 |
| 80o | 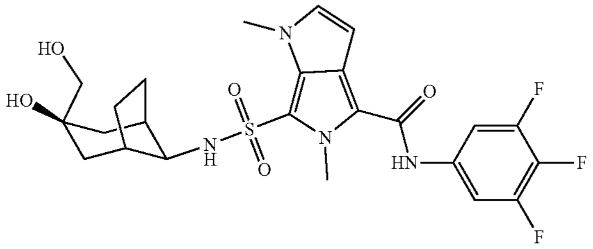 | 541 |
| 80p | 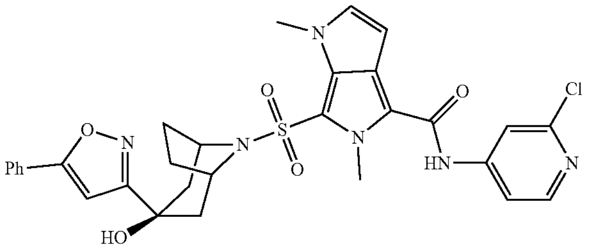 | 621 |

The following examples are the synthesis of 90 series of compounds:

Example 221 Synthesis of Compound 90a

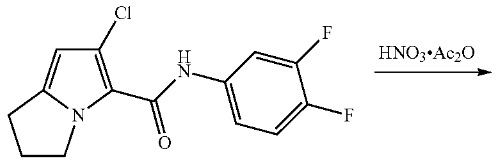

14

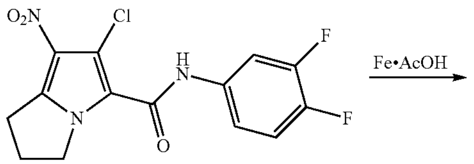

86

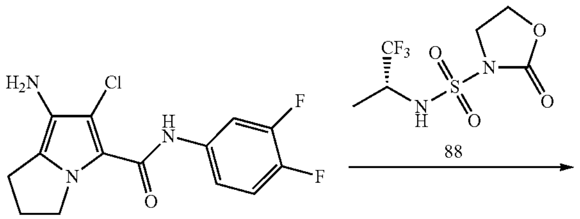

88

87

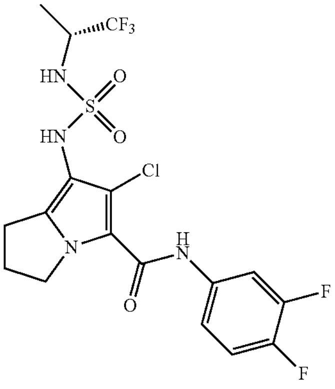

90a

Step 1:

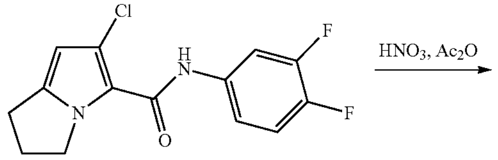

14

-continued

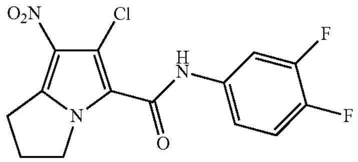

86

Compound 14 (5 g, 1 equiv) was dissolved in acid anhydride, nitric acid (4 equiv) was added under nitrogen atmosphere, and reaction was carried out at −30° C. After the reaction was completed, the mixture was directly poured into ice water, extracted with EA (3*40 mL), and washed with sodium hydrogen carbonate and dried. 200 mg of product was provided by column separation. ESI-MS (M+H=342)

Step 2:

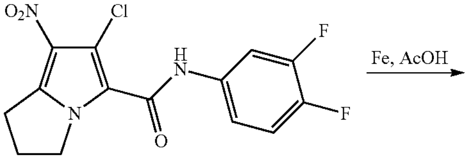

86

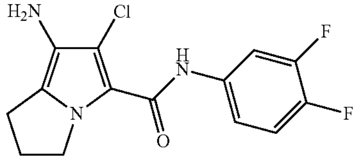

87

Under nitrogen atmosphere, the substrate 86 (200 mg) was dissolved in acetic acid, and iron powder (10 equiv) was added to react at room temperature overnight. The mixture was extracted with EA (3*40 mL), dried, and separated by column (heptane:EA=5:1) to provide 50 mg of product, ESI-MS (M+H=312).

Step 3:

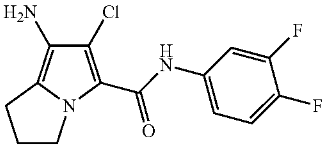

87

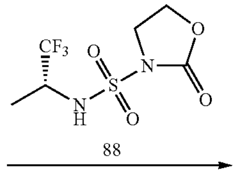

88

-continued

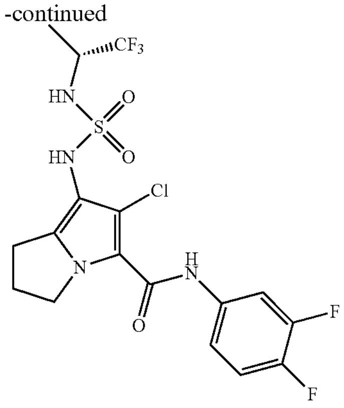

90a

Compound 87 (50 mg) was dissolved in acetonitrile (3 ml), and triethylamine (50 mg) and compound 88 (60 mg) were added to react at 80° C. After the reaction was completed, the mixture was spin dried and column purified (heptane:EA=3:1) to provide 10 mg product. $^{1}H$ NMR (400 MHz, DMSO-$d_6$) δ 9.62 (s, 1H), 8.86 (s, 1H), 7.92 (d, J=8.5 Hz, 1H), 7.86-7.73 (m, 1H), 7.53-7.33 (m, 1H), 4.22 (t, J=7.1 Hz, 2H), 3.96 (q, J=8.6, 7.5 Hz, 1H), 2.90 (t, J=7.5 Hz, 2H), 2.42-2.23 (m, 2H), 1.29 (d, J=7.0 Hz, 2H). ESI-MS (M+H=487)

The following 90 series of compounds were synthesized according to the method of example 221:

| Compound | Structure | Mass Spectrometry. ESI-MS, (M + H) |
|---|---|---|
| 90b | 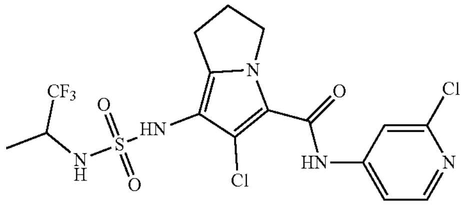 (R) | 486 |
| 90c | 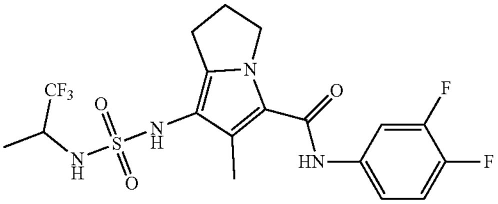 (R) | 467 |
| 90d | 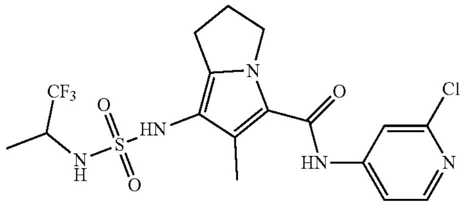 (R) | 466 |
| 90e | 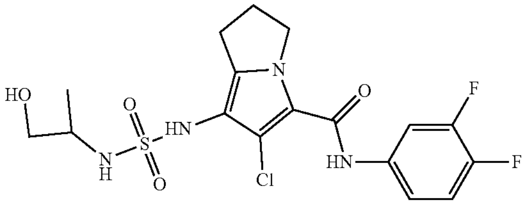 | 449 |

-continued
| Compound | Structure | Mass Spectrometry. ESI-MS, (M + H) |
|---|---|---|
| 90f | 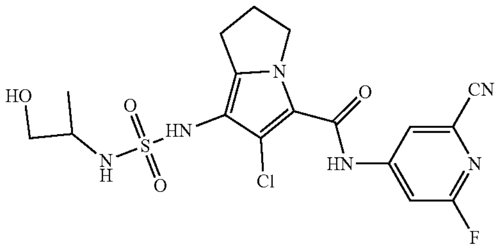 [SMILES: CC(CO)NS(=O)(=O)Nc1c(Cl)c(C(=O)Nc2cc(F)nc(C#N)c2)n2c1CCC2] | 457 |
| 90g | 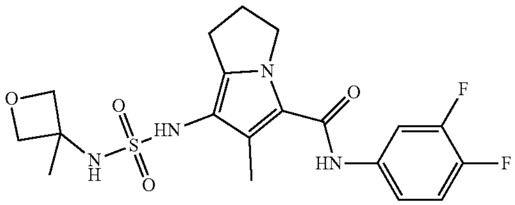 [SMILES: Cc1c(NS(=O)(=O)NC2(C)COC2)c2n(c1C(=O)Nc1ccc(F)c(F)c1)CCC2] | 441 |
| 90h | 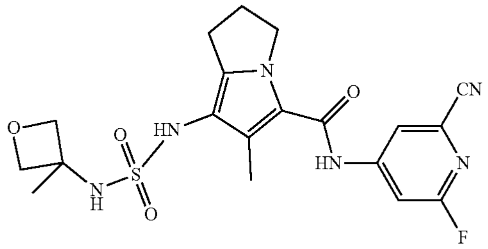 [SMILES: Cc1c(NS(=O)(=O)NC2(C)COC2)c2n(c1C(=O)Nc1cc(F)nc(C#N)c1)CCC2] | 449 |
| 90i | 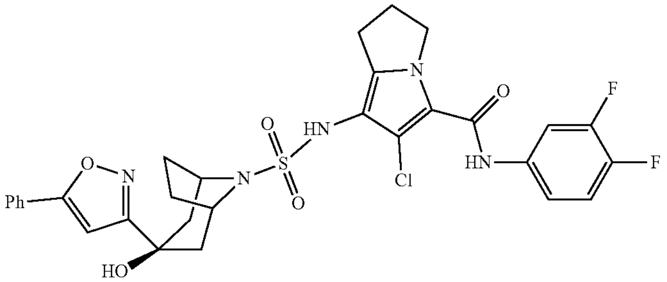 | 644 |
| 90j | 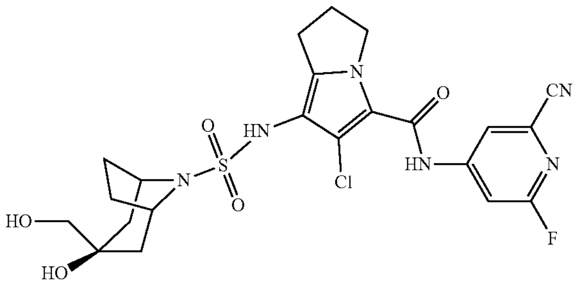 | 539 |
| 90k | 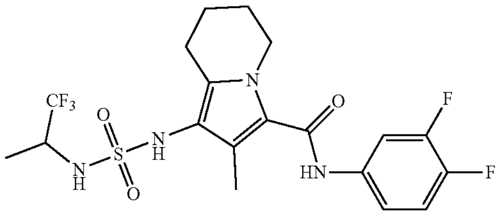 (R) | 481 |

-continued
| Compound | Structure | Mass Spectrometry. ESI-MS, (M + H) |
|---|---|---|
| 90l | 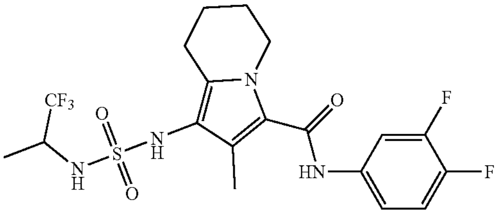 (R) | 480 |
| 90m | 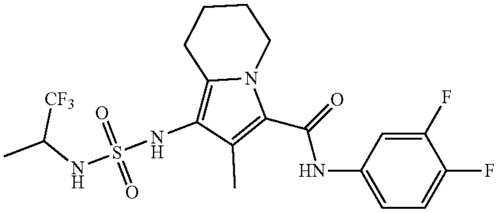 (R) | 501 |
| 90n | 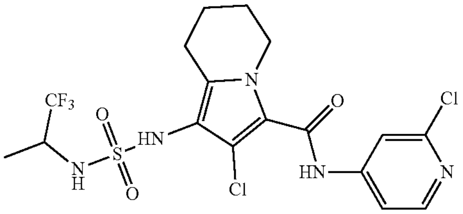 (R) | 500 |
| 90o | 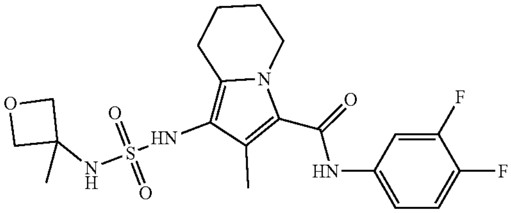 | 455 |
| 90p | 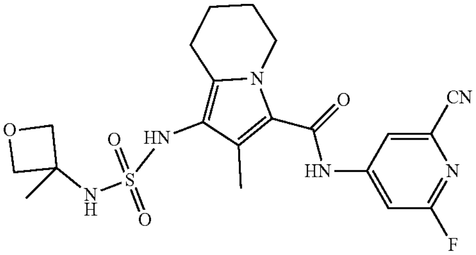 | 463 |
| 90r | 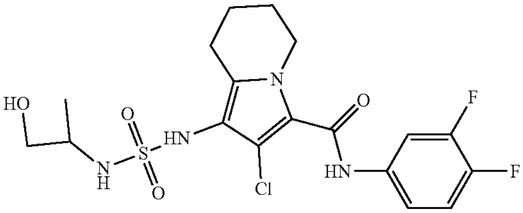 | 463 |

-continued
| Compound | Structure | Mass Spectrometry. ESI-MS, (M + H) |
|---|---|---|
| 90s | 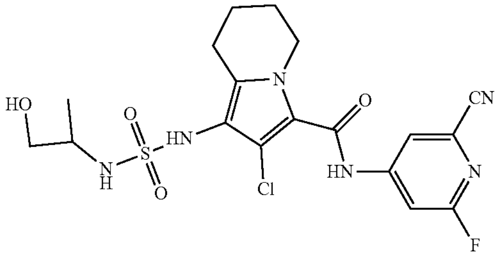 [SMILES: CC(CO)NS(=O)(=O)Nc1c(Cl)c(C(=O)Nc2cc(F)nc(C#N)c2)n2c1CCCC2] | 471 |
| 90t | 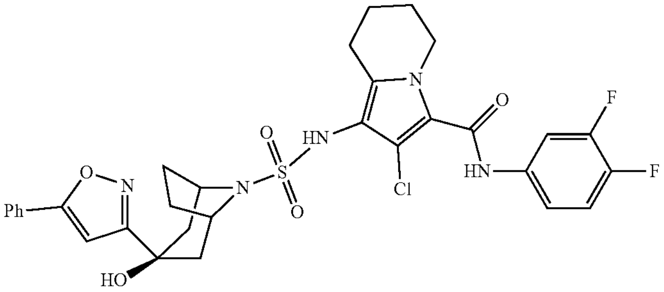 | 658 |
| 90u | 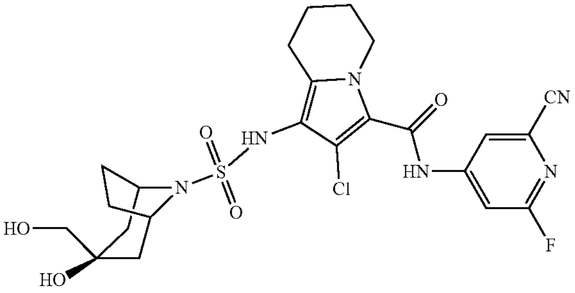 | 553 |
| 90v | 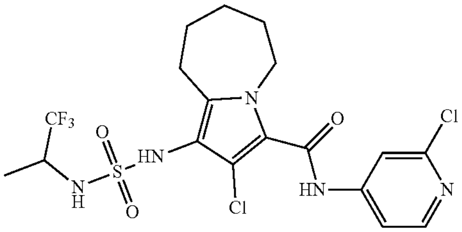 (R) | 514 |
| 90w | 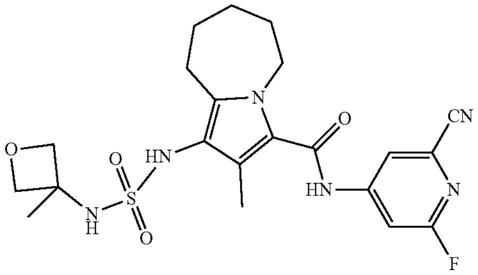 [SMILES: Cc1c(NS(=O)(=O)NC2(C)COC2)c2n(c1C(=O)Nc1cc(F)nc(C#N)c1)CCCCC2] | 477 |

-continued
| Compound | Structure | Mass Spectrometry. ESI-MS, (M + H) |
|---|---|---|
| 90x | 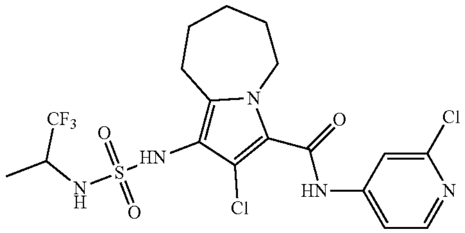 (R) | 514 |
| 90y | 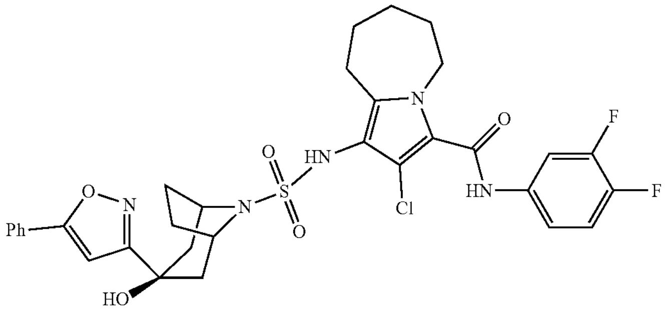 | 672 |
| 90z | 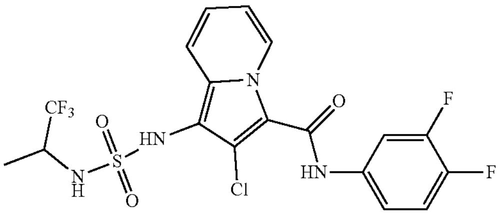 (R) | 497 |
| 90aa | 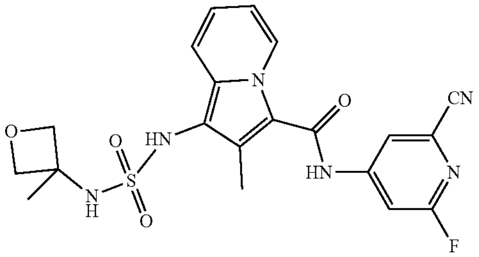 | 459 |
| 90bb | 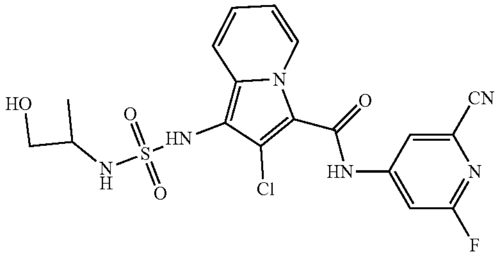 | 467 |

-continued
| Compound | Structure | Mass Spectrometry. ESI-MS, (M + H) |
|---|---|---|
| 90cc | 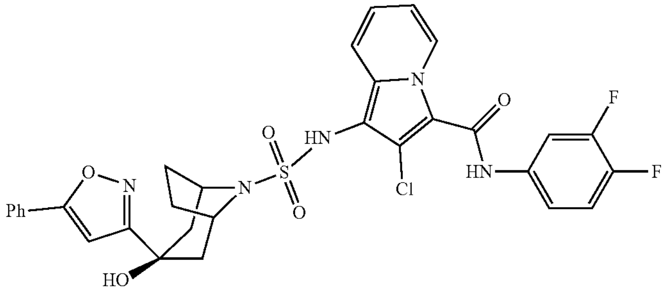 | 654 |
| 90dd | 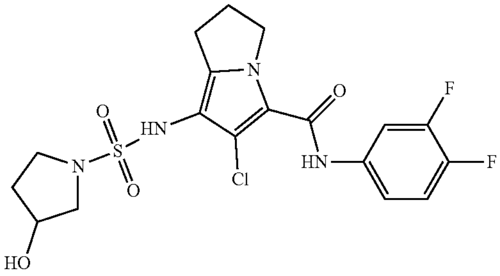 [SMILES: O=C(Nc1ccc(F)c(F)c1)c1c(Cl)c(NS(=O)(=O)N2CCC(O)C2)c2n1CCC2] | 461 |
| 90ee | 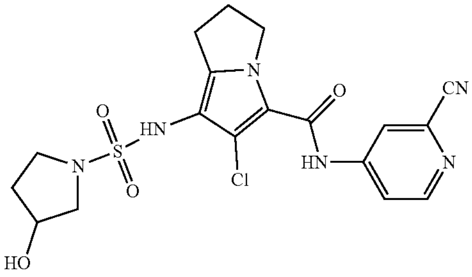 [SMILES: N#Cc1cc(NC(=O)c2c(Cl)c(NS(=O)(=O)N3CCC(O)C3)c3n2CCC3)ccn1] | 451 |
| 90ff | 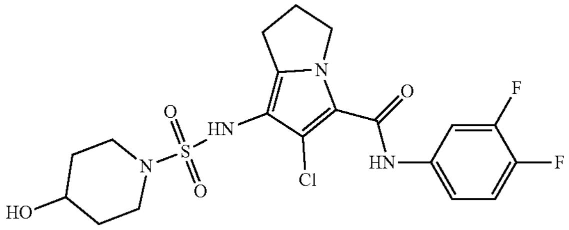 [SMILES: O=C(Nc1ccc(F)c(F)c1)c1c(Cl)c(NS(=O)(=O)N2CCC(O)CC2)c2n1CCC2] | 474 |
| 90gg | 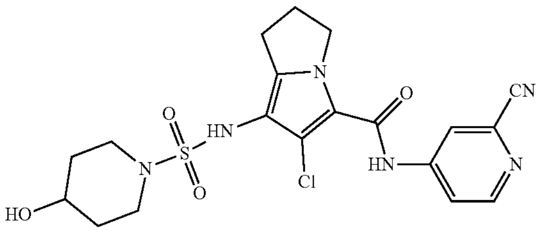 [SMILES: N#Cc1cc(NC(=O)c2c(Cl)c(NS(=O)(=O)N3CCC(O)CC3)c3n2CCC3)ccn1] | 465 |

-continued

| Compound | Structure | Mass Spectrometry. ESI-MS, (M + H) |
|---|---|---|
| 90hh | 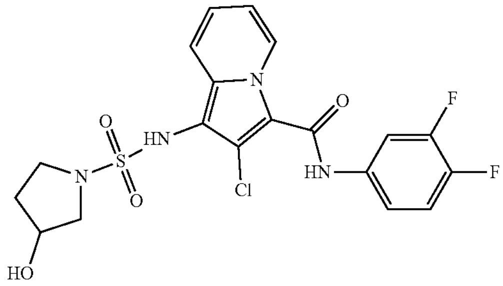 [SMILES: O=C(Nc1ccc(F)c(F)c1)c1c(Cl)c(NS(=O)(=O)N2CCC(O)C2)c2ccccn12] | 471 |
| 90ii | 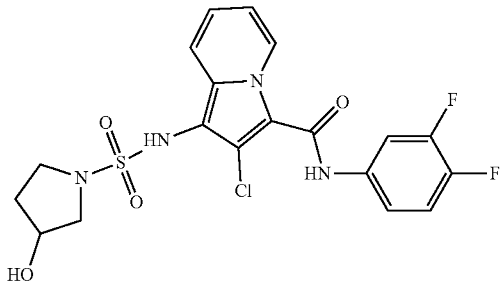 [SMILES: O=C(Nc1ccc(F)c(F)c1)c1c(Cl)c(NS(=O)(=O)N2CCC(O)C2)c2ccccn12] | 461 |

The following examples are the synthesis of 100 series of compounds:

Example 256 Synthesis of Compound 100a

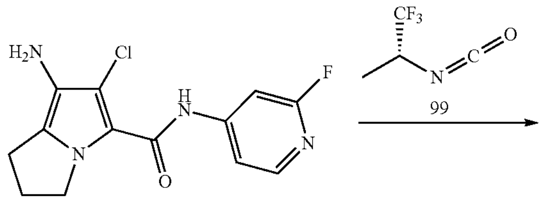

100

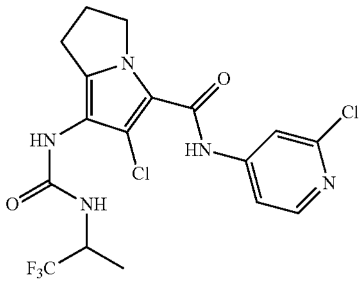

100 b

Step 1:

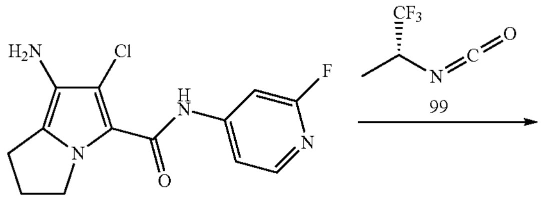

100

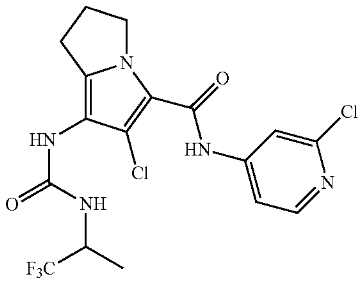

100 b

Compound 100 (50 mg) was dissolved in acetonitrile (3 ml), and triethylamine (50 mg) and compound 99 (60 mg) were added to react at 80° C. After the reaction was completed, the mixture was spin dried and column purified (heptane:EA=3:1) to provide 10 mg product. ESI-MS (M+H=450)

The following 100 series of compounds were synthesized according to the method of example 221:

| Compound | Structure | Mass Spectrometry. ESI-MS, (M + H) |
|---|---|---|
| 100b | 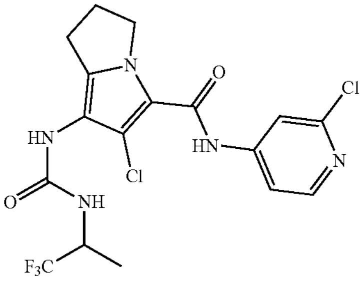 (R) | 450 |
| 100d | 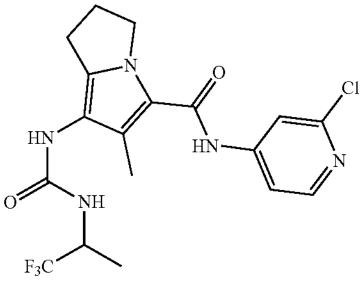 (R) | 430 |
| 100p | 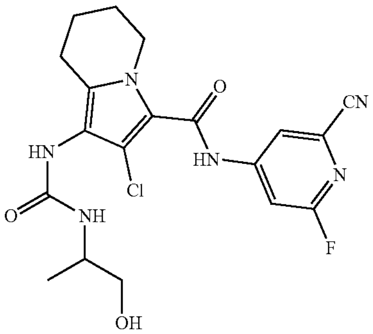 | 435 |
| 100q | 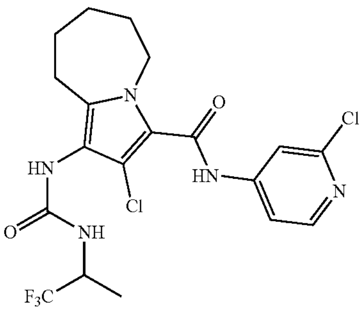 (R) | 478 |

-continued

| Compound | Structure | Mass Spectrometry. ESI-MS, (M + H) |
|---|---|---|
| 100r | 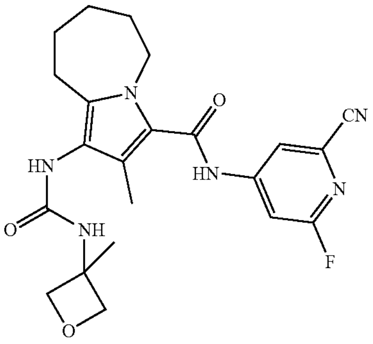 [SMILES: Cc1c(NC(=O)NC2(C)COC2)c2n(c1C(=O)Nc1cc(F)nc(C#N)c1)CCCCC2] | 441 |

Biological Examples—Anti-HBV Activity Experiment

Experiment 1: In Vitro Anti-HBV Nucleocapsid Assembly Activity Test

Main Reagents and Raw Materials:

C150 protein was expressed and purified by WuXi Apptec Co., Ltd.

BoDIPY® FL was purchased from Thermo Fisher Scientific.

Protein Fluorescent Label:

150 μL of 2% w/v skimmed milk was added into each well of 96-well plate, and incubated at room temperature for 2 hours. The skimmed milk was aspirated. The plate was washed with deionized water and dried, and stored at room temperature. C150 protein (3 mg per tube) was desalted with 5 ml Hitrap desalting column. The desalted C150 protein of each tube was added with 50 mM BoDIPY® FL Fluorescent Dye (20 μl), and incubated under 4° C. overnight in the dark after well mixed. Sephadex G-25 gel was used for filtration to remove fluorescent dyes that were not bounded onto C150. The C150 fluorescent labeling efficiency was calculated according to the following equation:

[BoDIPY®FL]=A504/78,000 $M^{-1}$;

[C150Bo]=(A280−[BoDIPY®FL]×1300 $M^{-1}$)/60,900 $M^{-1}$;

Fluorescent Labeling Efficiency=[BoDIPY®FL]/[C150Bo];

Wherein,

[BoDIPY®FL] represents the concentration of the fluorescent label;

[C150Bo] represents the concentration of fluorescently labeled protein;

A504 represents the absorbance value at 504 nM wavelength;

A280 represents the absorbance value at 280 nM wavelength;

$M^{-1}$ represents the reciprocal of the molar concentration.

Compound Dilution:

The mother liquor of compound was diluted with DMSO to 6 mM, then diluted to 600 μM with 50 mM HEPES, and then further 3-fold diluted with 10 DMSO/50 mM HEPES to 8 concentrations.

C150Bo was diluted to 2 μM with 50 mM HEPES. 37.5 μL of C150Bo and 2.5 μL of compound at each concentration were added into a 96 well plate and well mixed, then incubated at room temperature for 15 minutes. 10 μl of 750 mM NaCl/50 mM HEPES were added into the each reaction well, and the final concentration of NaCl was 150 mM.

Into the control wells in the 0% protein group 10 μL of 50 mM HEPES was added, and the final concentration of NaCl was 0 mM.

Into the control wells in the 100% protein group 10 μL of 5 M/50 mM HEPES was added, and the final concentration of NaCl was 1 M.

The final concentration of DMSO was 0.5%, the maximum final concentration of the compound was 30 μM, and final concentration of C150Bo was 1.5 μM. The mixture was incubated at room temperature for 1 hour. Fluorescence signal was measured (excitation light was 485 nm; emission light was 535 nm).

Data Analysis

% protein assembly=[1−(Sample fluorescence value−1 M NaCl fluorescence value)/(0 M NaCl fluorescence value−1 M NaCl fluorescence value)]×100.

$IC_{50}$ value was calculated by prism software, and the equation was as follows:

$$Y=Bottom+(Top-Bottom)/(1+10^{((LogIC50-X)HillSlope)});$$

wherein,

X represents the logarithm of the concentration, Y represents the effect value, and Y starts from the bottom and fits to the top by S type fitting.

Bottom represents the bottom of the curve;

Top represents the top of the curve;

HillSlope represents the absolute value of the maximum slope of the curve.

Experiment 2: Determination of Anti-HBV Activity in HepG2.2.15 Cell

Main Reagents:

QIAamp 96 DNA Blood Kit (12) (Qiagen, Item No. 51162);

FastStart Universal Probe Master (Roche, Item No. 04914058001);

Cell-titer Glo Testing Reagent (Promega, Item No. G7573).

Compound dilution. All the compounds for in vitro anti-HBV activity assay and cytotoxicity assay were 3-fold diluted into 8 concentrations. The final concentration of the tested compound was 30 μM, the final starting concentration of reference compound GLS4 was 1 μM, and the final concentration of DMSO was 0.5%.

HepG2.2.15 cell ($4\times10^4$ cell/well) was inoculated into 96 well plate, and cultured overnight in 37° C., 5% $CO_2$. On the second day, fresh culture medium containing different concentrations of the compound was added into the culture wells. On the fifth day, the old culture solution in the culture well was aspirated and fresh culture medium containing different concentrations of the compound was added.

On the eighth day, the supernatant in the culture well was collected for extraction of HBV DNA, and the content of DNA in the supernatant of HepG2.2.15 HBV was detected by qPCR. After the supernatant was collected, the medium and Cell-titer Glo reagent were added into the culture well, and the chemiluminescence value of each well was measured by microplate reader.

The activity calculation formula was as follows:

$$Y=Bottom+(Top-Bottom)/(1+10^{((LogIC50-X)*Hillslope)});$$

wherein,

X represents the logarithm of the concentration, Y represents the effect value, and Y starts from the bottom and fits to the top by S type fitting.

Bottom represents the bottom of the curve;

Top represents the top of the curve;

HillSlope represents the absolute value of the maximum slope of the curve.

Experiment 3: Determination of Cytotoxicity

The cytotoxicity of the test compound was tested using HepG2 cells. The cells were incubated for 4 days in the presence of the test compound. Cell activity was assessed using the resazurin assay.

The results showed that the compound of the present invention had good anti-HBV nucleocapsid assembly activity and anti-HBV activity in vitro, and had low cytotoxicity.

The activity data of Experiments 1 to 3 are shown in Table 13:

TABLE 13

| Compound No. | Experiment 1 Protein experiment $IC_{50}$ (μM) | Experiment 2 Cell experiment $EC_{50}$ (nM) | Experiment 3 Cytotoxicity $CC_{50}$ (nM) |
|---|---|---|---|
| 10a | ++ | +++ | >30000 |
| 10b | ++ | +++ | >30000 |
| 10c | ++ | +++ | >30000 |
| 10d | ++ | ++ | >30000 |
| 10e | ++ | ++ | >30000 |
| 10f | ++ | +++ | >30000 |
| 10g | ++ | +++ | >30000 |
| 10aa | ++ | ++ | >30000 |
| 10mm | ++ | ++ | >30000 |
| 10oo | ++ | ++ | >30000 |
| 10vv | ++ | +++ | >30000 |
| 10ww | ++ | +++ | >30000 |
| 20a | ++ | +++ | >30000 |
| 20b | +++ | +++ | >30000 |
| 20cc | ++ | ++ | >30000 |
| 20dd | ++ | ++ | >30000 |
| 20ee | ++ | +++ | >30000 |
| 20ff | ++ | +++ | >30000 |
| 20ii | ++ | ++ | >30000 |
| 20jj | ++ | ++ | >30000 |
| 20kk | ++ | +++ | >30000 |
| 20ll | ++ | +++ | >30000 |
| 30a | +++ | +++ | >30000 |
| 30b | ++ | +++ | >30000 |
| 30c | ++ | +++ | >30000 |
| 30r | ++ | +++ | >30000 |
| 30s | ++ | ++ | >30000 |
| 30t | ++ | ++ | >30000 |
| 40a | +++ | +++ | >30000 |
| 40b | ++ | +++ | >30000 |
| 40c | ++ | +++ | >30000 |
| 40d | ++ | +++ | >30000 |
| 40e | ++ | +++ | >30000 |
| 40f | ++ | +++ | >30000 |
| 50a | ++ | +++ | >30000 |
| 50b | + | +++ | >30000 |
| 60a | + | +++ | >30000 |
| 60b | ++ | +++ | >30000 |
| 70a | + | +++ | >30000 |
| 70b | + | +++ | >30000 |
| 80a | ++ | ++ | >30000 |
| 80b | ++ | ++ | >30000 |
| 80d | ++ | +++ | >30000 |
| 80f | ++ | +++ | >30000 |
| 90a | ++ | +++ | >30000 |
| 90b | ++ | +++ | >30000 |
| 90f | ++ | +++ | >30000 |
| 90g | ++ | +++ | >30000 |
| 90h | ++ | +++ | >30000 |
| 100b | ++ | +++ | >30000 |
| 100d | ++ | +++ | >30000 |
| 100p | ++ | +++ | >30000 |

TABLE 13-continued

| Compound No. | Experiment 1 Protein experiment $IC_{50}$ (μM) | Experiment 2 Cell experiment $EC_{50}$ (nM) | Experiment 3 Cytotoxicity $CC_{50}$ (nM) |
|---|---|---|---|
| 100q | ++ | +++ | >30000 |
| 100r | ++ | +++ | >30000 |

wherein in the second column of the table:
+++ indicates $IC_{50}$ is > 1 μM;
++ indicates that $IC_{50}$ is 1-100 μM;
+ indicates that $IC_{50}$ is > 100 μM;
and in the third column of the table:
++++ indicates $EC_{50}$ < 0.1 nM;
+++ indicates that $EC_{50}$ is 0.1-100 nM;
++ indicates that $EC_{50}$ is 100-1000 nM;
+ indicates that $EC_{50}$ is > 1000 nM.

Therefore, the compounds of the present application have excellent anti-HBV activity.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of formula (A1):

(A1)

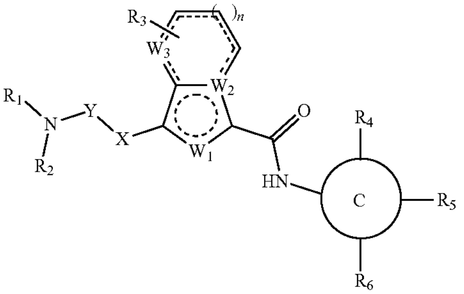

or a pharmaceutically acceptable salt, stereoisomer, or tautomer thereof, wherein:

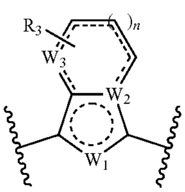

is

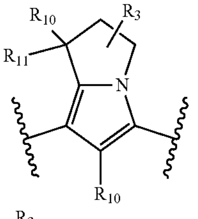

or

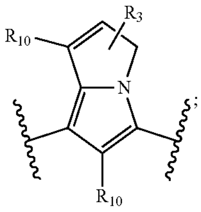

;

X is absent or —$NR_9$—;

Y is —$S(O)_2$—;

ring C is phenyl or pyridinyl, wherein the phenyl or pyridinyl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, =O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more halocycloalkyl, $C_6$-$C_{10}$ aryl, $C_6$-$C_{10}$ haloaryl, and 5- to 10-membered heteroaryl, and further wherein each 5-to 10-membered heteroaryl substituent independently has 1, 2, or 3 heteroatoms independently selected from the group consisting of N, O, and S, and is optionally and independently substituted with one or more substituents independently selected from the group consisting of halogen and phenyl.

2. The compound of claim 1, or a pharmaceutically acceptable salt, stereoisomer, or tautomer thereof, wherein ring C is phenyl.

3. The compound of claim 1, or a pharmaceutically acceptable salt, stereoisomer, or tautomer thereof, wherein:

$R_1$ is $C_1$-$C_4$ alkyl, wherein the $C_1$-$C_4$ alkyl is optionally substituted with one or more substituents independently selected from the group consisting of halogen and OH; and $R_2$ is H.

4. The compound of claim 1, wherein the compound is of formula (IX) or formula (X):

(IX)

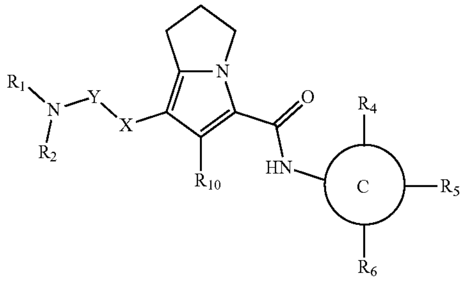

or (X)

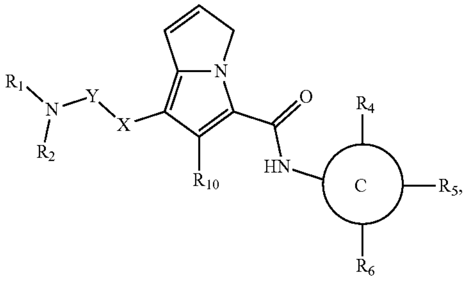

or a pharmaceutically acceptable salt, stereoisomer, or tautomer thereof, wherein:

$R_{10}$ is halogen or $C_1$-$C_4$ alkyl.

5. The compound of claim 1, or a stereoisomer thereof, wherein the compound, or stereoisomer thereof, is selected from the group consisting of:

-continued
10a
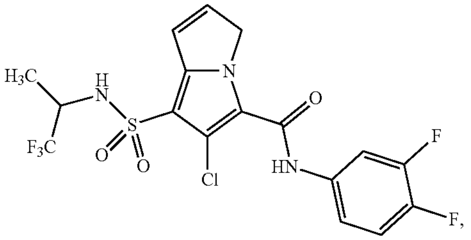
10b
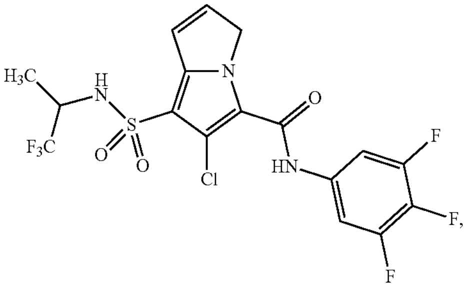
10c
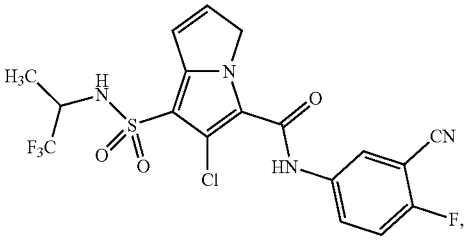
10d
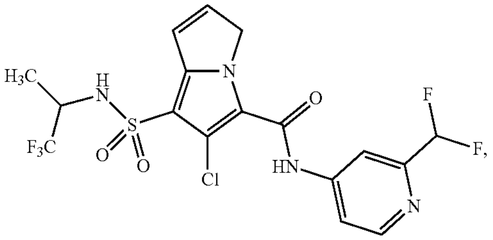
10e
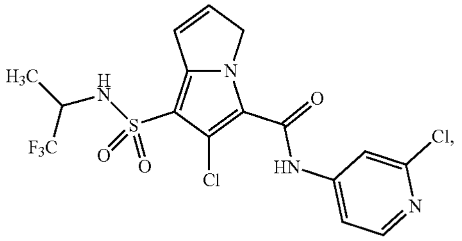
10f
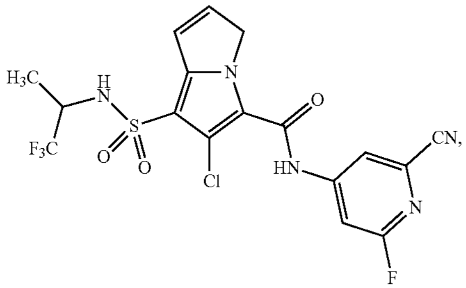
10g
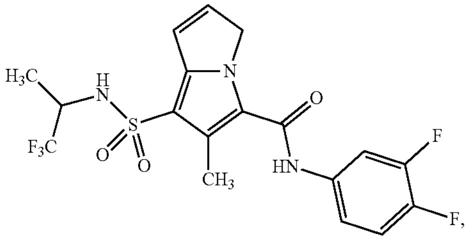
10h
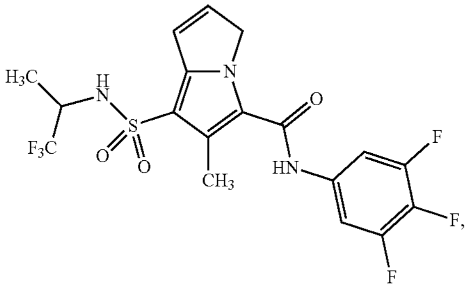
10i
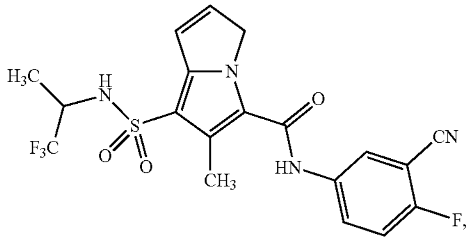
10j
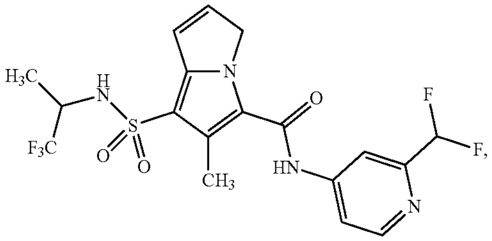
10k
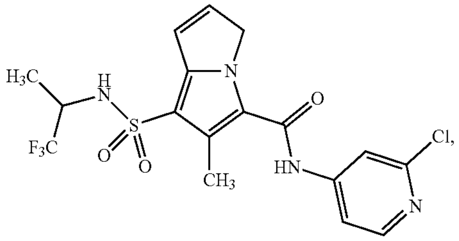
10l
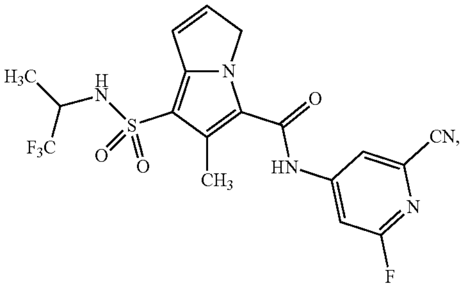

-continued
10m
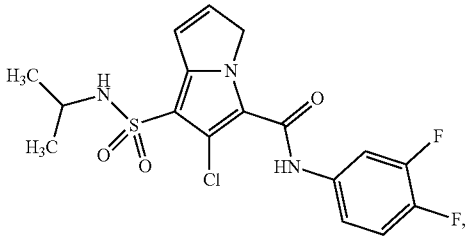
10n
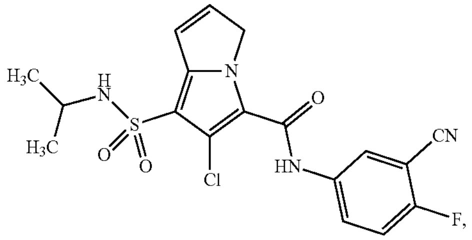
10o
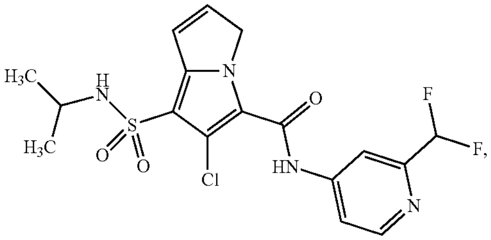
10p
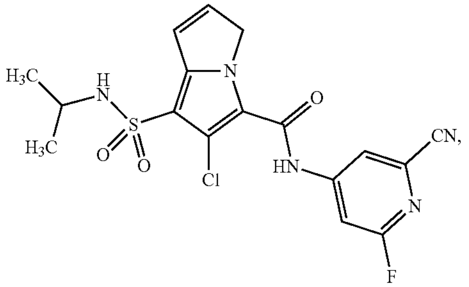
10q
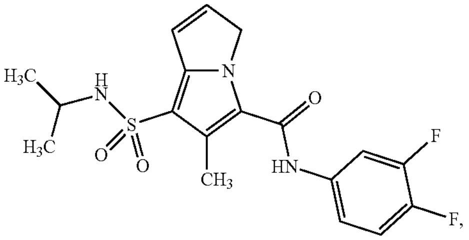
10r
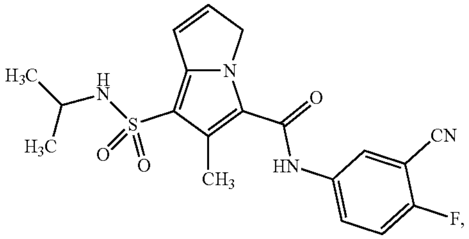
-continued
10s
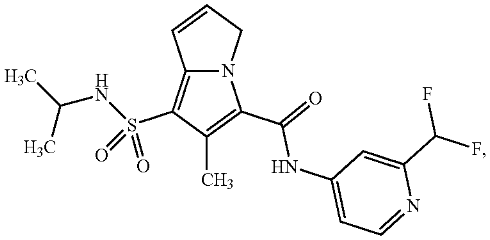
10t
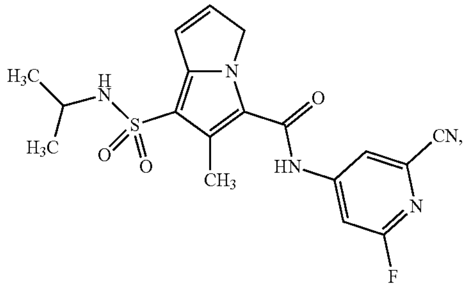
10u
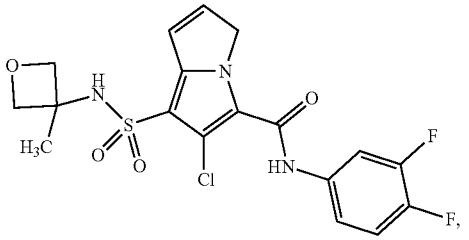
10v
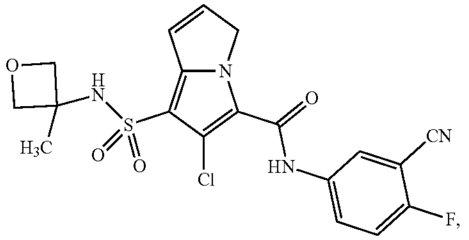
10w
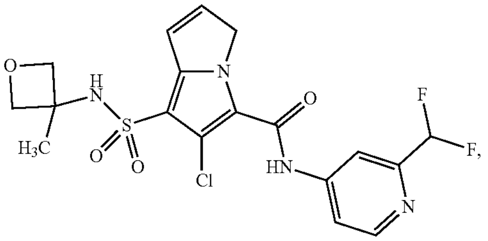
10x
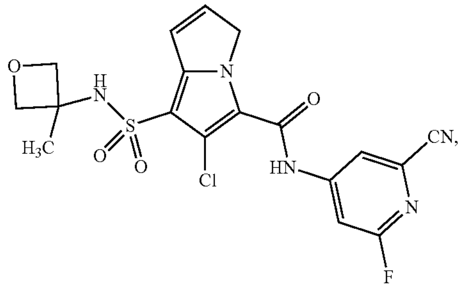

-continued
10y
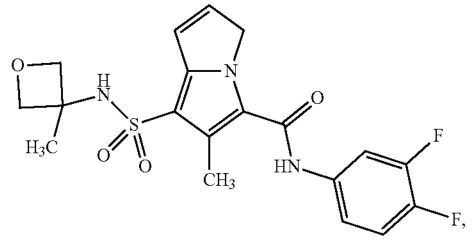
10z
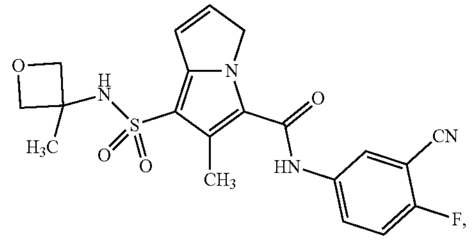
10aa
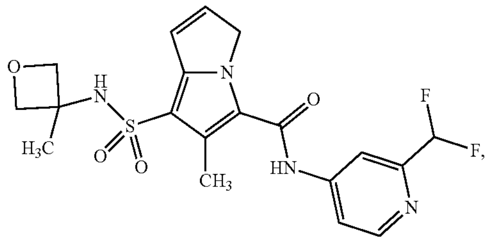
10bb
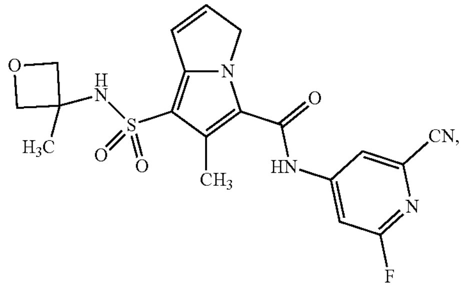
10cc
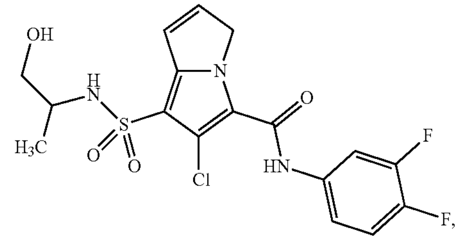
10dd
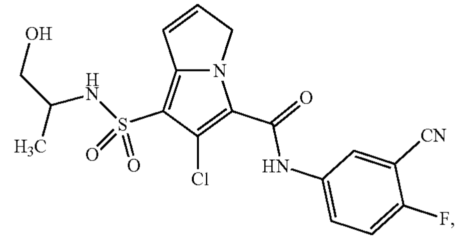
-continued
10ee
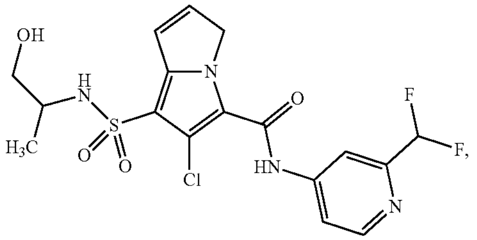
10ff
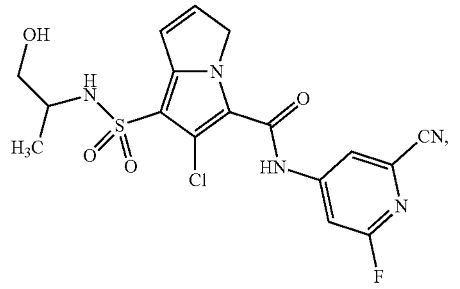
10gg
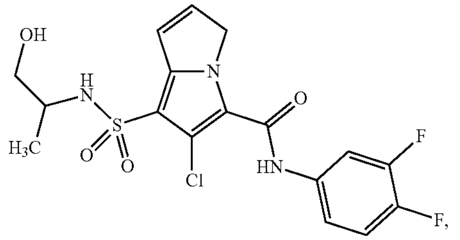
10hh
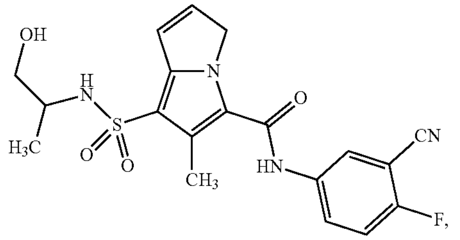
10ii
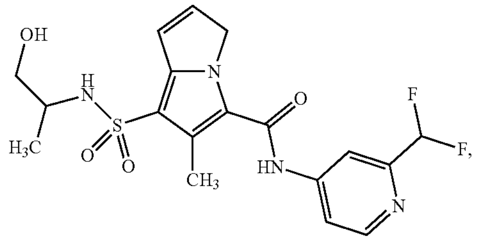
10jj
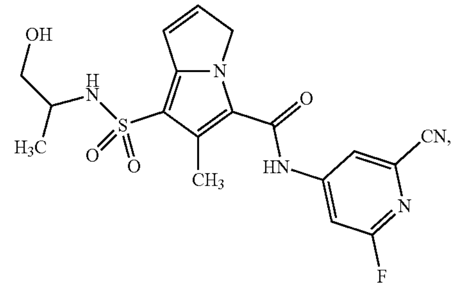

-continued
10kk
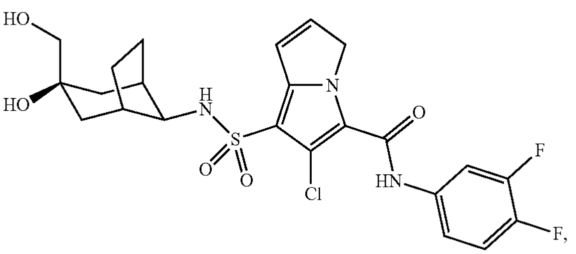
10ll
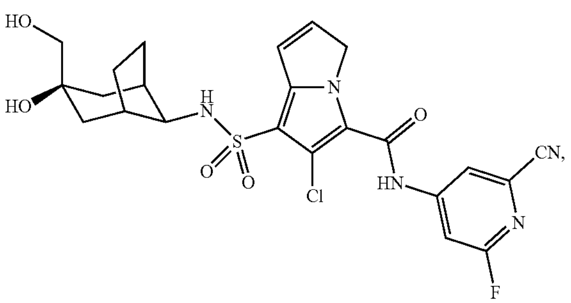
10mm
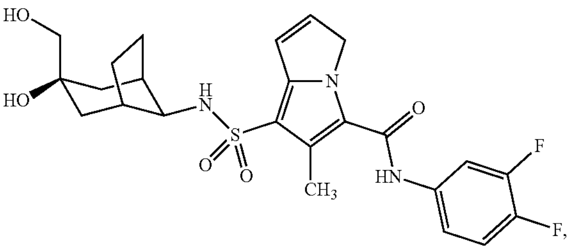
10nn
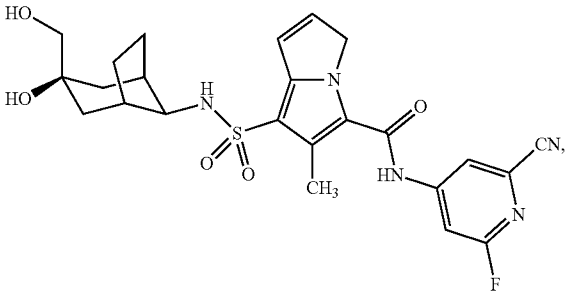
10oo
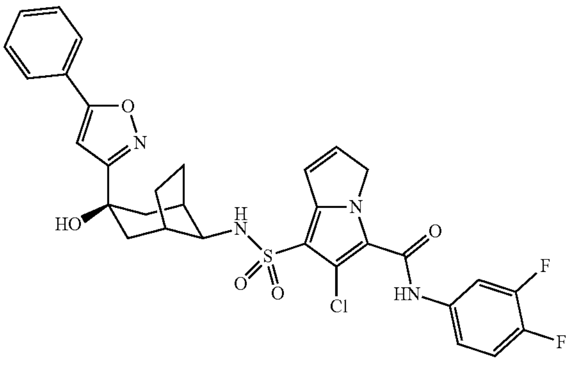
-continued
10pp
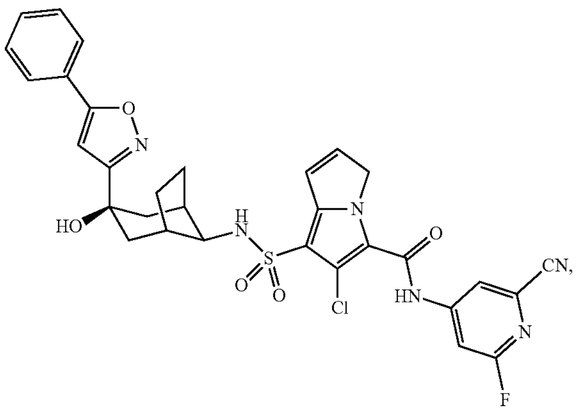
10qq
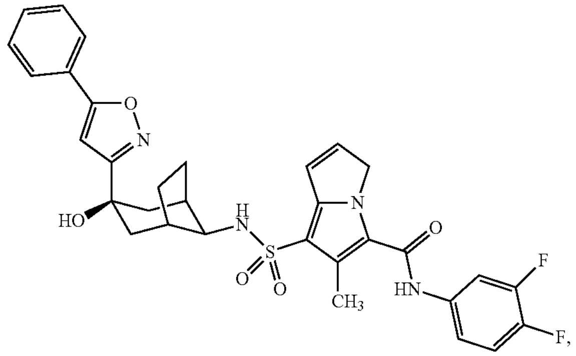
10rr
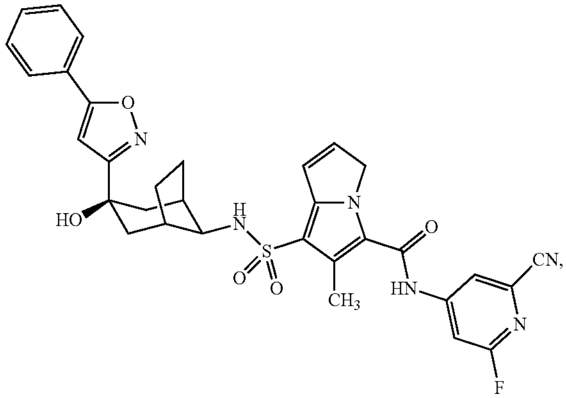
20a
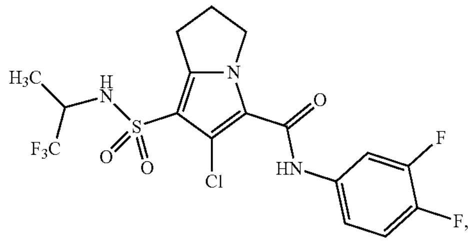

-continued
20b
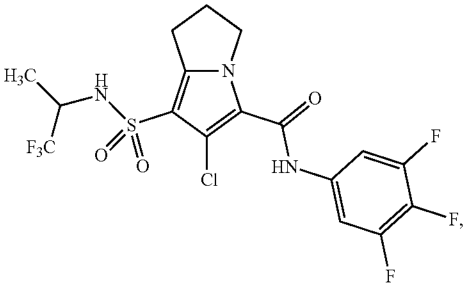
20c
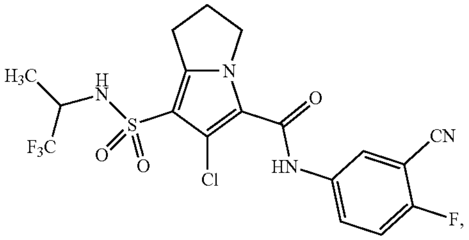
20d
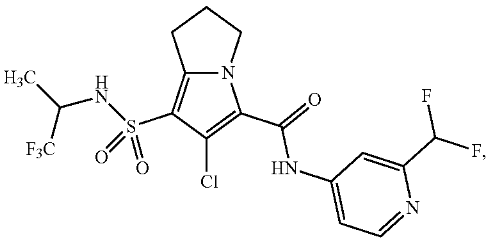
20e
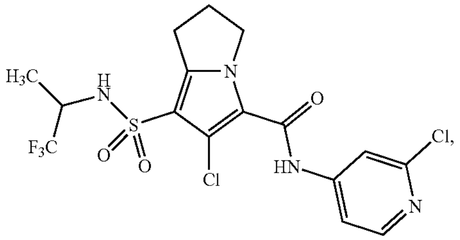
20f
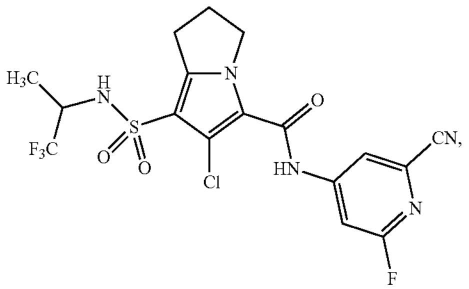
20g
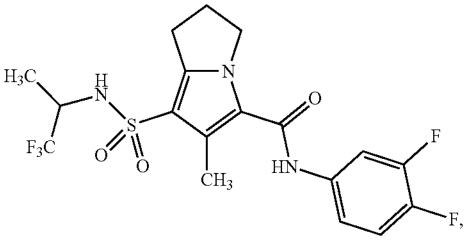
-continued
20h
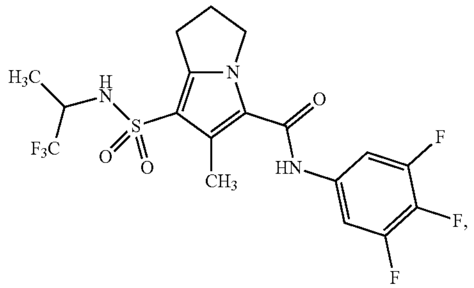
20i
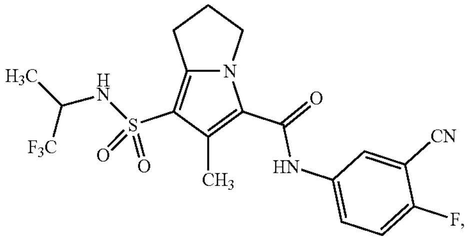
20j
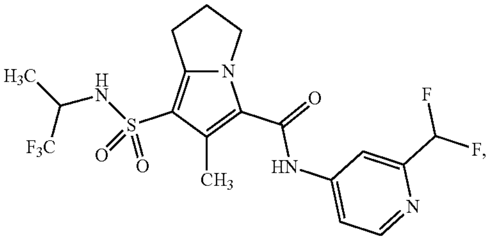
20k
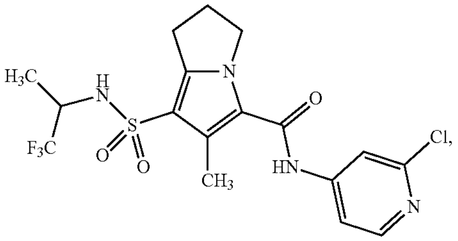
20l
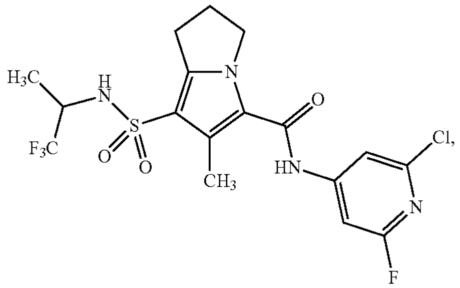
20m
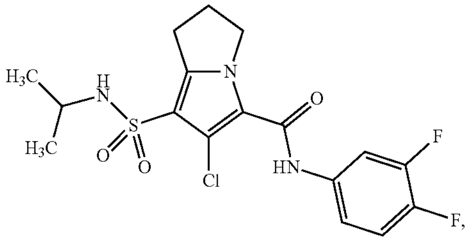

-continued
20n
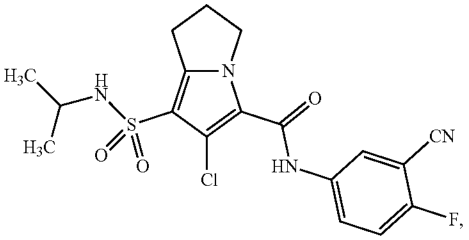
20o
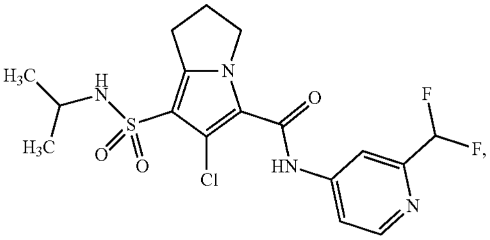
20p
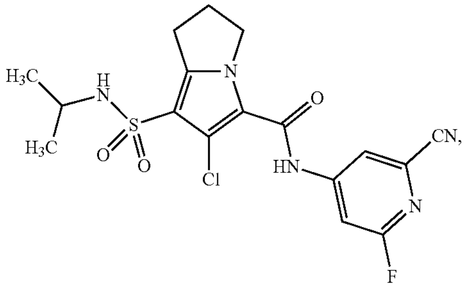
20q
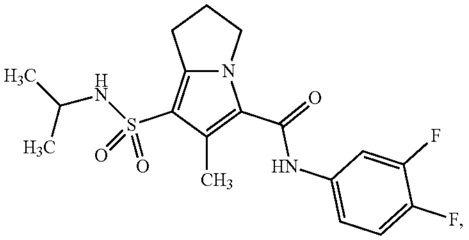
20r
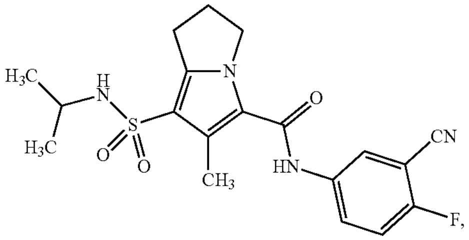
20s
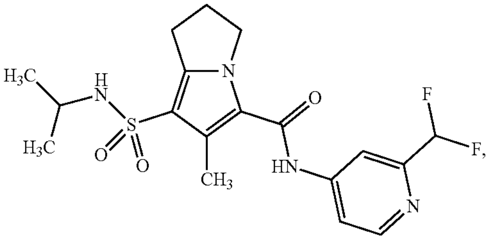
-continued
20t
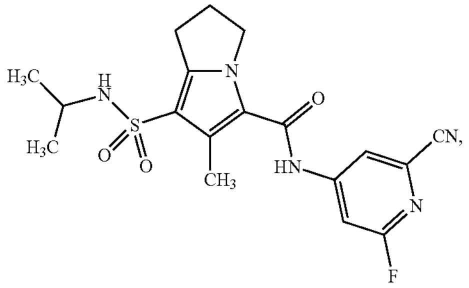
20u
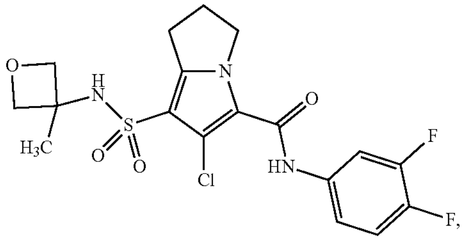
20v
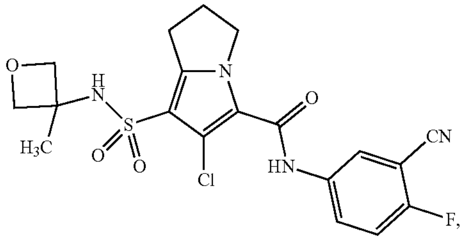
20w
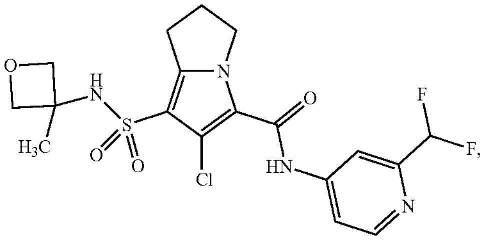
20x
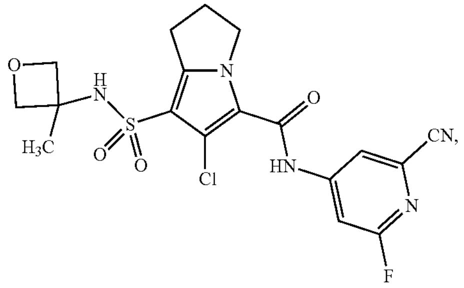

-continued
20y
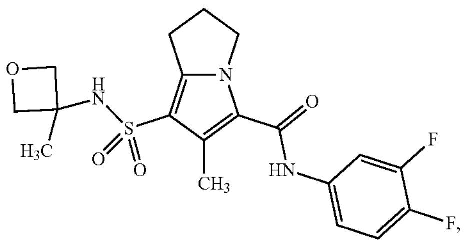
20z
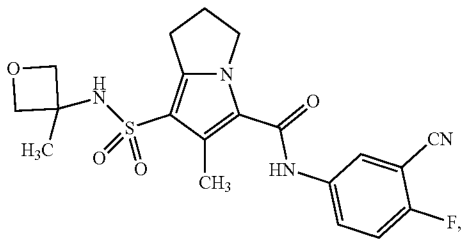
20aa
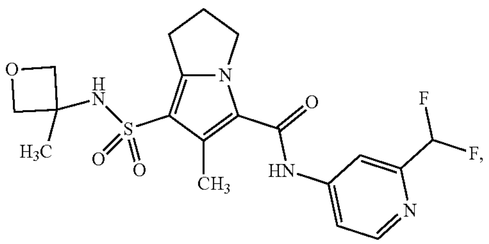
20bb
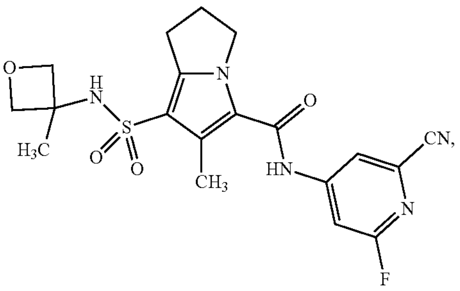
20cc
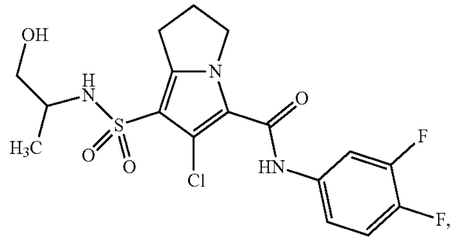
20dd
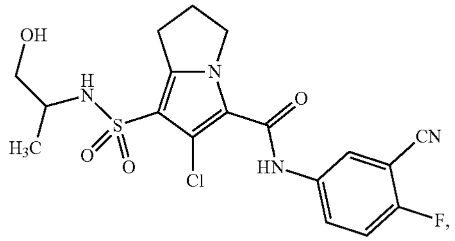
-continued
20ee
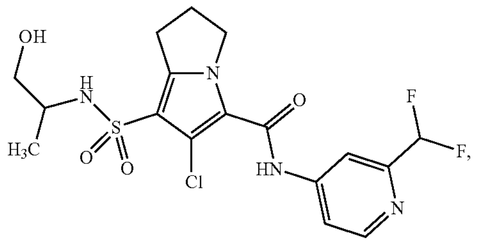
20ff
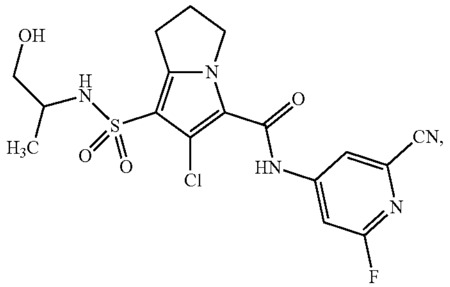
20gg
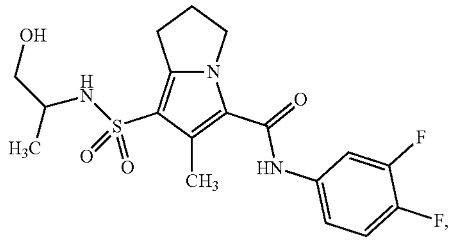
20hh
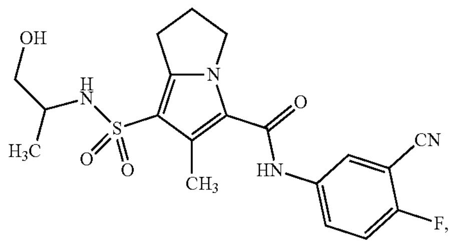
20ii
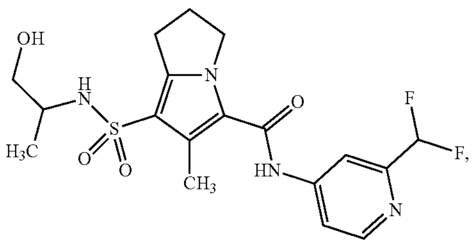
20jj
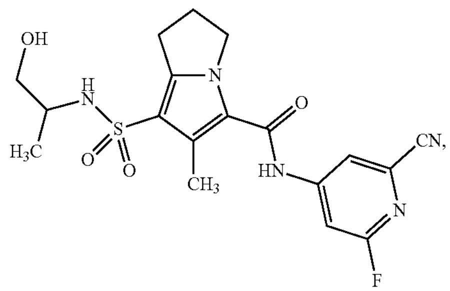

20kk
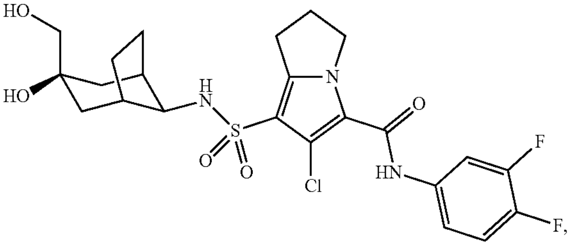
20ll
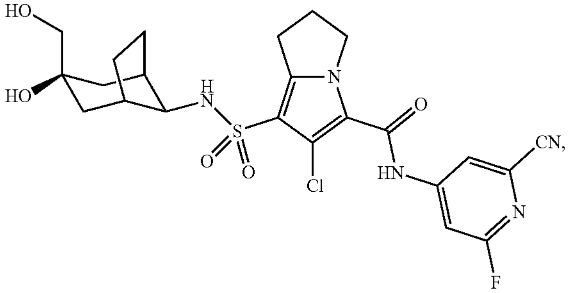
20mm
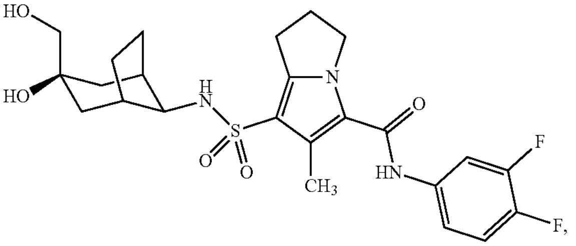
20nn
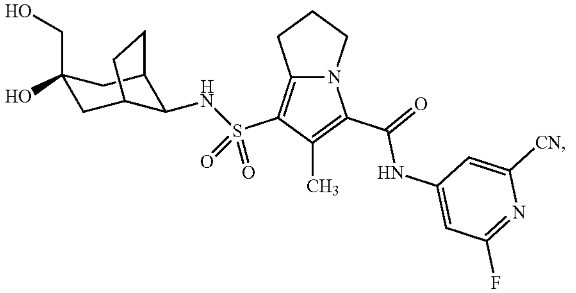
20oo
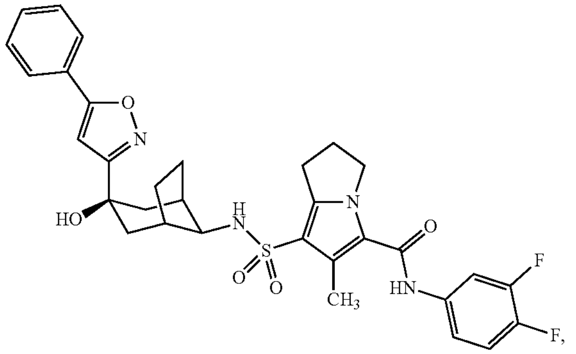
20pp
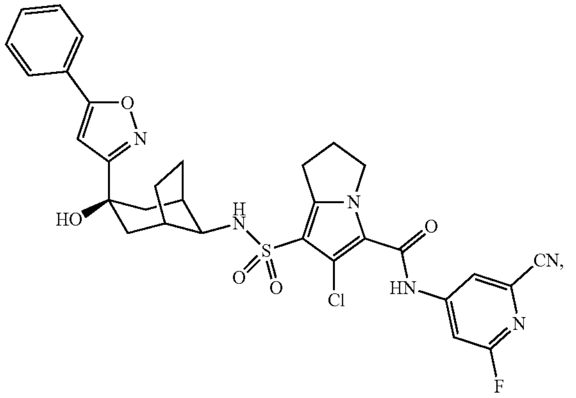
20qq
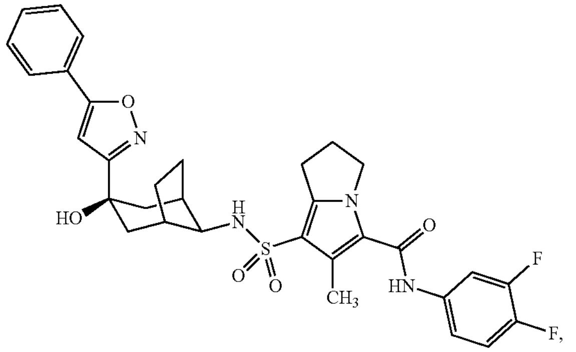
20rr
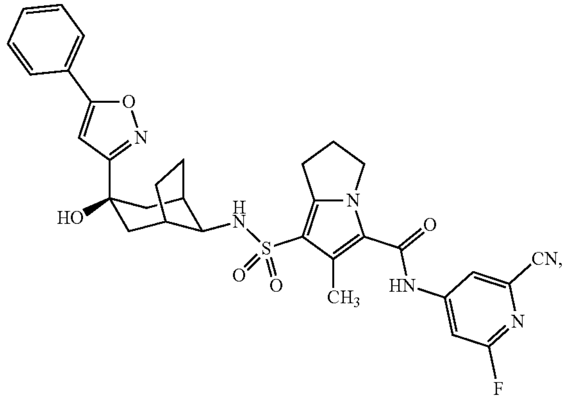
90a
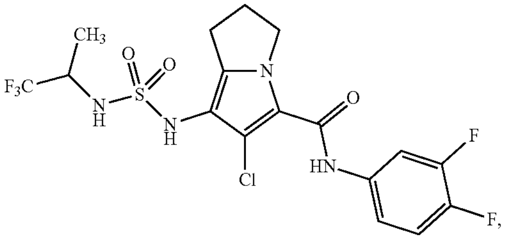

-continued

90b

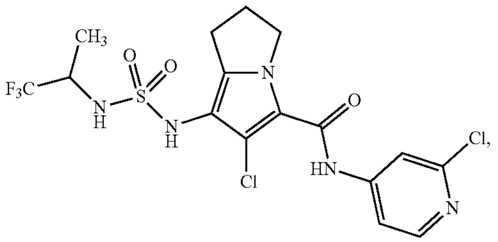

90c

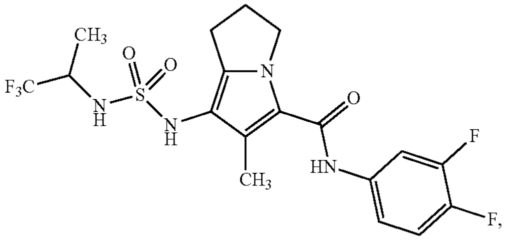

90d

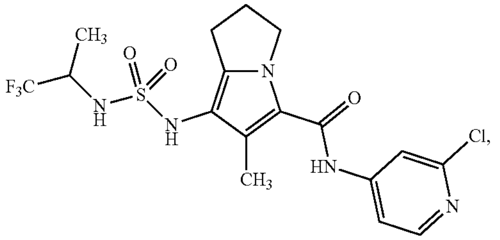

90e

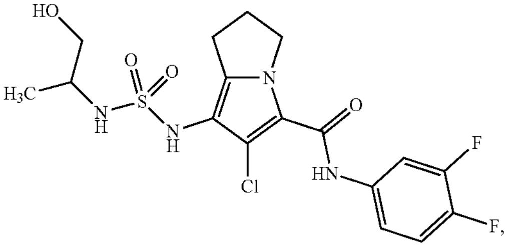

90f

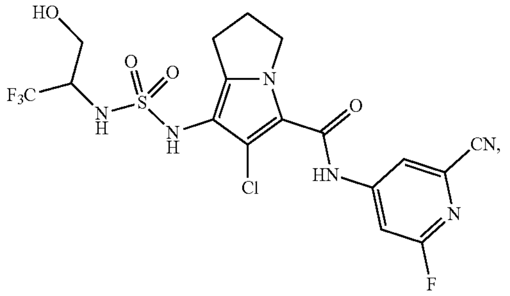

90g

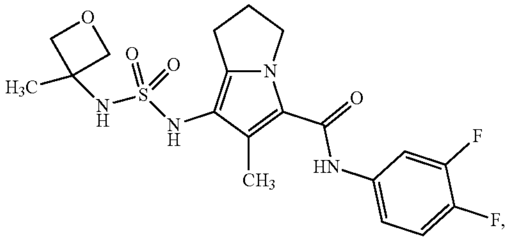

and

-continued

90h

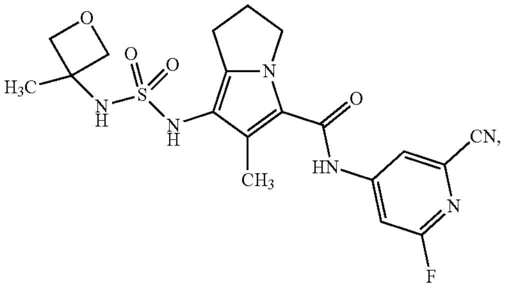

or a pharmaceutically acceptable salt or tautomer thereof.

6. A pharmaceutical composition comprising a compound of claim 1, or a pharmaceutically acceptable salt, stereoisomer, or tautomer thereof, and a pharmaceutically acceptable carrier.

7. A method for inhibiting hepatitis B virus in vitro, wherein the method comprises contacting a biological sample containing hepatitis B virus with a compound of claim 1, or a pharmaceutically acceptable salt, stereoisomer, or tautomer thereof.

8. A method for inhibiting hepatitis B virus in a subject, wherein the method comprises administering to the subject in need thereof a therapeutically effective amount of a compound of claim 1, or a pharmaceutically acceptable salt, stereoisomer, or tautomer thereof.

9. A method for treating hepatitis B in a subject, wherein the method comprises administering to the subject in need thereof a therapeutically effective amount of a compound of claim 1, or a pharmaceutically acceptable salt, stereoisomer, or tautomer thereof.

10. A method for treating hepatitis B in a subject, wherein the method comprises administering to the subject in need thereof a therapeutically effective amount of a pharmaceutical composition of claim 6.

11. A process for the preparation of a compound of formula (A1):

(A1)

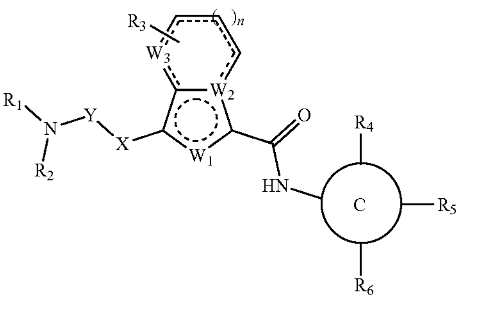

wherein:

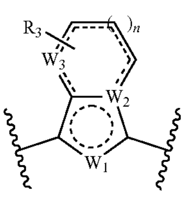

is

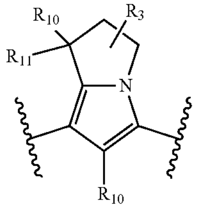

or

-continued

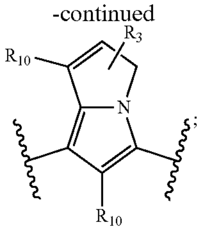

X is absent or —$NR_9$—;

Y is —$S(O)_2$—;

ring C is phenyl or pyridinyl, wherein the phenyl or pyridinyl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, ═O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl;

$R_1$ is H, $C_1$-$C_8$ alkyl, $C_3$-$C_{10}$ cycloalkyl, 3- to 10-membered heterocyclyl, $C_6$-$C_{10}$ aryl, or 5- to 10-membered heteroaryl, wherein the 3- to 10-membered heterocyclyl or 5- to 10-membered heteroaryl has 1, 2, or 3 heteroatoms independently selected from the group consisting of N, O, and S, and further wherein the $C_1$-$C_8$ alkyl, $C_3$-$C_{10}$ cycloalkyl, 3- to 10-membered heterocyclyl, $C_6$-$C_{10}$ aryl, or 5- to 10-membered heteroaryl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, ═O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl;

$R_2$ is H, $C_1$-$C_8$ alkyl, $C_3$-$C_{10}$ cycloalkyl, 3- to 10-membered heterocyclyl, $C_6$-$C_{10}$ aryl, or 5- to 10-membered heteroaryl, wherein the 3- to 10-membered heterocyclyl or 5- to 10-membered heteroaryl has 1, 2, or 3 heteroatoms independently selected from the group consisting of N, O, and S, and further wherein the $C_1$-$C_8$ alkyl, $C_3$-$C_{10}$ cycloalkyl, 3- to 10-membered heterocyclyl, $C_6$-$C_{10}$ aryl, or 5- to 10-membered heteroaryl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, ═O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl; or $R_1$ and $R_2$, together with the nitrogen atom to which they are attached, form a 3- to 10-membered heterocyclyl, wherein the 3- to 10-membered heterocyclyl has 1 N heteroatom and optionally 1, 2, or 3 additional heteroatoms independently selected from the group consisting of N, O, and S;

each $R_3$ is independently H, halogen, CN, $C_1$-$C_8$ alkyl, $C_2$-$C_6$ alkenyl, $C_2$-$C_6$ alkynyl, C(O)OH, $C(O)C_1$-$C_8$ alkyl, $NH_2$, $NHC_1$-$C_8$ alkyl, OH, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl, wherein each 3- to 10-membered heterocycloalkyl and 5- to 10-membered heteroaryl independently has 1, 2, or 3 heteroatoms independently selected from the group consisting of N, O, and S, and further wherein each $C_1$-$C_8$ alkyl, $C_2$-$C_6$ alkenyl, $C_2$-$C_6$ alkynyl, $C(O)C_1$-$C_8$ alkyl, $NHC_1$-$C_8$ alkyl, $OC_1$-$C_8$ alkyl, $C_3$-$C_{10}$ cycloalkyl, 3- to 10-membered heterocycloalkyl, $C_6$-$C_{10}$ aryl, and 5- to 10-membered heteroaryl is optionally and independently substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, ═O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl;

$R_4$ is H, halogen, CN, $C_1$-$C_6$ alkyl, $C_2$-$C_6$ alkenyl, $C_2$-$C_6$ alkynyl, C(O)OH, $C(O)C_1$-$C_8$ alkyl, $NH_2$, $NHC_1$-$C_8$ alkyl, OH, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl, wherein the 3- to 10-membered heterocycloalkyl or 5- to 10-membered heteroaryl has 1, 2, or 3 heteroatoms independently selected from the group consisting of N, O, and S, and further wherein the $C_1$-$C_8$ alkyl, $C_2$-$C_6$ alkenyl, $C_2$-$C_6$ alkynyl, $C(O)C_1$-$C_8$ alkyl, $NHC_1$-$C_8$ alkyl, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, ═O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl;

$R_5$ is H, halogen, CN, $C_1$-$C_8$ alkyl, $C_2$-$C_6$ alkenyl, $C_2$-$C_6$ alkynyl, C(O)OH, $C(O)C_1$-$C_8$ alkyl, $NH_2$, $NHC_1$-$C_8$ alkyl, OH, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl, wherein the 3- to 10-membered heterocycloalkyl or 5- to 10-membered heteroaryl has 1, 2, or 3 heteroatoms independently selected from the group consisting of N, O, and S, and further wherein the $C_1$-$C_8$ alkyl, $C_2$-$C_6$ alkenyl, $C_2$-$C_6$ alkynyl, $C(O)C_1$-$C_8$ alkyl, $NHC_1$-$C_8$ alkyl, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, =O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl;

$R_6$ is H, halogen, CN, $C_1$-$C_8$ alkyl, $C_2$-$C_6$ alkenyl, $C_2$-$C_6$ alkynyl, C(O)OH, $C(O)C_1$-$C_8$ alkyl, $NH_2$, $NHC_1$-$C_8$ alkyl, OH, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl, wherein the 3- to 10-membered heterocycloalkyl or 5- to 10-membered heteroaryl has 1, 2, or 3 heteroatoms independently selected from the group consisting of N, O, and S, and further wherein the $C_1$-$C_8$ alkyl, $C_2$-$C_6$ alkenyl, $C_2$-$C_6$ alkynyl, $C(O)C_1$-$C_8$ alkyl, $NHC_1$-$C_8$ alkyl, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, =O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl;

$R_9$ is H, $C_1$-$C_8$ alkyl, or $C_3$-$C_{10}$ cycloalkyl, wherein the $C_1$-$C_8$ alkyl or $C_3$-$C_{10}$ cycloalkyl is optionally substituted with one or more substituents independently selected from the group consisting of halogen, CN, $C_1$-$C_6$ alkyl, $C_1$-$C_6$ haloalkyl, C(O)OH, $NH_2$, and OH;

each $R_{10}$ is independently H, halogen, CN, $C_1$-$C_8$ alkyl, $C_2$-$C_6$ alkenyl, $C_2$-$C_6$ alkynyl, C(O)OH, $C(O)C_1$-$C_8$ alkyl, $NH_2$, $NHC_1$-$C_8$ alkyl, OH, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl, wherein the 3- to 10-membered heterocycloalkyl or 5- to 10-membered heteroaryl has 1, 2, or 3 heteroatoms independently selected from the group consisting of N, O, and S, and further wherein the $C_1$-$C_8$ alkyl, $C_2$-$C_6$ alkenyl, $C_2$-$C_6$ alkynyl, $C(O)C_1$-$C_8$ alkyl, $NHC_1$-$C_8$ alkyl, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, =O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl; and each $R_{11}$ is independently H, halogen, CN, $C_1$-$C_8$ alkyl, $C_2$-$C_6$ alkenyl, $C_2$-$C_6$ alkynyl, C(O)OH, $C(O)C_1$-$C_8$ alkyl, $NH_2$, $NHC_1$-$C_8$ alkyl, OH, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl, wherein each 3- to 10-membered heterocycloalkyl and 5- to 10-membered heteroaryl independently has 1, 2, or 3 heteroatoms independently selected from the group consisting of N, O, and S, and further wherein each $C_1$-$C_8$ alkyl, $C_2$-$C_6$ alkenyl, $C_2$-$C_6$ alkynyl, $C(O)C_1$-$C_8$ alkyl, $NHC_1$-$C_8$ alkyl, $OC_1$-$C_8$ alkyl, $C_3$-$C_{10}$ cycloalkyl, 3- to 10-membered heterocycloalkyl, $C_6$-$C_{10}$ aryl, and 5- to 10-membered heteroaryl is optionally and independently substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, =O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl;

wherein the process comprises the following steps:

reacting a compound of formula (A-1):

(A-1)

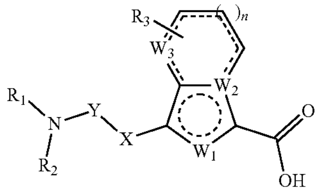

wherein:

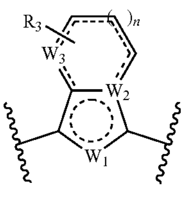

is

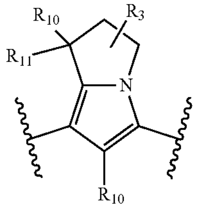

or

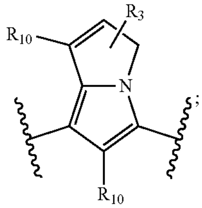

;

X is absent or —$NR_9$—;

Y is —$S(O)_2$—;

ring C is phenyl or pyridinyl, wherein the phenyl or pyridinyl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, =O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl;

$R_1$ is H, $C_1$-$C_8$ alkyl, $C_3$-$C_{10}$ cycloalkyl, 3- to 10-membered heterocyclyl, $C_6$-$C_{10}$ aryl, or 5- to 10-membered heteroaryl, wherein the 3- to 10-membered heterocyclyl or 5- to 10-membered heteroaryl has 1, 2, or 3 heteroatoms independently selected from the group consisting of N, O, and S, and further wherein the $C_1$-$C_8$ alkyl, $C_3$-$C_{10}$ cycloalkyl, 3- to 10-membered heterocyclyl, $C_6$-$C_{10}$ aryl, or 5- to 10-membered heteroaryl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, =O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl;

$R_2$ is H, $C_1$-$C_8$ alkyl, $C_3$-$C_{10}$ cycloalkyl, 3- to 10-membered heterocyclyl, $C_6$-$C_{10}$ aryl, or 5- to 10-membered heteroaryl, wherein the 3- to 10-membered heterocyclyl or 5- to 10-membered heteroaryl has 1, 2, or 3 heteroatoms independently selected from the group consisting of N, O, and S, and further wherein the $C_1$-$C_8$ alkyl, $C_3$-$C_{10}$ cycloalkyl, 3- to 10-membered heterocyclyl, $C_6$-$C_{10}$ aryl, or 5- to 10-membered heteroaryl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, =O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl; or $R_1$ and $R_2$, together with the nitrogen atom to which they are attached, form a 3- to 10-membered heterocyclyl, wherein the 3- to 10-membered heterocyclyl has 1 N heteroatom and optionally 1, 2, or 3 additional heteroatoms independently selected from the group consisting of N, O, and S;

each $R_3$ is independently H, halogen, CN, $C_1$-$C_8$ alkyl, $C_2$-$C_6$ alkenyl, $C_2$-$C_6$ alkynyl, C(O)OH, $C(O)C_1$-$C_8$ alkyl, $NH_2$, $NHC_1$-$C_8$ alkyl, OH, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl, wherein each 3- to 10-membered heterocycloalkyl and 5- to 10-membered heteroaryl independently has 1, 2, or 3 heteroatoms independently selected from the group consisting of N, O, and S, and further wherein each $C_1$-$C_8$ alkyl, C2-C6 alkenyl, C2-C6 alkynyl, $C(O)C_1$-$C_8$ alkyl, $NHC_1$-$C_8$ alkyl, $OC_1$-$C_8$ alkyl, $C_3$-$C_{10}$ cycloalkyl, 3- to 10-membered heterocycloalkyl, $C_6$-$C_{10}$ aryl, and 5- to 10-membered heteroaryl is optionally and independently substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, =O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl;

$R_9$ is H, $C_1$-$C_8$ alkyl, or $C_3$-$C_{10}$ cycloalkyl, wherein the $C_1$-$C_8$ alkyl or $C_3$-$C_{10}$ cycloalkyl is optionally substituted with one or more substituents independently selected from the group consisting of halogen, CN, $C_1$-$C_6$ alkyl, $C_1$-$C_6$ haloalkyl, C(O)OH, $NH_2$, and OH;

each $R_{10}$ is independently H, halogen, CN, $C_1$-$C_8$ alkyl, $C_2$-$C_6$ alkenyl, $C_2$-$C_6$ alkynyl, C(O)OH, $C(O)C_1$-$C_8$ alkyl, $NH_2$, $NHC_1$-$C_8$ alkyl, OH, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl, wherein the 3- to 10-membered heterocycloalkyl or 5- to 10-membered heteroaryl has 1, 2, or 3 heteroatoms independently selected from the group consisting of N, O, and S, and further wherein the $C_1$-$C_8$ alkyl, $C_2$-$C_6$ alkenyl, $C_2$-$C_6$ alkynyl, $C(O)C_1$-$C_8$ alkyl, $NHC_1$-$C_8$ alkyl, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, =O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl; and each $R_{11}$ is independently H, halogen, CN, $C_1$-$C_8$ alkyl, $C_2$-$C_6$ alkenyl, $C_2$-$C_6$ alkynyl, C(O)OH, $C(O)C_1$-$C_8$ alkyl, $NH_2$, $NHC_1$-$C_8$ alkyl, OH, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl, wherein each 3- to 10-membered heterocycloalkyl and 5- to 10-membered heteroaryl independently has 1, 2, or 3 heteroatoms independently selected from the group consisting of N, O, and S, and further wherein each $C_1$-$C_8$ alkyl, $C_2$-$C_6$ alkenyl, $C_2$-$C_6$ alkynyl, $C(O)C_1$-$C_8$ alkyl, $NHC_1$-$C_8$ alkyl, $OC_1$-$C_8$ alkyl, $C_3$-$C_{10}$ cycloalkyl, 3- to 10-membered heterocycloalkyl, $C_6$-$C_{10}$ aryl, and 5- to 10-membered heteroaryl is optionally and independently substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, =O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl;

with a compound of formula (A-2):

(A-2)

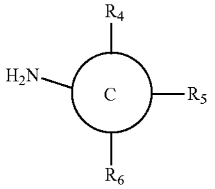

wherein:

$R_4$ is H, halogen, CN, $C_1$-$C_8$ alkyl, $C_2$-$C_6$ alkenyl, $C_2$-$C_6$ alkynyl, C(O)OH, C(O)$C_1$-$C_8$ alkyl, $NH_2$, $NHC_1$-$C_8$ alkyl, OH, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl, wherein the 3- to 10-membered heterocycloalkyl or 5- to 10-membered heteroaryl has 1, 2, or 3 heteroatoms independently selected from the group consisting of N, O, and S, and further wherein the $C_1$-$C_8$ alkyl, $C_2$-$C_6$ alkenyl, $C_2$-$C_6$ alkynyl, C(O)$C_1$-$C_8$ alkyl, $NHC_1$-$C_8$ alkyl, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, =O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl;

$R_5$ is H, halogen, CN, $C_1$-$C_8$ alkyl, $C_2$-$C_6$ alkenyl, $C_2$-$C_6$ alkynyl, C(O)OH, C(O)$C_1$-$C_8$ alkyl, $NH_2$, $NHC_1$-$C_8$ alkyl, OH, $OC_1$-$C_6$ alkyl, $C_3$-$C_{10}$ cycloalkyl, 3- to 10-membered heterocycloalkyl, $C_6$-$C_{10}$ aryl, or 5- to 10-membered heteroaryl, wherein the 3- to 10-membered heterocycloalkyl or 5- to 10-membered heteroaryl has 1, 2, or 3 heteroatoms independently selected from the group consisting of N, O, and S, and further wherein the $C_1$-$C_8$ alkyl, $C_2$-$C_6$ alkenyl, $C_2$-$C_6$ alkynyl, C(O)$C_1$-$C_8$ alkyl, $NHC_1$-$C_8$ alkyl, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, =O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl; and $R_6$ is H, halogen, CN, $C_1$-$C_8$ alkyl, $C_2$-$C_6$ alkenyl, $C_2$-$C_6$ alkynyl, C(O)OH, C(O)$C_1$-$C_8$ alkyl, $NH_2$, $NHC_1$-$C_8$ alkyl, OH, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl, wherein the 3- to 10-membered heterocycloalkyl or 5- to 10-membered heteroaryl has 1, 2, or 3 heteroatoms independently selected from the group consisting of N, O, and S, and further wherein the $C_1$-$C_8$ alkyl, $C_2$-$C_6$ alkenyl, $C_2$-$C_6$ alkynyl, C(O)$C_1$-$C_8$ alkyl, $NHC_1$-$C_8$ alkyl, $OC_1$-$C_8$ alkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more substituents independently selected from the group consisting of halogen, CN, $C_1$-$C_6$ alkyl, $C_1$-$C_6$ haloalkyl, $C_1$-$C_6$ hydroxyalkyl, C(O)OH, $NH_2$, OH, $OC_1$-$C_6$ alkyl, $OC_1$-$C_6$ haloalkyl, =O, $C_3$-$C_8$ cycloalkyl, $C_3$-$C_8$ halocycloalkyl, $C_6$-$C_{10}$ aryl, $C_6$-$C_{10}$ haloaryl, and 5- to 10-membered heteroaryl, and further wherein each 5- to 10-membered heteroaryl substituent independently has 1, 2, or 3 heteroatoms independently selected from the group consisting of N, O, and S, and is optionally and independently substituted with one or more substituents independently selected from the group consisting of halogen and phenyl;

in an inert solvent, to obtain the compound of formula (A1) above.

12. A compound selected from the group consisting of:

10ss

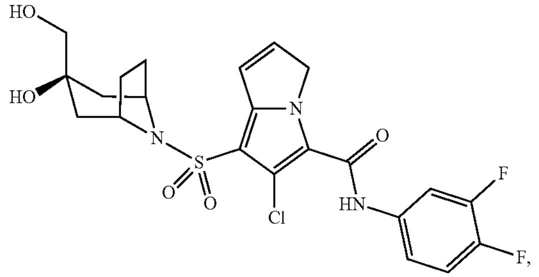

10tt

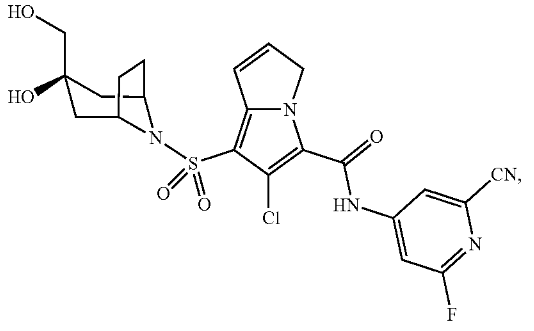

-continued
10uu
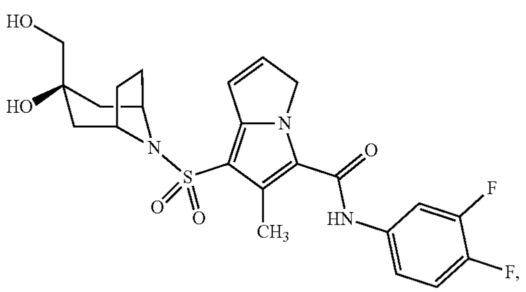
10vv
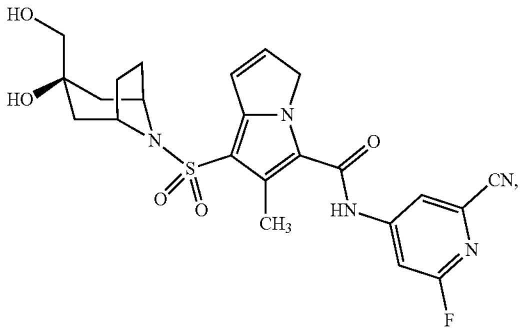
10ww
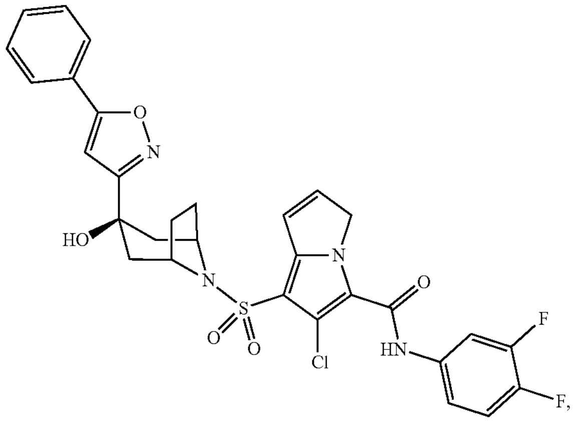
10xx
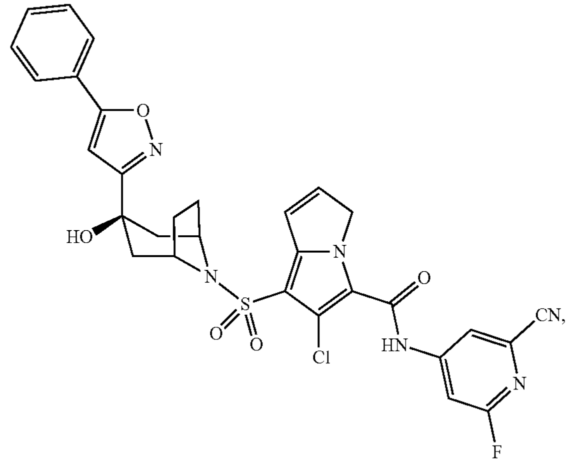
-continued
10yy
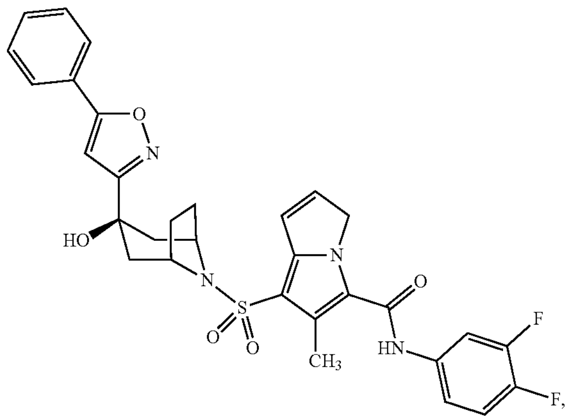
10zz
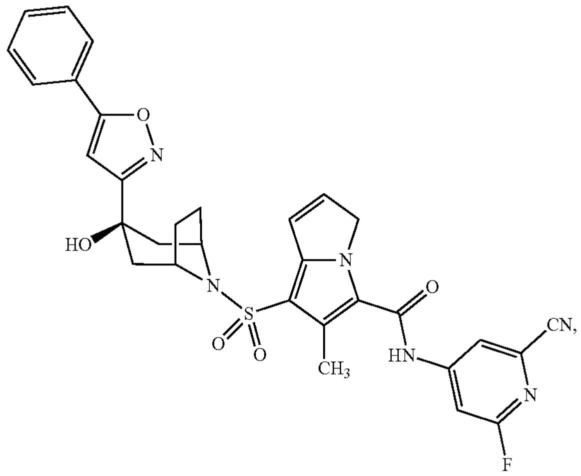
20ss
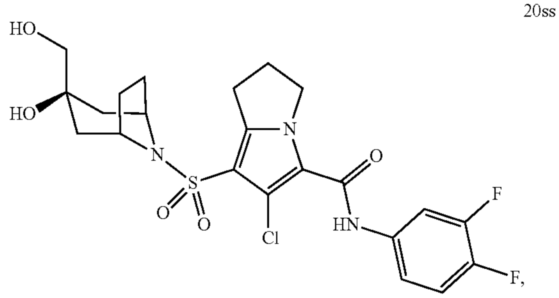
20tt
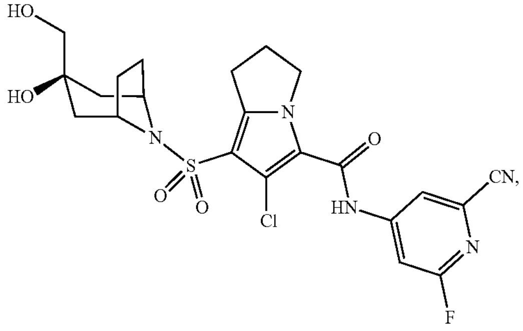

-continued
20uu
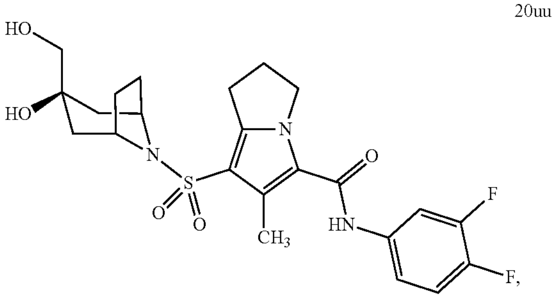
20vv
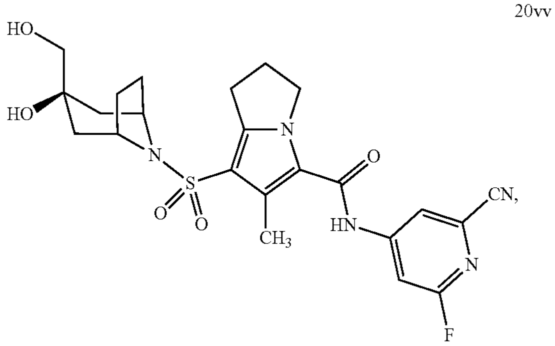
20ww
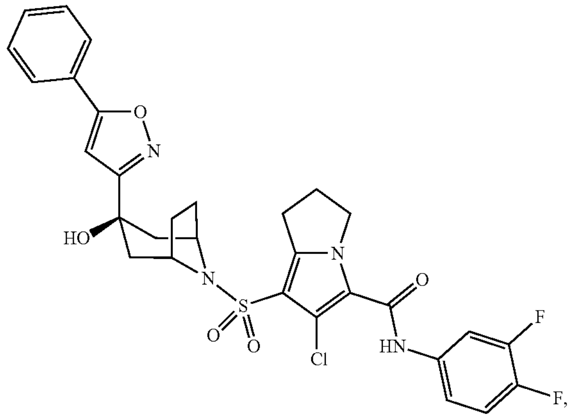
20xx
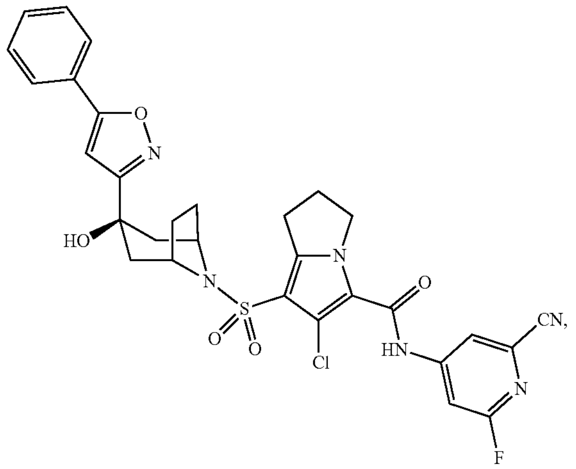
-continued
20yy
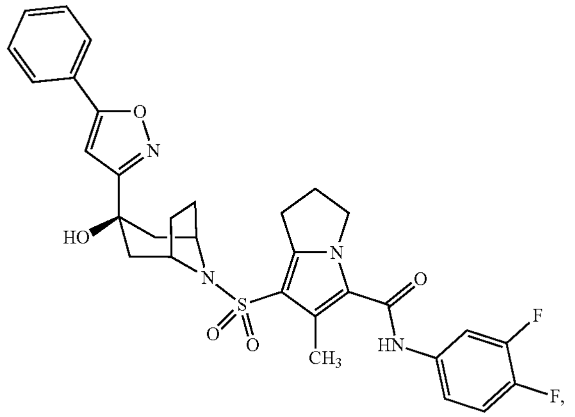
20zz
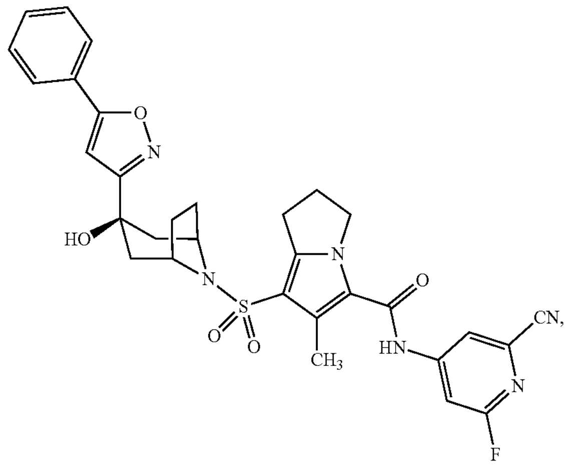
90i
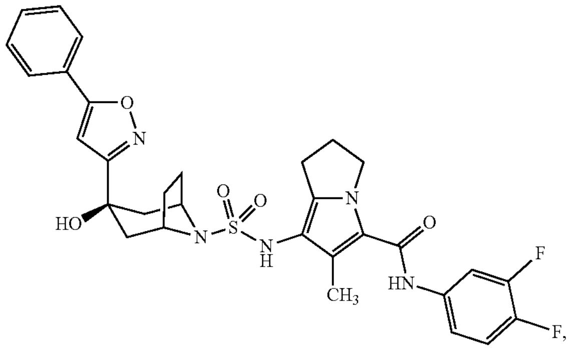
90j
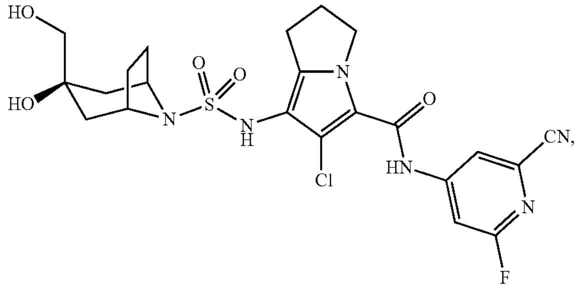

-continued
90dd
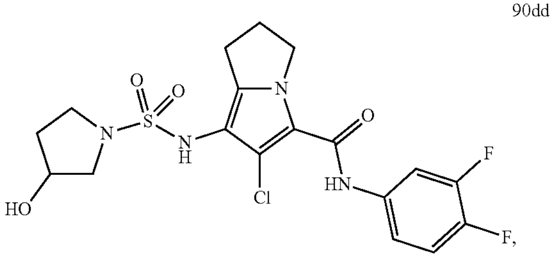
90ee
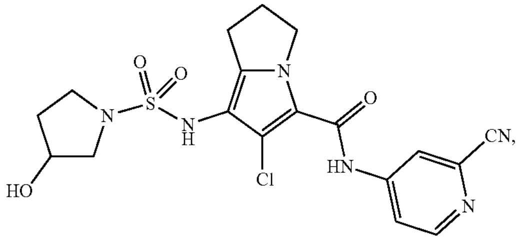
-continued
90ff
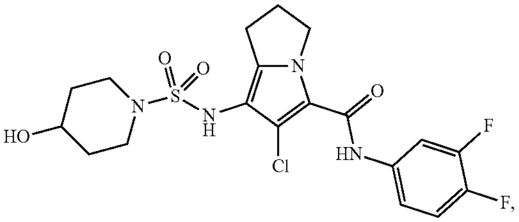
and
90gg
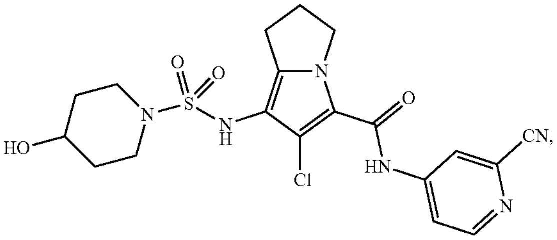
or a pharmaceutically acceptable salt or tautomer thereof.
* * * * *